US010787503B2

(12) United States Patent
Crowe, Jr. et al.

(10) Patent No.: US 10,787,503 B2
(45) Date of Patent: Sep. 29, 2020

(54) ANTIBODY-MEDIATED NEUTRALIZATION OF CHIKUNGUNYA VIRUS

(71) Applicant: VANDERBILT UNIVERSITY, Nashville, TN (US)

(72) Inventors: James E. Crowe, Jr., Nashville, TN (US); Scott A. Smith, White Bluff, TN (US); Terence Dermody, Brentwood, TN (US); Laurie Silva, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/566,283

(22) PCT Filed: Apr. 14, 2016

(86) PCT No.: PCT/US2016/027466
§ 371 (c)(1),
(2) Date: Oct. 13, 2017

(87) PCT Pub. No.: WO2016/168417
PCT Pub. Date: Oct. 20, 2016

(65) Prior Publication Data
US 2018/0079802 A1    Mar. 22, 2018

Related U.S. Application Data

(60) Provisional application No. 62/147,354, filed on Apr. 14, 2015.

(51) Int. Cl.
| | | |
|---|---|---|
| *C07K 16/10* | (2006.01) | |
| *A61K 39/395* | (2006.01) | |
| *G01N 33/569* | (2006.01) | |
| *A61K 39/12* | (2006.01) | |
| *A61K 39/00* | (2006.01) | |
| *C12Q 1/70* | (2006.01) | |

(52) U.S. Cl.
CPC .......... *C07K 16/1081* (2013.01); *A61K 39/12* (2013.01); *A61K 39/395* (2013.01); *G01N 33/56983* (2013.01); *A61K 39/00* (2013.01); *A61K 2039/505* (2013.01); *A61K 2039/507* (2013.01); *C07K 2317/21* (2013.01); *C07K 2317/34* (2013.01); *C07K 2317/565* (2013.01); *C07K 2317/76* (2013.01); *C07K 2317/92* (2013.01); *C12Q 1/70* (2013.01); *G01N 2333/181* (2013.01); *Y02A 50/383* (2018.01); *Y02A 50/51* (2018.01)

(58) Field of Classification Search
None
See application file for complete search history.

(56) References Cited

U.S. PATENT DOCUMENTS

| | | | |
|---|---|---|---|
| 9,441,032 B2 * | 9/2016 | Warter | ............... C07K 16/1081 |
| 9,738,704 B2 * | 8/2017 | Warter | ............... C07K 16/1081 |
| 2013/0189279 A1 | 7/2013 | Warter et al. | |
| 2018/0127487 A1 * | 5/2018 | Carter | .................... A61P 31/14 |

FOREIGN PATENT DOCUMENTS

| | | |
|---|---|---|
| WO | WO 2009/031045 | 3/2009 |
| WO | WO 2011/124635 | 10/2011 |
| WO | WO 2015/010125 | 1/2015 |

OTHER PUBLICATIONS

Office Communication issued in corresponding Eurasian Application No. 201792220, dated Mar. 26 2019.
Bréhin, Anne-Claire, et al. "Production and characterization of mouse monoclonal antibodies reactive to Chikungunya envelope E2 glycoprotein." *Virology* 371.1 (2008): 185-195.
Chu, Haiyan, et al. "Deciphering the protective role of adaptive immunity to CHIKV/IRES a novel candidate vaccine against Chikungunya in the A129 mouse model." *Vaccine* 31.33 (2013): 3353-3360.
Chua, Chong Long, Yoke Fun Chan, and I-Ching Sam. "Characterisation of mouse monoclonal antibodies targeting linear epitopes on Chikungunya virus E2 glycoprotein." *Journal of Virological Methods* 195 (2014): 126-133.
Couderc, Thérèse, et al. "Prophylaxis and therapy for Chikungunya virus infection" *The Journal of Infectious Diseases* 200.4 (2009): 516-523.
Extended European Search Report issued in European Application No. 16780715.5, dated Dec. 19, 2018.
Fong, Rachel H., et al. "Exposure of epitope residues on the outer face of the chikungunya virus envelope trimer determines antibody neutralizing efficacy." *Journal of Virology* (2014): JVI-01943.
Fric, Jan, et al. "Use of human monoclonal antibodies to treat Chikungunya virus infection." *The Journal of Infectious Diseases* 207.2 (2012): 319-322.
Goh, Lucas YH, et al. "Monoclonal antibodies specific for the capsid protein of chikungunya virus suitable for multiple applications." *Journal of General Virology* 96.3 (2015): 507-512.
Goh, Lucas YH, et al. "Neutralizing monoclonal antibodies to the E2 protein of chikungunya virus protects against disease in a mouse model." *Clinical Immunology* 149.3 (2013): 487-497.
Hallengärd, David, et al. "Prime-boost immunization strategies against Chikungunya, virus." *Journal of Virology* (2014): JVI-01926.
Hawman, David W., et al. "Chronic joint disease caused by persistent Chikungunya virus infection is controlled by the adaptive immune response." *Journal of Virology* (2013): JVI-02666.
International Search Report and Written Opinion issued in International Application No. PCT/US2016/027466, dated Oct. 7, 2016.
Invitation to Pay Additional Fees issued in International Application No. PCT/US2016/027466, dated Jun. 24, 2016.

(Continued)

*Primary Examiner* — Agnieszka Boesen
(74) *Attorney, Agent, or Firm* — Parker Highlander PLLC

(57) ABSTRACT

The present disclosure is directed to antibodies binding to and neutralizing Chikungunya virus (CHIKV) and methods for use thereof.

43 Claims, 34 Drawing Sheets

Specification includes a Sequence Listing.

(56) References Cited

OTHER PUBLICATIONS

Kam, Yiu-Wing, et al. "Early neutralizing IgG response to Chikungunya virus in infected patients targets a dominant linear epitope on the E2 glycoprotein." *EMBO Molecular Medicine* 4.4 (2012): 330-343.
Kam, Yin-Wing, et al. "Longitudinal analysis of the human antibody response to chikungunya virus infection: implications for serodiagnosis assays and vaccine development." *Journal of Virology* (2012): JVI-01780.
Kielian, Margaret, Chantal Chanel-Vos, and Maofu Liao. "Alphavirus entry and membrane fusion." *Viruses* 2.4 (2010): 796-825.
Lee, Chia Yin et al. "Chikungunya virus neutralization antigens and direct cell-to-cell transmission are revealed by human antibody-escape mutants." *PLoS Pathogens* 7.12 (2011), e1002390.
Lum, Fok-Moon, et al. "An essential role of antibodies in the control of Chikungunya virus infection." *The Journal of Immunology* (2013): 1300304.
Masrinoul, Promsin, et al. "Monoclonal antibody targeting chikungunya virus envelope 1 protein inhibits virus release." *Virology* 464 (2014): 111-117.
Pal, Pankaj, et al. "Chikunguaya viruses that escape monoclonal antibody therapy are clinically attenuated, stable, and not purified in mosquitoes." *Journal of Virology* (2014): JVI-01032.
Pal, Pankaj, et al. "Development of a highly protective combination monoclonal antibody therapy against Chikungunya virus." *PLoS Pathogens* 9.4 (2013): e1003312.
Schilte, Clémentine, et al. "Chikungunya virus-associated long-term arthralgia: a 36-month prospective longitudinal study." *PLoS Neglected Tropical Diseases* 7.3 (2013): e2137.
Search Report and Written Opinion issued in Singapore Application No. 11201708152S, dated Oct. 9, 2018.
Selvarajah, Suganya, et al. "A neutralizing monoclonal antibody targeting the acid-sensitive region in chikungunya virus E2 protects from disease." *PLoS Neglected Tropical Diseases* 7.9 (2013): e2423.
Sissoko, Daouda, et al. "Post-epidemic Chikungunya disease on Reunion Island: course of rheumatic manifestations and associated factors over a 15-month period." *PLoS Neglected Tropical Diseases* 3.3 (2009): e389.
Smith, Scott A., et al. "Isolation and characterization of broad and ultrapotent human monoclonal antibodies with therapeutic activity against chikungunya virus." *Cell Host & Microbe* 18.1 (2015): 86-95.
Staples, J. Erin, Robert F. Breiman, and Ann M. Powers. "Chikungunya fever: an epidemiological review of a re-emerging infectious disease," *Clinical Infectious Diseases* 49.6 (2009): 942-948.
Supplementary European Search Report issued in European Application No. 16780715.5, dated Oct. 8, 2018.
Warta, Lucile, et al. "Chikungunya virus envelope-specific human monoclonal antibodies with broad neutralization potency." *The Journal of Immunology* (2011): 1003139.
Office Communication issued in corresponding Chilean Application No. 201702596, dated May 29, 2019. Original—English Translation provided below.
Office Communication issued in corresponding Chilean Application No. 201702596, dated May 29, 2019. Machine Translation.
Office Communication issued in corresponding Eurasian Application No. 201792220/28, dated Dec. 17, 2019. English Translation with Original.
Office Communication issued in corresponding Japanese Application No. 2017-553887, dated Mar. 17, 2020. English Translation with Original.

\* cited by examiner

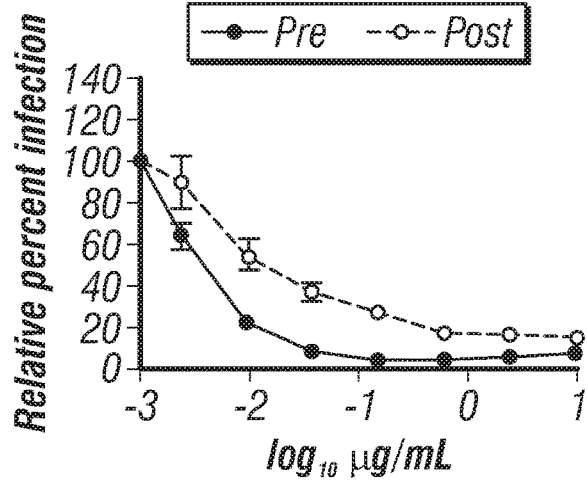
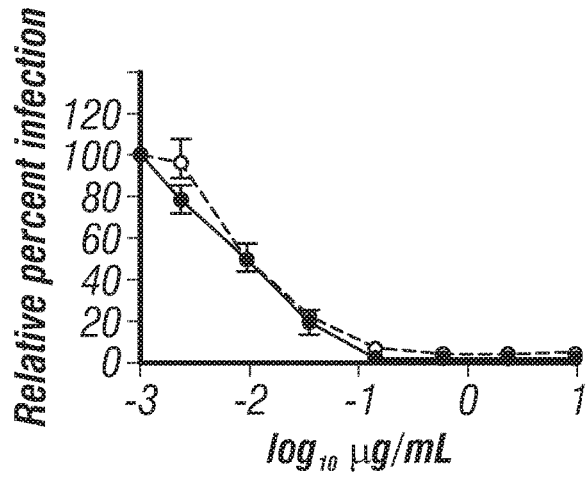
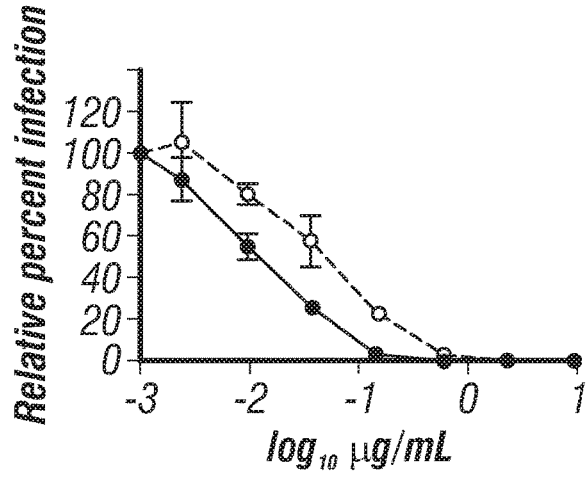
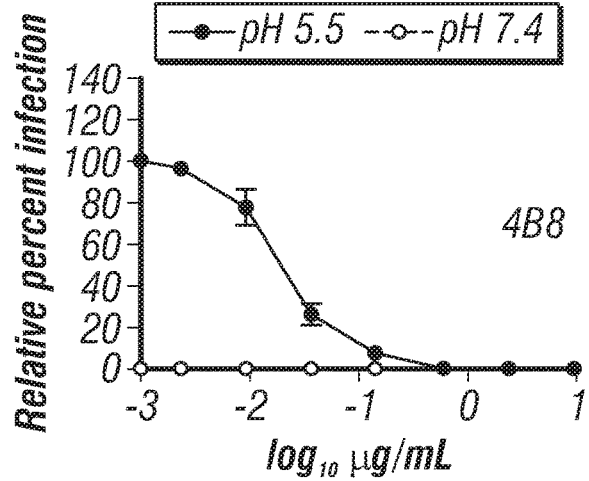
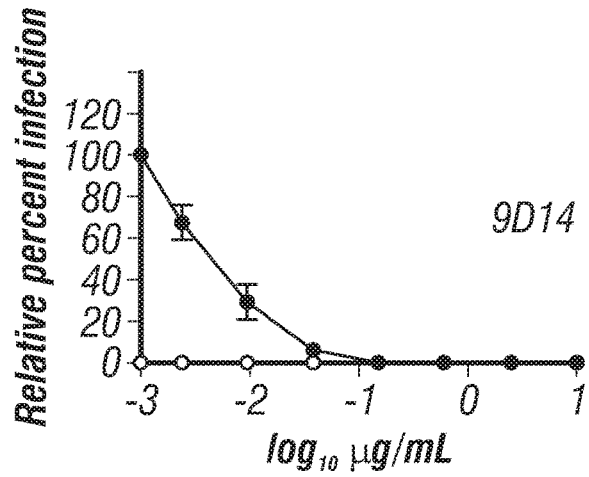
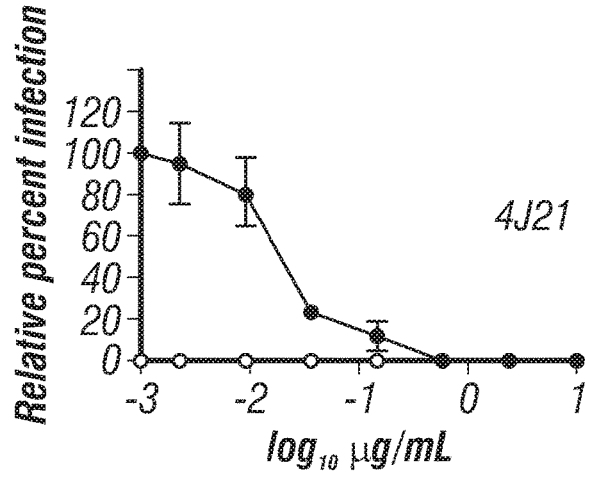
FIG. 2A
FIG. 2B

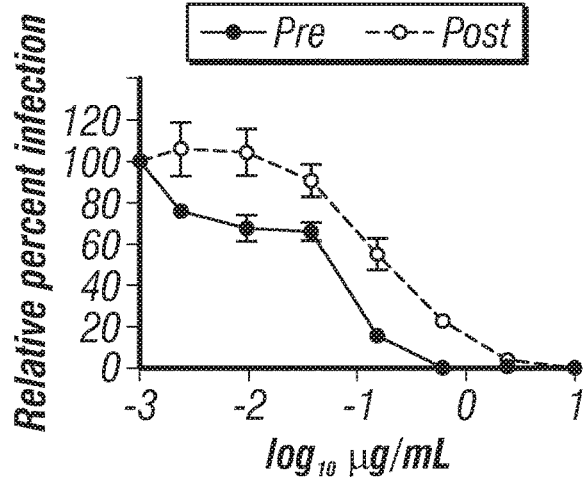
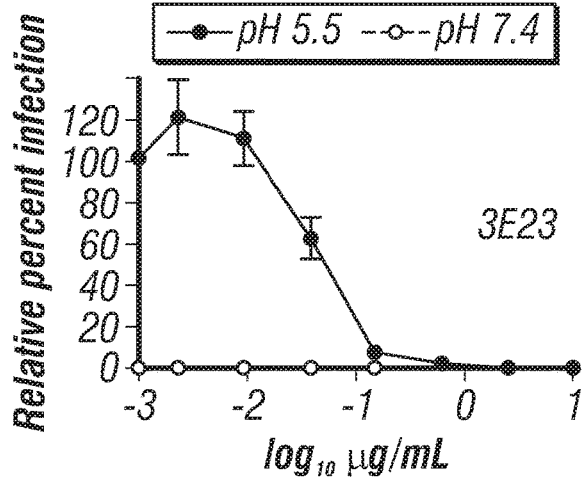
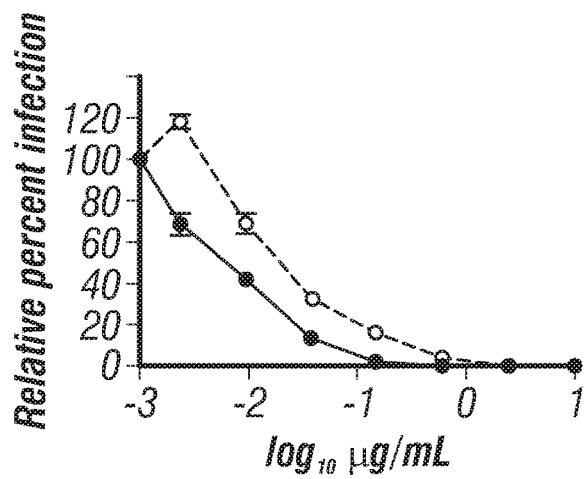
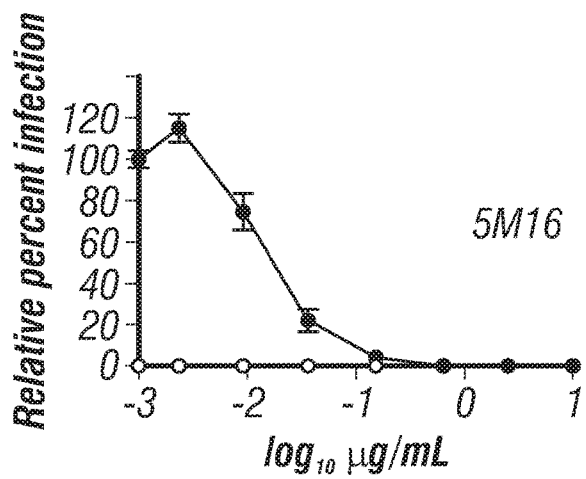
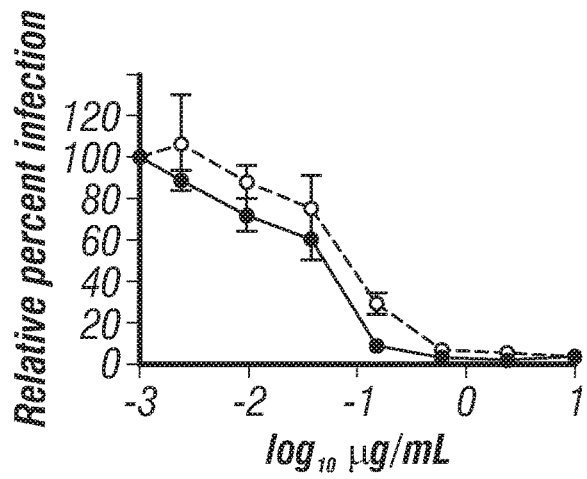
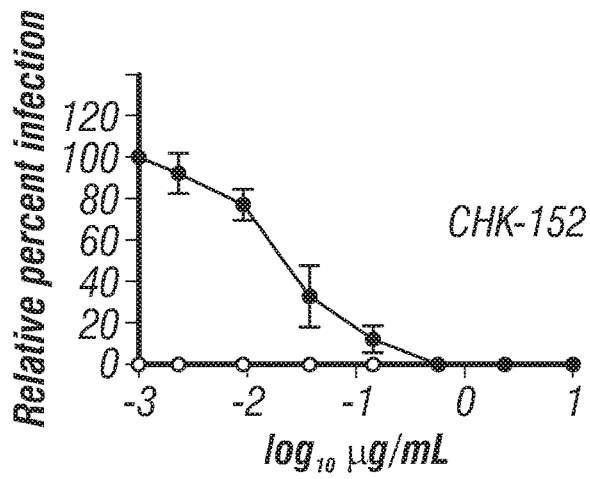
FIG. 2A
(Cont'd)
FIG. 2B
(Cont'd)

FIG. 5

| mAb | 5N23 | CHK-84 | CHK-141 | 5O14 | 5M16 | 106 | 9D14 | 4B8 | 1H12 | 5F10 | CHK-265 | CHK-88 | 3A2 | 5F19 | Domain(s) identified by mutagenesis studies |
|---|---|---|---|---|---|---|---|---|---|---|---|---|---|---|---|
| 5N23 | 0 | 5 | 5 | 77 | 93 | 89 | 98 | 92 | 31 | 92 | 100 | 97 | 92 | 96 | DA, Arch |
| CHK-84 | -1 | 2 | 5 | 47 | 21 | 68 | 105 | 88 | 39 | 94 | 94 | 85 | 95 | 81 | DA |
| CHK-141 | -3 | 4 | -1 | 49 | 34 | 79 | 98 | 94 | 54 | 101 | 100 | 101 | 94 | 80 | DA |
| 5O14 | 82 | 5 | -9 | -1 | -10 | -20 | 26 | -1 | 5 | 86 | 77 | 77 | 37 | 91 | NR |
| 5M16 | 92 | -2 | -38 | 27 | 5 | -12 | 25 | 6 | 26 | 95 | 90 | 91 | 72 | 88 | DA |
| 106 | 106 | 111 | 48 | 65 | 15 | -3 | -7 | 30 | 4 | 19 | 97 | 79 | 108 | 89 | DA |
| 9D14 | 79 | 103 | 97 | 44 | 20 | 34 | 23 | 4 | 48 | 84 | 80 | 89 | 71 | 94 | NotR |
| 4B8 | 96 | 102 | 101 | 33 | 18 | 3 | 27 | 6 | 36 | 90 | 88 | 91 | 92 | 103 | NR |
| 1H12 | -2 | -4 | 30 | 1 | -2 | -4 | 24 | 4 | -10 | 45 | 45 | 38 | 44 | 91 | DA/DB Arch |
| 5F10 | 103 | 100 | 96 | 89 | 96 | 82 | 118 | 96 | 52 | -3 | 2 | 3 | 88 | 99 | DB |
| CHK-265 | 98 | 92 | 86 | 85 | 84 | 85 | 105 | 92 | 52 | -3 | 2 | 3 | 95 | 96 | DB |
| CHK-88 | 96 | 90 | 85 | 89 | 87 | 110 | 116 | 91 | 49 | 5 | 10 | 8 | 44 | 97 | DB |
| 3A2 | 108 | 99 | 92 | 15 | 64 | 86 | 114 | 112 | 56 | 93 | 101 | 53 | 3 | 103 | DB |

Primary antibody (horizontal axis); Competing antibody (vertical axis)

trimer - side view trimer - top down view

| Clone | Hybridoma-produced mAb ('old') | Recombinant CHO cell-produced mAb ('new') |
| --- | --- | --- |
| 1H12 | 4.2 | 2.7 |
| 2H1 | 4 | 3.8 |
| (3E)23 | 34 | 13.8 |
| 3N23 | 2.1 | 4.5 |
| 4J14 | 8.6 | 5.7 |
| 4J21 | 11.4 | 4.8 |
| 4N12 | 4.8 | 5 |
| 5M16 | 5.9 | 1,094 |
| 5(O)14 | 14.3 | 34.8 |

*FIG. 14*

<u>Chikungunya virus E1/E2 alignment:</u>

ECSA Genotypes:  LR2006
 S27
 SL15649

Asian Genotypes:  181/25
 99659

West African Genotype:  IbH35

*Aligned sequences are shown as Protein_Strain_Genbank accession number*

*FIG. 15*

CLUSTAL O(1.2.1) multiple sequence alignment

| | |
|---|---|
| E1_S27_NC004162.2 | TACGAACACGTAACAGTGATCCCGAACACGGTGGGAGTACCGTATAAGACTTCTAGTCAAC |
| E1_SL15649_GU189061.1 | TACGAACACGTAACAGTGATCCCGAACACGGTGGGAGTACCGTATAAGACTTCTAGTCAAT |
| E1_LR2006_KT449801.1 | TACGAACACGTAACAGTGATCCCGAACACGGTGGGAGTACCGTATAAGACTTCTAGTCAAT |
| E1_181/25_L37661.3 | TACGAACACGTAACAGTGATCCCGAACACGGTGGGAGTACCGTATAAGACTTCTAGTCAAC |
| E1_99659_KJ451624.1 | TACGAACACGTAACAGTGATCCCGAACACGGTGGGAGTACCGTATAAGACTTCTAGTCAAC |
| E1_IbH35_HM045786.1 | TACGAACACGTAACAGTGATCCCGAACACGGTGGGAGTACCGTATAAGACTTGTCAAC |
| | ************************************************* ******* |
| E1_S27_NC004162.2 | AGACCGGCTACAGCCCCATGGTTGGAGATGGAGCTACTGTCAGTCACTTTGGAGCCA |
| E1_SL15649_GU189061.1 | AGACCTGGCTACAGCCCCATGGTATTGGAGATGGAGAACTACTGTCAGTCACTTTGGAGCCA |
| E1_LR2006_KT449801.1 | AGACCTGGCTACAGCCCCATGGTATTGGAGATGGAGAACTACTGTCAGTCACTTTGGAGCCA |
| E1_181/25_L37661.3 | AGACCGGGCTACAGCCCCATGGTACTGGAGATGGAGAGCTACTGTCAGTCACTTTGGAGCCA |
| E1_99659_KJ451624.1 | AGACCGGGCTACAGCCCCATGGTATTGGAGATGGAGAGCTACTGTCAGTCACTTTGGAACCA |
| E1_IbH35_HM045786.1 | AGACCGGGTTACAGCCCCATGGTATTGGAGATGGAGAGCTACTGTCAGTCACTTTGGAACCA |
| | ***** * ************* * *********** *:*************:* |
| E1_S27_NC004162.2 | ACGCTATCGCTTGATTACATCACGTGCGAATACAAAACCGTCATCCCGTCTCCCGTACGTG |
| E1_SL15649_GU189061.1 | ACACTATCGCTTGATTACATCACGTGCGAGTACAAAACCGTCATCCCGTCCCCGTACGTG |
| E1_LR2006_KT449801.1 | ACACTATCGCTTGATTACATCACGTGCGAGTACAAAACCGTCATCCCGTCCCCGTACGTG |
| E1_181/25_L37661.3 | ACGCTATCGCTTGATTACATCACGTGCGAGTACAAAACCGTCATCCCGTCTCCCGTACGTG |
| E1_99659_KJ451624.1 | ACGCTATCGCTTGATTACATCACGTGCGAGTATAAAACCGTTATCCCGTCTCCCGTACGTG |
| E1_IbH35_HM045786.1 | ACACTGTCACTTGACTTACATCACGTGCGAGTACAAAACTGTCATCCCGTCCCCGTACGTG |
| |   *  ** ***********: *****:*:******  ****** |
| E1_S27_NC004162.2 | AAATGCTGCGGTACAGCAGAGTGCAAGGACAAAAACCTACCTGACTACAGCTGTAAGGTC |
| E1_SL15649_GU189061.1 | AAGTGCTGCGGTACAGCAGAGTGCAAGGACAAAAACCTACCTGACTACAGCTGTAAGGTC |
| E1_LR2006_KT449801.1 | AAGTGCTGCGGTACAGCAGAGTGCAAGGACAAAAACCTACCTGACTACAGCTGTAAGGTC |
| E1_181/25_L37661.3 | AAATGCTGCGGTACAGCAGAGTGCAAGGACAAGAGCCTACCTGATTACAGCTGTAAGGTC |
| E1_99659_KJ451624.1 | AAGTGCTGCGGTACAGCAGAGTGTAAGGACAAGAGCCTACCTGATTACAGCTGTAAGGTC |
| E1_IbH35_HM045786.1 | AAGTGCTGTGGTACAGCAGAGTGCAAGGACAAGAGCCTACCTACCAGACTACAGCTGCAAGGTC |
| | .* ********* ******.*.  ****    *:**** **** |

FIG. 15 (Cont'd)

```
E1_S27_NC004162.2     TTCACCGGGCGTCTACCCATTTATGTGGGGCGGCCTACTGCTTCTGCGACGCTGAAAAC
E1_SL15649_GU189061.1 TTCACCGGGCGTCTACCCATTTATGTGGGGCGGCCTACTGCTTCTGCGACGCTGAAAAC
E1_LR2006_KT449801.1  TTCACCGGGCGTCTACCCATTTATGTGGGGCGGCCTACTGCTTCTGCGACGCTGAAAAC
E1_181/25_L37661.3    TTCACCGGGCGTCTACCCATTCATGTGGGGCGGCCTACTGCTTCTGCGACACTGAAAAC
E1_99659_KJ451624.1   TTCACCGGGCGTCTACCCATTCATGTGGGGCGGCCTACTGCTTCTGCGACACCGAAAAT
E1_IbH35_HM045786.1   TTTACTGGAGTCTACCCATTTATGTGGGGCGGCCTACTGCTTTTGCGACGCCGAAAAT
                      ** * ** * ************ ************* ***** ***** ***** *

E1_S27_NC004162.2     ACGCAATTGAGCGAAGCGACATGTGGAGAAGTCCGAATCATGCAAAACAGAATTTGCATCA
E1_SL15649_GU189061.1 ACGCAGTTGAGCGAAGCGACATGTGGAGAAGTCCGAATCATGCAAAACAGAATTTGCATCA
E1_LR2006_KT449801.1  ACGCAGTTGAGCGAAGCGACACGTGGAGAAGTCCGAATCATGCAAAACAGAATTTGCATCA
E1_181/25_L37661.3    ACGCAATTGAGCGAAGCGACATGTGGAGAAGTCCGAATCATGCAAAACAGAATTTGCATCA
E1_99659_KJ451624.1   ACGCAATTGAGCGAGGCGACATGTGGAGAAGTCCGAATCATGCAAAACAGAATTTGCATCA
E1_IbH35_HM045786.1   ACGCAATTGAGCGAGGCGACATGTAGAGAAATCTGAATCTTGCAAAACAGAGTTTGCATCG
                      ***** ******** ****** ** ****** ** **** **********  ********

E1_S27_NC004162.2     GCATACAGGGCTCATACCGCATCCGCATCAGCTAAGCTCCGCGTCCTTTACCAAGGAAAT
E1_SL15649_GU189061.1 GCATACAGGGCTCATACCGCATCTGCATCAGCTAAGCTCCGCGTCCTTTACCAAGGAAAT
E1_LR2006_KT449801.1  GCATACAGGGCTCATACCGCATCTGCATCAGCTAAGCTCCGCGTCCTTTACCAAGGAAAT
E1_181/25_L37661.3    GCATACAGGGCTCATACCGCATCCGCATCAGCTAAGCTCCGCGTCCTTTACCAAGGAAAT
E1_99659_KJ451624.1   GCATATACAGGGCTCATACCGCATCCGCATCAGCTAAGCTCCGCGTCCTTTACCAAGGAAAT
E1_IbH35_HM045786.1   GCCTACAGAGAGCCCACACCGCATCCGCGTCGGCGAAGCTCCGCGAAGCCAGTTAAGGAAAC
                      ** *** *   *  * ***** *     *    *******  *  *    ********

E1_S27_NC004162.2     AACATCACTGTAACTGCCTATGCAAACGGCGACCATGCCGTCACAGTTAAGGACGCCAAA
```

```
E1_S27_NC004162.2          TGCGAGGTACCAGCCTGCACCCATTCCTCAGACTTTGGGGGCGTTCGCCATTATTAAATAT
E1_SL15649_GU189061.1      TGCGAGGTACTAGCCTGCACCCATTCCTCAGACTTTGGGGGCGTTCGCCATTATTAAATAT
E1_LR2006_KT449801.1       TGCGAGGTACCAGCCTGCACCCATTCCTCAGACTTTGGGGGCGTTCGCCATTATTAAATAT
E1_181/25_L37661.3         TGCGAGGTACCAGCCTGCACCACTCCTCAGACTTTGGGGGCGTAGCCATCATTAAATAT
E1_99659_RJ451624.1        TGTGAGGTATCAGCCTGCACCCATTCCTCAGACTTTGGGGGCGTAGCCATCATTAAATAT
E1_IbH35_HM045786.1        TGCGAAGTACCAGCCTGCACCCATTCCCGACTTTGGGGGCGTTCGCCATCATCAAATAT
                           ** ** **  ******** *** ***** *****************  *** ** *****

E1_S27_NC004162.2          GCAGTCAAGAAAAGGCAAGTGTGCGGTGACCAACGCCGTCACTATCCGG
E1_SL15649_GU189061.1      GCAGCCAAGAAAAGGCAAGTGTGCGGTGCATTCGATGACTAACGCCGTCACTATTCGG
E1_LR2006_KT449801.1       GCAGCCAAGAAAAGGCAAGTGTGCGGTGCATTCGATGACTAACGCCGTCACTATTCGG
E1_181/25_L37661.3         GCAGCCAAGAAAAGGCAAGTGTGCGGTGCATTCGATGACTAACGCCGTCACTATTCGG
E1_99659_RJ451624.1        GCAGCCAGTAAAAGGCAAGTGTGCAGTGCACTCGATGCATTCGATGACTAACGCCGTCACTATTCGG
E1_IbH35_HM045786.1        ACAGCTAGCAAGAAAGTAAATGTGCAGTACATTGTGACCAACGCCGTTACCATTCGA
                            ***  *  *** * **** ****  * **  *  * **  * **** *** ** ** ***

E1_S27_NC004162.2          GAAGCTGAGATAGAAGTTGAAGGGAATTCTCAGCTGCAAATCTCTTTCTCGACGCCCTTG
E1_SL15649_GU189061.1      GAAGCTGAGATAGAAGTTGAAGGGAATTCTCAGCTGCAAATCTCTTTCTCGACGGCCTTA
E1_LR2006_KT449801.1       GAAGCTGAGATAGAAGTTGAAGGGAATTCTCAGCTGCAAATCTCTTTCTCGACGGCCTTA
E1_181/25_L37661.3         GAAGCTGAAATAGAAGTAGAAGGGAACTCTCAGTTGCAAATCTCTCTCTTTTTTCGACGGCCCTA
E1_99659_RJ451624.1        GAAGCTGAAATAGAAGTAGAAGGGAACTCTCAGTTGCAAATCTCTCTCTTTTTTCGACGGCCCTA
E1_IbH35_HM045786.1        GAAGCCGACGTAGAAGTAGAGGGGAATTCCCAGCTGCAAATATCCTTCTCAACAGCCTTG
                           ***** **  ****** **  ****  ** **** ******  **  **     * ***

E1_S27_NC004162.2          GCCAGCGCCCGAATTCCGCGTACAAGTACTGTTCTACACAAGTACACTGTGCAGCCGAGTGC
E1_SL15649_GU189061.1      GCCAGCGCCCGAATTCCGCGTACAAGTCTGTTCTACACAAGTACACTGTGCAGCCGAGTGC
E1_LR2006_KT449801.1       GCCAGCGCCCGAATTCCGCGTACAAGTCTGTTCTACACAAGTACACTGTGCAGCCGAGTGC
E1_181/25_L37661.3         GCCAGCGCCCGAATTCCGCGTACAAGTCTGTTCTACACAAGTACACTGTGCAGCCGAGTGC
E1_99659_RJ451624.1        GCCAGCGCCCGAATTTCGCGTTTCGCCGAGTTTCGCGTACAAGTCTGCTCCACACAAGTACACTGTGCAGCCGAGTGC
E1_IbH35_HM045786.1        GCAAGCGCCCGAGTTTCGCGTACAAGTGTGCTCCCACACAAGTACACTGCGCAGCCGCATGC
                           **  ******** **  ****    * **  * **   **    **  ** **   * **
```

CLUSTAL O(1.2.1) multiple sequence alignment

```
E1_IbH35_HM045786.1       YEHVTVIPNTVGVPYKTLVNRPGYSPMVLEMELQSVTLEPTLSLDYITCEYKTVIPSPYV
E1_S27_NC004162.2         YEHVTVIPNTVGVPYKTLVNRPGYSPMVLEMELLSVTLEPTLSLDYITCEYKTVIPSPYV
E1_SL15649_GUI89061.1     YEHVTVIPNTVGVPYKTLVNRPGYSPMVLEMELLSVTLEPTLSLDYITCEYKTVIPSPYV
E1_LR2006_KT449801.1      YEHVTVIPNTVGVPYKTLVNRPGYSPMVLEMELLSVTLEPTLSLDYITCEYKTVIPSPYV
E1_99659_KJ451624.1       YEHVTVIPNTVGVPYKTLVNRPGYSPMVLEMELLSVTLEPTLSLDYITCEYKTVIPSPYV
E1_181/25_L37661.3        YEHVTVIPNTVGVPYKTLVNRPGYSPMVLEMELLSVTLEPTLSLDYITCEYKTVIPSPYV
                          *********************************:**************************

E1_IbH35_HM045786.1       KCCGTAECKDKSLPDYSCKVFTGVYPFMWGGAYCFCDAENTQLSEAHVEKSESCKTEFAS
E1_S27_NC004162.2         KCCGTAECKDKNLPDYSCKVFTGVYPFMWGGAYCFCDAENTQLSEAHVEKSESCKTEFAS
E1_SL15649_GUI89061.1     KCCGTAECKDKNLPDYSCKVFTGVYPFMWGGAYCFCDAENTQLSEAHVEKSESCKTEFAS
E1_LR2006_KT449801.1      KCCGTAECKDKDKSLPDYSCKVFTGVYPFMWGGAYCFCDAENTQLSEAHVEKSESCKTEFAS
E1_99659_KJ451624.1       KCCGTAECKDKSLPDYSCKVFTGVYPFMWGGAYCFCDTENTQLSEAHVEKSESCKTEFAS
E1_181/25_L37661.3        KCCGTAECKDKSLPDYSCKVFTGVYPFMWGGAYCFCDTENTQLSEAHVEKSESCKTEFAS
                          ***********.********************:*******************

E1_IbH35_HM045786.1       AYRAHTASASAKLRVLYQGNNITVAAYANGDHAVTVKDAKFVVGPMSSAWTPFDNKIVVY
E1_S27_NC004162.2         AYRAHTASASAKLRVLYQGNNITVTAYANGDHAVTVKDAKFIVGPMSSAWTPFDNKIVVY
E1_SL15649_GUI89061.1     AYRAHTASASAKLRVLYQGNNITVTAYANGDHAVTVKDAKFIVGPMSSAWTPFDNKIVVY
E1_LR2006_KT449801.1      AYRAHTASASAKLRVLYQGNNITVAAYANGDHAVTVKDAKFIVGPMSSAWTPFDNKIVVY
E1_99659_KJ451624.1       AYRAHTASASAKLRVLYQGNNITVAAYANGDHAVTVKDAKFIVGPMSSAWTPFDNKIVVY
E1_181/25_L37661.3        AYRAHTASASAKLRVLYQGNNVTVSAYANGDHAVTVKDAKFIVGPMSSAWTPFDNKIVVY
                          *********************:**:***************:******************

E1_IbH35_HM045786.1       KGDVYNMDYPPFGAGRPGQFGDIQSRTPESKDVYANTQLVLQRPAAGTVHVPYSQAPSGF
E1_S27_NC004162.2         KGDVYNMDYPPFGAGRPGQFGDIQSRTPESKDVYANTQLVLQRPAAGTVHVPYSQAPSGF
E1_SL15649_GUI89061.1     KGDVYNMDYPPFGAGRPGQFGDIQSRTPESKDVYANTQLVLQRPAAGTVHVPYSQAPSGF
E1_LR2006_KT449801.1      KGDVYNMDYPPFGAGRPGQFGDIQSRTPESKDVYANTQLVLQRPAVGTVHVPYSQAPSGF
E1_99659_KJ451624.1       KGDVYNMDYPPFGAGRPGQFGDIQSRTPESEDVYANTQLVLQRPSAGTVHVPYSQAPSGF
E1_181/25_L37661.3        KGDVYNMDYPPFGAGRPGQFGDIQSRTPESEDVYANTQLVLQRPSAGTVHVPYSQAPSGF
                          ******************************:*************:**************
```

*FIG. 15 (Cont'd)*

| | |
|---|---|
| E1_IbH35_HM045786.1 | KYWLKERGASLQHTAPFGCQIATNPVRAVNCAVGNIPISIDIPDAAFTRVVDAPSVTDMS |
| E1_S27_NC004162.2 | KYWLKERGASLQHTAPFGCQIATNPVRAVNCAVGNMPISIDIPDAAFTRVVDAPSLTDMS |
| E1_SL15649_GUI89061.1 | KYWLKERGASLQHTAPFGCQIATNPVRAMNCAVGNMPISIDIPDAAFTRVVDAPSLTDMS |
| E1_LR2006_KT449801.1 | KYWLKERGASLQHTAPFGCQIATNPVRAVNCAVGNMPISIDIPEAAFTRVVDAPSLTDMS |
| E1_99659_KJ451624.1 | KYWLKERGASLQHTAPFGCQIATNPVRAVNCAVGNMPISIDIPDAAFTRVVDAPSLTDMS |
| E1_181/25_L37661.3 | KYWLKERGASLQHTAPFGCQIATNPVRAMNCAVGNMPISIDIPDAAFTRVVDAPSLTDMS |
| | ************************* :* :******:*****:** |

| | |
|---|---|
| E1_IbH35_HM045786.1 | CEVPACTHSSDFGGVAIIKYTASKKGKCAVHSMTNAVTIREADVEVEGNSQLQISFSTAL |
| E1_S27_NC004162.2 | CEVPACTHSSDFGGVAIIKYAVSKKGKCAVHSMTNAVTIREAEIEVEGNSQLQISFSTAL |
| E1_SL15649_GUI89061.1 | CEVLACTHSSDFGGVAIIKYAASKKGKCAVHSMTNAVTIREAEIEVEGNSQLQISFSTAL |
| E1_LR2006_KT449801.1 | CEVPACTHSSDFGGVAIIKYAASKKGKCAVHSMTNAVTIREAEIEVEGNSQLQISFSTAL |
| E1_99659_KJ451624.1 | CEVSACTHSSDFGGVAIIKYAASKKGKCAVHSMTNAVTIREAEIEVEGNSQLQISFSTAL |
| E1_181/25_L37661.3 | CEVPACTHSSDFGGVAIIKYAASKKGKCAVHSMTNAVTIREAEIEVEGNSQLQISFSTAL |
| | * ************: :*************:************* |

| | |
|---|---|
| E1_IbH35_HM045786.1 | ASAEFRVQVCSTQVHCAAACHPPKDHIVNYPASHTTLGVQDISTTAMSWVQKITGGVGLI |
| E1_S27_NC004162.2 | ASAEFRVQVCSTQVHCAAECHPPKDHIVNYPASHTTLGVQDISATAMSWVQKITGGVGLV |
| E1_SL15649_GUI89061.1 | ASAEFRVQVCSTQVHCAAECHPPKDHIVNYPASHTTLGVQDISATAMSWVQKITGGVGLV |
| E1_LR2006_KT449801.1 | ASAEFRVQVCSTQVHCAAECHPPKDHIVNYPASHTTLGVQDISATAMSWVQKITGGVGLV |
| E1_99659_KJ451624.1 | ASAEFRVQVCSTQVHCAAECHPPKDHIVNYPASHTTLGVQDISATAMSWVQKITGGVGLV |
| E1_181/25_L37661.3 | ASAEFRVQVCSTQVHCAAECHPPKDHIVNYPASHTTLGVQDISVTAMSWVQKITGGVGLV |
| | *****************:**********************:********: |

| | |
|---|---|
| E1_IbH35_HM045786.1 | VAVAALILIVVLCVSFSRH |
| E1_S27_NC004162.2 | VAVAALILIVVLCVSFSRH |
| E1_SL15649_GUI89061.1 | VAVAALILIVVLCVSFSRH |
| E1_LR2006_KT449801.1 | VAVAALILIVVLCVSFSRH |
| E1_99659_KJ451624.1 | VAVAALILIVVLCVSFSRH |
| E1_181/25_L37661.3 | VAVAALILIVVLCVSFSRH |
| | ******************* |

FIG. 15 (Cont'd)

CLUSTAL O(1.2.1) multiple sequence alignment

```
E2_181/25_L37661.3          AGTATTAAGGACAACTTCAATGTCTATAAAGCCATAAGACCGTACCTAGCTCACTGTCCC
E2_IbH35_HM045786.1         AGTACTAAGGACACAATTTTAATGTCTATAAAGACCATAAAGACCATATCTAGCTCATTGTCCT
E2_LR2006_KT449801.1        AGCACCAAGGACAACTTCAATGTCTATAAAGCCACAAGACCATTAGCTTAGCTCACTGTCCC
E2_SL15649_GU189061.1       AGCACCAAGGACAACTTCAATGTCTATAAAGCCACAAGACCATTAGCTCACTTAGCTCACTGTCCC
E2_S27_NC004162.2           AGCACCAAGGACAACTTCAATGTCTATAAAGACCACAAGACCATTAGCCTAGCTCACTGTCCC
E2_99659_KJ451624.1         AGTATTAAGGACCACTTCAATGTCTATAAAGACCATAAGACCGTACCTAGCTCACTGTCCC
                            ** * ******* * * ******** ******** ***** ** * ****** ** ***

E2_181/25_L37661.3          GACTGTGGAGAAGGGCACTCGTGCCATAGTCCCGTAGCGCTAGAACGCATCAGAAACGAA
E2_IbH35_HM045786.1         GACTGCGGAGAAGGGCATTCGTGCCACAGCCCTATCCGCCATTGGAGCGCATCAGAAATGAA
E2_LR2006_KT449801.1        GACTGTGGAGAAGGGCACTCGTGCCACAGTCCCGTAGCACTAGAACGCATCAGAAATGAA
E2_SL15649_GU189061.1       GACTGTGGAGAAGGGCACTCGTGCCACAGTCCCGTAGCACTAGAACGCATCAGAAATGAA
E2_S27_NC004162.2           GACTGTGGAGAAGGGCACTCGTGCCACAGTCCCGTAGCACTAGAACGCATCAGAAATGAA
E2_99659_KJ451624.1         GACTGTGGAGAAGGGCACTCGTGCCACAGTCCCGTAGCGCTAGAACGCATCAGAAACGAA
                            ***** *********** ******** ** ** *  *** ** **** *********  ***

E2_181/25_L37661.3          GCGACAGACGGGACGCTGAAAAATCCAGGTTTCCTTGCAAATCGGAATAAAGACGGATGAT
E2_IbH35_HM045786.1         GCAACGGACGGGAAACGCTGAAAAATCCAGGTCGTCTCTTTGCAGATCGGGATATCGGAGACGATGAC
E2_LR2006_KT449801.1        GCGACAGAGAGGGACGCTGAAAATCCAGGTCTCCGTTGCAAATCGGAATCGGAAATAAAGACGGATGAC
E2_SL15649_GU189061.1       GCGACAGAGGGGACGCTGAAAAATCCAGGTCTCCGTTGCAAATCGGAATAAAGACGGATGAC
E2_S27_NC004162.2           GCGACAGACGGGACGCTGAAAAATCCAGGTCTCCTTGCAAATCGGAATTGGAAATAGGACGGATGAT
E2_99659_KJ451624.1         GCGACAGACGGGACGTTGAAAAATCCAGGTTTCCTTGCAAATCGGAATAAAGACGGATGAT
                            ** ** ** **** * ******* ****** * * *  ***** ***** * * *****

E2_181/25_L37661.3          AGCCATGATTGGACCAAGCTGCGTTACATGGACAATCATATGCCAGCAGACGCAGAGAGG
E2_IbH35_HM045786.1         AGCCACGATTGGACCAAGCTGCGCTATATGGACAATATAGCCATCACGCCAGCAGACGCGGAGCGA
E2_LR2006_KT449801.1        AGCCACGATTGGACCAAGCTGCGTTATATGGACAACCACATGGACCAGCAGACGCAGAGAGG
E2_SL15649_GU189061.1       AGCCACGATTGGACCAAGCTGCGTTATATGGACAACCACATGCCAGCAGACGCAGAGAGG
E2_S27_NC004162.2           AGCCATGATTGGACCAAGCTGCGTTATATGGACAATCACATACCAGCAGACGCAGGGAGG
E2_99659_KJ451624.1         AGCCATGATTGGACCAAGCTGCGTTATATGGACAATCACATGCCAGCAGACGCAGAGCGG
                            ***** ***************** ** ******** ** ** ** ***********  **
```

```
E2_181/25_L376661.3      GAACTGACACCAGGAGCTACCGTCCCTTTCCTGCTTAGCCTAATATGCTGCATTAGAACA
E2_IbH35_HM045786.1      GAATTAACACCAGGAGCCACCGTTCCCTTTCTGCTTCAGCCTGCTATGTTGCGTCAGAACG
E2_LR2006_KT449801.1     GAACTGACACCAGGAGCTACCGTTCCCTTTCCTGCTTCAGCCTGCTAATATGCTGCATCAGAACA
E2_SL15649_GU189061.1    GAACTGACACCAGGAGCTACCGTCCCCTTTCCTGCTTAGCCTAATATGCTGCATCAGAACA
E2_S27_NC004162.2        GAACTGACACCAGGAGCTACCGTCCCCTTTCCTGCTTAGCCTAATATGCTGCATCAGAACA
E2_99659_KJ451624.1      GAACTGACACCAGGAGCTACCGTCCCCTTTCCTGCTTAGCCTAATATGCTGCATTAGAACA
                         *** * ******* **** ***  ****  ***** *** **  ** *** ** ****

E2_181/25_L376661.3      GCTAAAGCG
E2_IbH35_HM045786.1      ACCAAGCG
E2_LR2006_KT449801.1     GCTAAAGCG
E2_SL15649_GU189061.1    GCTAAAGCG
E2_S27_NC004162.2        GCTAAAGCG
E2_99659_KJ451624.1      GCTAAAGCG
                         . * ****
```

*FIG. 15 (Cont'd)*

```
CLUSTAL O(1.2.1) multiple sequence alignment

E2_IbH35_HM045786.1        STKDNFNVYKATRPYLAHCPDCGEGHSCHSPIALERIRNEATDGTLKIQVSLQIGIKTDD
E2_99659_KJ451624.1        SIKDHFNVYKAIRPYLAHCPDCGEGHSCHSPVALERIRNEATDGTLKIQVSLQIGIKTDD
E2_181/25_L37661.3         SIKDNFNVYKATRPYLAHCPDCGEGHSCHSPVALERIRNEATDGTLKIQVSLQIGIKTDD
E2_S27_NC_004162.2         STKDNFNVYKATRPYLAHCPDCGEGHSCHSPVALERIRNEATDGTLKIQVSLQIGTDD
E2_SL15649_GU189061.1      STKDNFNVYKATRPYLAHCPDCGEGHSCHSPVALERIRNEATDGTLKIQVSLQIGIKTDD
E2_LR2006_KT449801.1       STKDNFNVYKATRPYLAHCPDCGEGHSCHSPVALERIRNEATDGTLKIQIGIKTDD
                           * *:*:****** *********:********.********************* ****

E2_IbH35_HM045786.1        SHDWTKLRYMDSHTPADAERAGLLVRTSAPCTITGTMGHFILARCPKGETLTVGFTDSRK
E2_99659_KJ451624.1        SHDWTKLRYMDNHMPADAERAGLFVRTSAPCTITGTMGHFILARCPKGETLTAGFTDGRK
E2_181/25_L37661.3         SHDWTKLRYMDNHMPADAERARLFVRTSAPCTITGTMGHFILARCPKGETLTVGFTDSRK
E2_S27_NC_004162.2         SHDWTKLRYMDNHHTPADAGRAGLFVRTSAPCTITGTMGHFILARCPKGETLTVGFTDSRK
E2_SL15649_GU189061.1      SHDWTKLRYMDNHMPADAERAGLFVRTSAPCTITGTMGHFILARCPKGETLTVGFTDSRK
E2_LR2006_KT449801.1       SHDWTKLRYMDNHMPADAERAGLFVRTSAPCTITGTMGHFILARCPKGETLTVGFTDSRK
                           ***********.*:*** **.*:*********************.*** ****

E2_IbH35_HM045786.1        ISHTCTHPFHHEPPVIGREREHSRPQHGKELPCSTYVQSTAATAEEIEVHMPPDTPDRTL
E2_99659_KJ451624.1        ISHSCTHPFHHDPPVIGREKFHSRPQHGRELPCSTYAQSTAATAEEIEVHMPPDTPDRTL
E2_181/25_L37661.3         ISHSCTHPFHHDPPVIGREKFHSRPQHGRELPCSTYAQSTAATAEEIEVHMPPDTPDRTL
E2_S27_NC_004162.2         ISHSCTHPFHHDPPVIGREKFHSRPQHGRELPCSTYVQSNAATAEEIEVHMPPDTPDRTL
E2_SL15649_GU189061.1      ISHSCTHPFHHDPPVIGREKFHSRPQHGRELPCSTYVQSTAATTEEIEVHMPPDTPDRTL
E2_LR2006_KT449801.1       ISHSCTHPFHHDPPVIGREKFHSRPQHGRELPCSTYVQSTAATAEEIEVHMPPDTPDRTL
                           ***:*******:*******::**********:********.**.**:***************

E2_IbH35_HM045786.1        MTQQSGNVKITVNGQTVRYKCNCGGSNEGLTTTDKVINNCKIDQCHAAVTNHKKWQYNSP
E2_99659_KJ451624.1        MSQQSGNVKITVNSQTVRYKCNCGGSEGLTTTDKVINNCKVDQCHAAVTNHKKWQYNSP
E2_181/25_L37661.3         MSQQSGNVKITVNSQTVRYKCNCGDSNEGLTTTDKVINNCKVDQCHAAVTNHKKWQYNSP
E2_S27_NC_004162.2         LSQQSGNVKITVNSQTVRYKCNCGGSNEGLTTTDKVINNCKVDQCHAAVTNHKKWQYNSP
E2_SL15649_GU189061.1      MSQQSGNVKITVNGQTVRYKCNCGGSNEGLTTTDKVINNCKVDQCHAAVTNHKKWQYNSP
E2_LR2006_KT449801.1       MSQQSGNVKITVNGQTVRYKCNCGGSNEGLTTTDKVINNCKVDQCHAAVTNHKKWQYNSP
                           ::***********.*********.*:******************:*************
```

*FIG. 15 (Cont'd)*

| | |
|---|---|
| E2_IbH35_HM045786.1 | LVPRNAELGDRKGKIHIPFPLANVTCRVPKARNPTVTVTYGKNQVTMLLYPDHPTLLSYRNM |
| E2_99659_KJ451624.1 | LVPRNAEFGDRKGKIHIPFPLANVTCRVPKARNPTVTVTYGKNQVIMLLYPDHPTLLSYRNM |
| E2_181/25_L37661.3 | LVPRNAELGDRKGKVHIPFPLANVTCRVPKARNPTVTVTYGKNQVTMLLYPDHPTLLSYRNM |
| E2_S27_NC004162.2 | LVPRNAELGDRKGKIHIPFPLANVTCMVPKARNPTVTVTYGKNQVTMLLYPDHPTLLSYRNM |
| E2_SL15649_GU189061.1 | LVPRNAELGDRKGKIHIPFPLANVTCRVPKARNPTVTVTYGKNQVTMLLYPDHPTLLSYRSM |
| E2_LR2006_KT449801.1 | LVPRNAELGDRKGKIHIPFPLANVTCRVPKARNPTVTVTYGKNQVTMLLYPDHPTLLSYRNM |
| | :* * : ************.****:******.:**:* |

| | |
|---|---|
| E2_IbH35_HM045786.1 | GQEPNYHEEWTHKKEVTLTVPTEGLEVTWGNNEPYKYWPQMSTNGTAHGHPHEILLYYY |
| E2_99659_KJ451624.1 | GEEPNYQEEWTHKKEIRLTVPTEGLEVTWGNNEPYKYWPQLSTNGTAHGHPHEILLYYY |
| E2_181/25_L37661.3 | GEEPNYQEEWVTHKKEVLTVPTEGLEVTWGNNEPYKYWPQLSTNGTAHGHPHEILLYYY |
| E2_S27_NC004162.2 | GEEPNYQEEWVTHKKEVLTVPTEGLEVTWGNNEPYKYWPQLSANGTAHGHPHEILLYYY |
| E2_SL15649_GU189061.1 | GEEPNYQEEWVMHKKEVLTVPTEGLEVTWGNNEPYKYWPQLSTNGTAHGHPHEILLYYY |
| E2_LR2006_KT449801.1 | GEEPNYQEEWVMHKKEVVLTVPTEGLEVTWGNNEPYKYWPQLSTNGTAHGHPHEILLYYY |
| | *:*** *. **: ****************::******: |

| | |
|---|---|
| E2_IbH35_HM045786.1 | ELYPTMTVIIVSVASFVLLSMVGTAVGMCVCARRRCITPYELTPGATVPFLLSLLCCVRT |
| E2_99659_KJ451624.1 | ELYPTMTAVVLSVASFILLSMVGVAVGMCMCARRRCITPYELTPGATVPFLLSLICCIRT |
| E2_181/25_L37661.3 | ELYPTMTVVVVSVASFVLLSMVGVAVGMCMCARRRCITPYELTPGATVPFLLSLICCIRT |
| E2_S27_NC004162.2 | ELYPTMTVVVVSVASFILLSMVGMAVGMCMCARRRCITPYELTPGATVPFLLSLICCIRT |
| E2_SL15649_GU189061.1 | ELYPTMTVVVVSVATFILLSMVGMAVGMCMCARRRCITPYELTPGATVPFLLSLICCIRT |
| E2_LR2006_KT449801.1 | ELYPTMTVVVVSVATFILLSMVGMAAGMCMCARRRCITPYELTPGATVPFLLSLICCIRT |
| | *****.: :*:*:*****.*.**:******************::** |

| | |
|---|---|
| E2_IbH35_HM045786.1 | TKA |
| E2_99659_KJ451624.1 | AKA |
| E2_181/25_L37661.3 | AKA |
| E2_S27_NC004162.2 | AKA |
| E2_SL15649_GU189061.1 | AKA |
| E2_LR2006_KT449801.1 | AKA |
| | .*** |

*FIG. 15 (Cont'd)*

SEQUENCE LISTING

```
<160> NUMBER OF SEQ ID NOS: 276

<210> SEQ ID NO 1
<211> LENGTH: 423
<212> TYPE: PRT
<213> ORGANISM: Chikungunya virus

<400> SEQUENCE: 1

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45
```

Gln Val Ser Leu Gln Ile Gly Ile Gly Thr Asp Asp Ser His Asp Trp
 50                  55                  60

Thr Lys Leu Arg Tyr Met Asp Asn His Ile Pro Ala Asp Ala Gly Arg
 65                  70                  75                  80

Ala Gly Leu Phe Val Arg Thr Ser Ala Pro Cys Thr Ile Thr Gly Thr
                 85                  90                  95

Met Gly His Phe Ile Leu Ala Arg Cys Pro Lys Gly Glu Thr Leu Thr
                100                 105                 110

Val Gly Phe Thr Asp Ser Arg Lys Ile Ser His Ser Cys Thr His Pro
            115                 120                 125

Phe His His Asp Pro Pro Val Ile Gly Arg Glu Lys Phe His Ser Arg
130                 135                 140

Pro Gln His Gly Lys Glu Leu Pro Cys Ser Thr Tyr Val Gln Ser Asn
145                 150                 155                 160

Ala Ala Thr Ala Glu Glu Ile Glu Val His Met Pro Pro Asp Thr Pro
                165                 170                 175

Asp Arg Thr Leu Leu Ser Gln Gln Ser Gly Asn Val Lys Ile Thr Val
            180                 185                 190

Asn Ser Gln Thr Val Arg Tyr Lys Cys Asn Cys Gly Gly Ser Asn Glu
            195                 200                 205

Gly Leu Ile Thr Thr Asp Lys Val Ile Asn Cys Lys Val Asp Gln
210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Met Val Pro Lys Ala Arg
            260                 265                 270

Asn Pro Thr Val Thr Tyr Gly Lys Asn Gln Val Ile Met Leu Leu Tyr
            275                 280                 285

Pro Asp His Pro Thr Leu Leu Ser Tyr Arg Ser Met Gly Glu Glu Pro
290                 295                 300

Asn Tyr Gln Glu Glu Trp Val Thr His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Ala Asn Gly Thr Ala His Gly His Pro
            340                 345                 350

His Glu Ile Ile Leu Tyr Tyr Tyr Glu Leu Tyr Pro Thr Met Thr Val
            355                 360                 365

Val Val Val Ser Val Ala Ser Phe Ile Leu Leu Ser Met Val Gly Met
370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
                420

<210> SEQ ID NO 2
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 2

```
caggtgcagc tggtgcagtc tggagctgag gtgaagaagc ctggggcctc agtgaaggtc    60
tcctgcaagg cctctggtta cagctttacc agctacggta tcagctgggt gcgacaggcc   120
cctggacaag gcttgagtg gatgggatgg atcagcactt acaaaggtta cacacagtat   180
gcacagaact tccagggcag agtcaccatc accacagaca cacccgcgac tacagtctat   240
atggagctga ggagcctgag atctgacgac acggccgtgt attactgcgc gagagttctt   300
tccgagactg gttatttcta ctactactac tacggtatgg acgtctgggg ccaagggacc   360
ctggtcaccg tctcctca                                                  378
```

<210> SEQ ID NO 3
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 3

```
caggctgtgg tgactcagcc gccctcagtg tctggggccc cagggcagag ggtcaccatc    60
tcctgtactg ggagcagctc caacatcggg gcagattata atgtacactg gtaccagctg   120
cttccaggaa cagcccccaa actcctcatc tatggtaaca ccaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtgcttcg   300
gtattcggcg gagggaccaa actgaccgtc ctag                                334
```

<210> SEQ ID NO 4
<211> LENGTH: 312
<212> TYPE: DNA
<213> ORGANISM: Artificial sequence
<220> FEATURE:
<223> OTHER INFORMATION: Synthetic oligonucleotide

<400> SEQUENCE: 4

```
gcctcagtga aggtctcctg caaggcttct ggatacagtt tcactagcta ttctatcaac    60
tgggtgcgac aggcccctgg acaagggcct gagtggatgg gatggatcga caccaacact   120
gggaacccaa cctatgccca ggacttcgca ggacggtttg tcttctcctt ggacacctct   180
gtcaccacgg catatctgca gatcagcagc ctaaaggctg gggacactgc cgtttattac   240
tgtgcaacat attatgttga cctttggggg agttatcgcc aagactacta cggtatggac   300
gtctggggcc ac                                                        312
```

<210> SEQ ID NO 5
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 5

```
cagtctgtgc tgactcagcc accctcagcg tctgggaccc ccgggcagag ggtcaccatc    60
tcttgttctg gagggagctc caacatcggg agtaatcctg taaattggta ccagatggtc   120
ccaggaacgg cccccaaact cctcctctat actaataatc agcggccctc agggatccct   180
gaccgattct ctggctccaa gtctggcacc tcagcctccc tggccatcaa tggactccag   240
```

```
tctgaggatg aggctgatta ttactgtgca gtatgggatg acagcctgag tggccgttgg      300
gtgttcggcg agggaccaa ggtgaccgtc cta                                    333
```

<210> SEQ ID NO 6
<211> LENGTH: 411
<212> TYPE: DNA
<213> ORGANISM: Artificial sequence
<220> FEATURE:
<223> OTHER INFORMATION: Synthetic oligonucleotide

<400> SEQUENCE: 6

```
caggtgcagc tggtgcagtc tggagctgag gtgaagaagc ctggggcctc agtgagggtc       60
tcctgcaagg cgtctggtta cacctttacc agttatggta tcagctgggt gcgacaggcc      120
cctggacaag gcttgagtg gatgggatgg atcagcactt acaatggtga cacaaactat       180
gcacagaagt tccagggcag agtcaccttg acaacagaga catccacgag cacagcctac      240
atggagctga ggcgcctgag atctgacgac acggccgttt actactgtgc gagagatttt      300
gaatttcccg gagattgtag tggtggcagc tgctactcca ggttcatcta ccagcacaac      360
gacatggacg tctggggcca cgggaccctg gtcaccgtct cctcagcaag c               411
```

<210> SEQ ID NO 7
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 7

```
caggctgtgg tgactcagcc gccctcagtg tctgcggccc caggacagaa ggtcaccatc       60
tcctgctctg gaagcagctc caacattggg aatcattatg tatcctggta ccagcacctc      120
ccgggaacag cccccaaact cctcatttat gacaattata gcgaccctc agtgattcct       180 gaccgattct ctgcctccaa gtctggcgcg tcagccaccc tgggcatcat cggactccag      240
actggggacg aggccgatta ttactgcgga acatgggata gcagcctgag tgctgtggta      300
ttcggcggag ggaccaagct gaccgtccta                                       330
```

<210> SEQ ID NO 8
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 8

```
caggtgcagc tggtgcagtc gggcccagga ctggtgaagc cttcggacac cctgtccctc       60
acctgcagtg tctcaagtga cgccctccgc agcaggagtt attactgggg ctgggtccgc      120 cagcccccg ggaagggatt ggagtggatt gggactgtct cttatagtgg gggcacctac       180
tacaacccgt ccctccagag tcgagtcacc gtgtcggtgg acacgtccaa gaaccacttc      240
tccctgaggt tgaactctgt gaccgccgca gacgcggctg tttattactg tgcgagatct      300
tatttctatg atggcagtgg ttactactac ctgagctact ttgactcctg gggccaggga      360
accctggtca ccgtctcctc a                                                381
```

<210> SEQ ID NO 9
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 9

```
caggctgtgg tgactcagga gccctcactg actgtgtccc caggagggac agtcactctc    60
acctgtgctt ccagcactgg agcagtcacc agtggtcact atccaaactg gttccagcag   120
aaacctggac aaccacccag ggccctgatt tatagcacag acaacaagca ctcctggacc   180
cctgcccggt tctcaggctc cctcctaggg gtcaaggctg ccctgacact gtcagatgta   240
cagcctgagg acgaggctga ctattactgc ctgctccatt ttggtggtgt cgtggtcttc   300
ggcggaggga ccaagctgac cgtccta                                       327
```

<210> SEQ ID NO 10
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 10

```
caggtgcagc tggtgcagtc tggggaggc gtggtccagc ctgggaggtc cctgagactc     60
tcctgtgcag tgtctggatt caccttcagt aactatgcca tgcactgggt ccgccaggct   120
ccaggcaagg ggctggactg ggtggcagtt atatggtatg atggaagtaa taaatactat   180
gcagactccg tgaagggccg attcaccatc tccagagaca attccaagaa cacgctgtat   240
ctgcaagtga acagcctgag agccgaggac acggctgtgt attactgtgc gagggggtgac   300
tacgttcttg actactgggg ccagggaacc ctggtcaccg tctcctca                348
```

<210> SEQ ID NO 11
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 11

```
gacattgtga tgacccagtc tccatcctcc ctgtctgcat ctgtaggaga cagagtcacc    60
atcagttgcc gggccagtca gagcattccc agctatttaa attggtatca acagaaacca   120
gggaaagccc ctaaggtcct gatctatgct acatccactt tggaagctgg ggtcccatca   180
cggttcagtg gcagtggatc tgggacagat ttcactctca ccatcaccag tctgcaacct   240
gaagattttg caacttacta ctgtcaacag agttacaata cggggatatt cactttcggc   300
cctgggacca aagtggatat caaa                                          324
```

<210> SEQ ID NO 12
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 12

```
caggtgcagc tggtgcagtc tggggctgag gtgaagaagc ctgggtcctc ggtgaaggtc    60
tcctgcaagg cttctggagg cacttccagc acttatgcta tcagctgggt gcgacaggcc   120
cctggacaag ggcttgagtg gatgggaggc agcatccctg tctttgctac agtaaactac   180
gcacagaagt tccagggcag actcacgatt accgcggacg aatccacgag cacagtttac   240
```
atggaactga gcagcctgag atctgaggac acggccgttt atttctgtgc gagcccctat   300
tgtagtagta tgaactgcta tacgacctttt tactactttg acttctgggg ccagggaacc   360
ctggtcaccg tctcctca   378

<210> SEQ ID NO 13
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 13
caggctgtgg tgactcagcc tgcctccgtg tttgggtttc ctggacagtc gatcaccatc   60
tcctgcactg gaaccagcag tgactttggt acttataact atgtctcttg gtaccagcaa   120
cacccaggcc aagcccccaa actcatgatt tttgatgtca gtaatcggcc ctcagggggtt   180 tctaatcgct tctctggctc caagtctggc aacacggcct ccctgaccat ctctgggctc   240
caggctgagg acgaggcttc ttattactgc agctcctata aagcggcag cactctctac   300 ggcggaggga ccaagctgac cgtcctg   327

<210> SEQ ID NO 14
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 14
caggtgcagc tggtgcagtc tgggtctgag ttgaagaagc ctggggcctc agtgaaggtt   60
tcctgcaagg cttctggata cagtttcact agctattcta tcaactgggt gcgacaggcc   120
cctggacaag ggcctgagtg gatgggatgg atcgacacca acactgggaa cccaacctat   180
gcccaggact cgcaggacg gtttgtcttc tccttggaca cctctgtcac cacggcatat   240
ctgcagatca gcagcctaaa ggctggggac actgccgttt attactgtgc aacatattat   300
gttgaccttt gggggagtta tcgccaagac tactacggta tggacgtctg gggccacggg   360
accctggtca ccgtctcctc a   381

<210> SEQ ID NO 15
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 15
cagtctgtgg tgactcagcc accctcagtg tctgggaccc ccgggcaggg ggtcaccatc   60
tcttgttctg gagggagctc caacatcggg agtaatcctg taaattggta ccagatggtc   120
ccaggaacgg cccccaaaact cctcctctat actaataatc agcggccctc aggggtccct   180
gaccgattct ctggctccaa gtctggcacc tcagcctccc tggccatcaa tggactccag   240
tctgaggatg aggctgatta ttactgtgca gtatgggatg acagcctgag tggccgttgg   300
gtgttcggcg agggaccaa gctgaccgtc cta   333

<210> SEQ ID NO 16
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 16

```
caggtgcagc tggtgcagtc tggggctgag gtgaagaagc ctggggcctc agtgaaggtc    60
tcctgcaagg tttccggata catcctcagt aaattatccg tgcactgggt gcgacaggct   120
cctggaaaag gacttgaatg gatgggaggt tctgaacgtg aagatggcga acagtctac    180
gcacagaagt tccagggcag aatcagcttg accgaggaca catctataga gacagcctac   240
atggagctga gcagcctgag ttctgaggac acggccgtgt attattgtgc aacaggaggc   300
ttctggagta tgattggggg aaatggagtg gactactggg gccagggaac cctggtcacc   360
gtctcctca                                                           369
```

<210> SEQ ID NO 17
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 17

```
caggctgtgg tgactcagtc tccatcgtcc ctgcctgcat ctgtaggaga cagggtcacc    60
atcacttgcc gggcaagtca ggacattaga aataatttag ctggtatca gcagaaacca   120
gggaaagccc ctgagcgcct gatctatgga acctccaatt tgcagagtgg ggtcccgtca   180
aggttcagcg gcagtggatc tgggacagaa ttcactctca caatcagcag cctgcagcct   240
gaagattttg caacttatta ctgtctacag cataatagtt accctcccac gttcggccgc   300
gggaccaagg tggaaatcaa a                                             321
```

<210> SEQ ID NO 18
<211> LENGTH: 380
<212> TYPE: DNA
<213> ORGANISM: Artificial sequence
<220> FEATURE:
<223> OTHER INFORMATION: Synthetic oligonucleotide

<400> SEQUENCE: 18

```
caggtgcagc tggtgcagtc tggggctgag gtgaagaagc ctggggcctc agtgagagtt    60
tcctgcaagg catctgggta caccttcacc agttactttg tgcactgggt gcgacaggcc   120
cctggacaag gacttgagtg gatggcgata acttatcctg tggtggtag cccatcctac    180
gcaccgcagt tccagggcag actcaccatg accgacgaca cgtccgcgac acagtctac    240
atggacctga gtgacctgac ttctaaagac acggccgtgt attactgtgc gagaggtgcc   300
caccgttcca ttgggacgac ccccttgac tcgtggggcc agggaaccct ggtcaccgtc    360
tcctcagcaa gcttcaaggg                                               380
```

<210> SEQ ID NO 19
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 19

```
caggtgcagc tggtgcagtc tggggacgc gtggtccagg ctggaggtc cctgagactc      60
tcctgtgcag cgtctggatt caccttcagt atgtatggcg tccactgggt ccgccaggct   120
```

```
ccaggcaagg ggctggagtg ggtggcagtt atatggaatg atggatctaa agaatactat       180
ggagactccg tgaagggccg attcaccatc tccagagaca attccaggaa cacgttgtat       240
ctgcaaatga acagcctgag agtcgacgac acggcagtgt attttgtgc gagagatgga        300 attcctgacc ctgaacgcgg tgactacggg ggcttggact actggggcca gggaaccctg       360
gtcaccgtct cctca                                                       375
```

```
<210> SEQ ID NO 20
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 20
cagactgtgg tgactcagtt tccatcctcc ccgtttgcat ctgtaggaga cggagtcacc        60
atcacttgcc gggcaaggca gagcattagc agttatgtta attggtatca gcagaaacca       120
gggaaagccc ctaagctcct gatttacgct acatccagtt tgcaaagtgg ggtcccatca       180
aggttcagtg gcagtggata tgggacagat ttcactctca ccatcagcgg tctgcaacct       240
gaagattttg caacatacta ctgtcaacag agttacagtt ttcctcgaac gttcggccaa       300
gggaccaagg tggaaatcaa ac                                               322
```

```
<210> SEQ ID NO 21
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 21
caggtgcagc tggtgcagtc tggggctcag gtgaagaagc ctgggtcctc ggtgaaggtc        60
tcctgcaagc cctctggagg caccttcaac aacaatggga tcagttgggt gcgacaggcc       120
cctggacaag gcttgagtg gatgggaggc atcgtcccga actttggaac cccaacctat        180
ggacaagact ccagggcag agtcacgatc accgcggacg aatctacgag cacagtcttc        240
ttggagctga ccagactgag atctgacgac acggccgttt atttctgtgc gcgaggtcgc       300
acggcggtga ctccgatgca attgggttta cagttctact ttgacttctg gggccgggga       360
accctggtca ccgtctcctc a                                                381
```

```
<210> SEQ ID NO 22
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 22
cagactgtgg tgactcagga gccctcactg actgtgtccc caggagggac agtcactctc        60
acctgttctg ccaacagtgg agcagtcacc agtgattact atccaaactg gttccagcag       120
aaacctggac aagcacccag ggcactgatt tatagtgcaa gcaacaaatt ctcctggacg       180
cctgcccggt tctcaggctc cctccttggg ggcaaagctg ccctgacact gtcaggtgcg       240
cagcctgagg acgaggctga gtattactgc ctggtctact ctggtgatgg tgtggttttc       300
ggcggaggga ccaagctgac cgtcc                                            325
```

<210> SEQ ID NO 23
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 23

```
caggtgcagc tggtgcagtc tggggctgag gtgaagaagc ccggggcctc agtgaaggtc      60
tcctgcaaga cttctggata tacgttcacc gacaactctg tacactgggt gcgacaggcc     120
cctggacaag ggtttgagtg gatgggacgg atcaacccta acactggtgt ctcaacttct     180
gcccagaagt ttcagggcag ggtcaccatg accagggaca cgtccatcag cacaacctac     240
atggagctga gcagtttgag atctgacgac acggccgtct attactgtgc gagagaggag     300
aacgatagta gtgggtatta cctttgggt cagggaaccc tggtcaccgt ctcctca       357
```

<210> SEQ ID NO 24
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 24

```
cagattgtgg tgactcagtc tccatcctcc ctgtttgcat ctgtaggaga cagagtcacc      60
atcacttgcc gggcaagtca gagcattagc acctatttaa attggtatca gcaaaaacca     120
gggaaagccc ctaagctcct gatctatgct gcatccagtt tggagagtgg ggtcccatca     180
aggttcggtg gcagtagatc tgggacagat ttcactctca ccatcagcag tctgcaacct     240
gaagattttg caacttacta ctgtcaacag agttacagga ccccgtggac gttcggccaa     300
gggaccaagg tggacatcaa a                                                321
```

<210> SEQ ID NO 25
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 25

```
caggtgcagc tggtgcagtc tggtcctacg ctggtgaaac ccacacagac cctcacgctg      60
acctgcacct tctctgggtt ctcactcagt attagtggag tgggtgtggg ctggatccgt     120
cagcccccag gaaaggccct ggagtggctt gcactcattt attgggatga tgataagcgc     180
tacagcccat ctctgaagag caggctcacc atcaccaagg acacctccga aaaccaggtg     240
gtccttacaa tgaccaacat ggaccctgtg gacacagcca catattactg tgcacacagt     300
atgactaaag gcggggctat ctatggtcag gcctactttg aatactgggg ccagggaacc     360
ctggtc                                                                  366
```

<210> SEQ ID NO 26
<211> LENGTH: 276
<212> TYPE: DNA
<213> ORGANISM: Artificial sequence
<220> FEATURE:
<223> OTHER INFORMATION: Synthetic oligonucleotide

<400> SEQUENCE: 26

```
ccatctcctg cactggaacc agacagtgac gttggtggtt ataactatgt ctcctggtac      60
```

| | |
|---|---|
| caacaacacc caggcaaagc ccccaaactc atcatttatg atgtcactga tcggccctca | 120 |
| ggggtttcta atcgcttctc tgcctccaag tctgccaaca cggcctccct gaccatctct | 180 |
| gggctccagg ctgaggacga ggctgattat tactgcagct catatacaag cagcagcact | 240 |
| ctggttttcg gcggagggac caagctgacc gtccta | 276 |

<210> SEQ ID NO 27
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 27

| | |
|---|---|
| caggtccagc tggtacagtc tggggctgag gtgaagaagc ctggggcctc agtgaaggtc | 60 |
| tcctgcaagg tttccggata caccctcact gaattatcca tgcactgggt gcgacaggct | 120 |
| cctggaaaag gcctagagtg gatgggaggt tttgagcctg aagatggtga aacaatctac | 180 |
| gcacagaagt tccagggcag agtcaccatg accgaggaca catctagaga cacagcctac | 240 |
| atggagctga gtagcctgag atctgaggac acggccgtct attactgtac aacagatcag | 300 |
| gtctactatc gttcggggag ttattctgga tatgttgact actggggcca gggaaccctg | 360 |
| gtc | 363 |

<210> SEQ ID NO 28
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 28

| | |
|---|---|
| caggtccagc tggtgcagtc tggggctgag gtgaagaagc ctgggtcctc agtgaaggtc | 60 |
| tcctgcaagg cttctggacg cacctcagc agctatgtta tcagctgggt gcgacaggcc | 120 |
| cctggacaag gcttgagtg gatgggaggg atcatccctc tgtttggtac agcaaactac | 180 |
| gcacagaaat tccagggcag agtcacgatt accgcggacg aatccacgag cacagcctac | 240 |
| atggagctga gcagcctgag atctgacgac acggccgtct attactgtgc gaggggcgcc | 300 |
| cagctatatt acaatgatgg tagtggttac attttttgact actggggcca gggagccctg | 360 |
| gtc | 363 |

<210> SEQ ID NO 29
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 29

| | |
|---|---|
| caggtgcagc tggtgcagtc tgggcctgag gtgaagaagc ctgggacctc agtgaaggtc | 60 |
| tcctgcaagg cttctggatt cagctttatt agctctgctg tgcagtgggt gcgacaggct | 120 |
| cgtggacaac gccttgagtg gataggatgg atcgtcgttg ccagtgctaa cacaaactac | 180 |
| gcacagaagt tccgggaaag agtcaccatt actagggaca tgtccacaaa cacagcctat | 240 |
| atggaactga ccagcctgag atccgaggac acggccgttt attactgtgc ggcagagcac | 300 |
| cggtccccctt gtagtggtgg tgatagctgc tacagtctct actacggtat ggacgtctgg | 360 |
| ggccaaggga ccctggtcac cgtctcctca | 390 |

<210> SEQ ID NO 30
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 30

```
caggtgcagc tggtgcagtc tggggggaggc ttggttccgc ctgggggggtc cctgagactg      60 tcctgtacag cctctggatt caccgttagt aactatggca tgagctgggt ccgccagact     120
ccagggaagg gctggagtg gtctcaact attagtacta gtagtggtag aacattctac        180
gcagactccg tggagggccg gttcaccatc tccggagaca attccaagaa cacgctgtat     240
ctgcaaatga acagcctgag agtcgaagac acggccgtat attactgtgc gaaaggcccg     300 ttcggggggcg actttgacta ctggggccag ggaaccctgg tcaccgtctc ctca          354
```

<210> SEQ ID NO 31
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 31

```
caggctgtgg tgactcagtc tccagccacc ctgtctttgt ctccagggga aagagccacc      60
ctctcctgca gggccagtca gagtgttgcc atctacttag cctggtatca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtggcaact ggcagtacac ttttggccag     300
gggaccaaac tggagatcaa a                                                321
```

<210> SEQ ID NO 32
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 32

```
caggtgcagc tggtgcagtc tggggggaggc ctggtacagc ctggcaggtc cctgacactc      60
tcctgtgcag cctctggatt cacctttgat gtttatgcca tgcactgggt ccggcaagct     120
ccagggaagg gcttggagtg gtcgcaggt attagttgga atagtggtag cgtaggctat      180
gcggactcta tgaagggccg attcaccatc tccagagaca cgccaagaa ctccctgtat      240 ctgcaaatta acagtctgag agctgaggac acggccttat attactgtgc aaaagcattc     300
tggttcgggg agttatcggg ttacggtatg gacgtctggg gccaagggac cctggtcacc     360
gtctcctca                                                             369
```

<210> SEQ ID NO 33
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 33

```
caggctgtgg tgactcagcc tccctccgcg tccgggtttc ctggacagtc agtcaccatc    60
tcctgcactg gaaccagcag tgacgttggt agttataact atgtctcctg gtaccaacag   120
cacccaggca aagcccccaa actcataatt tatgcggtca ctaggcggcc ctcaggggtc   180
cctgagcgct tctctggctc caagtctggc aacacggcct ccctgaccgt ctctgggctc   240
caggctgagg atgaggctga ttattactgc acctcatatg caggcaacaa caaggatgtc   300
ttcggaactg ggaccaaggt caccgtccta                                    330

<210> SEQ ID NO 34
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 34
caggtgcagc tggtgcagtc tggagctgag gtgaagaagc ctggggcctc agtgaaggtc    60
tcctgcaagg cttctggtta cagctttaac atctatggta tcagctgggt gcgacaggcc   120
cctggacaag ggcttgagtg gatgggatgg atcagcgctt acaatggtaa cacaaactat   180
gcacagaaac tccagggcag agtcaccatg accacagaca catccacgag cacagcctac   240
atggaactga ggagcctgag atctgacgac acggccgtgt attactgtgc gagaccactt   300 tgggggggaat tttactatga tatctggggc caagggaccc tggtcaccgt ctcctca     357

<210> SEQ ID NO 35
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 35
caggctgtgg tgactcagtc tccaggcacc ctgtccttgt ctccagggga aagagccacc    60
ctctcttgca gggccagtca gagtgttagc agcgggtact cagcctggta ccagcagaaa   120
cctggccagg ctcccaggct cctcatctat ggtgcatcca aaagggccgc tggcatccca   180
gacaggttca gtggcagtgg gtctgggaca gacttcactc tcaccatcag cagactggag   240
cctgaagatt ttgcagtgta ttactgtcag ctgtttgcta cctcacctcc gcccttcggc   300
caagggacac gactggagat taaa                                         324

<210> SEQ ID NO 36
<211> LENGTH: 399
<212> TYPE: DNA
<213> ORGANISM: Artificial sequence
<220> FEATURE:
<223> OTHER INFORMATION: Synthetic oligonucleotide

<400> SEQUENCE: 36
caggtgcagc tggtgcagtc tgggggaggc gtggtccagc ctgggaggtc cctgagactc    60
tcctgtgcag cctctggatt caccttcagt aattatgtta tggagtgggt ccgccaggct   120
ccaggcaagg ggctgagtg gtggcagtt atatcatatg atggaagcaa taaatactat   180
gcagactccg tgaagggccg attcaccatc tccagagaca attccaagaa cacgttgtat   240
ctgcaaatga acagcctgag agctgaggac acggctgtgt attactgtgc gagatcagag   300
tgggagtctt cctatggttc ggggaattat tatacagatt acttctacta ctacgctatg   360
gacgtctggg gccaagggac cctggtcacc gtctcctca                          399
```

<210> SEQ ID NO 37
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 37
caggctgtgg tgactcagtc tccactctcc ctgcccgtca cccctggaga gccggcctcc      60
atctcctgca ggtctaatca gagcctcctg cgtggtatta gatacaacta tttggattgg     120
tacctgcaga aaccagggca gtctccacag ctcctgatct atttgggttc taatcgggcc     180
tccggggtcc ctgacaggtt cagtggcagt ggatcagcca cagatttttac actgaaaatc     240 agcagagtgg aggctgagga tgttggggtt tattactgca tgcaagctct acaaactcct     300
accaccttcg gccaagggac acgactggag attaaa                                336

<210> SEQ ID NO 38
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 38
caggtgcagc tggaggagtc tggtcctacg ctggtgaaac ccacacagac cctcacgctg      60
acctgttcct tctctgggtt ctcactcacc actactggag tgactgtggg ctggatccgt     120
cagcccccag gaaaggcctt ggagtggctt gcactcattt attgggatga tgataagcgc     180
tacagcccat ctctgaagag caggctcacc atcaccaagg acacctccaa aaaccaggtg     240
gtccttacca tgaccaacat ggaccctgtg acactgcca catattactg tgcgcactcc     300
accggctact atgatagtag tggctatcga ggggcccttg atgcttttgc tgtctggggc     360
caagggaccc tggtcaccgt ctcctca                                          387

<210> SEQ ID NO 39
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 39
cagattgtgg tgactcagtt tccagactcc ccggctgtgt ctttgggcga gagggccacc      60
atcaactgca gtccagcca gagtgtttta taccactcca acaataaaaa ctacttagct     120
tggtaccagc agaaaccagg acagcctcct aacctgctca tttactgggc atctgcccga     180
caatccgggg tccctgaccg attcagtggc agcgggtctg ggacagattt cactctcacc     240
atcagcagcc tgcaggctga agatgtggca gtttattact gtcagcaata ttatagtact     300
ccgtacactt ttggccaggg gaccaagctg gagatcaaa                             339

<210> SEQ ID NO 40
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 40

```
caggtgcagc tggtgcagtc gggcccagga ctggtgaagc cttcggacac cctgtccctc    60
acctgcagtg tctcaagtga cgccctccgc agcaggagtt attactgggg ctgggtccgc   120 cagcccccg ggaagggatt ggagtggatt gggactgtct cttatagtgg gggcacctac   180
tacaacccgt ccctccagag tcgagtcacc gtgtcggtgg acacgtccaa gaaccacttc   240
tccctgaggt tgaactctgt gaccgccgca gacgcggctg tttattactg tgcgagatct   300
tatttctatg atggcagtgg ttactactac ctgagctact ttgactcctg gggccaggga   360
accctggtca ccgtctcctc a                                             381

<210> SEQ ID NO 41
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 41
caggctgtgg tgactcagga gccctcactg actgtgtccc caggagggac agtcactctc    60
acctgtgctt ccagcactgg agcagtcacc agtggtcact atccaaactg gttccagcag   120
aaacctggac aaccacccag ggccctgatt tatagcacag acaacaagca ctcctggacc   180
cctgcccggt tctcaggctc cctcctaggg gtcaaggctg ccctgacact gtcagatgta   240
cagcctgagg acgaggctga ctattactgc ctgctccatt tggtggtgt cgtggtcttc   300 ggcggaggga ccaagctgac cgtccta                                       327

<210> SEQ ID NO 42
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 42
caggtgcagc tggtgcagtc tgggggaggc gtggtccagc ctgggaggtc cctgagactc    60
tcctgttcaa cgtctggatt caccttcagg atgtatggca tgcactgggt ccgccaggct   120
ccaggcaagg ggctggagtg ggtggccgtt attttaacg atggagttaa gaaatattat    180
ggagacgccg tgaagggccg attcaccgtc tccagagaca attccaggaa caccctgtat   240
ctggaaatga aaagcctgag agtcgacgac acggctgcct actactgtgc gagagacggg   300
attcctgacc ccgaacgcgg tgactacggg ggcttggact actggggcca gggaaccctg   360
gtcaccgtct cctca                                                    375

<210> SEQ ID NO 43
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 43
cagactgtgg tgactcagtc tccatcctcc ctgtctgcat ctgtaggaga cacagtcacc    60
atcacttgcc gggcaagtca gagcattacc agttatttaa actggtatca gcagaaacca   120
ggaaaagccc caaagctcct catctatgct acatccagtt tgcaaagtgg gctcccctca   180
aggttcagtg gcagtggcta tgggacagaa ttcactctca ccatcagtgg tctgcaacct   240
gaagattttg caacatacta ctgtcaacag agttacagtt ttcctcgaac gttcggccaa   300
```

```
gggaccaagg tggaaatgga ta                                             322

<210> SEQ ID NO 44
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 44
caggtgcagc tggtgcagtc tgggggaggc ttggtacagc ctggcaggtc cctgagactc    60
tcctgtgcaa cctctggatt catctttgat gattatgcca tgtactgggt ccggcaagct   120
ccagggaagg gcctggagtg gtctcaggt attagttgga atagtggaaa catagcctat    180
gcggactctg tgaagggccg attcaccatc tccagadaca cgccaagaa ctccctgtat    240 ttggaaatga acagtctgag agctgaggac acggccttgt attactgtgt aaaagatctt   300
tacgggtacg atattttgac tggtaatgga tatgattact ggggccaggg aaccctggtc    360
accgtctcct ca                                                       372

<210> SEQ ID NO 45
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 45
caggctgtgg tgactcagtc ttcactctcc ctgcccgtca cccctggaga gccggcctcc    60
atctcctgca ggtctagtca gagcctcctg caaagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagatttac actgaaaatc    240 agcagagtgg aggctgagga tgttggggtt tattactgca tgcaagctct acaaactcct   300
ccgacgttcg gccaagggac caaggtggaa atcaaaa                             337

<210> SEQ ID NO 46
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 46
caggtgcagc tggtgcagtc tggggctgag gtgaagaagc ctgggtcctc ggtgaaggtc     60
ccctgcaagg cttctggaga caccctcagt tactacggaa tcacttgggt gcgacgggcc   120
cctggacaag gcttgagtg gatgggacag atcatccctt tctttgctac aacaatctcc    180
gcacagaagt tccagggcag actcaccatg accgcggaag aatccacgag cactggctac   240
atggagcgca catttttacat ggacttgagt agccttagac ctgaggacac ggccgtatac   300
tactgtgcgg ggggctacta tggttcgggg agttcgggcg actacggttt ggacgtctgg   360
ggccaaggga ccctggtcac cgtctcctca                                    390

<210> SEQ ID NO 47
<211> LENGTH: 336
<212> TYPE: DNA
<213> ORGANISM: Artificial sequence
<220> FEATURE:
```

<223> OTHER INFORMATION: Synthetic oligonucleotide

<400> SEQUENCE: 47

```
caggctgtgg tgactcagcc gccctcagtg tctggggccc cagggcagag ggtcaccatc    60
tcctgcactg ggagcagctc caacatcggg gcaggttatg atgtaaactg gtaccagcag   120
cttccaggaa cagcccccaa actcctcatc tatggtaaca caatcggcc ctcagggtc    180
cctgaccgat tctctggctc caagtctggc acctcagcct ccctggccat cactgggctc   240
caggctgagg atgaggctga ttattactgc cagtcctatg acagcagcct gagtggttcg   300
ggagtcttcg gaactgggac cgaggtcacc gtccta                              336
```

<210> SEQ ID NO 48
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 48

```
caggtgcagc tggtgcagtc gggcccagga ctggtgaagc cttcggagac cctgtccctg    60
acgtgcgctg tttctggtga ctccatcggc agtagaagtt tctactgggg ctggatccgc   120
cagcccccag ggaaggggct ggagtggatt ggaagtatct attataatgg gaccacctac   180
tacaagccgt ccctcaagag tcgagtcacc atatccctag acacgtccaa gaaccagttc   240
tccctgaggc tgagctctct gaccgccaca gacacggggtg tctattactg tgcgcgggcg   300
ccaacctact gtagtccttc cagctgcgca gttcactggt acttcaatct ctggggccgt   360
ggcaccctgg tcaccgtctc ctca                                          384
```

<210> SEQ ID NO 49
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 49

```
caggtgcagc tggtgcagtc tggagctgag ctgaagaagc ctggggcctc agtgaaggtc    60
tcctgcaagg cttctggtta catatttacc aaatatggta tcagttggct gcgacaggcc   120
cctggacaag ggcttgagtg ggtgggatgg atcagcgctt acaatgaaaa cacaaactat   180
gcagagaagt tccagggcag agtcaccttg accacagatg catccacgag cacggcctac   240
atggagctga ggaacctgag atctgacgac acggccgtat acttctgtgc gagagaagtc   300
tggttcgcgg agtatattta ctggggccag ggaaccctgg tcaccgtctc ctca         354
```

<210> SEQ ID NO 50
<211> LENGTH: 300
<212> TYPE: DNA
<213> ORGANISM: Artificial sequence
<220> FEATURE:
<223> OTHER INFORMATION: Synthetic oligonucleotide

<400> SEQUENCE: 50

```
caggctgtgg tgactcagga gccctcactg actgtgtccc caggagggac agtcactctc    60
acctgttctg ccaacagtgg agcagtcacc agtgattact atccaaactg gttccagcag   120
aaacctggac aagcacccag ggcactgatt tatagtgcaa gcaacaaatt ctcctggacg   180
cctgcccggt tctcaggctc cctccttggg ggcaaagctg ccctgacact gtcaggtgcg   240
```
cagcctgagg acgaggctga gtattactgc ctggtctact ctggtgatgg tgtggttttc 300

<210> SEQ ID NO 51
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 51
cagtctgtgg tgactcagcc tgcctccgtg tctgggtctc ctggacagtc gatcaccatc 60
tcctgcactg gaaccagcag tgacgttggt gcttataact atgtctcctg gtaccaacaa 120
cacccaggca aagcccccaa actcgtgatt tatgatgtcg ctaatcggcc ctcagggatt 180
tctgaccgct tctctggctc caagtctggc aacacggcct ccctgaccat ctctgggctc 240
caggctgagg acgaggctga ttattactgc ggctcatata ccagcgacgt ctcgccggtt 300
ttcagcgggg ggaccaagct gaccgtcctc a 331

<210> SEQ ID NO 52
<211> LENGTH: 399
<212> TYPE: DNA
<213> ORGANISM: Artificial sequence
<220> FEATURE:
<223> OTHER INFORMATION: Synthetic oligonucleotide

<400> SEQUENCE: 52
caggtgcagc tggtgcagtc tgggtctgag ttgaagaagc ctggggcctc agtgaagctt 60
tcctgcaagg cttctggata caccttcaca agtcatccta tgaattgggt gcgacaggcc 120
cctggacaag gcttgagtg gatgggatgg atcaacacca agactgggaa cctaacttat 180
gcccagggct tcacaggacg gtttgtcttc tccttggaca cctctgtcag gacggcgtat 240
ctgcagatca gcggcctaaa ggctgaggac actgccattt attactgtgc gagagatgag 300
tatagtggct acgattcggt aggggtgttc cgtggttctt ttgacgactt ctacggtatg 360
gacgtctggg gccaagggac cctggtcacc gtctcctca 399

<210> SEQ ID NO 53
<211> LENGTH: 126
<212> TYPE: PRT
<213> ORGANISM: Artificial sequence
<220> FEATURE:
<223> OTHER INFORMATION: Synthetic peptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser
        115                 120                 125

<210> SEQ ID NO 54
<211> LENGTH: 111
<212> TYPE: PRT
<213> ORGANISM: Artificial sequence
<220> FEATURE:
<223> OTHER INFORMATION: Synthetic peptide

<400> SEQUENCE: 54

Gln Ala Val Val Thr Gln Pro Pro Ser Val Ser Gly Ala Pro Gly Gln
1               5                   10                  15

Arg Val Thr Ile Ser Cys Thr Gly Ser Ser Asn Ile Gly Ala Asp
            20                  25                  30

Tyr Asn Val His Trp Tyr Gln Leu Leu Pro Gly Thr Ala Pro Lys Leu
        35                  40                  45

Leu Ile Tyr Gly Asn Thr Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu
            100                 105                 110

<210> SEQ ID NO 55
<211> LENGTH: 119
<212> TYPE: PRT
<213> ORGANISM: Artificial sequence
<220> FEATURE:
<223> OTHER INFORMATION: Synthetic peptide

<400> SEQUENCE: 55

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Ser Tyr
            20                  25                  30

Ser Ile Asn Trp Val Arg Gln Ala Pro Gly Gln Gly Pro Glu Trp Met
        35                  40                  45

Gly Trp Ile Asp Thr Asn Thr Gly Asn Pro Thr Tyr Ala Gln Asp Phe
50                  55                  60

Ala Gly Arg Phe Val Phe Ser Leu Asp Thr Ser Val Thr Thr Ala Tyr
65                  70                  75                  80

Leu Gln Ile Ser Ser Leu Lys Ala Gly Asp Thr Ala Val Tyr Tyr Cys
                85                  90                  95

Ala Thr Tyr Tyr Val Asp Leu Trp Gly Ser Tyr Arg Gln Asp Tyr Tyr
            100                 105                 110

Gly Met Asp Val Trp Gly His
        115

<210> SEQ ID NO 56
<211> LENGTH: 111
<212> TYPE: PRT
<213> ORGANISM: Artificial sequence
<220> FEATURE:
<223> OTHER INFORMATION: Synthetic peptide

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
                20                  25                  30

Pro Val Asn Trp Tyr Gln Met Val Pro Gly Thr Ala Pro Lys Leu Leu
            35                  40                  45

Leu Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Asn Gly Leu Gln
65                  70                  75                  80

Ser Glu Asp Glu Ala Asp Tyr Tyr Cys Ala Val Trp Asp Asp Ser Leu
                85                  90                  95

Ser Gly Arg Trp Val Phe Gly Gly Gly Thr Lys Val Thr Val Leu
            100                 105                 110

<210> SEQ ID NO 57
<211> LENGTH: 137
<212> TYPE: PRT
<213> ORGANISM: Artificial sequence
<220> FEATURE:
<223> OTHER INFORMATION: Synthetic peptide

<400> SEQUENCE: 57

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Thr Tyr Asn Gly Asp Thr Asn Tyr Ala Gln Lys Phe
        50                  55                  60

Gln Gly Arg Val Thr Leu Thr Thr Glu Thr Ser Thr Ser Thr Ala Tyr
65                  70                  75                  80

Met Glu Leu Arg Arg Leu Arg Ser Asp Asp Thr Ala Val Tyr Tyr Cys
                85                  90                  95

Ala Arg Asp Phe Glu Phe Pro Gly Asp Cys Ser Gly Gly Ser Cys Tyr
            100                 105                 110

Ser Arg Phe Ile Tyr Gln His Asn Asp Met Asp Val Trp Gly His Gly
        115                 120                 125

Thr Leu Val Thr Val Ser Ser Ala Ser
    130                 135

<210> SEQ ID NO 58
<211> LENGTH: 110
<212> TYPE: PRT
<213> ORGANISM: Artificial sequence
<220> FEATURE:
<223> OTHER INFORMATION: Synthetic peptide

<400> SEQUENCE: 58

Gln Ala Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn His
                20                  25                  30

Tyr Val Ser Trp Tyr Gln His Leu Pro Gly Thr Ala Pro Lys Leu Leu
            35                  40                  45

Ile Tyr Asp Asn Tyr Lys Arg Pro Ser Val Ile Pro Asp Arg Phe Ser
        50                  55                  60

Ala Ser Lys Ser Gly Ala Ser Ala Thr Leu Gly Ile Ile Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 59
<211> LENGTH: 127
<212> TYPE: PRT
<213> ORGANISM: Artificial sequence
<220> FEATURE:
<223> OTHER INFORMATION: Synthetic peptide

<400> SEQUENCE: 59

Gln Val Gln Leu Val Gln Ser Gly Pro Gly Leu Val Lys Pro Ser Asp
1               5                   10                  15

Thr Leu Ser Leu Thr Cys Ser Val Ser Ser Asp Ala Leu Arg Ser Arg
            20                  25                  30

Ser Tyr Tyr Trp Gly Trp Val Arg Gln Pro Pro Gly Lys Gly Leu Glu
        35                  40                  45

Trp Ile Gly Thr Val Ser Tyr Ser Gly Gly Thr Tyr Tyr Asn Pro Ser
50                  55                  60

Leu Gln Ser Arg Val Thr Val Ser Val Asp Thr Ser Lys Asn His Phe
65                  70                  75                  80

Ser Leu Arg Leu Asn Ser Val Thr Ala Ala Asp Ala Ala Val Tyr Tyr
                85                  90                  95

Cys Ala Arg Ser Tyr Phe Tyr Asp Gly Ser Gly Tyr Tyr Leu Ser
            100                 105                 110

Tyr Phe Asp Ser Trp Gly Gln Gly Thr Leu Val Thr Val Ser Ser
        115                 120                 125

<210> SEQ ID NO 60
<211> LENGTH: 109
<212> TYPE: PRT
<213> ORGANISM: Artificial sequence
<220> FEATURE:
<223> OTHER INFORMATION: Synthetic peptide

<400> SEQUENCE: 60

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

His Tyr Pro Asn Trp Phe Gln Gln Lys Pro Gly Gln Pro Pro Arg Ala
        35                  40                  45

Leu Ile Tyr Ser Thr Asp Asn Lys His Ser Trp Thr Pro Ala Arg Phe
50                  55                  60

Ser Gly Ser Leu Leu Gly Val Lys Ala Ala Leu Thr Leu Ser Asp Val
65                  70                  75                  80

Gln Pro Glu Asp Glu Ala Asp Tyr Tyr Cys Leu Leu His Phe Gly Gly
                85                  90                  95

Val Val Val Phe Gly Gly Gly Thr Lys Leu Thr Val Leu
            100                 105

<210> SEQ ID NO 61
<211> LENGTH: 116
<212> TYPE: PRT

<213> ORGANISM: Artificial sequence
<220> FEATURE:
<223> OTHER INFORMATION: Synthetic peptide

<400> SEQUENCE: 61

```
Gln Val Gln Leu Val Gln Ser Gly Gly Val Val Gln Pro Gly Arg
1               5                   10                  15

Ser Leu Arg Leu Ser Cys Ala Val Ser Gly Phe Thr Phe Ser Asn Tyr
            20                  25                  30

Ala Met His Trp Val Arg Gln Ala Pro Gly Lys Gly Leu Asp Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Gly Asp Tyr Val Leu Asp Tyr Trp Gly Gln Gly Thr Leu Val
            100                 105                 110

Thr Val Ser Ser
        115
```

<210> SEQ ID NO 62
<211> LENGTH: 108
<212> TYPE: PRT
<213> ORGANISM: Artificial sequence
<220> FEATURE:
<223> OTHER INFORMATION: Synthetic peptide

<400> SEQUENCE: 62

```
Asp Ile Val Met Thr Gln Ser Pro Ser Ser Leu Ser Ala Ser Val Gly
1               5                   10                  15

Asp Arg Val Thr Ile Ser Cys Arg Ala Ser Gln Ser Ile Pro Ser Tyr
            20                  25                  30

Leu Asn Trp Tyr Gln Gln Lys Pro Gly Lys Ala Pro Lys Val Leu Ile
        35                  40                  45

Tyr Ala Thr Ser Thr Leu Glu Ala Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Asn Thr Gly Ile
                85                  90                  95

Phe Thr Phe Gly Pro Gly Thr Lys Val Asp Ile Lys
            100                 105
```

<210> SEQ ID NO 63
<211> LENGTH: 126
<212> TYPE: PRT
<213> ORGANISM: Artificial sequence
<220> FEATURE:
<223> OTHER INFORMATION: Synthetic peptide

<400> SEQUENCE: 63

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Ser Ser Thr Tyr
            20                  25                  30

Ala Ile Ser Trp Val Arg Gln Ala Pro Gly Gln Gly Leu Glu Trp Met
        35                  40                  45
```

```
Gly Gly Ser Ile Pro Val Phe Ala Thr Val Asn Tyr Ala Gln Lys Phe
         50                  55                  60

Gln Gly Arg Leu Thr Ile Thr Ala Asp Glu Ser Thr Ser Thr Val Tyr
 65                  70                  75                  80

Met Glu Leu Ser Ser Leu Arg Ser Glu Asp Thr Ala Val Tyr Phe Cys
                 85                  90                  95

Ala Ser Pro Tyr Cys Ser Ser Met Asn Cys Tyr Thr Thr Phe Tyr Tyr
                100                 105                 110

Phe Asp Phe Trp Gly Gln Gly Thr Leu Val Thr Val Ser Ser
            115                 120                 125

<210> SEQ ID NO 64
<211> LENGTH: 109
<212> TYPE: PRT
<213> ORGANISM: Artificial sequence
<220> FEATURE:
<223> OTHER INFORMATION: Synthetic peptide

<400> SEQUENCE: 64

Gln Ala Val Val Thr Gln Pro Ala Ser Val Phe Gly Phe Pro Gly Gln
 1               5                  10                  15

Ser Ile Thr Ile Ser Cys Thr Gly Thr Ser Ser Asp Phe Gly Thr Tyr
                 20                  25                  30

Asn Tyr Val Ser Trp Tyr Gln Gln His Pro Gly Gln Ala Pro Lys Leu
             35                  40                  45

Met Ile Phe Asp Val Ser Asn Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Ser Tyr Tyr Cys Ser Ser Tyr Thr Ser Gly
                 85                  90                  95

Ser Thr Leu Tyr Gly Gly Gly Thr Lys Leu Thr Val Leu
                100                 105

<210> SEQ ID NO 65
<211> LENGTH: 127
<212> TYPE: PRT
<213> ORGANISM: Artificial sequence
<220> FEATURE:
<223> OTHER INFORMATION: Synthetic peptide

<400> SEQUENCE: 65

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Ser Phe Thr Ser Tyr
                 20                  25                  30

Ser Ile Asn Trp Val Arg Gln Ala Pro Gly Gln Gly Pro Glu Trp Met
             35                  40                  45

Gly Trp Ile Asp Thr Asn Thr Gly Asn Pro Thr Tyr Ala Gln Asp Phe
         50                  55                  60

Ala Gly Arg Phe Val Phe Ser Leu Asp Thr Ser Val Thr Thr Ala Tyr
 65                  70                  75                  80

Leu Gln Ile Ser Ser Leu Lys Ala Gly Asp Thr Ala Val Tyr Tyr Cys
                 85                  90                  95

Ala Thr Tyr Tyr Val Asp Leu Trp Gly Ser Tyr Arg Gln Asp Tyr Tyr
                100                 105                 110

Gly Met Asp Val Trp Gly His Gly Thr Leu Val Thr Val Ser Ser
            115                 120                 125
```

-continued

<210> SEQ ID NO 66
<211> LENGTH: 111
<212> TYPE: PRT
<213> ORGANISM: Artificial sequence
<220> FEATURE:
<223> OTHER INFORMATION: Synthetic peptide

<400> SEQUENCE: 66

Gln Ser Val Val Thr Gln Pro Pro Ser Val Ser Gly Thr Pro Gly Gln
1               5                   10                  15

Gly Val Thr Ile Ser Cys Ser Gly Gly Ser Ser Asn Ile Gly Ser Asn
            20                  25                  30

Pro Val Asn Trp Tyr Gln Met Val Pro Gly Thr Ala Pro Lys Leu Leu
        35                  40                  45

Leu Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Asn Gly Leu Gln
65                  70                  75                  80

Ser Glu Asp Glu Ala Asp Tyr Tyr Cys Ala Val Trp Asp Asp Ser Leu
                85                  90                  95

Ser Gly Arg Trp Val Phe Gly Gly Gly Thr Lys Leu Thr Val Leu
            100                 105                 110

<210> SEQ ID NO 67
<211> LENGTH: 123
<212> TYPE: PRT
<213> ORGANISM: Artificial sequence
<220> FEATURE:
<223> OTHER INFORMATION: Synthetic peptide

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Gly Val Asp Tyr
            100                 105                 110

Trp Gly Gln Gly Thr Leu Val Thr Val Ser Ser
        115                 120

<210> SEQ ID NO 68
<211> LENGTH: 107
<212> TYPE: PRT
<213> ORGANISM: Artificial sequence
<220> FEATURE:
<223> OTHER INFORMATION: Synthetic peptide

<400> SEQUENCE: 68

Gln Ala Val Val Thr Gln Ser Pro Ser Ser Leu Pro Ala Ser Val Gly
1               5                   10                  15

```
Asp Arg Val Thr Ile Thr Cys Arg Ala Ser Gln Asp Ile Arg Asn Asn
            20                  25                  30

Leu Gly Trp Tyr Gln Gln Lys Pro Gly Lys Ala Pro Glu Arg Leu Ile
        35                  40                  45

Tyr Gly Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Arg Gly Thr Lys Val Glu Ile Lys
            100                 105

<210> SEQ ID NO 69
<211> LENGTH: 126
<212> TYPE: PRT
<213> ORGANISM: Artificial sequence
<220> FEATURE:
<223> OTHER INFORMATION: Synthetic peptide

<400> SEQUENCE: 69

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Phe Met His Trp Val Arg Gln Ala Pro Gly Gln Gly Leu Glu Trp Met
        35                  40                  45

Ala Ile Thr Tyr Pro Gly Gly Ser Pro Ser Tyr Ala Pro Gln Phe
    50                  55                  60

Gln Gly Arg Leu Thr Met Thr Asp Thr Ser Ala Thr Thr Val Tyr
65                  70                  75                  80

Met Asp Leu Ser Asp Leu Thr Ser Lys Asp Thr Ala Val Tyr Tyr Cys
                85                  90                  95

Ala Arg Gly Ala His Arg Ser Ile Gly Thr Thr Pro Leu Asp Ser Trp
            100                 105                 110

Gly Gln Gly Thr Leu Val Thr Val Ser Ser Ala Ser Phe Lys
        115                 120                 125

<210> SEQ ID NO 70
<211> LENGTH: 125
<212> TYPE: PRT
<213> ORGANISM: Artificial sequence
<220> FEATURE:
<223> OTHER INFORMATION: Synthetic peptide

<400> SEQUENCE: 70

Gln Val Gln Leu Val Gln Ser Gly Gly Arg Val Val Gln Ala Gly Arg
1               5                   10                  15

Ser Leu Arg Leu Ser Cys Ala Ala Ser Gly Phe Thr Phe Ser Met Tyr
            20                  25                  30

Gly Val His Trp Val Arg Gln Ala Pro Gly Lys Gly Leu Glu Trp Val
        35                  40                  45

Ala Val Ile Trp Asn Asp Gly Ser Lys Glu Tyr Tyr Gly Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Val Asp Asp Thr Ala Val Tyr Phe Cys
```

```
                    85                  90                  95
Ala Arg Asp Gly Ile Pro Asp Pro Glu Arg Gly Asp Tyr Gly Gly Leu
                100                 105                 110

Asp Tyr Trp Gly Gln Gly Thr Leu Val Thr Val Ser Ser
        115                 120                 125

<210> SEQ ID NO 71
<211> LENGTH: 107
<212> TYPE: PRT
<213> ORGANISM: Artificial sequence
<220> FEATURE:
<223> OTHER INFORMATION: Synthetic peptide

<400> SEQUENCE: 71

Gln Thr Val Val Thr Gln Phe Pro Ser Ser Pro Phe Ala Ser Val Gly
1               5                   10                  15

Asp Gly Val Thr Ile Thr Cys Arg Ala Arg Gln Ser Ile Ser Ser Tyr
            20                  25                  30

Val Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
50                  55                  60

Ser Gly Tyr Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Phe Pro Arg
                85                  90                  95

Thr Phe Gly Gln Gly Thr Lys Val Glu Ile Lys
            100                 105

<210> SEQ ID NO 72
<211> LENGTH: 127
<212> TYPE: PRT
<213> ORGANISM: Artificial sequence
<220> FEATURE:
<223> OTHER INFORMATION: Synthetic peptide

<400> SEQUENCE: 72

Gln Val Gln Leu Val Gln Ser Gly Ala Gln Val Lys Lys Pro Gly Ser
1               5                   10                  15

Ser Val Lys Val Ser Cys Lys Pro Ser Gly Gly Thr Phe Asn Asn Asn
            20                  25                  30

Gly Ile Ser Trp Val Arg Gln Ala Pro Gly Gln Gly Leu Glu Trp Met
        35                  40                  45

Gly Gly Ile Val Pro Asn Phe Gly Thr Pro Thr Tyr Gly Gln Asp Phe
50                  55                  60

Gln Gly Arg Val Thr Ile Thr Ala Asp Glu Ser Thr Ser Thr Val Phe
65                  70                  75                  80

Leu Glu Leu Thr Arg Leu Arg Ser Asp Asp Thr Ala Val Tyr Phe Cys
                85                  90                  95

Ala Arg Gly Arg Thr Ala Val Thr Pro Met Gln Leu Gly Leu Gln Phe
            100                 105                 110

Tyr Phe Asp Phe Trp Gly Arg Gly Thr Leu Val Thr Val Ser Ser
        115                 120                 125

<210> SEQ ID NO 73
<211> LENGTH: 108
<212> TYPE: PRT
<213> ORGANISM: Artificial sequence
<220> FEATURE:
```

<223> OTHER INFORMATION: Synthetic peptide

<400> SEQUENCE: 73

```
Gln Thr Val Val Thr Gln Glu Pro Ser Leu Thr Val Ser Pro Gly Gly
1               5                   10                  15

Thr Val Thr Leu Thr Cys Ser Ala Asn Ser Gly Ala Val Thr Ser Asp
            20                  25                  30

Tyr Tyr Pro Asn Trp Phe Gln Gln Lys Pro Gly Gln Ala Pro Arg Ala
        35                  40                  45

Leu Ile Tyr Ser Ala Ser Asn Lys Phe Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Val Tyr Ser Gly Asp
                85                  90                  95

Gly Val Val Phe Gly Gly Gly Thr Lys Leu Thr Val
            100                 105
```

<210> SEQ ID NO 74
<211> LENGTH: 119
<212> TYPE: PRT
<213> ORGANISM: Artificial sequence
<220> FEATURE:
<223> OTHER INFORMATION: Synthetic peptide

<400> SEQUENCE: 74

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asp Asn
            20                  25                  30

Ser Val His Trp Val Arg Gln Ala Pro Gly Gln Gly Phe Glu Trp Met
        35                  40                  45

Gly Arg Ile Asn Pro Asn Thr Gly Val Ser Thr Ser Ala Gln Lys Phe
    50                  55                  60

Gln Gly Arg Val Thr Met Thr Arg Asp Thr Ser Ile Ser Thr Thr Tyr
65                  70                  75                  80

Met Glu Leu Ser Ser Leu Arg Ser Asp Asp Thr Ala Val Tyr Tyr Cys
                85                  90                  95

Ala Arg Glu Glu Asn Asp Ser Ser Gly Tyr Tyr Leu Trp Gly Gln Gly
                100                 105                 110

Thr Leu Val Thr Val Ser Ser
        115
```

<210> SEQ ID NO 75
<211> LENGTH: 107
<212> TYPE: PRT
<213> ORGANISM: Artificial sequence
<220> FEATURE:
<223> OTHER INFORMATION: Synthetic peptide

<400> SEQUENCE: 75

```
Gln Ile Val Val Thr Gln Ser Pro Ser Ser Leu Phe Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Gly Gly
```

```
                    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Arg Thr Pro Trp
                     85                  90                  95

Thr Phe Gly Gln Gly Thr Lys Val Asp Ile Lys
                100                 105

<210> SEQ ID NO 76
<211> LENGTH: 122
<212> TYPE: PRT
<213> ORGANISM: Artificial sequence
<220> FEATURE:
<223> OTHER INFORMATION: Synthetic peptide

<400> SEQUENCE: 76

Gln Val Gln Leu Val Gln Ser Gly Pro Thr Leu Val Lys Pro Thr Gln
  1               5                  10                  15

Thr Leu Thr Leu Thr Cys Thr Phe Ser Gly Phe Ser Leu Ser Ile Ser
                 20                  25                  30

Gly Val Gly Val Gly Trp Ile Arg Gln Pro Pro Gly Lys Ala Leu Glu
             35                  40                  45

Trp Leu Ala Leu Ile Tyr Trp Asp Asp Lys Arg Tyr Ser Pro Ser
 50                  55                  60

Leu Lys Ser Arg Leu Thr Ile Thr Lys Asp Thr Ser Glu Asn Gln Val
 65                  70                  75                  80

Val Leu Thr Met Thr Asn Met Asp Pro Val Asp Thr Ala Thr Tyr Tyr
                 85                  90                  95

Cys Ala His Ser Met Thr Lys Gly Gly Ala Ile Tyr Gly Gln Ala Tyr
                100                 105                 110

Phe Glu Tyr Trp Gly Gln Gly Thr Leu Val
            115                 120

<210> SEQ ID NO 77
<211> LENGTH: 80
<212> TYPE: PRT
<213> ORGANISM: Artificial sequence
<220> FEATURE:
<223> OTHER INFORMATION: Synthetic peptide

<400> SEQUENCE: 77

Pro Ser Pro Ala Leu Glu Pro Asp Ser Asp Val Gly Gly Tyr Asn Tyr
  1               5                  10                  15

Val Ser Trp Tyr Gln Gln His Pro Gly Lys Ala Pro Lys Leu Ile Ile
                 20                  25                  30

Tyr Asp Val Thr Asp Arg Pro Ser Gly Val Ser Asn Arg Phe Ser Ala
             35                  40                  45

Ser Lys Ser Ala Asn Thr Ala Ser Leu Thr Ile Ser Gly Leu Gln Ala
 50                  55                  60

Glu Asp Glu Ala Asp Tyr Tyr Cys Ser Ser Tyr Thr Ser Ser Ser Thr
 65                  70                  75                  80

<210> SEQ ID NO 78
<211> LENGTH: 121
<212> TYPE: PRT
<213> ORGANISM: Artificial sequence
<220> FEATURE:
<223> OTHER INFORMATION: Synthetic peptide

<400> SEQUENCE: 78
```

-continued

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Glu Pro Glu Asp Gly Glu Thr Ile Tyr Ala Gln Lys Phe
    50                  55                  60

Gln Gly Arg Val Thr Met Thr Glu Asp Thr Ser Arg Asp Thr Ala Tyr
65                  70                  75                  80

Met Glu Leu Ser Ser Leu Arg Ser Glu Asp Thr Ala Val Tyr Tyr Cys
            85                  90                  95

Thr Thr Asp Gln Val Tyr Tyr Arg Ser Gly Ser Tyr Ser Gly Tyr Val
            100                 105                 110

Asp Tyr Trp Gly Gln Gly Thr Leu Val
        115                 120

<210> SEQ ID NO 79
<211> LENGTH: 121
<212> TYPE: PRT
<213> ORGANISM: Artificial sequence
<220> FEATURE:
<223> OTHER INFORMATION: Synthetic peptide

<400> SEQUENCE: 79

Gln Val Gln Leu Val Gln Ser Gly Ala Glu Val Lys Lys Pro Gly Ser
1               5                   10                  15

Ser Val Lys Val Ser Cys Lys Ala Ser Gly Arg Thr Phe Ser Ser Tyr
            20                  25                  30

Val Ile Ser Trp Val Arg Gln Ala Pro Gly Gln Gly Leu Glu Trp Met
        35                  40                  45

Gly Gly Ile Ile Pro Leu Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
            85                  90                  95

Ala Arg Gly Ala Gln Leu Tyr Tyr Asn Asp Gly Ser Tyr Ile Phe
            100                 105                 110

Asp Tyr Trp Gly Gln Gly Ala Leu Val
        115                 120

<210> SEQ ID NO 80
<211> LENGTH: 130
<212> TYPE: PRT
<213> ORGANISM: Artificial sequence
<220> FEATURE:
<223> OTHER INFORMATION: Synthetic peptide

<400> SEQUENCE: 80

Gln Val Gln Leu Val Gln Ser Gly Pro Glu Val Lys Lys Pro Gly Thr
1               5                   10                  15

Ser Val Lys Val Ser Cys Lys Ala Ser Gly Phe Ser Phe Ile Ser Ser
            20                  25                  30

Ala Val Gln Trp Val Arg Gln Ala Arg Gly Gln Arg Leu Glu Trp Ile
        35                  40                  45

Gly Trp Ile Val Val Ala Ser Ala Asn Thr Asn Tyr Ala Gln Lys Phe

```
            50                  55                  60
Arg Glu Arg Val Thr Ile Thr Arg Asp Met Ser Thr Asn Thr Ala Tyr
 65                  70                  75                  80

Met Glu Leu Thr Ser Leu Arg Ser Glu Asp Thr Ala Val Tyr Tyr Cys
                 85                  90                  95

Ala Ala Glu His Arg Ser Pro Cys Ser Gly Gly Asp Ser Cys Tyr Ser
            100                 105                 110

Leu Tyr Tyr Gly Met Asp Val Trp Gly Gln Gly Thr Leu Val Thr Val
        115                 120                 125

Ser Ser
    130

<210> SEQ ID NO 81
<211> LENGTH: 118
<212> TYPE: PRT
<213> ORGANISM: Artificial sequence
<220> FEATURE:
<223> OTHER INFORMATION: Synthetic peptide

<400> SEQUENCE: 81

Gln Val Gln Leu Val Gln Ser Gly Gly Gly Leu Val Pro Pro Gly Gly
 1               5                  10                  15

Ser Leu Arg Leu Ser Cys Thr Ala Ser Gly Phe Thr Val Ser Asn Tyr
             20                  25                  30

Gly Met Ser Trp Val Arg Gln Thr Pro Gly Lys Gly Leu Glu Trp Val
         35                  40                  45

Ser Thr Ile Ser Thr Ser Ser Gly Arg Thr Phe Tyr Ala Asp Ser Val
     50                  55                  60

Glu Gly Arg Phe Thr Ile Ser Gly Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Ala Lys Gly Pro Phe Gly Gly Asp Phe Asp Tyr Trp Gly Gln Gly Thr
            100                 105                 110

Leu Val Thr Val Ser Ser
        115

<210> SEQ ID NO 82
<211> LENGTH: 107
<212> TYPE: PRT
<213> ORGANISM: Artificial sequence
<220> FEATURE:
<223> OTHER INFORMATION: Synthetic peptide

<400> SEQUENCE: 82

Gln Ala Val Val Thr Gln Ser Pro Ala Thr Leu Ser Leu Ser Pro Gly
 1               5                  10                  15

Glu Arg Ala Thr Leu Ser Cys Arg Ala Ser Gln Ser Val Ala Ile Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Gly Asn Trp Gln Tyr
                 85                  90                  95
```

Thr Phe Gly Gln Gly Thr Lys Leu Glu Ile Lys
            100                 105

<210> SEQ ID NO 83
<211> LENGTH: 123
<212> TYPE: PRT
<213> ORGANISM: Artificial sequence
<220> FEATURE:
<223> OTHER INFORMATION: Synthetic peptide

<400> SEQUENCE: 83

Gln Val Gln Leu Val Gln Ser Gly Gly Gly Leu Val Gln Pro Gly Arg
1               5                   10                  15

Ser Leu Thr Leu Ser Cys Ala Ala Ser Gly Phe Thr Phe Asp Val Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Val Gly Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Ala Glu Asp Thr Ala Leu Tyr Tyr Cys
                85                  90                  95

Ala Lys Ala Phe Trp Phe Gly Glu Leu Ser Gly Tyr Gly Met Asp Val
            100                 105                 110

Trp Gly Gln Gly Thr Leu Val Thr Val Ser Ser
        115                 120

<210> SEQ ID NO 84
<211> LENGTH: 110
<212> TYPE: PRT
<213> ORGANISM: Artificial sequence
<220> FEATURE:
<223> OTHER INFORMATION: Synthetic peptide

<400> SEQUENCE: 84

Gln Ala Val Val Thr Gln Pro Pro Ser Ala Ser Gly Phe Pro Gly Gln
1               5                   10                  15

Ser Val Thr Ile Ser Cys Thr Gly Thr Ser Ser Asp Val Gly Ser Tyr
            20                  25                  30

Asn Tyr Val Ser Trp Tyr Gln Gln His Pro Gly Lys Ala Pro Lys Leu
        35                  40                  45

Ile Ile Tyr Ala Val Thr Arg Arg Pro Ser Gly Val Pro Glu Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Thr Ser Tyr Ala Gly Asn
                85                  90                  95

Asn Lys Asp Val Phe Gly Thr Gly Thr Lys Val Thr Val Leu
            100                 105                 110

<210> SEQ ID NO 85
<211> LENGTH: 119
<212> TYPE: PRT
<213> ORGANISM: Artificial sequence
<220> FEATURE:
<223> OTHER INFORMATION: Synthetic peptide

<400> SEQUENCE: 85

Gln Val Gln Leu Val Gln Ser Gly Ala Glu Val Lys Lys Pro Gly Ala

```
 1               5                  10                 15
Ser Val Lys Val Ser Cys Lys Ala Ser Gly Tyr Ser Phe Asn Ile Tyr
                20                  25                 30

Gly Ile Ser Trp Val Arg Gln Ala Pro Gly Gln Gly Leu Glu Trp Met
            35                  40                 45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Pro Leu Trp Gly Glu Phe Tyr Tyr Asp Ile Trp Gly Gln Gly
            100                 105                110

Thr Leu Val Thr Val Ser Ser
            115

<210> SEQ ID NO 86
<211> LENGTH: 108
<212> TYPE: PRT
<213> ORGANISM: Artificial sequence
<220> FEATURE:
<223> OTHER INFORMATION: Synthetic peptide

<400> SEQUENCE: 86

Gln Ala Val Val Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
                20                  25                  30

Tyr Ser Ala Trp Tyr Gln Gln Lys Pro Gly Gln Ala Pro Arg Leu Leu
            35                  40                  45

Ile Tyr Gly Ala Ser Lys Arg Ala Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Phe Ala Thr Ser Pro
                85                  90                  95

Pro Pro Phe Gly Gln Gly Thr Arg Leu Glu Ile Lys
            100                 105

<210> SEQ ID NO 87
<211> LENGTH: 133
<212> TYPE: PRT
<213> ORGANISM: Artificial sequence
<220> FEATURE:
<223> OTHER INFORMATION: Synthetic peptide

<400> SEQUENCE: 87

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Val Met Glu Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Glu Trp Glu Ser Ser Tyr Gly Ser Gly Asn Tyr Tyr Thr
            100                 105                 110

Asp Tyr Phe Tyr Tyr Tyr Ala Met Asp Val Trp Gly Pro Gly Thr Leu
        115                 120                 125

Val Thr Val Ser Ser
    130

<210> SEQ ID NO 88
<211> LENGTH: 112
<212> TYPE: PRT
<213> ORGANISM: Artificial sequence
<220> FEATURE:
<223> OTHER INFORMATION: Synthetic peptide

<400> SEQUENCE: 88

Gln Ala Val Val Thr Gln Ser Pro Leu Ser Leu Pro Val Thr Pro Gly
1               5                   10                  15

Glu Pro Ala Ser Ile Ser Cys Arg Ser Asn Gln Ser Leu Leu Arg Gly
            20                  25                  30

Ile Arg Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Ala Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Thr Thr Phe Gly Gln Gly Thr Arg Leu Glu Ile Lys
            100                 105                 110

<210> SEQ ID NO 89
<211> LENGTH: 129
<212> TYPE: PRT
<213> ORGANISM: Artificial sequence
<220> FEATURE:
<223> OTHER INFORMATION: Synthetic peptide

<400> SEQUENCE: 89

Gln Val Gln Leu Glu Glu Ser Gly Pro Thr Leu Val Lys Pro Thr Gln
1               5                   10                  15

Thr Leu Thr Leu Thr Cys Ser Phe Ser Gly Phe Ser Leu Thr Thr Thr
            20                  25                  30

Gly Val Thr Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Thr Gly Tyr Tyr Asp Ser Ser Gly Tyr Arg Gly Ala
            100                 105                 110

Leu Asp Ala Phe Ala Val Trp Gly Gln Gly Thr Leu Val Thr Val Ser
        115                 120                 125

Ser
```

```
<210> SEQ ID NO 90
<211> LENGTH: 113
<212> TYPE: PRT
<213> ORGANISM: Artificial sequence
<220> FEATURE:
<223> OTHER INFORMATION: Synthetic peptide

<400> SEQUENCE: 90

Gln Ile Val Val Thr Gln Phe Pro Asp Ser Pro Ala Val Ser Leu Gly
1               5                   10                  15

Glu Arg Ala Thr Ile Asn Cys Lys Ser Ser Gln Ser Val Leu Tyr His
            20                  25                  30

Ser Asn Asn Lys Asn Tyr Leu Ala Trp Tyr Gln Gln Lys Pro Gly Gln
        35                  40                  45

Pro Pro Asn Leu Leu Ile Tyr Trp Ala Ser Ala Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys

<210> SEQ ID NO 91
<211> LENGTH: 127
<212> TYPE: PRT
<213> ORGANISM: Artificial sequence
<220> FEATURE:
<223> OTHER INFORMATION: Synthetic peptide

<400> SEQUENCE: 91

Gln Val Gln Leu Val Gln Ser Gly Pro Gly Leu Val Lys Pro Ser Asp
1               5                   10                  15

Thr Leu Ser Leu Thr Cys Ser Val Ser Ser Asp Ala Leu Arg Ser Arg
            20                  25                  30

Ser Tyr Tyr Trp Gly Trp Val Arg Gln Pro Pro Gly Lys Gly Leu Glu
        35                  40                  45

Trp Ile Gly Thr Val Ser Tyr Ser Gly Gly Thr Tyr Tyr Asn Pro Ser
    50                  55                  60

Leu Gln Ser Arg Val Thr Val Ser Val Asp Thr Ser Lys Asn His Phe
65                  70                  75                  80

Ser Leu Arg Leu Asn Ser Val Thr Ala Ala Asp Ala Ala Val Tyr Tyr
                85                  90                  95

Cys Ala Arg Ser Tyr Phe Tyr Asp Gly Ser Gly Tyr Tyr Tyr Leu Ser
            100                 105                 110

Tyr Phe Asp Ser Trp Gly Gln Gly Thr Leu Val Thr Val Ser Ser
        115                 120                 125

<210> SEQ ID NO 92
<211> LENGTH: 109
<212> TYPE: PRT
<213> ORGANISM: Artificial sequence
<220> FEATURE:
<223> OTHER INFORMATION: Synthetic peptide

<400> SEQUENCE: 92

Gln Ala Val Val Thr Gln Glu Pro Ser Leu Thr Val Ser Pro Gly Gly
1               5                   10                  15
```

```
Thr Val Thr Leu Thr Cys Ala Ser Ser Thr Gly Ala Val Thr Ser Gly
             20                  25                  30

His Tyr Pro Asn Trp Phe Gln Lys Pro Gly Gln Pro Pro Arg Ala
         35                  40                  45

Leu Ile Tyr Ser Thr Asp Asn Lys His Ser Trp Thr Pro Ala Arg Phe
 50                  55                  60

Ser Gly Ser Leu Leu Gly Val Lys Ala Ala Leu Thr Leu Ser Asp Val
 65                  70                  75                  80

Gln Pro Glu Asp Glu Ala Asp Tyr Tyr Cys Leu Leu His Phe Gly Gly
                 85                  90                  95

Val Val Val Phe Gly Gly Gly Thr Lys Leu Thr Val Leu
            100                 105

<210> SEQ ID NO 93
<211> LENGTH: 125
<212> TYPE: PRT
<213> ORGANISM: Artificial sequence
<220> FEATURE:
<223> OTHER INFORMATION: Synthetic peptide

<400> SEQUENCE: 93

Gln Val Gln Leu Val Gln Ser Gly Gly Gly Val Val Gln Pro Gly Arg
 1               5                  10                  15

Ser Leu Arg Leu Ser Cys Ser Thr Ser Gly Phe Thr Phe Arg Met Tyr
             20                  25                  30

Gly Met His Trp Val Arg Gln Ala Pro Gly Lys Gly Leu Glu Trp Val
         35                  40                  45

Ala Val Ile Phe Asn Asp Gly Val Lys Lys Tyr Tyr Gly Asp Ala Val
 50                  55                  60

Lys Gly Arg Phe Thr Val Ser Arg Asp Asn Ser Arg Asn Thr Leu Tyr
 65                  70                  75                  80

Leu Glu Met Lys Ser Leu Arg Val Asp Asp Thr Ala Ala Tyr Tyr Cys
                 85                  90                  95

Ala Arg Asp Gly Ile Pro Asp Pro Glu Arg Gly Asp Tyr Gly Gly Leu
            100                 105                 110

Asp Tyr Trp Gly Gln Gly Thr Leu Val Thr Val Ser Ser
        115                 120                 125

<210> SEQ ID NO 94
<211> LENGTH: 107
<212> TYPE: PRT
<213> ORGANISM: Artificial sequence
<220> FEATURE:
<223> OTHER INFORMATION: Synthetic peptide

<400> SEQUENCE: 94

Gln Thr Val Val Thr Gln Ser Pro Ser Ser Leu Ser Ala Ser Val Gly
 1               5                  10                  15

Asp Thr Val Thr Ile Thr Cys Arg Ala Ser Gln Ser Ile Thr Ser Tyr
             20                  25                  30

Leu Asn Trp Tyr Gln Gln Lys Pro Gly Lys Ala Pro Lys Leu Leu Ile
         35                  40                  45

Tyr Ala Thr Ser Ser Leu Gln Ser Gly Leu Pro Ser Arg Phe Ser Gly
 50                  55                  60

Ser Gly Tyr Gly Thr Glu Phe Thr Leu Thr Ile Ser Gly Leu Gln Pro
 65                  70                  75                  80

Glu Asp Phe Ala Thr Tyr Tyr Cys Gln Gln Ser Tyr Ser Phe Pro Arg
```

85                  90                  95

Thr Phe Gly Gln Gly Thr Lys Val Glu Met Asp
                100                 105

<210> SEQ ID NO 95
<211> LENGTH: 124
<212> TYPE: PRT
<213> ORGANISM: Artificial sequence
<220> FEATURE:
<223> OTHER INFORMATION: Synthetic peptide

<400> SEQUENCE: 95

Gln Val Gln Leu Val Gln Ser Gly Gly Leu Val Gln Pro Gly Arg
1               5                   10                  15

Ser Leu Arg Leu Ser Cys Ala Thr Ser Gly Phe Ile Phe Asp Asp Tyr
                20                  25                  30

Ala Met Tyr Trp Val Arg Gln Ala Pro Gly Lys Gly Leu Glu Trp Val
            35                  40                  45

Ser Gly Ile Ser Trp Asn Ser Gly Asn Ile Ala Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Leu Tyr Tyr Cys
                85                  90                  95

Val Lys Asp Leu Tyr Gly Tyr Asp Ile Leu Thr Gly Asn Gly Tyr Asp
                100                 105                 110

Tyr Trp Gly Gln Gly Thr Leu Val Thr Val Ser Ser
            115                 120

<210> SEQ ID NO 96
<211> LENGTH: 112
<212> TYPE: PRT
<213> ORGANISM: Artificial sequence
<220> FEATURE:
<223> OTHER INFORMATION: Synthetic peptide

<400> SEQUENCE: 96

Gln Ala Val Val Thr Gln Ser Ser Leu Ser Leu Pro Val Thr Pro Gly
1               5                   10                  15

Glu Pro Ala Ser Ile Ser Cys Arg Ser Ser Gln Ser Leu Leu Gln Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gln Gly Thr Lys Val Glu Ile Lys
                100                 105                 110

<210> SEQ ID NO 97
<211> LENGTH: 130
<212> TYPE: PRT
<213> ORGANISM: Artificial sequence
<220> FEATURE:
<223> OTHER INFORMATION: Synthetic peptide

<400> SEQUENCE: 97

Gln Val Gln Leu Val Gln Ser Gly Ala Glu Val Lys Pro Gly Ser
1               5                   10                  15

Ser Val Lys Val Pro Cys Lys Ala Ser Gly Asp Thr Leu Ser Tyr Tyr
            20                  25                  30

Gly Ile Thr Trp Val Arg Arg Ala Pro Gly Gln Gly Leu Glu Trp Met
                35                  40                  45

Gly Gln Ile Ile Pro Phe Phe Ala Thr Thr Ile Ser Ala Gln Lys Phe
50                      55                  60

Gln Gly Arg Leu Thr Met Thr Ala Glu Glu Ser Ser Thr Gly Tyr
65                  70                  75                  80

Met Glu Arg Thr Phe Tyr Met Asp Leu Ser Ser Leu Arg Pro Glu Asp
                85                  90                  95

Thr Ala Val Tyr Tyr Cys Ala Gly Gly Tyr Tyr Gly Ser Gly Ser Ser
                100                 105                 110

Gly Asp Tyr Gly Leu Asp Val Trp Gly Gln Gly Thr Leu Val Thr Val
            115                 120                 125

Ser Ser
    130

<210> SEQ ID NO 98
<211> LENGTH: 112
<212> TYPE: PRT
<213> ORGANISM: Artificial sequence
<220> FEATURE:
<223> OTHER INFORMATION: Synthetic peptide

<400> SEQUENCE: 98

Gln Ala Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val Asn Trp Tyr Gln Gln Leu Pro Gly Thr Ala Pro Lys Leu
                35                  40                  45

Leu Ile Tyr Gly Asn Asn Asn Arg Pro Ser Gly Val Pro Asp Arg Phe
50                      55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Thr Gly Thr Glu Val Thr Val Leu
            100                 105                 110

<210> SEQ ID NO 99
<211> LENGTH: 128
<212> TYPE: PRT
<213> ORGANISM: Artificial sequence
<220> FEATURE:
<223> OTHER INFORMATION: Synthetic peptide

<400> SEQUENCE: 99

Gln Val Gln Leu Val Gln Ser Gly Pro Gly Leu Val Lys Pro Ser Glu
1               5                   10                  15

Thr Leu Ser Leu Thr Cys Ala Val Ser Gly Asp Ser Ile Gly Ser Arg
            20                  25                  30

Ser Phe Tyr Trp Gly Trp Ile Arg Gln Pro Pro Gly Lys Gly Leu Glu
                35                  40                  45

Trp Ile Gly Ser Ile Tyr Tyr Asn Gly Thr Thr Tyr Tyr Lys Pro Ser

```
                50                  55                  60
Leu Lys Ser Arg Val Thr Ile Ser Leu Asp Thr Ser Lys Asn Gln Phe
 65                  70                  75                  80

Ser Leu Arg Leu Ser Ser Leu Thr Ala Thr Asp Thr Gly Val Tyr Tyr
                 85                  90                  95

Cys Ala Arg Ala Pro Thr Tyr Cys Ser Pro Ser Cys Ala Val His
                100                 105                 110

Trp Tyr Phe Asn Leu Trp Gly Arg Gly Thr Leu Val Thr Val Ser Ser
            115                 120                 125
```

<210> SEQ ID NO 100
<211> LENGTH: 118
<212> TYPE: PRT
<213> ORGANISM: Artificial sequence
<220> FEATURE:
<223> OTHER INFORMATION: Synthetic peptide

<400> SEQUENCE: 100

```
Gln Val Gln Leu Val Gln Ser Gly Ala Glu Leu Lys Lys Pro Gly Ala
  1               5                  10                  15

Ser Val Lys Val Ser Cys Lys Ala Ser Gly Tyr Ile Phe Thr Lys Tyr
                 20                  25                  30

Gly Ile Ser Trp Leu Arg Gln Ala Pro Gly Gln Gly Leu Glu Trp Val
             35                  40                  45

Gly Trp Ile Ser Ala Tyr Asn Glu Asn Thr Asn Tyr Ala Glu Lys Phe
         50                  55                  60

Gln Gly Arg Val Thr Leu Thr Thr Asp Ala Ser Thr Ser Thr Ala Tyr
 65                  70                  75                  80

Met Glu Leu Arg Asn Leu Arg Ser Asp Asp Thr Ala Val Tyr Phe Cys
                 85                  90                  95

Ala Arg Glu Val Trp Phe Ala Glu Tyr Ile Tyr Trp Gly Gln Gly Thr
                100                 105                 110

Leu Val Thr Val Ser Ser
            115
```

<210> SEQ ID NO 101
<211> LENGTH: 110
<212> TYPE: PRT
<213> ORGANISM: Artificial sequence
<220> FEATURE:
<223> OTHER INFORMATION: Synthetic peptide

<400> SEQUENCE: 101

```
Gln Ser Val Val Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ala Tyr
                 20                  25                  30

Asn Tyr Val Ser Trp Tyr Gln Gln His Pro Gly Lys Ala Pro Lys Leu
             35                  40                  45

Val Ile Tyr Asp Val Ala Asn Arg Pro Ser Gly Ile Ser Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Tyr Thr Ser Asp
                 85                  90                  95

Val Ser Pro Val Phe Ser Gly Gly Thr Lys Leu Thr Val Leu
                100                 105                 110
```

```
<210> SEQ ID NO 102
<211> LENGTH: 133
<212> TYPE: PRT
<213> ORGANISM: Artificial sequence
<220> FEATURE:
<223> OTHER INFORMATION: Synthetic peptide

<400> SEQUENCE: 102

Gln Val Gln Leu Val Gln Ser Gly Ser Glu Leu Lys Lys Pro Gly Ala
1               5                   10                  15

Ser Val Lys Leu Ser Cys Lys Ala Ser Gly Tyr Thr Phe Thr Ser His
            20                  25                  30

Pro Met Asn Trp Val Arg Gln Ala Pro Gly Gln Gly Leu Glu Trp Met
        35                  40                  45

Gly Trp Ile Asn Thr Lys Thr Gly Asn Leu Thr Tyr Ala Gln Gly Phe
    50                  55                  60

Thr Gly Arg Phe Val Phe Ser Leu Asp Thr Ser Val Arg Thr Ala Tyr
65                  70                  75                  80

Leu Gln Ile Ser Gly Leu Lys Ala Glu Asp Thr Ala Ile Tyr Tyr Cys
                85                  90                  95

Ala Arg Asp Glu Tyr Ser Gly Tyr Asp Ser Val Gly Val Phe Arg Gly
            100                 105                 110

Ser Phe Asp Asp Phe Tyr Gly Met Asp Val Trp Gly Gln Gly Thr Leu
        115                 120                 125

Val Thr Val Ser Ser
    130

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Gly Tyr Ser Phe Thr Ser Tyr Gly
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

Ile Ser Thr Tyr Lys Gly Tyr Thr
1               5

<210> SEQ ID NO 105
<211> LENGTH: 19
<212> TYPE: PRT
<213> ORGANISM: Artificial sequence
<220> FEATURE:
<223> OTHER INFORMATION: Synthetic peptide

<400> SEQUENCE: 105

Ala Arg Val Leu Ser Glu Thr Gly Tyr Phe Tyr Tyr Tyr Tyr Tyr Gly
1               5                   10                  15

Met Asp Val
```

-continued

```
<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Gly Tyr Ser Phe Thr Ser Tyr Ser
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide

<400> SEQUENCE: 107

Ile Asp Thr Asn Thr Gly Asn Pro
1               5

<210> SEQ ID NO 108
<211> LENGTH: 20
<212> TYPE: PRT
<213> ORGANISM: Artificial sequence
<220> FEATURE:
<223> OTHER INFORMATION: Synthetic peptide

<400> SEQUENCE: 108

Ala Thr Tyr Tyr Val Asp Leu Trp Gly Ser Tyr Arg Gln Asp Tyr Tyr
1               5                   10                  15

Gly Met Asp Val
            20

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109

Gly Tyr Thr Phe Thr Ser Tyr Gly
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic peptide

<400> SEQUENCE: 110

Ile Ser Thr Tyr Asn Gly Asp Thr
1               5

<210> SEQ ID NO 111
<211> LENGTH: 28
<212> TYPE: PRT
<213> ORGANISM: Artificial sequence
<220> FEATURE:
<223> OTHER INFORMATION: Synthetic peptide

<400> SEQUENCE: 111

Ala Arg Asp Phe Glu Phe Pro Gly Asp Cys Ser Gly Gly Ser Cys Tyr
1               5                   10                  15
```

Ser Arg Phe Ile Tyr Gln His Asn Asp Met Asp Val
            20                  25

<210> SEQ ID NO 112
<211> LENGTH: 10
<212> TYPE: PRT
<213> ORGANISM: Artificial sequence
<220> FEATURE:
<223> OTHER INFORMATION: Synthetic peptide

<400> SEQUENCE: 112

Ser Asp Ala Leu Arg Ser Arg Ser Tyr Tyr
1               5                   10

<210> SEQ ID NO 113
<211> LENGTH: 7
<212> TYPE: PRT
<213> ORGANISM: Artificial sequence
<220> FEATURE:
<223> OTHER INFORMATION: Synthetic peptide

<400> SEQUENCE: 113

Val Ser Tyr Ser Gly Gly Thr
1               5

<210> SEQ ID NO 114
<211> LENGTH: 19
<212> TYPE: PRT
<213> ORGANISM: Artificial sequence
<220> FEATURE:
<223> OTHER INFORMATION: Synthetic peptide

<400> SEQUENCE: 114

Ala Arg Ser Tyr Phe Tyr Asp Gly Ser Gly Tyr Tyr Tyr Leu Ser Tyr
1               5                   10                  15

Phe Asp Ser

<210> SEQ ID NO 115
<211> LENGTH: 8
<212> TYPE: PRT
<213> ORGANISM: Artificial sequence
<220> FEATURE:
<223> OTHER INFORMATION: Synthetic peptide

<400> SEQUENCE: 115

Gly Phe Thr Phe Ser Asn Tyr Ala
1               5

<210> SEQ ID NO 116
<211> LENGTH: 8
<212> TYPE: PRT
<213> ORGANISM: Artificial sequence
<220> FEATURE:
<223> OTHER INFORMATION: Synthetic peptide

<400> SEQUENCE: 116

Ile Trp Tyr Asp Gly Ser Asn Lys
1               5

<210> SEQ ID NO 117
<211> LENGTH: 9
<212> TYPE: PRT
<213> ORGANISM: Artificial sequence
<220> FEATURE:
<223> OTHER INFORMATION: Synthetic peptide

```
<400> SEQUENCE: 117

Ala Arg Gly Asp Tyr Val Leu Asp Tyr
1               5

<210> SEQ ID NO 118
<211> LENGTH: 8
<212> TYPE: PRT
<213> ORGANISM: Artificial sequence
<220> FEATURE:
<223> OTHER INFORMATION: Synthetic peptide

<400> SEQUENCE: 118

Gly Gly Thr Ser Ser Thr Tyr Ala
1               5

<210> SEQ ID NO 119
<211> LENGTH: 8
<212> TYPE: PRT
<213> ORGANISM: Artificial sequence
<220> FEATURE:
<223> OTHER INFORMATION: Synthetic peptide

<400> SEQUENCE: 119

Ser Ile Pro Val Phe Ala Thr Val
1               5

<210> SEQ ID NO 120
<211> LENGTH: 19
<212> TYPE: PRT
<213> ORGANISM: Artificial sequence
<220> FEATURE:
<223> OTHER INFORMATION: Synthetic peptide

<400> SEQUENCE: 120

Ala Ser Pro Tyr Cys Ser Ser Met Asn Cys Tyr Thr Thr Phe Tyr Tyr
1               5                   10                  15

Phe Asp Phe

<210> SEQ ID NO 121
<211> LENGTH: 8
<212> TYPE: PRT
<213> ORGANISM: Artificial sequence
<220> FEATURE:
<223> OTHER INFORMATION: Synthetic peptide

<400> SEQUENCE: 121

Gly Tyr Ser Phe Thr Ser Tyr Ser
1               5

<210> SEQ ID NO 122
<211> LENGTH: 8
<212> TYPE: PRT
<213> ORGANISM: Artificial sequence
<220> FEATURE:
<223> OTHER INFORMATION: Synthetic peptide

<400> SEQUENCE: 122

Ile Asp Thr Asn Thr Gly Asn Pro
1               5

<210> SEQ ID NO 123
<211> LENGTH: 20
<212> TYPE: PRT
<213> ORGANISM: Artificial sequence
<220> FEATURE:
<223> OTHER INFORMATION: Synthetic peptide
```

```
<400> SEQUENCE: 123

Ala Thr Tyr Tyr Val Asp Leu Trp Gly Ser Tyr Arg Gln Asp Tyr Tyr
1               5                   10                  15

Gly Met Asp Val
            20

<210> SEQ ID NO 124
<211> LENGTH: 8
<212> TYPE: PRT
<213> ORGANISM: Artificial sequence
<220> FEATURE:
<223> OTHER INFORMATION: Synthetic peptide

<400> SEQUENCE: 124

Gly Tyr Ile Leu Ser Lys Leu Ser
1               5

<210> SEQ ID NO 125
<211> LENGTH: 8
<212> TYPE: PRT
<213> ORGANISM: Artificial sequence
<220> FEATURE:
<223> OTHER INFORMATION: Synthetic peptide

<400> SEQUENCE: 125

Ser Glu Arg Glu Asp Gly Glu Thr
1               5

<210> SEQ ID NO 126
<211> LENGTH: 16
<212> TYPE: PRT
<213> ORGANISM: Artificial sequence
<220> FEATURE:
<223> OTHER INFORMATION: Synthetic peptide

<400> SEQUENCE: 126

Ala Thr Gly Gly Phe Trp Ser Met Ile Gly Gly Asn Gly Val Asp Tyr
1               5                   10                  15

<210> SEQ ID NO 127
<211> LENGTH: 8
<212> TYPE: PRT
<213> ORGANISM: Artificial sequence
<220> FEATURE:
<223> OTHER INFORMATION: Synthetic peptide

<400> SEQUENCE: 127

Gly Tyr Thr Phe Thr Ser Tyr Phe
1               5

<210> SEQ ID NO 128
<211> LENGTH: 8
<212> TYPE: PRT
<213> ORGANISM: Artificial sequence
<220> FEATURE:
<223> OTHER INFORMATION: Synthetic peptide

<400> SEQUENCE: 128

Thr Tyr Pro Gly Gly Gly Ser Pro
1               5

<210> SEQ ID NO 129
<211> LENGTH: 15
<212> TYPE: PRT
<213> ORGANISM: Artificial sequence
```

```
<220> FEATURE:
<223> OTHER INFORMATION: Synthetic peptide

<400> SEQUENCE: 129

Ala Arg Gly Ala His Arg Ser Ile Gly Thr Thr Pro Leu Asp Ser
1               5                   10                  15

<210> SEQ ID NO 130
<211> LENGTH: 8
<212> TYPE: PRT
<213> ORGANISM: Artificial sequence
<220> FEATURE:
<223> OTHER INFORMATION: Synthetic peptide

<400> SEQUENCE: 130

Gly Phe Thr Phe Ser Met Tyr Gly
1               5

<210> SEQ ID NO 131
<211> LENGTH: 8
<212> TYPE: PRT
<213> ORGANISM: Artificial sequence
<220> FEATURE:
<223> OTHER INFORMATION: Synthetic peptide

<400> SEQUENCE: 131

Ile Trp Asn Asp Gly Ser Lys Glu
1               5

<210> SEQ ID NO 132
<211> LENGTH: 18
<212> TYPE: PRT
<213> ORGANISM: Artificial sequence
<220> FEATURE:
<223> OTHER INFORMATION: Synthetic peptide

<400> SEQUENCE: 132

Ala Arg Asp Gly Ile Pro Asp Pro Glu Arg Gly Asp Tyr Gly Gly Leu
1               5                   10                  15

Asp Tyr

<210> SEQ ID NO 133
<211> LENGTH: 8
<212> TYPE: PRT
<213> ORGANISM: Artificial sequence
<220> FEATURE:
<223> OTHER INFORMATION: Synthetic peptide

<400> SEQUENCE: 133

Gly Gly Thr Phe Asn Asn Asn Gly
1               5

<210> SEQ ID NO 134
<211> LENGTH: 8
<212> TYPE: PRT
<213> ORGANISM: Artificial sequence
<220> FEATURE:
<223> OTHER INFORMATION: Synthetic peptide

<400> SEQUENCE: 134

Ile Val Pro Asn Phe Gly Thr Pro
1               5

<210> SEQ ID NO 135
<211> LENGTH: 20
<212> TYPE: PRT
```

<213> ORGANISM: Artificial sequence
<220> FEATURE:
<223> OTHER INFORMATION: Synthetic peptide

<400> SEQUENCE: 135

Ala Arg Gly Arg Thr Ala Val Thr Pro Met Gln Leu Gly Leu Gln Phe
1               5                   10                  15

Tyr Phe Asp Phe
            20

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

Gly Tyr Thr Phe Thr Asp Asn Ser
1               5

<210> SEQ ID NO 137
<211> LENGTH: 8
<212> TYPE: PRT
<213> ORGANISM: Artificial sequence
<220> FEATURE:
<223> OTHER INFORMATION: Synthetic peptide

<400> SEQUENCE: 137

Ile Asn Pro Asn Thr Gly Val Ser
1               5

<210> SEQ ID NO 138
<211> LENGTH: 12
<212> TYPE: PRT
<213> ORGANISM: Artificial sequence
<220> FEATURE:
<223> OTHER INFORMATION: Synthetic peptide

<400> SEQUENCE: 138

Ala Arg Glu Glu Asn Asp Ser Ser Gly Tyr Tyr Leu
1               5                   10

<210> SEQ ID NO 139
<211> LENGTH: 10
<212> TYPE: PRT
<213> ORGANISM: Artificial sequence
<220> FEATURE:
<223> OTHER INFORMATION: Synthetic peptide

<400> SEQUENCE: 139

Gly Phe Ser Leu Ser Ile Ser Gly Val Gly
1               5                   10

<210> SEQ ID NO 140
<211> LENGTH: 7
<212> TYPE: PRT
<213> ORGANISM: Artificial sequence
<220> FEATURE:
<223> OTHER INFORMATION: Synthetic peptide

<400> SEQUENCE: 140

Ile Tyr Trp Asp Asp Asp Lys
1               5

<210> SEQ ID NO 141

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 141

Ala His Ser Met Thr Lys Gly Gly Ala Ile Tyr Gly Gln Ala Tyr Phe
1               5                   10                  15
Glu Tyr

<210> SEQ ID NO 142
<211> LENGTH: 8
<212> TYPE: PRT
<213> ORGANISM: Artificial sequence
<220> FEATURE:
<223> OTHER INFORMATION: Synthetic peptide

<400> SEQUENCE: 142

Gly Tyr Thr Leu Thr Glu Leu Ser
1               5

<210> SEQ ID NO 143
<211> LENGTH: 8
<212> TYPE: PRT
<213> ORGANISM: Artificial sequence
<220> FEATURE:
<223> OTHER INFORMATION: Synthetic peptide

<400> SEQUENCE: 143

Phe Glu Pro Glu Asp Gly Glu Thr
1               5

<210> SEQ ID NO 144
<211> LENGTH: 18
<212> TYPE: PRT
<213> ORGANISM: Artificial sequence
<220> FEATURE:
<223> OTHER INFORMATION: Synthetic peptide

<400> SEQUENCE: 144

Thr Thr Asp Gln Val Tyr Tyr Arg Ser Gly Ser Tyr Ser Gly Tyr Val
1               5                   10                  15
Asp Tyr

<210> SEQ ID NO 145
<211> LENGTH: 8
<212> TYPE: PRT
<213> ORGANISM: Artificial sequence
<220> FEATURE:
<223> OTHER INFORMATION: Synthetic peptide

<400> SEQUENCE: 145

Gly Arg Thr Phe Ser Ser Tyr Val
1               5

<210> SEQ ID NO 146
<211> LENGTH: 8
<212> TYPE: PRT
<213> ORGANISM: Artificial sequence
<220> FEATURE:
<223> OTHER INFORMATION: Synthetic peptide

<400> SEQUENCE: 146

Ile Ile Pro Leu Phe Gly Thr Ala
1               5
```

<210> SEQ ID NO 147
<211> LENGTH: 18
<212> TYPE: PRT
<213> ORGANISM: Artificial sequence
<220> FEATURE:
<223> OTHER INFORMATION: Synthetic peptide

<400> SEQUENCE: 147

Ala Arg Gly Ala Gln Leu Tyr Tyr Asn Asp Gly Ser Gly Tyr Ile Phe
1               5                   10                  15

Asp Tyr

<210> SEQ ID NO 148
<211> LENGTH: 8
<212> TYPE: PRT
<213> ORGANISM: Artificial sequence
<220> FEATURE:
<223> OTHER INFORMATION: Synthetic peptide

<400> SEQUENCE: 148

Gly Phe Ser Phe Ile Ser Ser Ala
1               5

<210> SEQ ID NO 149
<211> LENGTH: 8
<212> TYPE: PRT
<213> ORGANISM: Artificial sequence
<220> FEATURE:
<223> OTHER INFORMATION: Synthetic peptide

<400> SEQUENCE: 149

Ile Val Val Ala Ser Ala Asn Thr
1               5

<210> SEQ ID NO 150
<211> LENGTH: 23
<212> TYPE: PRT
<213> ORGANISM: Artificial sequence
<220> FEATURE:
<223> OTHER INFORMATION: Synthetic peptide

<400> SEQUENCE: 150

Ala Ala Glu His Arg Ser Pro Cys Ser Gly Gly Asp Ser Cys Tyr Ser
1               5                   10                  15

Leu Tyr Tyr Gly Met Asp Val
            20

<210> SEQ ID NO 151
<211> LENGTH: 8
<212> TYPE: PRT
<213> ORGANISM: Artificial sequence
<220> FEATURE:
<223> OTHER INFORMATION: Synthetic peptide

<400> SEQUENCE: 151

Gly Phe Thr Val Ser Asn Tyr Gly
1               5

<210> SEQ ID NO 152
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 152

Ile Ser Thr Ser Ser Gly Arg Thr
1               5

<210> SEQ ID NO 153
<211> LENGTH: 11
<212> TYPE: PRT
<213> ORGANISM: Artificial sequence
<220> FEATURE:
<223> OTHER INFORMATION: Synthetic peptide

<400> SEQUENCE: 153

Ala Lys Gly Pro Phe Gly Gly Asp Phe Asp Tyr
1               5                   10

<210> SEQ ID NO 154
<211> LENGTH: 8
<212> TYPE: PRT
<213> ORGANISM: Artificial sequence
<220> FEATURE:
<223> OTHER INFORMATION: Synthetic peptide

<400> SEQUENCE: 154

Gly Phe Thr Phe Asp Val Tyr Ala
1               5

<210> SEQ ID NO 155
<211> LENGTH: 8
<212> TYPE: PRT
<213> ORGANISM: Artificial sequence
<220> FEATURE:
<223> OTHER INFORMATION: Synthetic peptide

<400> SEQUENCE: 155

Ile Ser Trp Asn Ser Gly Ser Val
1               5

<210> SEQ ID NO 156
<211> LENGTH: 16
<212> TYPE: PRT
<213> ORGANISM: Artificial sequence
<220> FEATURE:
<223> OTHER INFORMATION: Synthetic peptide

<400> SEQUENCE: 156

Ala Lys Ala Phe Trp Phe Gly Glu Leu Ser Gly Tyr Gly Met Asp Val
1               5                   10                  15

<210> SEQ ID NO 157
<211> LENGTH: 8
<212> TYPE: PRT
<213> ORGANISM: Artificial sequence
<220> FEATURE:
<223> OTHER INFORMATION: Synthetic peptide

<400> SEQUENCE: 157

Gly Tyr Ser Phe Asn Ile Tyr Gly
1               5

<210> SEQ ID NO 158
<211> LENGTH: 8
<212> TYPE: PRT
<213> ORGANISM: Artificial sequence
<220> FEATURE:
<223> OTHER INFORMATION: Synthetic peptide

<400> SEQUENCE: 158
```

```
Ile Ser Ala Tyr Asn Gly Asn Thr
1               5

<210> SEQ ID NO 159
<211> LENGTH: 12
<212> TYPE: PRT
<213> ORGANISM: Artificial sequence
<220> FEATURE:
<223> OTHER INFORMATION: Synthetic peptide

<400> SEQUENCE: 159

Ala Arg Pro Leu Trp Gly Glu Phe Tyr Tyr Asp Ile
1               5                  10

<210> SEQ ID NO 160
<211> LENGTH: 8
<212> TYPE: PRT
<213> ORGANISM: Artificial sequence
<220> FEATURE:
<223> OTHER INFORMATION: Synthetic peptide

<400> SEQUENCE: 160

Gly Phe Thr Phe Ser Asn Tyr Val
1               5

<210> SEQ ID NO 161
<211> LENGTH: 8
<212> TYPE: PRT
<213> ORGANISM: Artificial sequence
<220> FEATURE:
<223> OTHER INFORMATION: Synthetic peptide

<400> SEQUENCE: 161

Ile Ser Tyr Asp Gly Ser Asn Lys
1               5

<210> SEQ ID NO 162
<211> LENGTH: 26
<212> TYPE: PRT
<213> ORGANISM: Artificial sequence
<220> FEATURE:
<223> OTHER INFORMATION: Synthetic peptide

<400> SEQUENCE: 162

Ala Arg Ser Glu Trp Glu Ser Ser Tyr Gly Ser Gly Asn Tyr Tyr Thr
1               5                   10                  15

Asp Tyr Phe Tyr Tyr Tyr Ala Met Asp Val
            20                  25

<210> SEQ ID NO 163
<211> LENGTH: 10
<212> TYPE: PRT
<213> ORGANISM: Artificial sequence
<220> FEATURE:
<223> OTHER INFORMATION: Synthetic peptide

<400> SEQUENCE: 163

Gly Phe Ser Leu Thr Thr Thr Gly Val Thr
1               5                   10

<210> SEQ ID NO 164
<211> LENGTH: 7
<212> TYPE: PRT
<213> ORGANISM: Artificial sequence
<220> FEATURE:
<223> OTHER INFORMATION: Synthetic peptide
```

<400> SEQUENCE: 164

Ile Tyr Trp Asp Asp Asp Lys
1               5

<210> SEQ ID NO 165
<211> LENGTH: 21
<212> TYPE: PRT
<213> ORGANISM: Artificial sequence
<220> FEATURE:
<223> OTHER INFORMATION: Synthetic peptide

<400> SEQUENCE: 165

Ala His Ser Thr Gly Tyr Tyr Asp Ser Ser Gly Tyr Arg Gly Ala Leu
1               5                   10                  15

Asp Ala Phe Ala Val
            20

<210> SEQ ID NO 166
<211> LENGTH: 10
<212> TYPE: PRT
<213> ORGANISM: Artificial sequence
<220> FEATURE:
<223> OTHER INFORMATION: Synthetic peptide

<400> SEQUENCE: 166

Ser Asp Ala Leu Arg Ser Arg Ser Tyr Tyr
1               5                   10

<210> SEQ ID NO 167
<211> LENGTH: 7
<212> TYPE: PRT
<213> ORGANISM: Artificial sequence
<220> FEATURE:
<223> OTHER INFORMATION: Synthetic peptide

<400> SEQUENCE: 167

Val Ser Tyr Ser Gly Gly Thr
1               5

<210> SEQ ID NO 168
<211> LENGTH: 19
<212> TYPE: PRT
<213> ORGANISM: Artificial sequence
<220> FEATURE:
<223> OTHER INFORMATION: Synthetic peptide

<400> SEQUENCE: 168

Ala Arg Ser Tyr Phe Tyr Asp Gly Ser Gly Tyr Tyr Tyr Leu Ser Tyr
1               5                   10                  15

Phe Asp Ser

<210> SEQ ID NO 169
<211> LENGTH: 8
<212> TYPE: PRT
<213> ORGANISM: Artificial sequence
<220> FEATURE:
<223> OTHER INFORMATION: Synthetic peptide

<400> SEQUENCE: 169

Gly Phe Thr Phe Arg Met Tyr Gly
1               5

<210> SEQ ID NO 170
<211> LENGTH: 8

```
<212> TYPE: PRT
<213> ORGANISM: Artificial sequence
<220> FEATURE:
<223> OTHER INFORMATION: Synthetic peptide

<400> SEQUENCE: 170

Ile Phe Asn Asp Gly Val Lys Lys
1               5

<210> SEQ ID NO 171
<211> LENGTH: 18
<212> TYPE: PRT
<213> ORGANISM: Artificial sequence
<220> FEATURE:
<223> OTHER INFORMATION: Synthetic peptide

<400> SEQUENCE: 171

Ala Arg Asp Gly Ile Pro Asp Pro Glu Arg Gly Asp Tyr Gly Gly Leu
1               5                   10                  15

Asp Tyr

<210> SEQ ID NO 172
<211> LENGTH: 8
<212> TYPE: PRT
<213> ORGANISM: Artificial sequence
<220> FEATURE:
<223> OTHER INFORMATION: Synthetic peptide

<400> SEQUENCE: 172

Gly Phe Ile Phe Asp Asp Tyr Ala
1               5

<210> SEQ ID NO 173
<211> LENGTH: 8
<212> TYPE: PRT
<213> ORGANISM: Artificial sequence
<220> FEATURE:
<223> OTHER INFORMATION: Synthetic peptide

<400> SEQUENCE: 173

Ile Ser Trp Asn Ser Gly Asn Ile
1               5

<210> SEQ ID NO 174
<211> LENGTH: 17
<212> TYPE: PRT
<213> ORGANISM: Artificial sequence
<220> FEATURE:
<223> OTHER INFORMATION: Synthetic peptide

<400> SEQUENCE: 174

Val Lys Asp Leu Tyr Gly Tyr Asp Ile Leu Thr Gly Asn Gly Tyr Asp
1               5                   10                  15

Tyr

<210> SEQ ID NO 175
<211> LENGTH: 8
<212> TYPE: PRT
<213> ORGANISM: Artificial sequence
<220> FEATURE:
<223> OTHER INFORMATION: Synthetic peptide

<400> SEQUENCE: 175

Gly Asp Thr Leu Ser Tyr Tyr Gly
1               5
```

<210> SEQ ID NO 176
<211> LENGTH: 8
<212> TYPE: PRT
<213> ORGANISM: Artificial sequence
<220> FEATURE:
<223> OTHER INFORMATION: Synthetic peptide

<400> SEQUENCE: 176

Ile Ile Pro Phe Phe Ala Thr Thr
1               5

<210> SEQ ID NO 177
<211> LENGTH: 23
<212> TYPE: PRT
<213> ORGANISM: Artificial sequence
<220> FEATURE:
<223> OTHER INFORMATION: Synthetic peptide

<400> SEQUENCE: 177

Thr Ala Val Tyr Tyr Cys Ala Gly Gly Tyr Tyr Gly Ser Gly Ser Ser
1               5                   10                  15

Gly Asp Tyr Gly Leu Asp Val
            20

<210> SEQ ID NO 178
<211> LENGTH: 10
<212> TYPE: PRT
<213> ORGANISM: Artificial sequence
<220> FEATURE:
<223> OTHER INFORMATION: Synthetic peptide

<400> SEQUENCE: 178

Gly Asp Ser Ile Gly Ser Arg Ser Phe Tyr
1               5                   10

<210> SEQ ID NO 179
<211> LENGTH: 7
<212> TYPE: PRT
<213> ORGANISM: Artificial sequence
<220> FEATURE:
<223> OTHER INFORMATION: Synthetic peptide

<400> SEQUENCE: 179

Ile Tyr Tyr Asn Gly Thr Thr
1               5

<210> SEQ ID NO 180
<211> LENGTH: 20
<212> TYPE: PRT
<213> ORGANISM: Artificial sequence
<220> FEATURE:
<223> OTHER INFORMATION: Synthetic peptide

<400> SEQUENCE: 180

Ala Arg Ala Pro Thr Tyr Cys Ser Pro Ser Ser Cys Ala Val His Trp
1               5                   10                  15

Tyr Phe Asn Leu
            20

<210> SEQ ID NO 181
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 181

Gly Tyr Ile Phe Thr Lys Tyr Gly
1               5

<210> SEQ ID NO 182
<211> LENGTH: 8
<212> TYPE: PRT
<213> ORGANISM: Artificial sequence
<220> FEATURE:
<223> OTHER INFORMATION: Synthetic peptide

<400> SEQUENCE: 182

Ile Ser Ala Tyr Asn Glu Asn Thr
1               5

<210> SEQ ID NO 183
<211> LENGTH: 11
<212> TYPE: PRT
<213> ORGANISM: Artificial sequence
<220> FEATURE:
<223> OTHER INFORMATION: Synthetic peptide

<400> SEQUENCE: 183

Ala Arg Glu Val Trp Phe Ala Glu Tyr Ile Tyr
1               5                   10

<210> SEQ ID NO 184
<211> LENGTH: 8
<212> TYPE: PRT
<213> ORGANISM: Artificial sequence
<220> FEATURE:
<223> OTHER INFORMATION: Synthetic peptide

<400> SEQUENCE: 184

Gly Tyr Thr Phe Thr Ser His Pro
1               5

<210> SEQ ID NO 185
<211> LENGTH: 8
<212> TYPE: PRT
<213> ORGANISM: Artificial sequence
<220> FEATURE:
<223> OTHER INFORMATION: Synthetic peptide

<400> SEQUENCE: 185

Ile Asn Thr Lys Thr Gly Asn Leu
1               5

<210> SEQ ID NO 186
<211> LENGTH: 26
<212> TYPE: PRT
<213> ORGANISM: Artificial sequence
<220> FEATURE:
<223> OTHER INFORMATION: Synthetic peptide

<400> SEQUENCE: 186

Ala Arg Asp Glu Tyr Ser Gly Tyr Asp Ser Val Gly Val Phe Arg Gly
1               5                   10                  15

Ser Phe Asp Asp Phe Tyr Gly Met Asp Val
            20                  25

<210> SEQ ID NO 187
<211> LENGTH: 9
<212> TYPE: PRT
<213> ORGANISM: Artificial sequence
<220> FEATURE:
```

```
<223> OTHER INFORMATION: Synthetic peptide

<400> SEQUENCE: 187

Ser Ser Asn Ile Gly Ala Asp Tyr Asn
1               5

<210> SEQ ID NO 188
<211> LENGTH: 3
<212> TYPE: PRT
<213> ORGANISM: Artificial sequence
<220> FEATURE:
<223> OTHER INFORMATION: Synthetic peptide

<400> SEQUENCE: 188

Gly Asn Thr
1

<210> SEQ ID NO 189
<211> LENGTH: 11
<212> TYPE: PRT
<213> ORGANISM: Artificial sequence
<220> FEATURE:
<223> OTHER INFORMATION: Synthetic peptide

<400> SEQUENCE: 189

Gln Ser Tyr Asp Ser Ser Leu Ser Ala Ser Val
1               5                   10

<210> SEQ ID NO 190
<211> LENGTH: 8
<212> TYPE: PRT
<213> ORGANISM: Artificial sequence
<220> FEATURE:
<223> OTHER INFORMATION: Synthetic peptide

<400> SEQUENCE: 190

Ser Ser Asn Ile Gly Ser Asn Pro
1               5

<210> SEQ ID NO 191
<211> LENGTH: 3
<212> TYPE: PRT
<213> ORGANISM: Artificial sequence
<220> FEATURE:
<223> OTHER INFORMATION: Synthetic peptide

<400> SEQUENCE: 191

Thr Asn Asn
1

<210> SEQ ID NO 192
<211> LENGTH: 12
<212> TYPE: PRT
<213> ORGANISM: Artificial sequence
<220> FEATURE:
<223> OTHER INFORMATION: Synthetic peptide

<400> SEQUENCE: 192

Ala Val Trp Asp Asp Ser Leu Ser Gly Arg Trp Val
1               5                   10

<210> SEQ ID NO 193
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 193

Ser Ser Asn Ile Gly Asn His Tyr
1               5

<210> SEQ ID NO 194
<211> LENGTH: 3
<212> TYPE: PRT
<213> ORGANISM: Artificial sequence
<220> FEATURE:
<223> OTHER INFORMATION: Synthetic peptide

<400> SEQUENCE: 194

Asp Asn Tyr
1

<210> SEQ ID NO 195
<211> LENGTH: 11
<212> TYPE: PRT
<213> ORGANISM: Artificial sequence
<220> FEATURE:
<223> OTHER INFORMATION: Synthetic peptide

<400> SEQUENCE: 195

Gly Thr Trp Asp Ser Ser Leu Ser Ala Val Val
1               5                   10

<210> SEQ ID NO 196
<211> LENGTH: 9
<212> TYPE: PRT
<213> ORGANISM: Artificial sequence
<220> FEATURE:
<223> OTHER INFORMATION: Synthetic peptide

<400> SEQUENCE: 196

Thr Gly Ala Val Thr Ser Gly His Tyr
1               5

<210> SEQ ID NO 197
<211> LENGTH: 3
<212> TYPE: PRT
<213> ORGANISM: Artificial sequence
<220> FEATURE:
<223> OTHER INFORMATION: Synthetic peptide

<400> SEQUENCE: 197

Ser Thr Asp
1

<210> SEQ ID NO 198
<211> LENGTH: 9
<212> TYPE: PRT
<213> ORGANISM: Artificial sequence
<220> FEATURE:
<223> OTHER INFORMATION: Synthetic peptide

<400> SEQUENCE: 198

Leu Leu His Phe Gly Gly Val Val Val
1               5

<210> SEQ ID NO 199
<211> LENGTH: 6
<212> TYPE: PRT
<213> ORGANISM: Artificial sequence
<220> FEATURE:
<223> OTHER INFORMATION: Synthetic peptide
```

```
<400> SEQUENCE: 199

Gln Ser Ile Pro Ser Tyr
1               5

<210> SEQ ID NO 200
<211> LENGTH: 3
<212> TYPE: PRT
<213> ORGANISM: Artificial sequence
<220> FEATURE:
<223> OTHER INFORMATION: Synthetic peptide

<400> SEQUENCE: 200

Ala Thr Ser
1

<210> SEQ ID NO 201
<211> LENGTH: 10
<212> TYPE: PRT
<213> ORGANISM: Artificial sequence
<220> FEATURE:
<223> OTHER INFORMATION: Synthetic peptide

<400> SEQUENCE: 201

Gln Gln Ser Tyr Asn Thr Gly Ile Phe Thr
1               5                   10

<210> SEQ ID NO 202
<211> LENGTH: 9
<212> TYPE: PRT
<213> ORGANISM: Artificial sequence
<220> FEATURE:
<223> OTHER INFORMATION: Synthetic peptide

<400> SEQUENCE: 202

Ser Ser Asp Phe Gly Thr Tyr Asn Tyr
1               5

<210> SEQ ID NO 203
<211> LENGTH: 3
<212> TYPE: PRT
<213> ORGANISM: Artificial sequence
<220> FEATURE:
<223> OTHER INFORMATION: Synthetic peptide

<400> SEQUENCE: 203

Asp Val Ser
1

<210> SEQ ID NO 204
<211> LENGTH: 13
<212> TYPE: PRT
<213> ORGANISM: Artificial sequence
<220> FEATURE:
<223> OTHER INFORMATION: Synthetic peptide

<400> SEQUENCE: 204

Ser Ser Tyr Thr Ser Gly Ser Thr Leu Tyr Gly Gly Gly
1               5                   10

<210> SEQ ID NO 205
<211> LENGTH: 8
<212> TYPE: PRT
<213> ORGANISM: Artificial sequence
<220> FEATURE:
<223> OTHER INFORMATION: Synthetic peptide

<400> SEQUENCE: 205
```

```
Ser Ser Asn Ile Gly Ser Asn Pro
1               5
```

<210> SEQ ID NO 206
<211> LENGTH: 3
<212> TYPE: PRT
<213> ORGANISM: Artificial sequence
<220> FEATURE:
<223> OTHER INFORMATION: Synthetic peptide

<400> SEQUENCE: 206

```
Thr Asn Asn
1
```

<210> SEQ ID NO 207
<211> LENGTH: 12
<212> TYPE: PRT
<213> ORGANISM: Artificial sequence
<220> FEATURE:
<223> OTHER INFORMATION: Synthetic peptide

<400> SEQUENCE: 207

```
Ala Val Trp Asp Asp Ser Leu Ser Gly Arg Trp Val
1               5                   10
```

<210> SEQ ID NO 208
<211> LENGTH: 6
<212> TYPE: PRT
<213> ORGANISM: Artificial sequence
<220> FEATURE:
<223> OTHER INFORMATION: Synthetic peptide

<400> SEQUENCE: 208

```
Gln Asp Ile Arg Asn Asn
1               5
```

<210> SEQ ID NO 209
<211> LENGTH: 3
<212> TYPE: PRT
<213> ORGANISM: Artificial sequence
<220> FEATURE:
<223> OTHER INFORMATION: Synthetic peptide

<400> SEQUENCE: 209

```
Gly Thr Ser
1
```

<210> SEQ ID NO 210
<211> LENGTH: 9
<212> TYPE: PRT
<213> ORGANISM: Artificial sequence
<220> FEATURE:
<223> OTHER INFORMATION: Synthetic peptide

<400> SEQUENCE: 210

```
Leu Gln His Asn Ser Tyr Pro Pro Thr
1               5
```

<210> SEQ ID NO 211
<211> LENGTH: 6
<212> TYPE: PRT
<213> ORGANISM: Artificial sequence
<220> FEATURE:
<223> OTHER INFORMATION: Synthetic peptide

<400> SEQUENCE: 211

```
Gln Ser Ile Ser Ser Tyr
1               5

<210> SEQ ID NO 212
<211> LENGTH: 3
<212> TYPE: PRT
<213> ORGANISM: Artificial sequence
<220> FEATURE:
<223> OTHER INFORMATION: Synthetic peptide

<400> SEQUENCE: 212

Ala Thr Ser
1

<210> SEQ ID NO 213
<211> LENGTH: 9
<212> TYPE: PRT
<213> ORGANISM: Artificial sequence
<220> FEATURE:
<223> OTHER INFORMATION: Synthetic peptide

<400> SEQUENCE: 213

Gln Gln Ser Tyr Ser Phe Pro Arg Thr
1               5

<210> SEQ ID NO 214
<211> LENGTH: 9
<212> TYPE: PRT
<213> ORGANISM: Artificial sequence
<220> FEATURE:
<223> OTHER INFORMATION: Synthetic peptide

<400> SEQUENCE: 214

Ser Gly Ala Val Thr Ser Asp Tyr Tyr
1               5

<210> SEQ ID NO 215
<211> LENGTH: 3
<212> TYPE: PRT
<213> ORGANISM: Artificial sequence
<220> FEATURE:
<223> OTHER INFORMATION: Synthetic peptide

<400> SEQUENCE: 215

Ser Ala Ser
1

<210> SEQ ID NO 216
<211> LENGTH: 9
<212> TYPE: PRT
<213> ORGANISM: Artificial sequence
<220> FEATURE:
<223> OTHER INFORMATION: Synthetic peptide

<400> SEQUENCE: 216

Leu Val Tyr Ser Gly Asp Gly Val Val
1               5

<210> SEQ ID NO 217
<211> LENGTH: 6
<212> TYPE: PRT
<213> ORGANISM: Artificial sequence
<220> FEATURE:
<223> OTHER INFORMATION: Synthetic peptide

<400> SEQUENCE: 217

Gln Ser Ile Ser Thr Tyr
```

<210> SEQ ID NO 218
<211> LENGTH: 3
<212> TYPE: PRT
<213> ORGANISM: Artificial sequence
<220> FEATURE:
<223> OTHER INFORMATION: Synthetic peptide

<400> SEQUENCE: 218

Ala Ala Ser
1

<210> SEQ ID NO 219
<211> LENGTH: 9
<212> TYPE: PRT
<213> ORGANISM: Artificial sequence
<220> FEATURE:
<223> OTHER INFORMATION: Synthetic peptide

<400> SEQUENCE: 219

Gln Gln Ser Tyr Arg Thr Pro Trp Thr
1               5

<210> SEQ ID NO 220
<211> LENGTH: 9
<212> TYPE: PRT
<213> ORGANISM: Artificial sequence
<220> FEATURE:
<223> OTHER INFORMATION: Synthetic peptide

<400> SEQUENCE: 220

Asp Ser Asp Val Gly Gly Tyr Asn Tyr
1               5

<210> SEQ ID NO 221
<211> LENGTH: 3
<212> TYPE: PRT
<213> ORGANISM: Artificial sequence
<220> FEATURE:
<223> OTHER INFORMATION: Synthetic peptide

<400> SEQUENCE: 221

Asp Val Thr
1

<210> SEQ ID NO 222
<211> LENGTH: 10
<212> TYPE: PRT
<213> ORGANISM: Artificial sequence
<220> FEATURE:
<223> OTHER INFORMATION: Synthetic peptide

<400> SEQUENCE: 222

Ser Ser Tyr Thr Ser Ser Ser Thr Leu Val
1               5                   10

<210> SEQ ID NO 223
<211> LENGTH: 6
<212> TYPE: PRT
<213> ORGANISM: Artificial sequence
<220> FEATURE:
<223> OTHER INFORMATION: Synthetic peptide

<400> SEQUENCE: 223

Gln Ser Val Ala Ile Tyr
1               5

<210> SEQ ID NO 224
<211> LENGTH: 3
<212> TYPE: PRT
<213> ORGANISM: Artificial sequence
<220> FEATURE:
<223> OTHER INFORMATION: Synthetic peptide

<400> SEQUENCE: 224

Asp Ala Ser
1

<210> SEQ ID NO 225
<211> LENGTH: 9
<212> TYPE: PRT
<213> ORGANISM: Artificial sequence
<220> FEATURE:
<223> OTHER INFORMATION: Synthetic peptide

<400> SEQUENCE: 225

Gln Gln Arg Gly Asn Trp Gln Tyr Thr
1               5

<210> SEQ ID NO 226
<211> LENGTH: 9
<212> TYPE: PRT
<213> ORGANISM: Artificial sequence
<220> FEATURE:
<223> OTHER INFORMATION: Synthetic peptide

<400> SEQUENCE: 226

Ser Ser Asp Val Gly Ser Tyr Asn Tyr
1               5

<210> SEQ ID NO 227
<211> LENGTH: 3
<212> TYPE: PRT
<213> ORGANISM: Artificial sequence
<220> FEATURE:
<223> OTHER INFORMATION: Synthetic peptide

<400> SEQUENCE: 227

Ala Val Thr
1

<210> SEQ ID NO 228
<211> LENGTH: 10
<212> TYPE: PRT
<213> ORGANISM: Artificial sequence
<220> FEATURE:
<223> OTHER INFORMATION: Synthetic peptide

<400> SEQUENCE: 228

Thr Ser Tyr Ala Gly Asn Asn Lys Asp Val
1               5                   10

<210> SEQ ID NO 229
<211> LENGTH: 7
<212> TYPE: PRT
<213> ORGANISM: Artificial sequence
<220> FEATURE:
<223> OTHER INFORMATION: Synthetic peptide

<400> SEQUENCE: 229

Gln Ser Val Ser Ser Gly Tyr
1               5

```
<210> SEQ ID NO 230
<211> LENGTH: 3
<212> TYPE: PRT
<213> ORGANISM: Artificial sequence
<220> FEATURE:
<223> OTHER INFORMATION: Synthetic peptide

<400> SEQUENCE: 230

Gly Ala Ser
1

<210> SEQ ID NO 231
<211> LENGTH: 9
<212> TYPE: PRT
<213> ORGANISM: Artificial sequence
<220> FEATURE:
<223> OTHER INFORMATION: Synthetic peptide

<400> SEQUENCE: 231

Gln Leu Phe Ala Thr Ser Pro Pro Pro
1               5

<210> SEQ ID NO 232
<211> LENGTH: 11
<212> TYPE: PRT
<213> ORGANISM: Artificial sequence
<220> FEATURE:
<223> OTHER INFORMATION: Synthetic peptide

<400> SEQUENCE: 232

Gln Ser Leu Leu Arg Gly Ile Arg Tyr Asn Tyr
1               5                   10

<210> SEQ ID NO 233
<211> LENGTH: 3
<212> TYPE: PRT
<213> ORGANISM: Artificial sequence
<220> FEATURE:
<223> OTHER INFORMATION: Synthetic peptide

<400> SEQUENCE: 233

Leu Gly Ser
1

<210> SEQ ID NO 234
<211> LENGTH: 9
<212> TYPE: PRT
<213> ORGANISM: Artificial sequence
<220> FEATURE:
<223> OTHER INFORMATION: Synthetic peptide

<400> SEQUENCE: 234

Met Gln Ala Leu Gln Thr Pro Thr Thr
1               5

<210> SEQ ID NO 235
<211> LENGTH: 12
<212> TYPE: PRT
<213> ORGANISM: Artificial sequence
<220> FEATURE:
<223> OTHER INFORMATION: Synthetic peptide

<400> SEQUENCE: 235

Gln Ser Val Leu Tyr His Ser Asn Asn Lys Asn Tyr
1               5                   10
```

<210> SEQ ID NO 236
<211> LENGTH: 3
<212> TYPE: PRT
<213> ORGANISM: Artificial sequence
<220> FEATURE:
<223> OTHER INFORMATION: Synthetic peptide

<400> SEQUENCE: 236

Trp Ala Ser
1

<210> SEQ ID NO 237
<211> LENGTH: 9
<212> TYPE: PRT
<213> ORGANISM: Artificial sequence
<220> FEATURE:
<223> OTHER INFORMATION: Synthetic peptide

<400> SEQUENCE: 237

Gln Gln Tyr Tyr Ser Thr Pro Tyr Thr
1               5

<210> SEQ ID NO 238
<211> LENGTH: 9
<212> TYPE: PRT
<213> ORGANISM: Artificial sequence
<220> FEATURE:
<223> OTHER INFORMATION: Synthetic peptide

<400> SEQUENCE: 238

Thr Gly Ala Val Thr Ser Gly His Tyr
1               5

<210> SEQ ID NO 239
<211> LENGTH: 3
<212> TYPE: PRT
<213> ORGANISM: Artificial sequence
<220> FEATURE:
<223> OTHER INFORMATION: Synthetic peptide

<400> SEQUENCE: 239

Ser Thr Asp
1

<210> SEQ ID NO 240
<211> LENGTH: 9
<212> TYPE: PRT
<213> ORGANISM: Artificial sequence
<220> FEATURE:
<223> OTHER INFORMATION: Synthetic peptide

<400> SEQUENCE: 240

Leu Leu His Phe Gly Gly Val Val Val
1               5

<210> SEQ ID NO 241
<211> LENGTH: 6
<212> TYPE: PRT
<213> ORGANISM: Artificial sequence
<220> FEATURE:
<223> OTHER INFORMATION: Synthetic peptide

<400> SEQUENCE: 241

Gln Ser Ile Thr Ser Tyr
1               5

<210> SEQ ID NO 242

```
<211> LENGTH: 3
<212> TYPE: PRT
<213> ORGANISM: Artificial sequence
<220> FEATURE:
<223> OTHER INFORMATION: Synthetic peptide

<400> SEQUENCE: 242

Ala Thr Ser
1

<210> SEQ ID NO 243
<211> LENGTH: 9
<212> TYPE: PRT
<213> ORGANISM: Artificial sequence
<220> FEATURE:
<223> OTHER INFORMATION: Synthetic peptide

<400> SEQUENCE: 243

Gln Gln Ser Tyr Ser Phe Pro Arg Thr
1               5

<210> SEQ ID NO 244
<211> LENGTH: 11
<212> TYPE: PRT
<213> ORGANISM: Artificial sequence
<220> FEATURE:
<223> OTHER INFORMATION: Synthetic peptide

<400> SEQUENCE: 244

Gln Ser Leu Leu Gln Ser Asn Gly Tyr Asn Tyr
1               5                   10

<210> SEQ ID NO 245
<211> LENGTH: 3
<212> TYPE: PRT
<213> ORGANISM: Artificial sequence
<220> FEATURE:
<223> OTHER INFORMATION: Synthetic peptide

<400> SEQUENCE: 245

Leu Gly Ser
1

<210> SEQ ID NO 246
<211> LENGTH: 9
<212> TYPE: PRT
<213> ORGANISM: Artificial sequence
<220> FEATURE:
<223> OTHER INFORMATION: Synthetic peptide

<400> SEQUENCE: 246

Met Gln Ala Leu Gln Thr Pro Pro Thr
1               5

<210> SEQ ID NO 247
<211> LENGTH: 9
<212> TYPE: PRT
<213> ORGANISM: Artificial sequence
<220> FEATURE:
<223> OTHER INFORMATION: Synthetic peptide

<400> SEQUENCE: 247

Ser Ser Asn Ile Gly Ala Gly Tyr Asp
1               5

<210> SEQ ID NO 248
<211> LENGTH: 3
```

```
<212> TYPE: PRT
<213> ORGANISM: Artificial sequence
<220> FEATURE:
<223> OTHER INFORMATION: Synthetic peptide

<400> SEQUENCE: 248

Gly Asn Asn
1

<210> SEQ ID NO 249
<211> LENGTH: 12
<212> TYPE: PRT
<213> ORGANISM: Artificial sequence
<220> FEATURE:
<223> OTHER INFORMATION: Synthetic peptide

<400> SEQUENCE: 249

Gln Ser Tyr Asp Ser Ser Leu Ser Gly Ser Gly Val
1               5                   10

<210> SEQ ID NO 250
<211> LENGTH: 9
<212> TYPE: PRT
<213> ORGANISM: Artificial sequence
<220> FEATURE:
<223> OTHER INFORMATION: Synthetic peptide

<400> SEQUENCE: 250

Ser Ser Asp Val Gly Ala Tyr Asn Tyr
1               5

<210> SEQ ID NO 251
<211> LENGTH: 3
<212> TYPE: PRT
<213> ORGANISM: Artificial sequence
<220> FEATURE:
<223> OTHER INFORMATION: Synthetic peptide

<400> SEQUENCE: 251

Asp Val Ala
1

<210> SEQ ID NO 252
<211> LENGTH: 10
<212> TYPE: PRT
<213> ORGANISM: Artificial sequence
<220> FEATURE:
<223> OTHER INFORMATION: Synthetic peptide

<400> SEQUENCE: 252

Gly Ser Tyr Thr Ser Asp Val Ser Pro Val
1               5                   10

<210> SEQ ID NO 253
<211> LENGTH: 1317
<212> TYPE: DNA
<213> ORGANISM: Chikungunya virus

<400> SEQUENCE: 253
tacgaacacg taacagtgat cccgaacacg gtgggagtac cgtataagac tctagtcaac      60
agaccgggct acagccccat ggtactggag atggagctac tgtcagtcac tttggagcca     120
acgctatcgc ttgattacat cacgtgcgaa tacaaaaccg tcatcccgtc tccgtacgtg     180
aaatgctgcg gtacagcaga gtgcaaggac aaaaacctac tgactacag ctgtaaggtc     240 ttcaccggcg tctacccatt tatgtgggc ggcgcctact gcttctgcga cgctgaaaac     300
```

-continued

```
acgcaattga gcgaagcaca tgtggagaag tccgaatcat gcaaaacaga atttgcatca    360
gcatacaggg ctcataccgc atccgcatca gctaagctcc gcgtccttta ccaaggaaat    420
aacatcactg taactgccta tgcaaacggc gaccatgccg tcacagttaa ggacgccaaa    480
ttcattgtgg ggccaatgtc ttcagcctgg acaccttttg acaacaaaat cgtggtgtac    540
aaaggtgacg tttacaacat ggactacccg ccctttggcg caggaagacc aggacaattt    600
ggcgatatcc aaagtcgcac gcctgagagc aaagacgtct atgctaacac acaactggta    660
ctgcagagac cggctgcggg tacggtacac gtgccatact ctcaggcacc atctggcttt    720
aagtattggt taaaagaacg aggggcgtcg ctacagcaca cagcaccatt tggctgccaa    780
atagcaacaa acccggtaag agcgatgaac tgcgccgtag ggaacatgcc catctccatc    840
gacataccgg atgcggcctt cactagggtc gtcgacgcgc cctctttaac ggacatgtca    900
tgcgaggtac cagcctgcac ccattcctca gactttgggg gcgtcgccat tattaaatat    960
gcagtcagca agaaaggcaa gtgtgcggtg cattcgatga ccaacgccgt cactatccgg   1020
gaagctgaga tagaagttga agggaattct cagctgcaaa tctctttctc gacggccttg   1080
gccagcgccg aattccgcgt acaagtctgt tctacacaag tacactgtgc agccgagtgc   1140
caccctccga aggaccacat agtcaactac ccggcgtcac ataccaccct cggggtccag   1200
gacatttccg ctacggcgat gtcatgggtg cagaagatca cgggaggtgt gggactggtt   1260
gtcgctgttg cagcactgat tctaatcgtg gtgctatgcg tgtcgttcag caggcac      1317
```

<210> SEQ ID NO 254
<211> LENGTH: 1317
<212> TYPE: DNA
<213> ORGANISM: Chikungunya virus

<400> SEQUENCE: 254

```
tacgaacacg taacagtgat cccgaacacg gtgggagtac cgtataagac tctagtcaat     60
agacctggct acagccccat ggtattggag atggaactac tgtcagtcac tttggagcca    120
acactatcgc ttgattacat cacgtgcgag tacaaaaccg tcatcccgtc tccgtacgtg    180
aagtgctgcg gtacagcaga gtgcaaggac aaaaacctac ctgactacag ctgtaaggtc    240
ttcaccggcg tctacccatt tatgtggggc ggcgcctact gcttctgcga cgctgaaaac    300
acgcagttga gcgaagcaca tgtggagaag tccgaatcat gcaaaacaga atttgcatca    360
gcatacaggg ctcataccgc atctgcatca gctaagctcc gcgtccttta ccaaggaaat    420
aacatcactg taactgccta tgcaaacggc gaccatgccg tcacagttaa ggacgccaaa    480
ttcattgtgg ggccaatgtc ttcagcctgg acacctttcg acaacaaaat tgtggtgtac    540
aaaggtgacg tctataacat ggactacccg ccctttggcg caggaagacc aggacaattt    600
ggcgatatcc aaagtcgcac acctgagagt aaagacgtct atgctaatac acaactggta    660
ctgcagagac cggctgcggg tacggtacac gtgccatact ctcaggcacc atctggcttt    720
aagtattggc taaaagaacg cggggcgtca ctgcagcaca cagcaccatt tggctgccaa    780
atagcaacaa acccggtaag agcggtgaac tgcgccgtag ggaacatgcc catctccatc    840
gacataccgg aagcggcctt cactagggtc gtcgacgcgc cctctttaac ggacatgtcg    900
tgcgaggtac tagcctgcac ccattcctca gactttgggg gcgtcgccat tattaaatat    960
gcagccagca agaaaggcaa gtgtgcggtg cattcgatga ctaacgccgt cactattcgg   1020
gaagctgaga tagaagttga agggaattct cagctgcaaa tctctttctc gacggcctta   1080
```

| | |
|---|---|
| gccagcgccg aattccgcgt acaagtctgt tctacacaag tacactgtgc agctgagtgc | 1140 |
| caccccccga aggaccacat agtcaactac ccggcgtcac ataccaccct cggggtccag | 1200 |
| gacatctccg ctacggcgat gtcatgggtg cagaagatca cgggaggtgt gggactggtt | 1260 |
| gttgctgttg ccgcactgat tctaatcgtg gtgctatgcg tgtcgttcag caggcac | 1317 |

<210> SEQ ID NO 255
<211> LENGTH: 1317
<212> TYPE: DNA
<213> ORGANISM: Chikungunya virus

<400> SEQUENCE: 255

| | |
|---|---|
| tacgaacacg taacagtgat cccgaacacg gtgggagtac cgtataagac tctagtcaat | 60 |
| agacctggct acagccccat ggtattggag atggaactac tgtcagtcac tttggagcca | 120 |
| acactatcgc ttgattacat cacgtgcgag tacaaaaccg tcatcccgtc tccgtacgtg | 180 |
| aagtgctgcg gtacagcaga gtgcaaggac aaaaacctac ctgactacag ctgtaaggtc | 240 |
| ttcaccggcg tctacccatt tatgtggggc ggcgcctact gcttctgcga cgctgaaaac | 300 |
| acgcagttga gcgaagcaca cgtggagaag tccgaatcat gcaaaacaga atttgcatca | 360 |
| gcatacaggc tcataccgc atctgcatca gctaagctcc gcgtccttta ccaaggaaat | 420 |
| aacatcactg taactgccta tgcaaacggc gaccatgccg tcacagttaa ggacgccaaa | 480 |
| ttcattgtgg ggccaatgtc ttcagcctgg acacctttcg acaacaaaat tgtggtgtac | 540 |
| aaaggtgacg tctataacat ggactacccg ccctttggcg caggaagacc aggacaattt | 600 |
| ggcgatatcc aaagtcgcac acctgagagt aaagacgtct atgctaatac acaactggta | 660 |
| ctgcagagac cggctgtggg tacggtacac gtgccatact ctcaggcacc atctggcttt | 720 |
| aagtattggc taaagaaacg cggggcgtcg ctgcagcaca cagcaccatt tggctgccaa | 780 |
| atagcaacaa acccggtaag agcggtgaac tgcgccgtag ggaacatgcc catctccatc | 840 |
| gacataccgg aagcggcctt cactagggtc gtcgacgcgc cctctttaac ggacatgtcg | 900 |
| tgcgaggtac cagcctgcac ccattcctca gactttgggg gcgtcgccat tattaaatat | 960 |
| gcagccagca aagaaggcaa gtgtgcggtg cattcgatga ctaacgccgt cactattcgg | 1020 |
| gaagctgaga tagaagttga agggaattct cagctgcaaa tctctttctc gacggcctta | 1080 |
| gccagcgccg aattccgcgt acaagtctgt tctacacaag tacactgtgc agccgagtgc | 1140 |
| caccccccga aggaccacat agtcaactac ccggcgtcac ataccaccct cggggtccag | 1200 |
| gacatctccg ctacggcgat gtcatgggtg cagaagatca cgggaggtgt gggactggtt | 1260 |
| gttgctgttg ccgcactgat tctaatcgtg gtgctatgcg tgtcgttcag caggcac | 1317 |

<210> SEQ ID NO 256
<211> LENGTH: 1317
<212> TYPE: DNA
<213> ORGANISM: Chikungunya virus

<400> SEQUENCE: 256

| | |
|---|---|
| tacgaacacg taacagtgat cccgaacacg gtgggagtac cgtataagac tctagtcaac | 60 |
| agaccgggct acagccccat ggtactggag atggagcttc tgtcagtcac tttggagcca | 120 |
| acgctatcgc ttgattacat cacgtgcgag tataaaaccg tcatcccgtc tccgtacgtg | 180 |
| aaatgctgcg gtacagcaga gtgcaaggac aagagcctac tgattacag ctgtaaggtc | 240 |
| ttcaccggcg tctacccatt catgtggggc ggcgcctact gcttctgcga cactgaaaat | 300 |
| acgcaattga gcgaagcaca tgtggagaag tccgaatcat gcaaaacaga atttgcatca | 360 |

```
gcatataggg ctcataccgc atccgcatca gctaagctcc gcgtcccttta ccaaggaaat    420 aatgttactg tatctgctta tgcaaacggc gatcatgccg tcacagttaa ggacgctaaa    480
ttcattgtgg ggccaatgtc ttcagcctgg acaccttttg acaataaaat cgtggtgtac    540
aaaggcgacg tctacaacat ggactacccg cccttcggcg caggaagacc aggacaattt    600
ggcgacatcc aaagtcgcac gcctgagagc gaagacgtct atgctaacac acaactggta    660
ctgcagagac cgtccgcggg tacggtgcac gtgccgtact ctcaggcacc atctggcttc    720
aagtattggc taaaagaacg aggggcgtcg ctgcagcaca cagcaccatt tggctgtcaa    780
atagcaacaa acccggtaag agcgatgaac tgcgccgtag ggaacatgcc tatctccatc    840
gacataccgg acgcggcctt cactagggtc gtcgacgcgc catctttaac ggacatgtcg    900
tgtgaggtac cagcctgcac ccactcctca gactttgggg gcgtagccat cattaaatat    960
gcagccagca agaaaggcaa gtgtgcggtg cattcgatga ctaacgccgt cactattcgg   1020
gaagctgaaa tagaagtaga agggaactct cagttgcaaa tctctttttc gacggcccta   1080
gccagcgccg aattccgcgt acaagtctgt tctacacaag tacactgtgc agccgagtgc   1140
catccaccga aagaccatat agtcaattac ccggcgtcac acaccaccct cggggtccaa   1200
gacatttccg ttacggcgat gtcatgggtg cagaagatca cgggaggtgt gggactggtt   1260
gtcgctgttg cagcactgat cctaatcgtg gtgctatgcg tgtcgtttag caggcac      1317

<210> SEQ ID NO 257
<211> LENGTH: 1317
<212> TYPE: DNA
<213> ORGANISM: Chikungunya virus

<400> SEQUENCE: 257
tacgaacacg taacagtgat cccgaacacg gtgggagtac cgtataagac tctagtcaac     60
agaccgggct acagccccat ggtattggag atggagcttc tgtctgtcac cttggaacca    120
acgctatcgc ttgattacat cacgtgcgag tataaaaccg ttatcccgtc tccgtacgtg    180
aaatgctgcg gtacagcaga gtgtaaggac aagagcctac ctgattacag ctgtaaggtc    240
ttcaccggcg tctacccatt catgtggggc ggcgcctact gcttctgcga caccgaaaat    300
acgcaattga gcgaagcaca tgtggagaag tccgaatcat gcaaaacaga atttgcatca    360
gcatacaggg ctcataccgc atccgcatca gctaagctcc gcgtcccttta ccaaggaaat    420 aatatcactg tggctgctta tgcaaacggc gaccatgccg tcacagttaa ggacgctaaa    480
ttcatagtgg ggccaatgtc ttcagcctgg acaccttttcg acaataaaat cgtggtgtac    540
aaaggcgacg tctacaacat ggactacccg cccttcggcg caggaagacc aggacaattt    600
ggcgacatcc aaagtcgcac gcctgagagc gaagacgtct atgctaatac acaactggta    660
ctgcagagac cgtccgcggg tacggtgcac gtgccgtact ctcaggcacc atctggcttc    720
aagtattggc taaaagaacg aggggcgtcg ctgcagcaca cagcaccatt tggctgtcaa    780
atagcaacaa acccggtaag agcgatgaac tgcgccgtag ggaacatgcc tatctccatc    840
gacataccgg acgcggcctt taccagggtc gtcgacgcgc catctttaac ggacatgtcg    900
tgtgaggtat cagcctgcac ccattcctca gactttgggg gcgtagccat cattaaatat    960
gcagccagta agaaaggcaa gtgtgcagtg cactcgatga ctaacgccgt cactattcgg   1020
gaagctgaaa tagaagtaga agggaactct cagttgcaaa tctctttttc gacggcccta   1080
gccagcgccg aattccgcgt acaagtctgt tctacacaag tacactgtgc agccgagtgc   1140
```

-continued

```
catccaccga aagaccatat agtcaattac ccggcgtcac acaccaccct cggggtccaa   1200
gacatttccg ctacggcgat gtcatgggtg cagaagatca cgggaggtgt gggactggtt   1260
gtcgctgttg cagcactgat cctaatcgtg gtgctatgcg tgtcgtttag caggcac      1317
```

<210> SEQ ID NO 258
<211> LENGTH: 1317
<212> TYPE: DNA
<213> ORGANISM: Chikungunya virus

<400> SEQUENCE: 258

```
tacgaacacg taacagtgat cccgaacacg gtgggagtac cgtataagac tcttgtcaac    60
agaccgggtt acagccccat ggtattggag atggagctac aatcggtcac cttggaacca   120
acactgtcac ttgactacat cacgtgcgag tacaaaactg tcatccctc cccgtacgtg    180 aagtgctgtg gtacagcaga gtgcaaggac aagagcctac cagactacag ctgcaaggtc   240
tttactggag tctacccatt tatgtggggc ggcgcctact gcttttgcga cgccgaaaat   300
acgcaattga gcgaggcaca tgtagagaaa tctgaatctt gcaaaacaga gtttgcatcg   360
gcctacagag cccacaccgc atcggcgtcg gcgaagctcc gcgtccttta ccaaggaaac   420
aacattactg tagctgccta cgctaacggc gaccatgccg tcacagtaaa ggacgccaag   480
tttgtcgtgg gaccaatgtc ctccgcctgg acaccttttg acaacaaaat cgtggtgtac   540
aaaggcgacg tctacaacat ggactaccca ccttttggcg caggaagacc aggacaattt   600
ggtgacattc aaagtcgtac accggaaagt aaagacgttt atgccaacac tcagttggta   660
ctacagaggc cagcagcagg cacggtacat gtaccatact ctcaggcacc atctggcttc   720
aagtattggc tgaaggaacg aggagcatcg ctacagcaca cggcaccgtt cggttgccag   780
attgcgacaa acccggtaag agctgtaaat tgcgctgtgg ggaacatacc aatttccatc   840
gacataccgg atgcggcctt tactagggtt gtcgatgcac cctctgtaac ggacatgtca   900
tgcgaagtac cagcctgcac tcactcctcc gactttgggg cgtcgccat catcaaatat   960 acagctagca agaaaggtaa atgtgcagta cattcgatga ccaacgccgt taccattcga   1020
gaagccgacg tagaagtaga ggggaattcc cagctgcaaa tatccttctc aacagccttg   1080
gcaagcgccg agtttcgcgt gcaagtgtgc tccacacaag tacactgcgc agccgcatgc   1140
caccctccaa aggaccacat agtcaattac ccagcatcac acaccaccct tggggtccag   1200
gatatatcca acggcaatgt cttgggtg cagaagatta cgggaggagt aggattaatt   1260
gttgctgttg ctgccttaat tttaattgtg gtgctatgcg tgtcgtttag caggcac      1317
```

<210> SEQ ID NO 259
<211> LENGTH: 439
<212> TYPE: PRT
<213> ORGANISM: Chikungunya virus

<400> SEQUENCE: 259

```
Tyr Glu His Val Thr Val Ile Pro Asn Thr Val Gly Val Pro Tyr Lys
 1               5                  10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
```

```
            65                  70                  75                  80
        Phe Thr Gly Val Tyr Pro Phe Met Trp Gly Gly Ala Tyr Cys Phe Cys
                            85                  90                  95
        Asp Ala Glu Asn Thr Gln Leu Ser Glu Ala His Val Glu Lys Ser Glu
                        100                 105                 110
        Ser Cys Lys Thr Glu Phe Ala Ser Ala Tyr Arg Ala His Thr Ala Ser
                        115                 120                 125
        Ala Ser Ala Lys Leu Arg Val Leu Tyr Gln Gly Asn Asn Ile Thr Val
                    130                 135                 140
        Ala Ala Tyr Ala Asn Gly Asp His Ala Val Thr Val Lys Asp Ala Lys
        145                 150                 155                 160
        Phe Val Val Gly Pro Met Ser Ser Ala Trp Thr Pro Phe Asp Asn Lys
                        165                 170                 175
        Ile Val Val Tyr Lys Gly Asp Val Tyr Asn Met Asp Tyr Pro Pro Phe
                    180                 185                 190
        Gly Ala Gly Arg Pro Gly Gln Phe Gly Asp Ile Gln Ser Arg Thr Pro
                    195                 200                 205
        Glu Ser Lys Asp Val Tyr Ala Asn Thr Gln Leu Val Leu Gln Arg Pro
                210                 215                 220
        Ala Ala Gly Thr Val His Val Pro Tyr Ser Gln Ala Pro Ser Gly Phe
        225                 230                 235                 240
        Lys Tyr Trp Leu Lys Glu Arg Gly Ala Ser Leu Gln His Thr Ala Pro
                        245                 250                 255
        Phe Gly Cys Gln Ile Ala Thr Asn Pro Val Arg Ala Val Asn Cys Ala
                        260                 265                 270
        Val Gly Asn Ile Pro Ile Ser Ile Asp Ile Pro Asp Ala Ala Phe Thr
                    275                 280                 285
        Arg Val Val Asp Ala Pro Ser Val Thr Asp Met Ser Cys Glu Val Pro
                290                 295                 300
        Ala Cys Thr His Ser Ser Asp Phe Gly Gly Val Ala Ile Ile Lys Tyr
        305                 310                 315                 320
        Thr Ala Ser Lys Lys Gly Lys Cys Ala Val His Ser Met Thr Asn Ala
                        325                 330                 335
        Val Thr Ile Arg Glu Ala Asp Val Glu Val Glu Gly Asn Ser Gln Leu
                    340                 345                 350
        Gln Ile Ser Phe Ser Thr Ala Leu Ala Ser Ala Glu Phe Arg Val Gln
                    355                 360                 365
        Val Cys Ser Thr Gln Val His Cys Ala Ala Cys His Pro Pro Lys
                370                 375                 380
        Asp His Ile Val Asn Tyr Pro Ala Ser His Thr Thr Leu Gly Val Gln
        385                 390                 395                 400
        Asp Ile Ser Thr Thr Ala Met Ser Trp Val Gln Lys Ile Thr Gly Gly
                        405                 410                 415
        Val Gly Leu Ile Val Ala Val Ala Ala Leu Ile Leu Ile Val Val Leu
                        420                 425                 430
        Cys Val Ser Phe Ser Arg His
                    435

<210> SEQ ID NO 260
<211> LENGTH: 439
<212> TYPE: PRT
<213> ORGANISM: Chikungunya virus

<400> SEQUENCE: 260
```

-continued

```
Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
                20                  25                  30

Leu Leu Ser Val Thr Leu Glu Pro Thr Leu Ser Leu Asp Tyr Ile Thr
            35                  40                  45

Cys Glu Tyr Lys Thr Val Ile Pro Ser Pro Tyr Val Lys Cys Cys Gly
50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Ala Tyr Cys Phe Cys
                85                  90                  95

Asp Ala Glu Asn Thr Gln Leu Ser Glu Ala His Val Glu Lys Ser Glu
                100                 105                 110

Ser Cys Lys Thr Glu Phe Ala Ser Ala Tyr Arg Ala His Thr Ala Ser
            115                 120                 125

Ala Ser Ala Lys Leu Arg Val Leu Tyr Gln Gly Asn Asn Ile Thr Val
130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
                180                 185                 190

Gly Ala Gly Arg Pro Gly Gln Phe Gly Asp Ile Gln Ser Arg Thr Pro
            195                 200                 205

Glu Ser Lys Asp Val Tyr Ala Asn Thr Gln Leu Val Leu Gln Arg Pro
            210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Met Asn Cys Ala
            260                 265                 270

Val Gly Asn Met Pro Ile Ser Ile Asp Ile Pro Asp Ala Ala Phe Thr
                275                 280                 285

Arg Val Val Asp Ala Pro Ser Leu Thr Asp Met Ser Cys Glu Val Pro
            290                 295                 300

Ala Cys Thr His Ser Ser Asp Phe Gly Gly Val Ala Ile Ile Lys Tyr
305                 310                 315                 320

Ala Val Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350

Gln Ile Ser Phe Ser Thr Ala Leu Ala Ser Ala Glu Phe Arg Val Gln
            355                 360                 365

Val Cys Ser Thr Gln Val His Cys Ala Ala Glu Cys His Pro Pro Lys
370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
```

```
                    420             425             430
Cys Val Ser Phe Ser Arg His
            435

<210> SEQ ID NO 261
<211> LENGTH: 439
<212> TYPE: PRT
<213> ORGANISM: Chikungunya virus

<400> SEQUENCE: 261

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Met Pro Ile Ser Ile Asp Ile Pro Glu Ala Ala Phe Thr
        275                 280                 285

Arg Val Val Asp Ala Pro Ser Leu Thr Asp Met Ser Cys Glu Val Leu
    290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350
```

Gln Ile Ser Phe Ser Thr Ala Leu Ala Ser Ala Glu Phe Arg Val Gln
            355                 360                 365

Val Cys Ser Thr Gln Val His Cys Ala Ala Glu Cys His Pro Pro Lys
    370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
            420                 425                 430

Cys Val Ser Phe Ser Arg His
            435

<210> SEQ ID NO 262
<211> LENGTH: 439
<212> TYPE: PRT
<213> ORGANISM: Chikungunya virus

<400> SEQUENCE: 262

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Val Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Met Pro Ile Ser Ile Asp Ile Pro Glu Ala Ala Phe Thr
        275                 280                 285

Arg Val Val Asp Ala Pro Ser Leu Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Glu Cys His Pro Pro Lys
370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
                420                 425                 430

Cys Val Ser Phe Ser Arg His
            435

<210> SEQ ID NO 263
<211> LENGTH: 439
<212> TYPE: PRT
<213> ORGANISM: Chikungunya virus

<400> SEQUENCE: 263

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
130                 135                 140

Ala Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Glu Asp Val Tyr Ala Asn Thr Gln Leu Val Leu Gln Arg Pro

```
                210                 215                 220
Ser Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Met Asn Cys Ala
                260                 265                 270

Val Gly Asn Met Pro Ile Ser Ile Asp Ile Pro Asp Ala Ala Phe Thr
                275                 280                 285

Arg Val Val Asp Ala Pro Ser Leu Thr Asp Met Ser Cys Glu Val Ser
                290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
                340                 345                 350

Gln Ile Ser Phe Ser Thr Ala Leu Ala Ser Ala Glu Phe Arg Val Gln
                355                 360                 365

Val Cys Ser Thr Gln Val His Cys Ala Ala Glu Cys His Pro Pro Lys
                370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
                420                 425                 430

Cys Val Ser Phe Ser Arg His
                435

<210> SEQ ID NO 264
<211> LENGTH: 439
<212> TYPE: PRT
<213> ORGANISM: Chikungunya virus

<400> SEQUENCE: 264

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
                20                  25                  30

Leu Leu Ser Val Thr Leu Glu Pro Thr Leu Ser Leu Asp Tyr Ile Thr
                35                  40                  45

Cys Glu Tyr Lys Thr Val Ile Pro Ser Pro Tyr Val Lys Cys Cys Gly
                50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Leu Ser Glu Ala His Val Glu Lys Ser Glu
                100                 105                 110

Ser Cys Lys Thr Glu Phe Ala Ser Ala Tyr Arg Ala His Thr Ala Ser
                115                 120                 125

Ala Ser Ala Lys Leu Arg Val Leu Tyr Gln Gly Asn Asn Val Thr Val
                130                 135                 140
```

Ser Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Glu Asp Val Tyr Ala Asn Thr Gln Leu Val Leu Gln Arg Pro
210                 215                 220

Ser Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Met Asn Cys Ala
            260                 265                 270

Val Gly Asn Met Pro Ile Ser Ile Asp Ile Pro Asp Ala Ala Phe Thr
        275                 280                 285

Arg Val Val Asp Ala Pro Ser Leu Thr Asp Met Ser Cys Glu Val Pro
290                 295                 300

Ala Cys Thr His Ser Ser Asp Phe Gly Gly Val Ala Ile Ile Lys Tyr
305                 310                 315                 320

Ala Ala Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Glu Cys His Pro Pro Lys
370                 375                 380

Asp His Ile Val Asn Tyr Pro Ala Ser His Thr Thr Leu Gly Val Gln
385                 390                 395                 400

Asp Ile Ser Val Thr Ala Met Ser Trp Val Gln Lys Ile Thr Gly Gly
                405                 410                 415

Val Gly Leu Val Val Ala Val Ala Ala Leu Ile Leu Ile Val Val Leu
            420                 425                 430

Cys Val Ser Phe Ser Arg His
        435

<210> SEQ ID NO 265
<211> LENGTH: 1269
<212> TYPE: DNA
<213> ORGANISM: Chikungunya virus

<400> SEQUENCE: 265
agtattaagg acaacttcaa tgtctataaa gccataagac cgtacctagc tcactgtccc     60
gactgtggag aagggcactc gtgccatagt cccgtagcgc tagaacgcat cagaaacgaa    120
gcgacagacg ggacgctgaa atccaggtt tccttgcaaa tcggaataaa gacggatgat    180
agccatgatt ggaccaagct gcgttacatg gacaatcata tgccagcaga cgcagagagg    240
gccaggctat ttgtaagaac gtcagcaccg tgcacgatta ctggaacaat gggacacttc    300
atcctggccc gatgtccgaa aggagaaact ctgacggtgg gattcactga cggtaggaag    360
atcagtcact catgtacgca cccatttcac acgaccctc ctgtgatagg ccgggaaaaa    420

```
tttcattccc gaccgcagca cggtagagaa ctaccttgca gcacgtacgc gcagagcacc     480
gctgcaactg ccgaggagat agaggtacat atgcccccag acaccccaga tcgcacattg     540
atgtcacaac agtccggtaa tgtaaagatc acagtcaata gtcagacggt gcggtacaag     600
tgtaattgcg gtgactcaaa tgaaggacta accactacag acaaagtgat taataactgc     660
aaggttgatc aatgccatgc cgcggtcacc aatcacaaaa aatggcagta taattcccct     720
ctggtcccgc gtaatgctga actcggggac cgaaaaggaa aagttcacat tccgtttcct     780
ctggcaaatg tgacatgcag ggtgcctaag gcaaggaacc ccaccgtgac gtacggaaaa     840
aaccaagtca tcatgctgct gtatcctgac acccaacgc tcctgtccta ccggaatatg     900
ggagaagaac caaactatca agaagagtgg gtgacgcata agaaggagat caggttaacc     960
gtgccgactg aagggctcga ggtcacgtgg ggcaacaacg agccgtacaa gtattggccg    1020
cagttatcca caaacggtac agcccacggc caccccgcatg agataatttt gtattattat    1080
gagctgtacc ctactatgac tgtggtagtt gtgtcagtgg cctcgttcgt actcctgtcg    1140
atggtgggtg tggcagtggg gatgtgcatg tgtgcacgac gcagatgcat tacaccgtac    1200
gaactgacac caggagctac cgtccctttc ctgcttagcc taatatgctg cattagaaca    1260
gctaaagcg                                                            1269

<210> SEQ ID NO 266
<211> LENGTH: 1269
<212> TYPE: DNA
<213> ORGANISM: Chikungunya virus

<400> SEQUENCE: 266
agtactaagg acaattttaa tgtctataaa gctacaagac catatctagc tcattgtcct     60
gactgcggag aagggcattc gtgccacagc cctatcgcat ggagcgcat cagaaatgaa    120 gcaacggacg gaacgctgaa aatccaggtc tctttgcaga tcgggataaa gacagatgac    180
agccacgatt ggaccaagct gcgctatatg gatagccata cgccagcgga cgcggagcga    240
gccggattgc ttgtaaggac ttcagcaccg tgcacgatca ccgggaccat gggacacttt    300
attctcgccc gatgcccgaa aggagagacg ctgacagtgg gatttacgga cagcagaaag    360
atcagccaca catgcacaca cccgttccat catgaaccac ctgtgatagg tagggagagg    420
ttccactctc gaccacaaca tggtaaagag ttaccttgca gcacgtacgt gcagagcacc    480
gctgccactg ccgaggagat agaggtgcat atgcccccag atactcctga ccgcacgctg    540
atgacgcagc agtctggcaa cgtgaagatc acagttaatg gcagacggt gcggtacaag    600 tgcaactgcg gcggctcaaa cgagggactg acaaccacag acaaagtgat caataactgc    660
aaaattgatc agtgccatgc tgcagtcact aatcacaaga gtggcaata caactccccct    720 ttagtcccgc gtaacgctga actcggggac cgtaaaggaa agattcacat cccattccca    780
ttggcaaacg tgacttgcag agtgccaaaa gcaagaaacc cacagtaac gtacggaaaa    840 aaccaagtca ccatgctgct gtatcctgac catccgacac tcttgtctta tcgtaacatg    900
ggacaggaac caaattacca cgaggagtgg gtgacacaca agaaggaggt taccttgacc    960
gtgcctactg agggtctgga ggtcacttgg ggcaacaacg aaccatacaa gtactggccg    1020
cagatgtcta cgaacggtac tgctcatggt cacccacatg agataatctt gtactattat    1080
gagctgtacc ccactatgac tgtaatcatt gtgtcggtgg cctcgttcgt gcttctgtcg    1140
atggtgggca cagcagtggg gatgtgtgtg tgcgcacggc gcagatgcat tacaccatat    1200
gaattaacac caggagccac cgttcccttt ctgctcagcc tgctatgttg cgtcagaacg    1260
``` accaaggcg                                                                1269

<210> SEQ ID NO 267
<211> LENGTH: 1269
<212> TYPE: DNA
<213> ORGANISM: Chikungunya virus

<400> SEQUENCE: 267
agcaccaagg acaacttcaa tgtctataaa gccacaagac catacttagc tcactgtccc    60
gactgtggag aagggcactc gtgccatagt cccgtagcac tagaacgcat cagaaatgaa   120
gcgacagacg ggacgctgaa aatccaggtc tccttgcaaa tcggaataaa gacggatgac   180
agccacgatt ggaccaagct gcgttatatg gacaaccaca tgccagcaga cgcagagagg   240
gcggggctat ttgtaagaac atcagcaccg tgtacgatta ctggaacaat gggacacttc   300
atcctggccc gatgtccaaa agggaaaact ctgacggtgg gattcactga cagtaggaag   360
attagtcact catgtacgca cccatttcac cacgaccctc ctgtgatagg tcgggaaaaa   420
ttccattccc gaccgcagca cggtaaagag ctaccttgca gcacgtacgt gcagagcacc   480
gccgcaacta ccgaggagat agaggtacac atgccccag acacccctga tcgcacatta   540
atgtcacaac agtccggcaa cgtaaagatc acagtcaatg ccagacggt gcggtacaag   600
tgtaattgcg gtggctcaaa tgaaggacta acaactacag acaaagtgat taataactgc   660
aaggttgatc aatgtcatgc cgcggtcacc aatcacaaaa agtggcagta taactcccct   720
ctggtcccgc gtaatgctga acttgggac cgaaaaggaa aaattcacat cccgtttccg   780
ctggcaaatg taacatgcag ggtgcctaaa gcaaggaacc ccaccgtgac gtacgggaaa   840
aaccaagtca tcatgctact gtatcctgac cacccaacac tcctgtccta ccggaatatg   900
ggagaagaac caaactatca agaagagtgg gtgatgcata agaaggaagt cgtgctaacc   960
gtgccgactg aagggctcga ggtcacgtgg ggcaacaacg agccgtataa gtattggccg  1020
cagttatcta caaacggtac agcccatggc caccccgcatg agataattct gtattattat  1080
gagctgtacc ccactatgac tgtagtagtt gtgtcagtgg ccacgttcat actcctgtcg  1140
atggtgggta tggcagcggg gatgtgcatg tgtgcacgac gcagatgcat cacaccgtat  1200
gaactgacac caggagctac cgtcccttc ctgcttagcc taatatgctg catcagaaca  1260
gctaaagcg                                                          1269

<210> SEQ ID NO 268
<211> LENGTH: 1269
<212> TYPE: DNA
<213> ORGANISM: Chikungunya virus

<400> SEQUENCE: 268
agcaccaagg acaacttcaa tgtctataaa gccacaagac catacttagc tcactgtccc    60
gactgtggag aagggcactc gtgccatagt cccgtagcac tagaacgcat cagaaatgaa   120
gcgacagacg ggacgctgaa aatccaggtc tccttgcaaa tcggaataaa gacggacgac   180
agccacgatt ggaccaagct gcgttatatg gacaaccaca tgccagcaga cgcagagagg   240
gcggggctat ttgtaagaac atcagcaccg tgtacgatta ctggaacaat gggacacttc   300
atcctggccc gatgtccaaa agggaaaact ctgacggtgg gattcactga cagtaggaag   360
attagtcatt catgtacgca cccatttcac cacgaccctc ctgtgatagg tcgggaaaaa   420
ttccattccc gaccgcagca cggtaaagag ctaccttgca gcacgtacgt gcagagcacc   480

```
gccgcaacta ccgaggagat agaggtacac atgcccccag acacccctga tcgcacatta      540
atgtcacaac agtccggcaa cgtaaagatc acagtcaatg ccagacggt gcggtacaag       600 tgtaattgcg gtggctcaaa tgaaggacta acaactacag acaaagtgat taataactgc     660
aaggttgatc aatgtcatgc cgcggtcacc aatcacaaaa agtggcagta taactcccct     720
ctggtcccgc gtaatgctga acttggggac cgaaaaggaa aaattcacat cccgtttccg     780
ctggcaaatg taacatgcag ggtgcctaaa gcaaggaacc ccaccgtgac gtacgggaaa     840
aaccaagtca tcatgctact gtatcctgac cacccaacac tcctgtccta ccggaatatg     900
ggagaagaac caaactatca agaagagtgg gtgatgcata gaaggaagt cgtgctaacc      960 gtgccgactg aagggctcga ggtcacgtgg ggcaacaacg agccgtataa gtattggccg    1020
cagttatcta caaacggtac agcccatggc caccgcatg ataattct gtattattat       1080 gagctgtacc ctactatgac tgtagtagtt gtgtcagtgg ccacgttcat actcctgtcg    1140
atggtgggta tggcagtggg gatgtgcatg tgtgcacgac gcagatgcat cacaccgtat    1200
gaactgacac aggagctac cgtccctttc ctgcttagcc taatatgctg catcagaaca     1260
gctaaagcg                                                             1269

<210> SEQ ID NO 269
<211> LENGTH: 1269
<212> TYPE: DNA
<213> ORGANISM: Chikungunya virus

<400> SEQUENCE: 269
agcaccaagg acaacttcaa tgtctataaa gccacaagac catacctagc tcactgtccc      60
gactgtggag aagggcactc gtgccatagt cccgtagcac tagaacgcat cagaaatgaa    120
gcgacagacg ggacgctgaa aatccaggtc tccttgcaaa ttggaatagg acgcgatgat    180
agccatgatt ggaccaagct gcgttacatg acaatcaca taccagcaga cgcagggagg    240
gccgggctat ttgtaagaac atcagcacca tgcacgatta ctggaacaat gggacacttc    300
atcctggccc gatgtccgaa aggagaaact ctgacggtgg gattcactga cagtaggaag    360
attagtcact catgtacgca cccatttcac cacgacctc ctgtgatagg ccgggaaaaa    420
ttccattccc gaccgcagca cggtaaagag ctaccttgca gcacgtacgt gcagagcaac    480
gccgcaactg ccgaggagat agaggtacac atgcccccag acacccctga tcgcacattg    540
ctgtcacaac agtccggcaa cgtaaagatc acagtcaata gtcagacggt gcggtataag    600
tgtaattgcg gtggctcaaa tgaaggacta ataactacag ataaagtgat taataactgc    660
aaggttgatc aatgtcatgc cgcggtcacc aatcacaaaa agtggcagta taactcccct    720
ctggtcccgc gtaacgctga actcggggac cgaaaaggaa aaattcacat cccgtttccg    780
ctggcaaatg taacatgcat ggtgcctaaa gcaaggaacc ccaccgtgac gtacgggaaa    840
aaccaagtca tcatgctact gtatcctgac cacccaacac tcctgtccta ccggagtatg    900
ggagaagaac caaactatca agaagagtgg gtgacgcaca gaaggaggt cgtgctaacc    960 gtgccgactg aagggctcga ggttacgtgg ggcaacaacg agccgtataa gtattggccg   1020
cagttatctg caaacggtac agcccacggc caccgcatg ataatctt gtactattat     1080 gagctgtacc ctactatgac tgtagtagtt gtgtcagtgg cctcgttcat actcctgtcg   1140
atggtgggta tggcagtggg gatgtgcatg tgtgcacgac gcagatgcat cacaccatac   1200
gaactgacac aggagctac cgtccctttc ctgcttagcc taatatgctg catcagaaca    1260
gctaaagcg                                                           1269
```

<210> SEQ ID NO 270
<211> LENGTH: 1269
<212> TYPE: DNA
<213> ORGANISM: Chikungunya virus

<400> SEQUENCE: 270

```
agtattaagg accacttcaa tgtctataaa gccacaagac cgtacctagc tcactgtccc      60
gactgtggag aagggcactc gtgccatagt cccgtagcgc tagaacgcat cagaaacgaa     120
gcgacagacg ggacgttgaa atccaggtt tccttgcaaa tcggaataaa gacggatgat      180
agccatgatt ggaccaagct gcgttatatg acaatcaca tgccagcaga cgcagagcgg      240
gccgggctat ttgtaagaac gtcagcaccg tgcacgatta ctggaacaat gggacacttc     300
attctggccc gatgtccgaa aggagaaact ctgacggcgg ggttcactga cggtaggaag    360
atcagtcact catgtacgca cccatttcac catgaccctc ctgtgatagg ccgggaaaaa     420
ttccattccc gaccgcagca cggtagggaa ctaccttgca gcacgtacgc gcagagcacc     480
gctgcaactg ccgaggagat agaggtacac atgcccccag acaccccaga tcgcacatta     540
atgtcacaac agtccggcaa tgtaaagatc acagtcaata gtcagacggt gcggtacaag     600
tgcaattgtg gtgactcaag tgaaggatta accactacag ataaagtgat taataactgc     660
aaggtcgatc aatgccatgc cgcggtcacc aatcacaaaa atggcagta taattcccct     720
ctggtcccgc gtaatgctga attcggggac cggaaaggaa aagttcacat tccatttcct     780
ctggcaaatg tgacatgcag ggtgcctaaa gcaagaaacc ccaccgtgac gtacggaaaa     840
aaccaagtca tcatgttgct gtatcctgac acccaacgc tcctgtccta caggaatatg     900
ggagaagaac caaactatca agaagagtgg gtgacgcata agaaggagat caggttaacc     960
gtgccgactg aggggctcga ggtcacgtgg ggtaacaatg agccgtacaa gtattggccg    1020
cagttatcca caaacggtac agcccacggc caccgcatg agataattct gtattattat    1080
gagctgtacc caactatgac tgcggtagtt ttgtcagtgg cctcgttcat actcctgtcg    1140
atggtgggtg tggcagtggg gatgtgcatg tgtgcacgac gcagatgcat tacaccgtac    1200
gaactgacac caggagctac cgtcccttc ctgcttagcc taatatgctg cattagaaca    1260
gctaaagcg                                                            1269
```

<210> SEQ ID NO 271
<211> LENGTH: 423
<212> TYPE: PRT
<213> ORGANISM: Chikungunya virus

<400> SEQUENCE: 271

```
Ser Thr Lys Asp Asn Phe Asn Val Tyr Lys Ala Thr Arg Pro Tyr Leu
 1               5                  10                  15

Ala His Cys Pro Asp Cys Gly Glu Gly His Ser Cys His Ser Pro Ile
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95
```

Met Gly His Phe Ile Leu Ala Arg Cys Pro Lys Gly Glu Thr Leu Thr
              100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140

Pro Gln His Gly Lys Glu Leu Pro Cys Ser Thr Tyr Val Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Thr Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Ile Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Thr Met Leu Leu Tyr
        275                 280                 285

Pro Asp His Pro Thr Leu Leu Ser Tyr Arg Asn Met Gly Gln Glu Pro
    290                 295                 300

Asn Tyr His Glu Glu Trp Val Thr His Lys Lys Glu Val Thr Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Met Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Ile Ile Val Ser Val Ala Ser Phe Val Leu Ser Met Val Gly Thr
    370                 375                 380

Ala Val Gly Met Cys Val Cys Ala Arg Arg Arg Cys Ile Thr Pro Tyr
385                 390                 395                 400

Glu Leu Thr Pro Gly Ala Thr Val Pro Phe Leu Leu Ser Leu Leu Cys
                405                 410                 415

Cys Val Arg Thr Thr Lys Ala
            420

<210> SEQ ID NO 272
<211> LENGTH: 423
<212> TYPE: PRT
<213> ORGANISM: Chikungunya virus

<400> SEQUENCE: 272

Ser Ile Lys Asp His Phe Asn Val Tyr Lys Ala Thr Arg Pro Tyr Leu
1               5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
                100                 105                 110

Ala Gly Phe Thr Asp Gly Arg Lys Ile Ser His Ser Cys Thr His Pro
                115                 120                 125

Phe His His Asp Pro Pro Val Ile Gly Arg Glu Lys Phe His Ser Arg
                130                 135                 140

Pro Gln His Gly Arg Glu Leu Pro Cys Ser Thr Tyr Ala Gln Ser Thr
145                 150                 155                 160

Ala Ala Thr Ala Glu Glu Ile Glu Val His Met Pro Pro Asp Thr Pro
                165                 170                 175

Asp Arg Thr Leu Met Ser Gln Gln Ser Gly Asn Val Lys Ile Thr Val
                180                 185                 190

Asn Ser Gln Thr Val Arg Tyr Lys Cys Asn Cys Gly Asp Ser Ser Glu
                195                 200                 205

Gly Leu Thr Thr Thr Asp Lys Val Ile Asn Asn Cys Lys Val Asp Gln
                210                 215                 220

Cys His Ala Ala Val Thr Asn His Lys Lys Trp Gln Tyr Asn Ser Pro
225                 230                 235                 240

Leu Val Pro Arg Asn Ala Glu Phe Gly Asp Arg Lys Gly Lys Val His
                245                 250                 255

Ile Pro Phe Pro Leu Ala Asn Val Thr Cys Arg Val Pro Lys Ala Arg
                260                 265                 270

Asn Pro Thr Val Thr Tyr Gly Lys Asn Gln Val Ile Met Leu Leu Tyr
                275                 280                 285

Pro Asp His Pro Thr Leu Leu Ser Tyr Arg Asn Met Gly Glu Glu Pro
                290                 295                 300

Asn Tyr Gln Glu Glu Trp Val Thr His Lys Lys Glu Ile Arg Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
                340                 345                 350

His Glu Ile Ile Leu Tyr Tyr Tyr Glu Leu Tyr Pro Thr Met Thr Ala
                355                 360                 365

Val Val Leu Ser Val Ala Ser Phe Ile Leu Leu Ser Met Val Gly Val
                370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
                420

<210> SEQ ID NO 273
<211> LENGTH: 423
<212> TYPE: PRT
<213> ORGANISM: Chikungunya virus

<400> SEQUENCE: 273

```
Ser Ile Lys Asp Asn Phe Asn Val Tyr Lys Ala Ile Arg Pro Tyr Leu
1               5                   10                  15
Ala His Cys Pro Asp Cys Gly Glu Gly His Ser Cys His Ser Pro Val
            20                  25                  30
Ala Leu Glu Arg Ile Arg Asn Glu Ala Thr Asp Gly Thr Leu Lys Ile
        35                  40                  45
Gln Val Ser Leu Gln Ile Gly Ile Lys Thr Asp Ser His Asp Trp
    50                  55                  60
Thr Lys Leu Arg Tyr Met Asp Asn His Met Pro Ala Asp Ala Glu Arg
65                  70                  75                  80
Ala Arg Leu Phe Val Arg Thr Ser Ala Pro Cys Thr Ile Thr Gly Thr
                85                  90                  95
Met Gly His Phe Ile Leu Ala Arg Cys Pro Lys Gly Glu Thr Leu Thr
            100                 105                 110
Val Gly Phe Thr Asp Gly Arg Lys Ile Ser His Ser Cys Thr His Pro
        115                 120                 125
Phe His His Asp Pro Pro Val Ile Gly Arg Glu Lys Phe His Ser Arg
    130                 135                 140
Pro Gln His Gly Arg Glu Leu Pro Cys Ser Thr Tyr Ala Gln Ser Thr
145                 150                 155                 160
Ala Ala Thr Ala Glu Glu Ile Glu Val His Met Pro Pro Asp Thr Pro
                165                 170                 175
Asp Arg Thr Leu Met Ser Gln Gln Ser Gly Asn Val Lys Ile Thr Val
            180                 185                 190
Asn Ser Gln Thr Val Arg Tyr Lys Cys Asn Cys Gly Asp Ser Asn Glu
        195                 200                 205
Gly Leu Thr Thr Thr Asp Lys Val Ile Asn Asn Cys Lys Val Asp Gln
    210                 215                 220
Cys His Ala Ala Val Thr Asn His Lys Lys Trp Gln Tyr Asn Ser Pro
225                 230                 235                 240
Leu Val Pro Arg Asn Ala Glu Leu Gly Asp Arg Lys Gly Lys Val His
                245                 250                 255
Ile Pro Phe Pro Leu Ala Asn Val Thr Cys Arg Val Pro Lys Ala Arg
            260                 265                 270
Asn Pro Thr Val Thr Tyr Gly Lys Asn Gln Val Ile Met Leu Leu Tyr
        275                 280                 285
Pro Asp His Pro Thr Leu Leu Ser Tyr Arg Asn Met Gly Glu Glu Pro
    290                 295                 300
Asn Tyr Gln Glu Glu Trp Val Thr His Lys Lys Glu Ile Arg Leu Thr
305                 310                 315                 320
Val Pro Thr Glu Gly Leu Glu Val Thr Trp Gly Asn Asn Glu Pro Tyr
                325                 330                 335
Lys Tyr Trp Pro Gln Leu Ser Thr Asn Gly Thr Ala His Gly His Pro
            340                 345                 350
His Glu Ile Ile Leu Tyr Tyr Tyr Glu Leu Tyr Pro Thr Met Thr Val
        355                 360                 365
Val Val Val Ser Val Ala Ser Phe Val Leu Leu Ser Met Val Gly Val
    370                 375                 380
Ala Val Gly Met Cys Met Cys Ala Arg Arg Arg Cys Ile Thr Pro Tyr
385                 390                 395                 400
Glu Leu Thr Pro Gly Ala Thr Val Pro Phe Leu Leu Ser Leu Ile Cys
                405                 410                 415
```

Cys Ile Arg Thr Ala Lys Ala
            420

<210> SEQ ID NO 274
<211> LENGTH: 423
<212> TYPE: PRT
<213> ORGANISM: Chikungunya virus

<400> SEQUENCE: 274

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Gly Thr Asp Asp Ser His Asp Trp
    50                  55                  60

Thr Lys Leu Arg Tyr Met Asp Asn His Ile Pro Ala Asp Ala Gly Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Lys Glu Leu Pro Cys Ser Thr Tyr Val Gln Ser Asn
145                 150                 155                 160

Ala Ala Thr Ala Glu Glu Ile Glu Val His Met Pro Pro Asp Thr Pro
                165                 170                 175

Asp Arg Thr Leu Leu Ser Gln Gln Ser Gly Asn Val Lys Ile Thr Val
            180                 185                 190

Asn Ser Gln Thr Val Arg Tyr Lys Cys Asn Cys Gly Gly Ser Asn Glu
        195                 200                 205

Gly Leu Ile Thr Thr Asp Lys Val Ile Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Met Val Pro Lys Ala Arg
            260                 265                 270

Asn Pro Thr Val Thr Tyr Gly Lys Asn Gln Val Ile Met Leu Leu Tyr
        275                 280                 285

Pro Asp His Pro Thr Leu Leu Ser Tyr Arg Ser Met Gly Glu Glu Pro
    290                 295                 300

Asn Tyr Gln Glu Glu Trp Val Thr His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Ala Asn Gly Thr Ala His Gly His Pro
            340                 345                 350

His Glu Ile Ile Leu Tyr Tyr Tyr Glu Leu Tyr Pro Thr Met Thr Val

```
                355                 360                 365
Val Val Val Ser Val Ala Ser Phe Ile Leu Leu Ser Met Val Gly Met
            370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
            420

<210> SEQ ID NO 275
<211> LENGTH: 423
<212> TYPE: PRT
<213> ORGANISM: Chikungunya virus

<400> SEQUENCE: 275

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Ser His Asp Trp
    50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp Arg Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
        275                 280                 285

Pro Asp His Pro Thr Leu Leu Ser Tyr Arg Asn Met Gly Glu Glu Pro
    290                 295                 300
```

```
Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Val Val Ser Val Ala Thr Phe Ile Leu Leu Ser Met Val Gly Met
    370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
            420

<210> SEQ ID NO 276
<211> LENGTH: 423
<212> TYPE: PRT
<213> ORGANISM: Chikungunya virus

<400> SEQUENCE: 276

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
                20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
    50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
    115                 120                 125

Phe His His Asp Pro Pro Val Ile Gly Arg Glu Lys Phe His Ser Arg
130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp Arg Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
    195                 200                 205

Gly Leu Thr Thr Thr Asp Lys Val Ile Asn Asn Cys Lys Val Asp Gln
210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255
```

```
Ile Pro Phe Pro Leu Ala Asn Val Thr Cys Arg Val Pro Lys Ala Arg
            260                 265                 270
Asn Pro Thr Val Thr Tyr Gly Lys Asn Gln Val Ile Met Leu Leu Tyr
275             280                     285
Pro Asp His Pro Thr Leu Leu Ser Tyr Arg Asn Met Gly Glu Glu Pro
        290             295                 300
Asn Tyr Gln Glu Glu Trp Val Met His Lys Lys Glu Val Val Leu Thr
305             310                 315                 320
Val Pro Thr Glu Gly Leu Glu Val Thr Trp Gly Asn Asn Glu Pro Tyr
                325                 330                 335
Lys Tyr Trp Pro Gln Leu Ser Thr Asn Gly Thr Ala His Gly His Pro
                340                 345                 350
His Glu Ile Ile Leu Tyr Tyr Tyr Glu Leu Tyr Pro Thr Met Thr Val
            355                 360                 365
Val Val Val Ser Val Ala Thr Phe Ile Leu Leu Ser Met Val Gly Met
        370                 375                 380
Ala Ala Gly Met Cys Met Cys Ala Arg Arg Arg Cys Ile Thr Pro Tyr
385                 390                 395                 400
Glu Leu Thr Pro Gly Ala Thr Val Pro Phe Leu Leu Ser Leu Ile Cys
                405                 410                 415
Cys Ile Arg Thr Ala Lys Ala
                420
```

ANTIBODY-MEDIATED NEUTRALIZATION OF CHIKUNGUNYA VIRUS

This application is a national phase application under 35 U.S.C § 371 of International Application No. PCT/US2016/027466, filed Apr. 14, 2016, which claims benefit of priority to U.S. Provisional Application Ser. No. 62/147,354, filed Apr. 14, 2015, the entire contents of which are hereby incorporated by reference.

This invention was made with government support under grant numbers AI103038, AI096833, AI057157, AI114816 and HHSN272201400018C awarded by the National Institutes of Health and under grant number W911NF-13-1-0417 awarded by the Department of Defense. The government has certain rights in the invention.

BACKGROUND

1. Field of the Disclosure

The present disclosure relates generally to the fields of medicine, infectious disease, and immunology. More particular, the disclosure relates to antibodies that neutralize Chikungunya virus.

2. Background

Chikungunya virus (CHIKV) is an enveloped, positive-sense RNA virus in the Alphavirus genus of the Togaviridae family and is transmitted by *Aedes* mosquitoes. The mature CHIKV virion contains two glycoproteins, E1 and E2, which are generated from a precursor polyprotein, p62-E1, by proteolytic cleavage. E2 functions in viral attachment, whereas E1 mediates membrane fusion to allow viral entry (Kielian et al., 2010). In humans, CHIKV infection causes fever and joint pain, which may be severe and last in some cases for years (Schilte et al., 2013; Sissoko et al., 2009; Staples et al., 2009). CHIKV has caused outbreaks in most regions of sub-Saharan Africa and also in parts of Asia, Europe, and the Indian and Pacific Oceans. In December 2013, the first transmission of CHIKV in the Western Hemisphere occurred, with autochthonous cases identified in St. Martin (CDC 2013). The virus spread rapidly to virtually all islands in the Caribbean as well as Central, South, and North America. In less than one year, over a million suspected CHIKV cases in the Western Hemisphere were reported, and endemic transmission in more than 40 countries, including the United States was documented (CDC, 2014). At present, there is no licensed vaccine or antiviral therapy to prevent or treat CHIKV infection.

Although mechanisms of protective immunity to CHIKV infection in humans are not fully understood, the humoral response controls infection and limits tissue injury (Chu et al., 2013; Hallengard et al., 2014; Hawman et al., 2013; Kam et al., 2012b; Lum et al., 2013; Pal et al., 2013). Immune human γ-globulin neutralizes infectivity in cultured cells and prevents morbidity in mice when administered up to 24 hours after viral inoculation (Couderc et al., 2009). Several murine monoclonal antibodies (mAbs) that neutralize CHIKV infection have been described (Brehin et al., 2008; Goh et al., 2013; Masrinoul et al., 2014; Pal et al., 2013; Pal et al., 2014), including some with efficacy when used in combination to treat mice or nonhuman primates following CHIKV challenge (Pal et al., 2013; Pal et al., 2014). In comparison, a limited number of human CHIKV mAbs have been reported, the vast majority of which exhibit modest neutralizing activity (Fong et al., 2014; Fric et al., 2013; Lee et al., 2011; Selvarajah et al., 2013; Warter et al., 2011).

SUMMARY

Thus, in accordance with the present disclosure, there is provided a method of detecting a Chikungunya virus infection in a subject comprising (a) contacting a sample from said subject with an antibody or antibody fragment having clone-paired heavy and light chain CDR sequences from Tables 3 and 4, respectively; and (b) detecting Chikungunya virus glycoprotein E2 in said sample by binding of said antibody or antibody fragment to E2 in said sample. The sample may be a body fluid, such as blood, sputum, tears, saliva, mucous or serum, urine or feces. Detection may comprise ELISA, RIA or Western blot. The method may further comprise performing steps (a) and (b) a second time and determining a change in the E2 levels as compared to the first assay. The antibody may be encoding by clone-paired variable sequences as set forth in Table 1, or encoded by light and heavy chain variable sequences having 70%, 80%, 90% or 95% identity to clone-paired variable sequences as set forth in Table 1, or having light and heavy chain variable sequences characterized by clone-paired sequences as set forth in Table 2, or having 70%, 80%, 90% or 95% identity to clone-paired sequences from Table 2. The antibody fragment may be a recombinant ScFv (single chain fragment variable) antibody, Fab fragment, F(ab')2 fragment, or Fv fragment. The antibody may be an IgG, and/or a chimeric antibody.

In another embodiment, there is provided a method of treating a subject infected with Chikungunya Virus, or reducing the likelihood of infection of a subject at risk of contracting Chikungunya virus, comprising delivering to said subject an antibody or antibody fragment having clone-paired heavy and light chain CDR sequences from Tables 3 and 4, respectively. The antibody may be encoding by clone-paired variable sequences as set forth in Table 1, or encoded by light and heavy chain variable sequences having 70%, 80%, 90% or 95% identity to clone-paired variable sequences as set forth in Table 1, or having light and heavy chain variable sequences characterized by clone-paired sequences as set forth in Table 2, or having 70%, 80%, 90% or 95% identity to clone-paired sequences from Table 2. The antibody fragment may be a recombinant ScFv (single chain fragment variable) antibody, Fab fragment, F(ab')2 fragment, or Fv fragment. The antibody may be an IgG, and/or a chimeric antibody. The antibody or antibody fragment may be administered prior to infection, or after infection. Delivering may comprise antibody or antibody fragment administration, or genetic delivery with an RNA or DNA sequence or vector encoding the antibody or antibody fragment.

In still yet another embodiment, there is provided a monoclonal antibody, wherein the antibody is characterized by clone-paired heavy and light chain CDR sequences from Tables 3 and 4, respectively. The antibody may be encoding by clone-paired variable sequences as set forth in Table 1, or encoded by light and heavy chain variable sequences having 70%, 80%, 90% or 95% identity to clone-paired variable sequences as set forth in Table 1, or having light and heavy chain variable sequences characterized by clone-paired sequences as set forth in Table 2, or having 70%, 80%, 90% or 95% identity to clone-paired sequences from Table 2. The antibody fragment may be a recombinant ScFv (single chain fragment variable) antibody, Fab fragment, F(ab')2 fragment, or Fv fragment. The antibody may be a chimeric antibody, or a bispecific antibody that targets a Chikungunya virus antigen other than glycoprotein. The antibody may be an IgG. The antibody or antibody fragment further comprises a cell penetrating peptide and/or is an intrabody.

Also provided is a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoding by clone-paired variable sequences as set forth in Table 1, or encoded by light and heavy chain variable sequences having 70%, 80%, 90% or 95% identity to clone-paired variable sequences as set forth in Table 1, or having light and heavy chain variable sequences characterized by clone-paired sequences as set forth in Table 2, or having 70%, 80%, 90% or 95% identity to clone-paired sequences from Table 2. The antibody fragment may be a recombinant ScFv (single chain fragment variable) antibody, Fab fragment, F(ab')2 fragment, or Fv fragment. The antibody may be a chimeric antibody, and/or an IgG. The antibody or antibody fragment further may comprise a cell penetrating peptide and/or is an intrabody.

In one embodiment, the isolated monoclonal antibody or antigen-binding fragment thereof that specifically binds to Chikungunya virus glycoprotein E2, comprises heavy and light chain variable sequence pairs selected from the group consisting of SEQ ID NOs: 53/54, 55/56. 57/58. 59/60, 61/62, 63/64, 65/66, 67/68, 70/71, 72/73, 74/75, 76/77, 81/82, 83/84, 85/86. 87/88, 89/90, 91/92, 93/94, 95/96, and 97/98.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 103, 104 and 105, respectively and CDRL1, CDRL2 and CDRL3 amino acid sequences of SEQ ID NOs: 187, 188 and 189, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 106, 107 and 108, respectively and CDRL1, CDRL2 and CDRL3 amino acid sequences of SEQ ID NOs: 190, 191 and 192, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 109, 110 and 111, respectively and CDRL1, CDRL2 and CDRL3 amino acid sequences of SEQ ID NOs: 193, 194 and 195, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 112, 113 and 114, respectively and CDRL1, CDRL2 and CDRL3 amino acid sequences of SEQ ID NOs: 196, 197 and 198, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 115, 116 and 117, respectively and CDRL1, CDRL2 and CDRL3 amino acid sequences of SEQ ID NOs: 199, 200 and 201, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 118, 119 and 120, respectively and CDRL1, CDRL2 and CDRL3 amino acid sequences of SEQ ID NOs: 202, 203 and 204, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 121, 122 and 123, respectively and CDRL1, CDRL2 and CDRL3 amino acid sequences of SEQ ID NOs: 205, 206 and 207, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 124, 125 and 126, respectively and CDRL1, CDRL2 and CDRL3 amino acid sequences of SEQ ID NOs: 208, 209 and 210, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 130, 131 and 132, respectively and CDRL1, CDRL2 and CDRL3 amino acid sequences of SEQ ID NOs: 211, 212 and 213, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 133, 134 and 135, respectively and CDRL1, CDRL2 and CDRL3 amino acid sequences of SEQ ID NOs: 214, 215 and 216, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 136, 137 and 138, respectively and CDRL1, CDRL2 and CDRL3 amino acid sequences of SEQ ID NOs: 217, 218 and 219, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 139, 140 and 141, respectively and CDRL1, CDRL2 and CDRL3 amino acid sequences of SEQ ID NOs: 220, 221 and 222, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 151, 152 and 153, respectively and CDRL1, CDRL2 and CDRL3 amino acid sequences of SEQ ID NOs: 223, 224 and 225, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 154, 155 and 156, respectively and CDRL1, CDRL2 and CDRL3 amino acid sequences of SEQ ID NOs: 226, 227 and 228, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 157, 158 and 159, respectively and CDRL1, CDRL2 and CDRL3 amino acid sequences of SEQ ID NOs: 229, 230 and 231, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 160, 161 and 162, respectively and CDRL1, CDRL2 and CDRL3 amino acid sequences of SEQ ID NOs: 232, 233 and 234, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 163, 164 and 165, respectively and CDRL1, CDRL2 and CDRL3 amino acid sequences of SEQ ID NOs: 235, 236 and 237, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 166, 167 and 168, respectively and CDRL1, CDRL2 and CDRL3 amino acid sequences of SEQ ID NOs: 238, 239 and 240, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 169, 170 and 171, respectively and CDRL1, CDRL2 and CDRL3 amino acid sequences of SEQ ID NOs: 241, 242 and 243, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 172, 173 and 174, respectively and CDRL1, CDRL2 and CDRL3 amino acid sequences of SEQ ID NOs: 244, 245, and 246, respectively.

In one embodiment, the isolated monoclonal antibody or antigen binding fragment thereof that specifically binds to Chikungunya virus glycoprotein E2 comprises the CDRH1, CDRH2 and CDRH3 amino acid sequences of SEQ ID NOs: 175, 176 and 177, respectively and CDRL1, CDRL2 and CDRL3 amino acid sequences of SEQ ID NOs: 247, 248 and 249, respectively.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Sequence alignment of E2 from the CHIKV strains used in this study. Strain name is indicated on the left (S27, SEQ ID NO: 1, Accession number AF369024.2; SL15649, Accession number GU189061; LR2006_OPY1, Accession number DQ443544.2; 99659, Accession number KJ451624; RSU1, Accession number HM045797.1; NI 64 IbH35, Accession number HM045786.1). The numbers above the sequence correspond to the amino acid position in the mature E2 protein. Amino acids identical to strain S27 are indicated by a dash. Domains of E2 determined from the crystal structure of the CHIKV E2/E1 heterodimer (Voss et al., 2010) are depicted in the diagram above the sequence alignment and are color-coded (cyan: domain A, purple: β-ribbon connector, green: domain B, pink: domain C, taupe shades: regions not present in the crystal structure). The position of residues at which alanine substitution disrupts mAb binding, as determined by alanine-scanning mutagenesis, are designated by color-coded dots above the alignment for each specific antibody. Residues that influence the binding of multiple antibodies are indicated by squares shaded in gray, with the darker the shade of gray, the greater number of antibodies influenced by the alanine substitution at that residue. (FIG. 1B) Location of residues required for mAb binding mapped onto the crystal structure of the mature envelope glycoprotein complex (PDB ID 3N41). A side view of a ribbon trace of a single heterodimer of E1/E2 is shown with E1 colored in light cyan and the domains of E2 colored as in panel A. The side chains of the amino acids required for antibody binding are shown as space-filling forms and color-coded for each of the 20 individual antibodies according to the legend in panel A. Residues that influence the binding of multiple antibodies are depicted in shades of gray with the darker the shade, the greater the number of antibodies influenced by alanine substitution at that residue (legend shown on the left). (FIG. 1C) A top view of the E1/E2 heterodimer, rotated 90° from the structure in FIG. 1B.

FIGS. 2A-B. Mechanism of neutralization by human anti-CHIKV mAbs. (FIG. 2A) Pre- and post-attachment neutralization assays. SL15649 VRPs were (i) incubated with the mAbs shown (including CHK-152, a positive control mAb) at 4° C. for 1 hour prior to addition to pre-chilled Vero cells, followed by removal of unbound virus by three washes (pre-attachment; filled circle) or (ii) allowed to adsorb to pre-chilled Vero cells at 4° C. for 1 hour, followed by addition of the indicated mAbs at 4° C. for 1 hour (post-attachment; open circles). (FIG. 2B) FFWO assay. SL15649 VRPs were adsorbed to pre-chilled Vero cells at 4° C. for 1 hour, followed by addition of the mAbs shown (including CHK-152, a positive control murine mAb) for 1 hour. Unbound virus was removed, and cells were exposed to low pH medium (pH 5.5; filled circles) at 37° C. for 2 min to trigger viral fusion at the plasma membrane. As a negative control, cells were exposed to neutral pH medium (pH 7.4; open circles) at 37° C. for 2 min. For both FIG. 2A and FIG. 2B, cells were incubated at 37° C. until 18 hours after infection, and GFP-positive cells were quantified using fluorescence microscopy. The data are combined from two independent experiments, each performed in triplicate.

(FIG. 3A) Mice were administered 50 μg of indicated CHIKV-specific or control mAb by intraperitoneal injection 24 hours before a lethal challenge of CHIKV (n=3 to 6 mice per mAb tested). (FIG. 3B) Mice were administered 50 μg of indicated CHIKV-specific or control mAb by intraperitoneal injection 24 hours after a lethal challenge of CHIKV (n=4 to 6 mice per mAb tested). (FIG. 3C) Mice were administered 250 μg of indicated CHIKV-specific or control mAb by intraperitoneal injection 48 hours after a lethal challenge of CHIKV (n=7 to 10 mice per mAb tested). (FIG. 3D) Mice were administered 250 μg of indicated pair of CHIKV-specific mAbs or a control mAb by intraperitoneal injection 60 hours after a lethal challenge of CHIKV (n=8 mice per mAb combination tested with the exception of 4J21+2H1, which is an n=3). For monotherapy with 4J21 or 4N12, a single dose of 500 μg was given (n=4 to 5 mice per mAb tested).

FIG. 5. Identification of mAb competition groups. Quantitative competition binding using Octet-based biolayer interferometry was used to assign mAbs to competition groups. Anti-Penta-His biosensor tips covered with immobilized CHIKV-LR2006 E2 ectodomain were immersed into wells containing primary mAb, followed by immersion into wells containing competing mAbs. The values shown are the percent binding of the competing mAb in the presence of the first mAb (determined by comparing the maximal signal of competing mAb applied after the first mAb complex to the maximal signal of competing mAb alone). MAbs were judged to compete well for binding to the same site if maximum binding of the competing mAb was reduced to <30% of its non-competed binding (black squares) or to exhibit partial completion if the binding of the competing mAb was reduced to <70% of its non-competed binding (gray squares). MAbs were considered non-competing if maximum binding of the competing mAb was >70% of its non-competed binding (white squares). Four competition-binding groups were identified, indicated by colored boxes. The corresponding major antigenic sites for mAbs discovered by alanine-scanning mutagenesis (Table 1 and FIGS. 1A-C) are summarized in the columns to the right of the competition matrix. DA indicates domain A; DB indicates domain B, e indicates both arch 1 and 2; NT indicates not tested; NotReact indicates that the mAb did not react against the wild-type envelope proteins; NoReduct indicates the mAb did bind to the wild-type E proteins, but no reduction was noted reproducibly for any mutant. The data are combined from one experiment, with multiple readings for each mAb alone and a single reading of a mAb in combination with each competing antibody.

FIG. 14. Half maximal effective inhibitory concentration ($EC_{50}$; ng/mL) for hybridoma-produced versus recombinant CHO cell-produced antibodies. Data are similar for hybridoma-produced versus recombinant.

Figure 15:
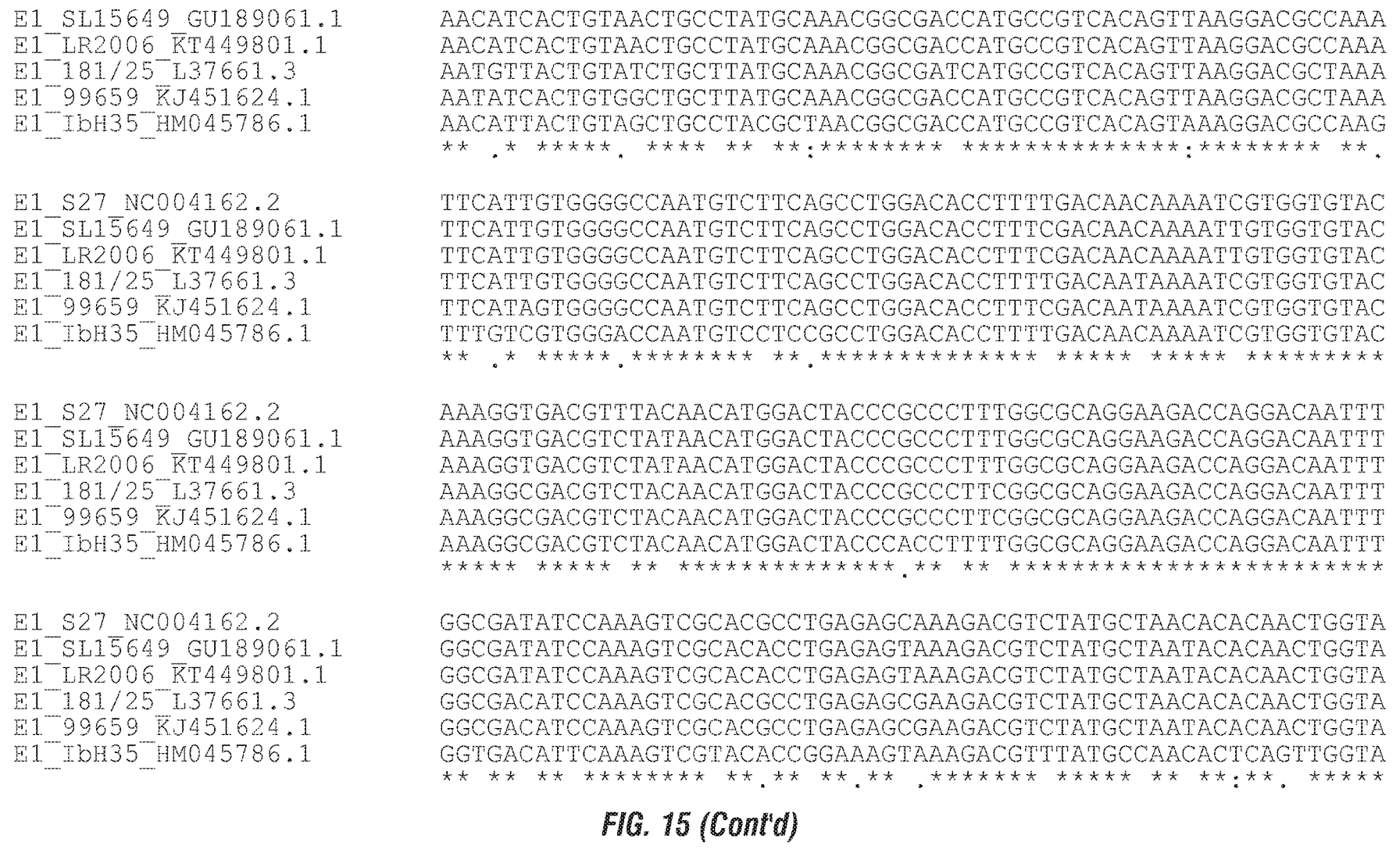
Figure 15:
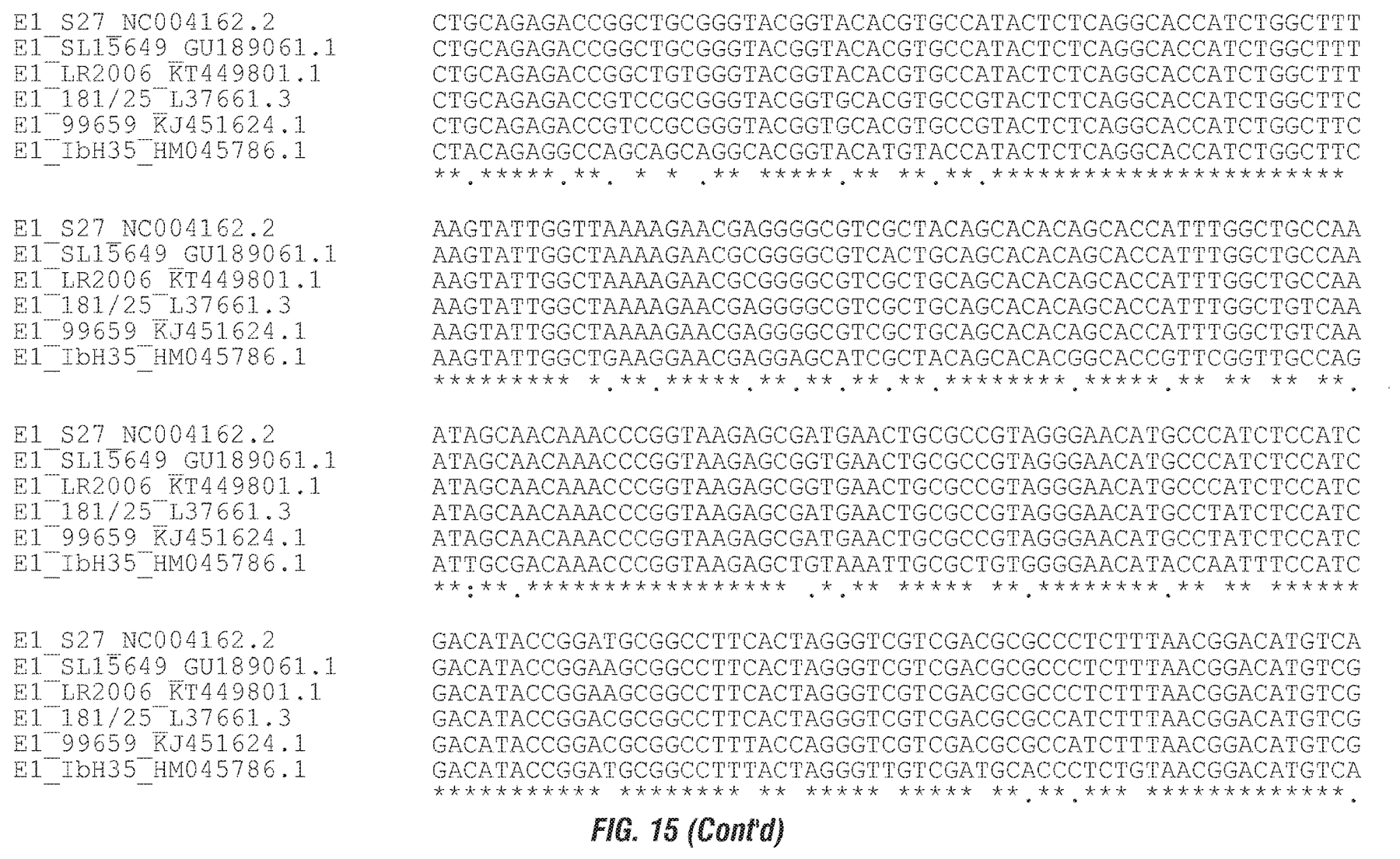
Figure 15:
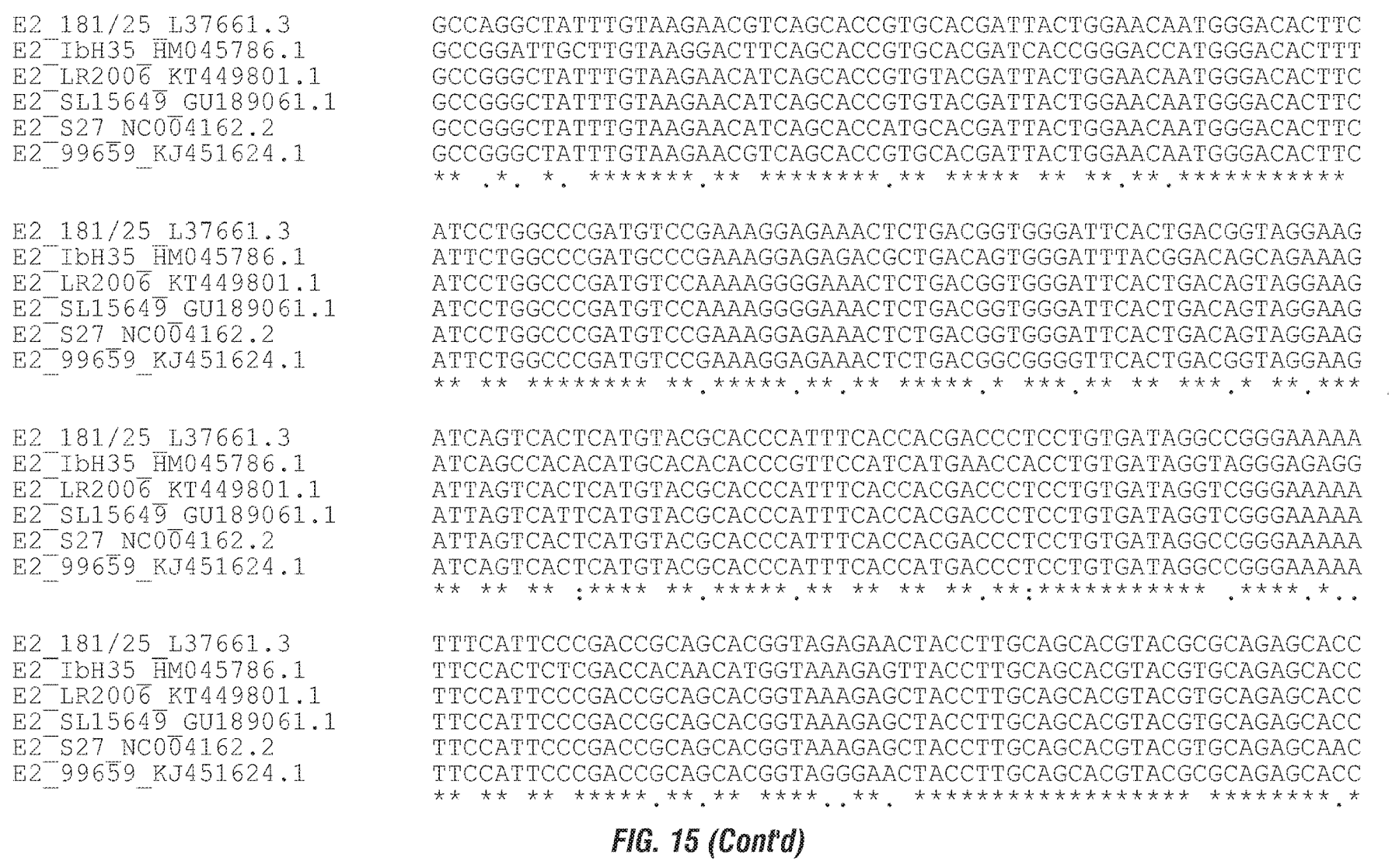
Figure 15:
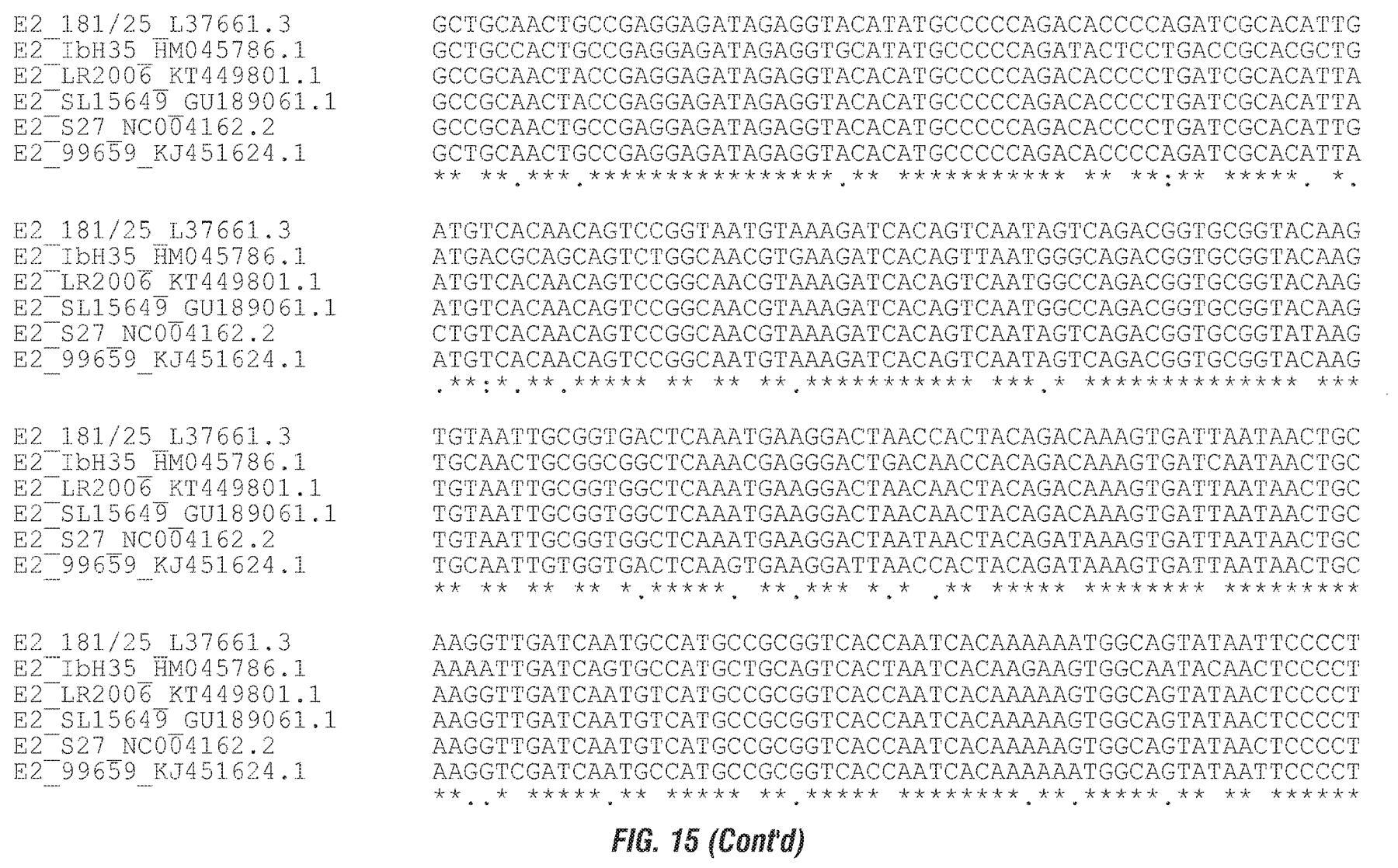
Figure 15:
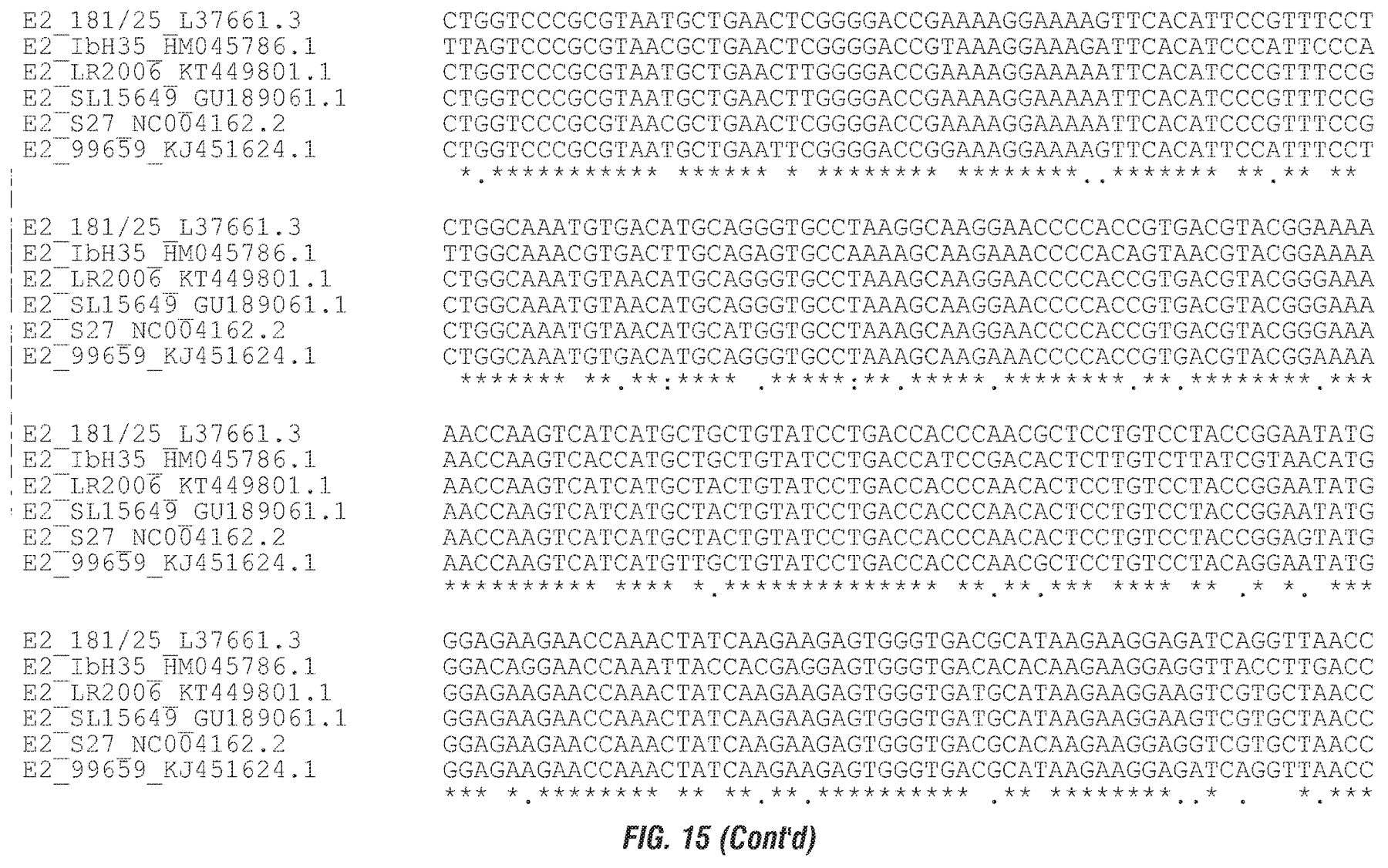
Figure 15:
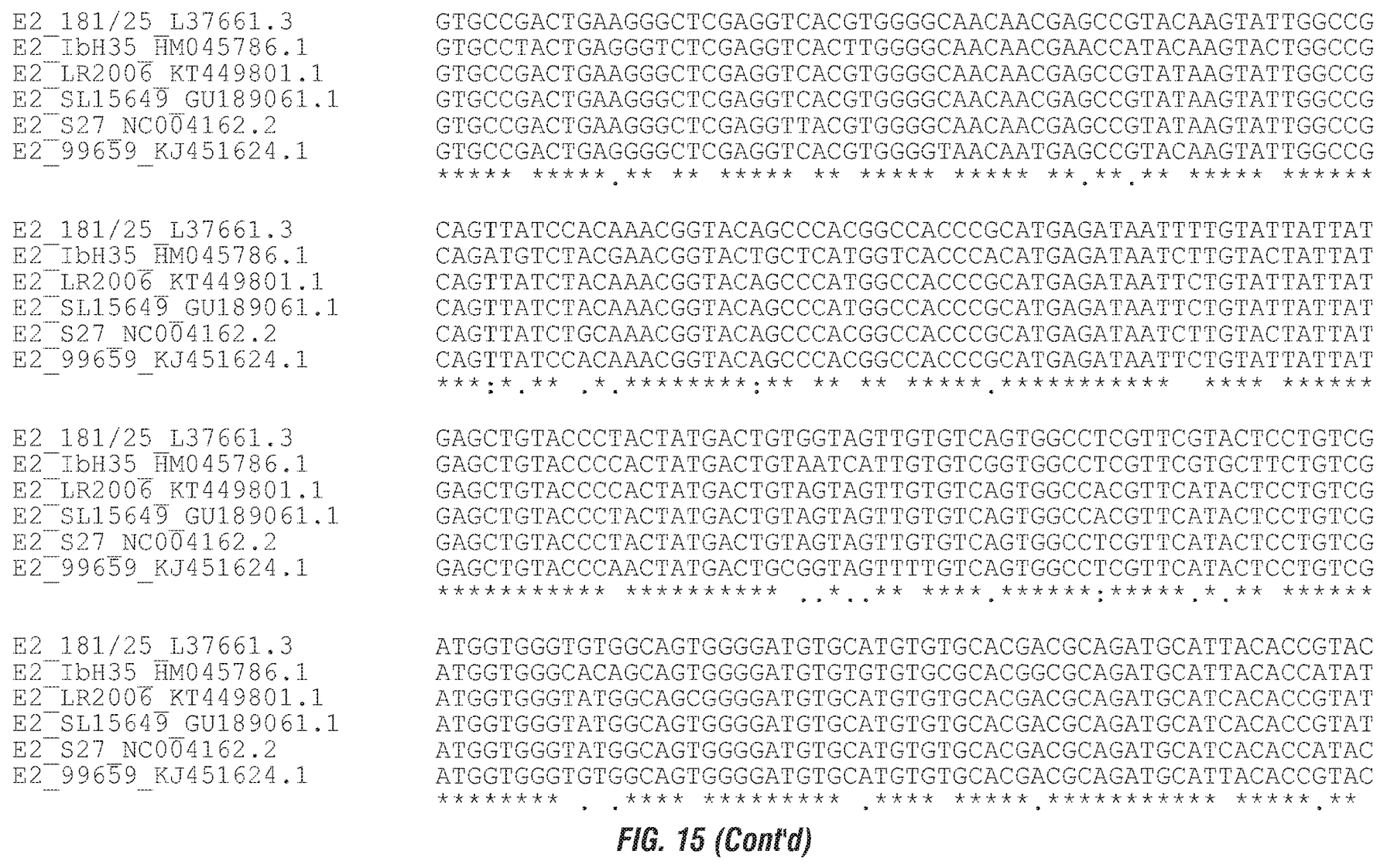

FIG. 15. Alignments of both the E1 and E2 proteins as amino acids, and the nucleotides for the genes that encode the proteins. Genbank accession number for proteins is listed with the virus strain. Three strains for viruses from the prototypic groups: East.Central.South Africa (ECSA), two for Asian, and the one West African strain are provided. These antibodies cross react across all strains.

DESCRIPTION OF ILLUSTRATIVE EMBODIMENTS

Figure 1A:
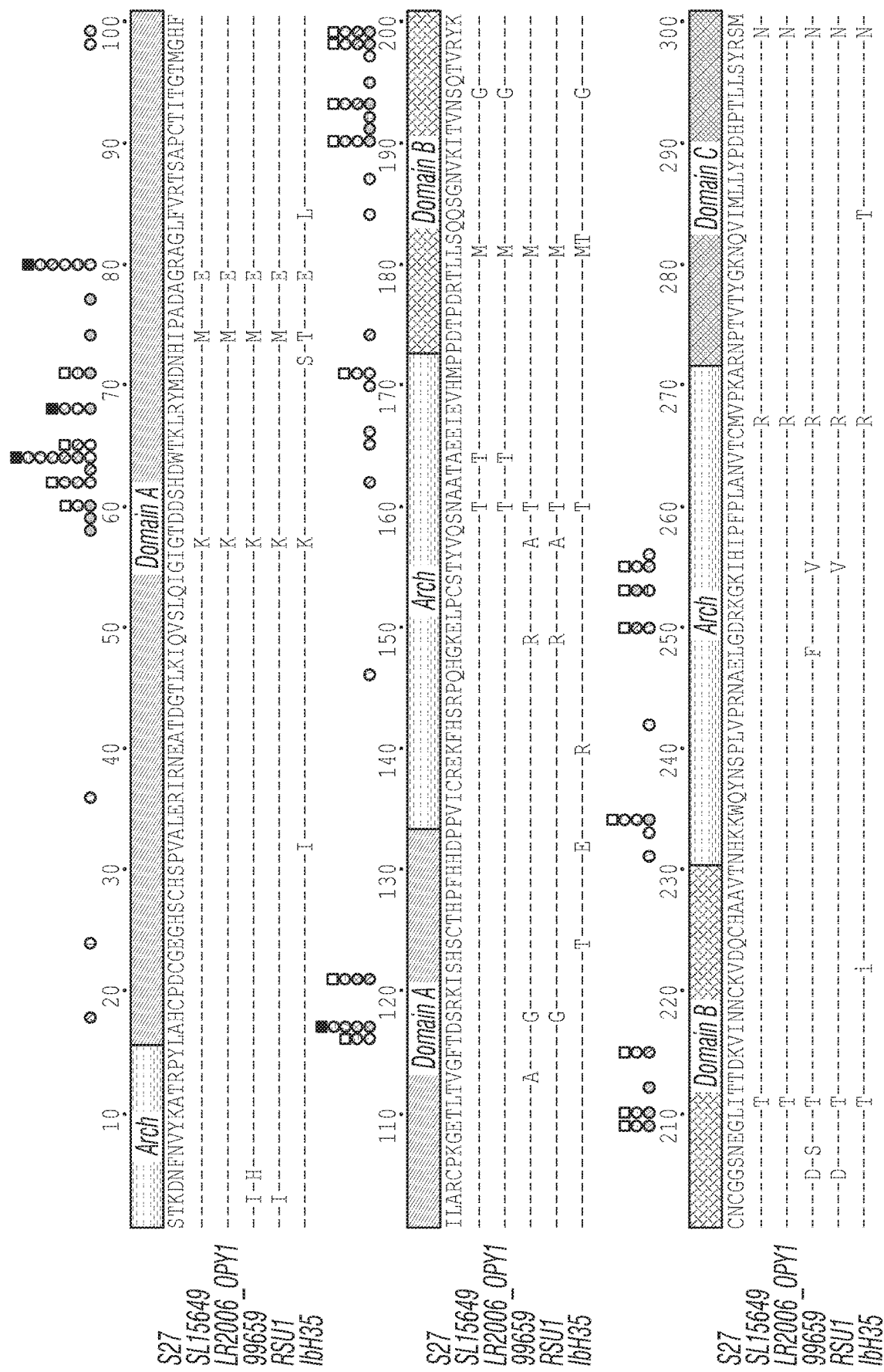
FIGS. 1A-C. Structural analysis of E2 residues important for mAb binding.
Figure 1A:
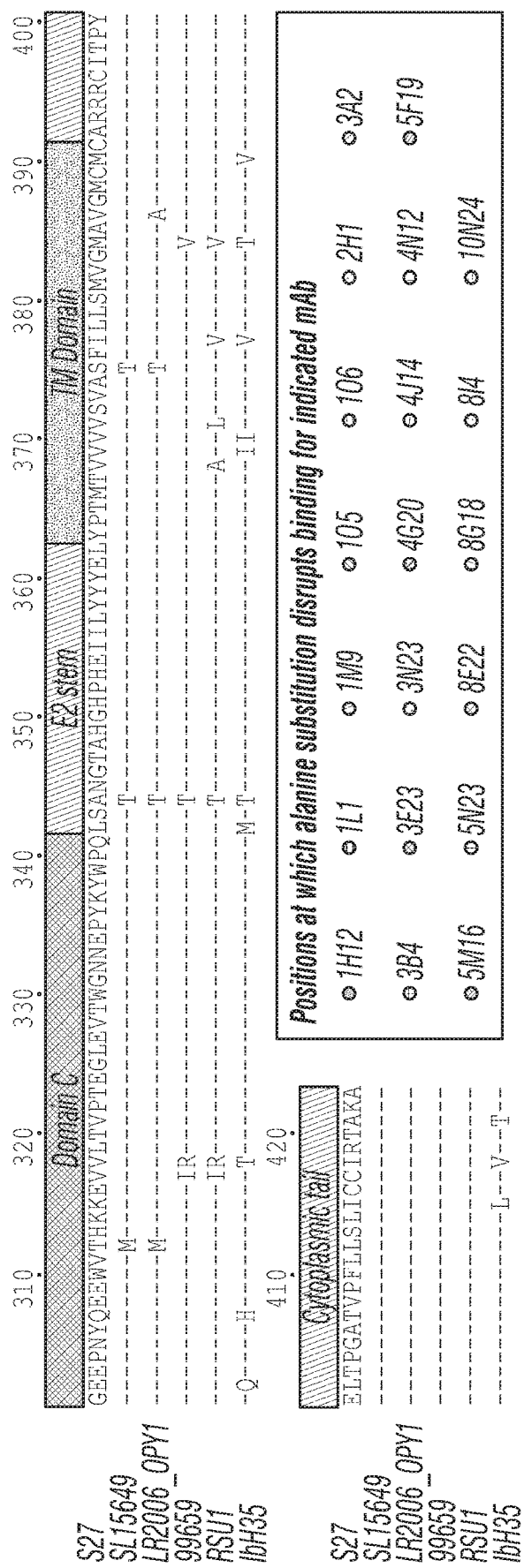

The inventors isolated a large panel of human mAbs that neutralize CHIKV infectivity in cell culture and successfully treated Ifnar$^{-/-}$ mice (lacking type I interferon receptors) inoculated with a lethal dose of CHIKV, even when administered as late as 60 hours after infection. They identified the A domain of E2 as the major antigenic site for recognition by mAbs that broadly neutralize CHIKV infection with ultrapotent activity and showed that the principal mechanism of inhibition is to prevent fusion. These and other aspects of the disclosure are described in detail below.

I. Chikungunya and Chikungunya Virus

Chikungunya is an infection caused by the chikungunya virus. It features sudden onset fever usually lasting two to seven days, and joint pains typically lasting weeks or months but sometimes years. The mortality rate is a little less than 1 in 1000, with the elderly most likely to die. The virus is passed to humans by two species of mosquito of the genus Aedes: *A. albopictus* and *A. aegypti*. Animal reservoirs of the virus include monkeys, birds, cattle, and rodents. This is in contrast to dengue, for which only primates are hosts.

The best means of prevention is overall mosquito control and the avoidance of bites by any infected mosquitoes. No specific treatment is known, but medications can be used to reduce symptoms. Rest and fluids may also be useful.

The incubation period of chikungunya disease ranges from two to twelve days, typically three to seven. Between 72 and 97% of those infected will develop symptoms. Symptoms include sudden onset, sometimes biphasic fever typically lasting from a few days to a week, sometimes up to ten days, usually above 39° C. (102° F.) and sometimes reaching 41° C. (104° F.), and strong joint pain or stiffness usually lasting weeks or months but sometimes lasting years. Rash (usually maculopapular), muscle pain, headache, fatigue, nausea or vomiting may also be present. Inflammation of the eyes may present as iridocyclitis, or uveitis, and retina lesions may occur. Typically, the fever lasts for two days and then ends abruptly. However, headache, insomnia and an extreme degree of prostration last for a variable period, usually about five to seven days.

Observations during recent epidemics have suggested chikungunya may cause long-term symptoms following acute infection. During the La Reunion outbreak in 2006, more than 50% of subjects over the age of 45 reported long-term musculoskeletal pain with up to 60% of people reporting prolonged painful joints three years following initial infection. A study of imported cases in France reported that 59% of people still suffered from arthralgia two years after acute infection. Following a local epidemic of chikungunya in Italy, 66% of people reported muscle pains, joint pains, or asthenia at one year after acute infection. Long-term symptoms are not an entirely new observation; long-term arthritis was observed following an outbreak in 1979. Common predictors of prolonged symptoms are increased age and prior rheumatological disease. The cause of these chronic symptoms is currently not fully known. Markers of autoimmune or rheumatoid disease have not been found in people reporting chronic symptoms. However, some evidence from humans and animal models suggests chikungunya may be able to establish chronic infections within the host. Viral antigen was detected in a muscle biopsy of a people suffering a recurrent episode of disease three months after initial onset. Additionally, viral antigen and RNA were found in synovial macrophages of a person during a relapse of musculoskeletal disease 18 months after initial infection. Several animal models have also suggested chikungunya virus may establish persistent infections. In a mouse model, viral RNA was detected specifically in joint-associated tissue for at least 16 weeks after inoculation, and was associated with chronic synovitis. Similarly, another study reported detection of a viral reporter gene in joint tissue of mice for weeks after inoculation. In a non-human primate model, chikungunya virus was found to persist in the spleen for at least six weeks.

Chikungunya virus is an alphavirus with a positive-sense single-stranded RNA genome of about 11.6 kb. It is a member of the Semliki Forest virus complex and is closely related to Ross River virus, O'nyong'nyong virus, and Semliki Forest virus. In the United States, it is classified as a category C priority pathogen and work requires biosafety level III precautions. Human epithelial and endothelial cells, primary fibroblasts, and monocyte-derived macrophages are permissive for chikungunya virus in vitro, and viral replication is highly cytopathic, but susceptible to type-I and -II interferon. In vivo, chikungunya virus appears to replicate in fibroblasts, skeletal muscle progenitor cells, and myofibers.

Chikungunya virus is an alphavirus, as are the viruses that cause eastern equine encephalitis and western equine encephalitis. Chikungunya is generally spread through bites from *A. aegypti* mosquitoes, but recent research by the Pasteur Institute in Paris has suggested chikungunya virus strains in the 2005-2006 Reunion Island outbreak incurred a mutation that facilitated transmission by the Asian tiger mosquito (*A. albopictus*).

Chikungunya virus infection of *A. albopictus* was caused by a point mutation in one of the viral envelope genes (E1). Enhanced transmission of chikungunya virus by *A. albopic-* tus could mean an increased risk for outbreaks in other areas where the Asian tiger mosquito is present. A recent epidemic in Italy was likely perpetuated by *A. albopictus*. In Africa, chikungunya is spread by a sylvatic cycle in which the virus largely resides in other primates between human outbreaks.

Upon infection with chikungunya, the host's fibroblasts produce type-1 (alpha and beta) interferon. Mice that lack the interferon alpha receptor die in two to three days upon being exposed to $10^2$ chikungunya PFUs, while wild-type mice survive even when exposed to as many as $10^6$ PFUs of the virus. At the same time, mice that are partially type-1 deficient (IFN $\alpha/\beta+/-$) are mildly affected and experience symptoms such as muscle weakness and lethargy. Partidos et al. (2011) saw similar results with the live attenuated strain CHIKV181/25. However, rather than dying, the type-1 interferon-deficient (IFN $\alpha/\beta-/-$) mice were temporarily disabled and the partially type-1 interferon-deficient mice did not have any problems.

Several studies have attempted to find the upstream components of the type-1 interferon pathway involved in the host's response to chikungunya infection. So far, no one knows the chikungunya-specific pathogen associated molecular pattern. Nonetheless, IPS-1—also known as Cardif, MAVS, and VISA—has been found to be an important factor. In 2011, White et al. found that interfering with IPS-1 decreased the phosphorylation of interferon regulatory factor 3 (IRF3) and the production of IFN-$\beta$. Other studies have found that IRF3 and IRF7 are important in an age-dependent manner. Adult mice that lack both of these regulatory factors die upon infection with chikungunya. Neonates, on the other hand, succumb to the virus if they are deficient in one of these factors.

Chikungunya counters the type-I interferon response by producing NS2, a nonstructural protein that degrades RBP1 and turns off the host cell's ability to transcribe DNA. NS2 interferes with the JAK-STAT signaling pathway and prevents STAT from becoming phosphorylated.

Common laboratory tests for chikungunya include RT-PCR, virus isolation, and serological tests. Virus isolation provides the most definitive diagnosis, but takes one to two weeks for completion and must be carried out in biosafety level III laboratories. The technique involves exposing specific cell lines to samples from whole blood and identifying chikungunya virus-specific responses. RT-PCR using nested primer pairs is used to amplify several chikungunya-specific genes from whole blood. Results can be determined in one to two days.

Serological diagnosis requires a larger amount of blood than the other methods, and uses an ELISA assay to measure chikungunya-specific IgM levels. Results require two to three days, and false positives can occur with infection via other related viruses, such as o'nyong'nyong virus and Semliki Forest virus.

The differential diagnosis may include infection with other mosquito-borne viruses, such as dengue, and influenza. Chronic recurrent polyarthralgia occurs in at least 20% of chikungunya patients one year after infection, whereas such symptoms are uncommon in dengue.

Currently, no specific treatment is available. Attempts to relieve the symptoms include the use of NSAIDs such as naproxen or paracetamol (acetaminophen) and fluids. Aspirin is not recommended. In those who have more than two weeks of arthritis, ribavirin may be useful. The effect of chloroquine is not clear. It does not appear to help acute disease, but tentative evidence indicates it might help those with chronic arthritis. Steroids do not appear useful, either.

Chikungunya is mostly present in the developing world. The epidemiology of chikungunya is related to mosquitoes, their environments, and human behavior. The adaptation of mosquitoes to the changing climate of North Africa around 5,000 years ago made them seek out environments where humans stored water. Human habitation and the mosquitoes' environments were then very closely connected. During periods of epidemics humans are the reservoir of the virus. During other times, monkey, birds and other vertebrates have served as reservoirs.

Three genotypes of this virus have been described: West African, East/Central/South African, and Asian genotypes. Explosive epidemics in Indian Ocean in 2005 and Pacific Islands in 2011, as well as now in the Americas, continue to change the distribution of genotypes.

On 28 May 2009 in Changwat Trang of Thailand, where the virus is endemic, the provincial hospital decided to deliver by Caesarean section a male baby from his chikungunya-infected mother, Khwanruethai Sutmueang, 28, a Trang native, to prevent mother-fetus virus transmission. However, after delivering the baby, the physicians discovered the baby was already infected with the virus, and put him into intensive care because the infection had left the baby unable to breathe by himself or to drink milk. The physicians presumed the virus might be able to be transmitted from a mother to her fetus, but without laboratory confirmation.

In December 2013, chikungunya was confirmed on the Caribbean island of St. Martin with 66 confirmed cases and suspected cases of around 181. This outbreak is the first time in the Western Hemisphere that the disease has spread to humans from a population of infected mosquitoes. By January 2014, the Public Health Agency of Canada reported that cases were confirmed on the British Virgin Islands, Saint-Barthélemy, Guadeloupe, Dominica, Martinique, and French Guyana. In April 2014, chikungunya was also confirmed in the Dominican Republic by the Centers for Disease Control and Prevention (CDC). By the end of April, it had spread to 14 countries in all, including Jamaica, St. Lucia, St. Kitts and Nevis, and Haiti where an epidemic was declared.

By the end of May 2014, over ten imported cases of the virus had been reported in the United States by people traveling to Florida from areas where the virus is endemic. The strain of chikungunya spreading to the U.S. from the Caribbean is most easily spread by *A. aegypti*. Concern exists that this strain of chikungunya could mutate to make the *A. albopictus* vector more efficient. If this mutation were to occur, chikungunya would be more of a public health concern to the US because the *A. albopictus* or Asian tiger mosquito is more widespread in the U.S. and is more aggressive than the *A. aegypti*.

On June 2014 six cases of the virus were confirmed in Brazil, two in the city of Campinas in the state of Sao Paulo. The six cases are Brazilian army soldiers who had recently returned from Haiti, where they were participating in the reconstruction efforts as members of the United Nations Stabilisation Mission in Haiti. The information was officially released by Campinas municipality, which considers that it has taken the appropriate actions.

On 16 Jun. 2014, Florida had a cumulative total of 42 cases. As of 11 Sep. 2014, the number of reported cases in Puerto Rico for the year was 1,636. By 28 October, that number had increased to 2,974 confirmed cases with over 10,000 cases suspected. On 17 Jun. 2014, Department of Health officials in the U.S. state of Mississippi confirmed they are investigating the first potential case in a Mississippi resident who recently travelled to Haiti. On 19 Jun. 2014, the virus had spread to Georgia, USA. On 24 Jun. 2014, a case was reported in Poinciana, Polk County, Fla., USA. On 25 Jun. 2014, the Health Department of the U.S. state of Arkansas confirmed that one person from that state is carrying chikungunya. On 26 Jun. 2014, a case was reported in the Mexican state of Jalisco.

On 17 Jul. 2014, the first chikungunya case acquired in the United States was reported in Florida by the Centers for Disease Control and Prevention. Since 2006, over 200 cases have been reported in the United States, but only in people who had traveled to other countries. This is the first time the virus was passed by mosquitoes to a person on the U.S. mainland. On 2 Sep. 2014, the Centers for Disease Control and Prevention reported that there had been seven confirmed cases of chikungunya in the United States in people who had acquired the disease locally.

On 25 Sep. 2014, official authorities in El Salvador report over 30,000 confirmed cases of this new epidemy. The new epidemic is also on the rise in Jamaica and in Barbados. There is a risk that tourists to those countries may bring the virus to their own countries. November 2014: Brazil has reported a local transmission of a different strain (genotype) of chikungunya that has never been documented in the Americas. This is an African genotype, but oddly fails to explain if it is South African or West African. The new genotype (in the Americas) is more severe than the Asian genotype which is currently spreading through the Americas, and immunity to one genotype does not confer immunity to others. French Polynesia is among other regions experiencing ongoing outbreaks.

On 7 Nov. 2014 Mexico reported an outbreak of chikungunya, acquired by local transmission, in southern state of Chiapas. The outbreak extends across the coastline from the Guatemala border to the neighbouring state of Oaxaca. Health authorities have reported a cumulative load of 39 laboratory-confirmed cases (by the end of week 48). No suspect cases have been reported. In January 2015, there were 90,481 reported cases of chikungunya in Colombia.

II. Monoclonal Antibodies and Production Thereof

A. General Methods

It will be understood that monoclonal antibodies binding to Chikungunya virus will have several applications. These include the production of diagnostic kits for use in detecting and diagnosing Chikungunya virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, which in this case is for Chikungunya virus glycoprotein (GP). Those of skill in the art, by assessing the binding specificity/affinity of a given antibody using techniques well known to those of skill in the art, can determine whether such antibodies fall within the scope of the instant claims. In one aspect, there are provided monoclonal antibodies having clone-paired CDR's from the heavy and light chains as illustrated in Tables 3 and 4, respectively. Such antibodies may be produced by the clones discussed below in the Examples section using methods described herein.

In a second aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (0 the amino acids may vary from those set out above by permitting conservative substitutions (discussed below). Each of the foregoing applies to the nucleic acid sequences set forth as Table 1 and the amino acid sequences of Table 2.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido)ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Chikungunya Infection A. Formulation and Administration The present disclosure provides pharmaceutical compositions comprising anti-Chikungunya virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those that are disclosed are produced in vivo in a subject at risk of Chikungunya virus infection. Sequences for the E1 and E2 are listed as SEQ ID NOS: 253-276 in the appended sequence listing. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{99}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting Chikungunya virus and its associated antigens. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Chikungunya virus antibodies directed to specific parasite epitopes in samples also is provided. The steps of various useful immunodetection methods have been described in the scientific literature, such as, e.g., Doolittle and Ben-Zeev (1999), Gulbis and Galand 0993), De Jager et al. (1993), and Nakamura et al. (1987). In general, the immunobinding methods include obtaining a sample suspected of containing Chikungunya virus, and contacting the sample with a first antibody in accordance with the present disclosure, as the case may be, under conditions effective to allow the formation of immunocomplexes.

These methods include methods for purifying Chikungunya virus or related antigens from a sample. The antibody will preferably be linked to a solid support, such as in the form of a column matrix, and the sample suspected of containing the Chikungunya virus or antigenic component will be applied to the immobilized antibody. The unwanted components will be washed from the column, leaving the Chikungunya virus antigen immunocomplexed to the immobilized antibody, which is then collected by removing the organism or antigen from the column.

The immunobinding methods also include methods for detecting and quantifying the amount of Chikungunya virus or related components in a sample and the detection and quantification of any immune complexes formed during the binding process. Here, one would obtain a sample suspected of containing Chikungunya virus or its antigens, and contact the sample with an antibody that binds Chikungunya virus or components thereof, followed by detecting and quantifying the amount of immune complexes formed under the specific conditions. In terms of antigen detection, the biological sample analyzed may be any sample that is suspected of containing Chikungunya virus or Chikungunya virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Chikungunya virus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Chikungunya virus or Chikungunya virus antigen is added to the wells. After binding and washing to remove non-specifically bound immune complexes, the bound antigen may be detected. Detection may be achieved by the addition of another anti-Chikungunya virus antibody that is linked to a detectable label. This type of ELISA is a simple "sandwich ELISA." Detection may also be achieved by the addition of a second anti-Chikungunya virus antibody, followed by the addition of a third antibody that has binding affinity for the second antibody, with the third antibody being linked to a detectable label.

In another exemplary ELISA, the samples suspected of containing the Chikungunya virus or Chikungunya virus antigen are immobilized onto the well surface and then contacted with the anti-Chikungunya virus antibodies of the disclosure. After binding and washing to remove non-specifically bound immune complexes, the bound anti-Chikungunya virus antibodies are detected. Where the initial anti-Chikungunya virus antibodies are linked to a detectable label, the immune complexes may be detected directly. Again, the immune complexes may be detected using a second antibody that has binding affinity for the first anti-Chikungunya virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material.

A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Chikungunya virus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled Chikungunya virus monoclonal antibodies to determine the amount of Chikungunya virus antibodies in a sample. The basic format would include contacting a known amount of Chikungunya virus monoclonal antibody (linked to a detectable label) with Chikungunya virus antigen or particle. The Chikungunya virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Chikungunya virus or Chikungunya virus antigens, the antibodies may be included in the kit. The immunodetection kits will thus comprise, in suitable container means, a first antibody that binds to Chikungunya virus or Chikungunya virus antigen, and optionally an immunodetection reagent.

In certain embodiments, the Chikungunya virus antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Chikungunya virus or Chikungunya virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Isolation of human mAbs. PBMCs were obtained from a human ~5 years after documented symptomatic CHKV infection in Sri Lanka. B cells were transformed in 384-well plates with EBV in the presence of CpG. The supernatants from the resulting B cell lymphoblastic cells lines were screened for the presence of human CHKV-specific binding antibodies by ELISA using live CHIKV vaccine strain 181/25 virus as antigen. Transformed B cells were collected and fused to a myeloma cell line, distributed into culture plates and expansion, and selected by growth in hypoxanthine-aminopterin-thymidine medium containing ouabain. Hybridomas were cloned by single-cell sorting. Supernatants from cloned hybridomas growing in serum-free medium were collected, purified and concentrated from clarified medium by protein G chromatography.

Neutralization assays. Purified IgG mAb proteins were tested for neutralizing activity using CHKV virus replicon particles (VRPs) or each of 4 live chikungunya viruses representing diverse genetic and geographic profile. A CHIKV VRP that encoded GFP was generated by development of a three-plasmid CHIKV replicon helper system based on a plasmid containing the full-length cDNA of the CHIKV strain SL15649 (GenBank: GU189061.1) genome sequence, using PCR-based cloning methodologies. VRP were incubated with mAb in dilutions then inoculated onto Vero 81 cell monolayers for 18 hrs; infected cells and total cells (identified with a nuclear marker) were identified with a fluorescence imaging system. To determine mAb breadth and neutralization potency, the inventors used four representative live virus strains with at least one representative from each CHIKV genotype, including one prototype virus from each of the three genotypes and also a strain from the current Caribbean outbreak. Neutralizing activity was determined in a focus reduction neutralization test. Serial dilutions of purified human mAbs were incubated with 100 focus-forming units of CHIKV at 37° C. for 1 hour. MAb-virus complexes were added to Vero cells in 96-well plates, and then plaques were detected after cell fixation using immunoperoxidase detection and quantified using an ImmunoSpot 5.0.37 macroanalyzer (Cellular Technologies Ltd). $EC_{50}$ values were calculated using nonlinear regression analysis after comparison to wells inoculated with CHIKV in the absence of antibody.

E2 ELISA. Recombinant CHIKV E2 ectodomain protein (corresponding to the CHIKV-LR2006 strain) was generated in *E. coli* and adsorbed to microtiter plates. Human mAbs were applied, then bound CHKV-specific mAbs were detected with biotin-conjugated goat anti-human IgG.

Competition binding assay. The inventors identified groups of antibodies binding to the same major antigenic site by competing pairs of antibodies for binding to CHIKV-LR2006 E2 ectodomain protein containing a polyhistidine-tag attached to an Anti-Penta-His biosensor tip (ForteBio #18-5077) in an Octet Red biosensor (ForteBio).

Alanine scanning mutagenesis for epitope mapping. A CHIKV envelope protein expression construct (strain S27, Uniprot Reference #Q8JUX5) with a C-terminal V5 tag was subjected to alanine-scanning mutagenesis to generate a comprehensive mutation library. Primers were designed to mutate each residue within the E2, 6K, and E1 regions of the envelope proteins (residues Y326 to H1248 in the structural polyprotein) to alanine; alanine codons were mutated to serine. In total, 910 CHIKV envelope protein mutants were generated. Loss of binding of mAbs to each construct was tested using an immunofluorescence binding assay, using cellular fluorescence detected with a high-throughput flow cytometer.

Mechanism of neutralization. MAbs were interacted with VRPs before or after attachment to Vero 81 cells, and then cells were stained, imaged, and analyzed as described for VRP neutralization assays to determine at what stage mAbs exerted the antiviral effect. Fusion from within and fusion from without assays were performed as detailed in Supplemental Experimental Procedures.

In vivo protection studies in mice. Ifnar$^{-/-}$ mice were bred in pathogen-free animal facilities and infection experiments were performed in A-BSL3 facilities. Footpad injections were performed under anesthesia. For prophylaxis studies, human mAbs were administered by intraperitoneal injection to 6 week-old Ifnar$^{-/-}$ mice 1 day prior to subcutaneous inoculation in the footpad with 10 FFU of CHIKV-LR. For therapeutic studies, 10 FFU of CHIKV-LR was delivered 24, 48, or 60 hours prior to administration of a single dose of individual or combinations of human mAbs at specified doses.

Human subject and peripheral blood cell isolation. An otherwise healthy adult subject presented in October of 2006 with CHIKV infection. The symptoms of CHIKV infection coincided with return from a one-year visit to Sri Lanka, during which the patient spent time in urban areas (primarily Colombo), and rural settings, including rainforests and coastal areas. The patient experienced multiple insect bites over the course of the visit, but remained in good health throughout the stay. On return to the U.S., the subject presented to the primary care physician with a fever (102° F.) of three days duration. The patient reported the concurrent development of bilateral joint pain in elbows and fingers, and a raised, non-pruritic rash on the back and abdomen, accompanied by general "body ache" and headache. On presentation, he appeared to be well, and in no acute distress. A mild, blanching, papular rash extended across the back, chest and abdomen (see FIG. 4). A mild conjunctivitis was noted. The skeletal exam was remarkable for tender swollen fingers, knees and elbows, which were without erythema or effusions. Muscle strength and range of motion of the affected joints were intact, but joint movement elicited pain.

Blood was drawn for a CBC, serologies and malaria smears, and the patient was discharged. The white blood cell count was $4.0 \times 10^4$ cells/mm$^3$, the hematocrit was 41% and platelet count was 180,000/mm$^3$. The total lymphocyte count was $1.0 \times 10^4$ cells/mm$^3$. Malaria smears and serologies were negative, and the patient was diagnosed tentatively as having a viral illness of unknown etiology.

The patient returned to the clinic two weeks later, afebrile, but with persistent arthralgia, most prominent in the fingers. The patient described the pain and stiffness as no better, and perhaps worse, than during his previous visit. The patient reported that an outbreak of chikungunya was occurring in the area of previous travel. Blood was drawn and serum separated and sent to CDC for PCR and serological testing, which confirmed the diagnosis of chikungunya infection.

In April 2012, five and a half years after the index infection, peripheral blood mononuclear cells (PBMCs) were isolated by density gradient separation on Ficoll without known exposure to CHIKV or other arthritogenic alphaviruses in the intervening period while living in the United States. The cells were cryopreserved and stored in liquid nitrogen until study. The protocol for recruiting and collecting blood samples from subjects was approved by the Institutional Review Boards of the University of North Carolina at Chapel Hill and the Vanderbilt University Medical Center.

Generation of human hybridomas. Cryopreserved PBMC samples were thawed rapidly at 37° C. and washed prior to transformation with Epstein-Barr virus, as described (Smith et al., 2012). Cultures were incubated at 37° C. with 5% CO$_2$ for 10 days and screened for the presence of cells secreting CHIKV-specific antibodies in the supernatant using VRP neutralizing assays and an ELISA. The inventors performed two independent transformations using separate aliquots of the same blood sample.

In the first transformation, the inventors established 3,840 cultures (10×384-well plates) containing an average of 42 transformed B cell colonies per culture, for an estimated total of about 161,000 individual B cell colonies. To screen for antibodies that display neutralizing activity against CHIKV under BSL2 conditions, the inventors developed a high-throughput fluorescence reduction neutralization assay using CHIKV replicon particles (VRPs) that express green fluorescent protein as a reporter. VRPs are virions that display the native viral glycoproteins but lack the full-length viral genome and thus are incapable of generating infectious progeny (Vander Veen et al., 2012). The inventors used VRPs derived from strain SL15649 (Morrison et al., 2011), which was isolated from Sri Lanka in 2006. SL15649 is contemporaneous to the strain that infected the donor and is likely very similar in sequence. From this experiment, the inventors identified 160 B cell cultures with supernatants that mediated neutralization at 90% inhibition, suggesting a frequency of 0.099% virus-specific B cells per total B cells (~1 in 1,000). A total of 60 of these lines inhibited at a level of >98%, and in the secondary screen, supernatants from 58 of the 60 lines contained antibodies that bound in ELISA to cell-culture-produced CHIKV (strain 181/25) captured on an immunoassay plate. The inventors selected 35 of the 58 lines with the highest neutralizing and binding activity for hybridoma fusion, identified 22 hybridomas with virus-binding supernatants after fusion and plating, and successfully isolated 14 clones for further study. In the second transformation, the inventors established 1,536 cultures (4×384-well plates) containing an average of 38 transformed B cell colonies per culture, for an estimated total of about 58,000 individual B cell colonies tested, suggesting a virus-specific B cell frequency of 0.1% (again, ~1 in 1,000). In this experiment, they used a primary screen of ELISA binding to CHIKV strain 181/25 without a prior neutralizing test. The inventors identified 60 lines with ELISA optical density signal greater than four times the background level, selected the 30 B cell lines with the highest optical density signal in ELISA for fusion, identified 18 hybridomas with virus-binding supernatants after fusion and plating, and successfully isolated 16 clones for further study.

Fusion with myeloma cells. Cells from wells with supernatants capable of neutralizing CHIKV infectivity were fused with HMMA2.5 non-secreting myeloma cells as described (Smith et al., 2012). Resultant hybridomas were selected by growth in hypoxanthine-aminopterin-thymidine (HAT) medium containing ouabain, biologically cloned by single-cell FACS using a FACSAria III cell sorter (BD Biosciences), and expanded.

Human mAb production and purification. Wells containing hybridomas producing CHIKV-specific antibodies were cloned by three rounds of limiting dilution or with a ClonePix device (Molecular Devices) according to the manufacturer's instructions. Once individual clones were obtained, each hybridoma was expanded until 50% confluent in 75 cm² flasks. For antibody expression, cells were collected with a cell scraper, washed in serum-free medium (GIBCO Hybridoma-SFM from Invitrogen, 12045084), and divided equally into four 225 cm² flasks (Corning, 431082) containing 250 mL serum-free medium. Cells were incubated for 21 days before medium was clarified by centrifugation and passed through a 0.2 µm sterile filter. Antibodies were purified from clarified medium by protein G chromatography (GE Life Sciences, Protein G HP Columns).

Cells. BHK-21 cells (ATCC CCL-10) were maintained in alpha minimal essential medium (αMEM; Gibco) supplemented to contain 10% fetal bovine serum (FBS) and 10% tryptose phosphate (Sigma). Vero 81 cells (ATCC CCL-81) were maintained in αMEM supplemented to contain 5% FBS. Medium for all cells was supplemented to contain 0.29 mg/mL L-glutamine (Gibco), 100 U/mL penicillin (Gibco), 100 µg/mL streptomycin (Gibco), and 500 ng/mL amphotericin B. Cells were maintained at 37° C. in a humidified atmosphere of 5% $CO_2$.

Generation of CHIKV VRP plasmid constructs. A three-plasmid CHIKV replicon helper system was derived from a plasmid containing the full-length cDNA of the CHIKV strain SL15649 (GenBank: GU189061.1) genome sequence using PCR-based cloning methodologies. A CHIKV replicon genome was constructed using a two-step process that involved the generation of an intermediate cloning vector with the CHIKV full-length structural cassette substituted with a multiple cloning site (MCS). Enhanced green fluorescent protein (eGFP) was subcloned into the multiple cloning site of this plasmid to generate pMH41 (CHIKV SL15649 eGFP replicon). The construction of a two-plasmid helper system included a multi-step cloning process that first involved the generation of a full-length structural gene helper plasmid via removal of the majority (6,891 nt) of the CHIKV non-structural cassette. The full-length structural cassette was further subdivided into two constructs, pMH38 (CHIKV SL15649 capsid helper), which is comprised of the capsid gene sequence followed by a unique AvrII restriction site, and pMH39 (CHIKV SL15649 glycoprotein helper), which contains an in-frame deletion of the capsid RNA-binding domain followed by the intact envelope glycoprotein (E3-E1) coding sequence.

Recombinant CHIKV p62-E1 production. A plasmid containing CHIKV p62 (i.e., E3 [aa S1-R64]-E2 [aa S1-E361]-16 amino acid linker-E1 [aa Y1-Q411] followed by a His tag) (Voss et al., 2010) was transfected into 293F cells using 293fectin reagent (Invitrogen). After 72 hours incubation, the supernatant was removed, and the cells were cultured for an additional 72 hours. The pooled supernatants were loaded onto a nickel agarose bead column (GoldBio) and eluted with imidazole. The protein was further purified using a Superdex S200 gel filtration column (GE Life Sciences). Fractions containing the CHIKV p62-E1 protein were pooled, frozen, and stored at −80° C.

Generation of CHIKV strain SL15649-derived VRP stocks. VRP stocks were recovered from recombinant CHIKV plasmids in a certified biological safety level 3 (BSL3) facility in biological safety cabinets in accordance with protocols approved by the Vanderbilt University Department of Environment, Health, and Safety and the Vanderbilt Institutional Biosafety Committee. The three SL15649 replicon system plasmids were linearized by digestion with NotI-HF, purified by phenol-chloroform extraction, and used as templates in transcription reactions using an mMessage mMachine SP6 transcription kit (Life Technologies) to produce capped, full-length RNA transcripts in vitro. Viral RNA transcripts were introduced into BHK21 cells by electroporation using a GenePulser electroporator. Culture supernatants containing VRPs were collected 24 hours after electroporation; supernatants were clarified by centrifugation at 855×g for 20 min, aliquoted, and stored at −80° C. VRP stocks were evaluated for propagation-competent recombinant virus by serial passage of 20% of the stock and 10% of passage 1 culture supernatant using Vero 81 cells, which were examined for cytopathic effect (CPE) 72 hours after infection. Stocks were considered to have passed this safety test when CPE was not detected in the final passage. Stocks were then removed from the BSL3 laboratory.

VRP neutralization and GFP reporter assay. Vero 81 cells ($2.25 \times 10^3$ cells/well) were seeded into wells of 384-well plates and incubated at 37° C. for 24 hours. Neat hybridoma supernatant or serial dilutions of purified mAbs were incubated with VRPs at an MOI of ~5 infectious units/cell in virus dilution buffer (VDB; RPMI medium containing 20 mM HEPES supplemented to contain 1% FBS) at 37° C. for 1 hour and then adsorbed to cells. Cells were incubated at 37° C. for 18 hours, stained with Hoechst stain to label nuclei, and imaged using an ImageXpress Micro XL imaging system (Molecular Devices) at the Vanderbilt High-Throughput Screening Facility. Total and CHIKV-infected cells (marked by GFP expression) were quantified using MetaXpress software (Molecular Devices) in two fields of view per well. For each antibody, $EC_{50}$ values with 95% confidence intervals were determined using nonlinear regression to fit separate logistic growth curves using the R statistics program (R.C. Team, 2014).

Virus stocks prepared as antigen for ELISA. The infectious clone plasmid for CHIKV vaccine strain 181/25 (Levitt et al., 1986 and Mainou et al., 2013) was linearized with NotI-HF and transcribed in vitro using an mMessage mMachine SP6 transcription kit (Life Technologies). Viral RNA was introduced into BHK21 cells by electroporation. Culture supernatants were harvested 24 hours later, clarified by centrifugation at 855×g for 20 min, aliquoted, and stored at −80° C.

Virus capture ELISA for hybridoma screening. Antibody binding to virus particles was performed by coating assay plates with purified mouse mAb CHK-187 (Pal et al., 2013), prepared at 1 µg/mL in 0.1 M $Na_2CO_3$ and 0.1 M $NaHCO_3$ pH 9.3 binding buffer, was used to coat ELISA plates (Nunc 242757) and incubated at 4° C. overnight. After incubating plates for 1 hour with blocking buffer (1% powdered milk and 2% goat serum in PBS with Tween 20 [PBS-T]), plates were washed five times with PBS-T and incubated with 25 µL of culture supernatant from BHK21 cell monolayers infected with CHIKV vaccine strain 181/25. After incubation at room temperature for 1 hour, plates were washed ten times with PBS, and 10 µL of B cell culture supernatant was added into 25 µL/well of blocking buffer. Plates were incubated at room temperature for 1 hour prior to washing five times with PBS-T. A secondary antibody conjugated to alkaline phosphatase (goat anti-human Fc; Meridian Life Science, W99008A) was applied at a 1:5,000 dilution in 25 µL/well of blocking buffer, and plates were incubated at room temperature for 1 hour. Following five washes with PBS-T, phosphatase substrate solution (1 mg/mL phosphatase substrate in 1 M Tris aminomethane [Sigma, S0942]) was added at 25 µL/well, and plates were incubated at room temperature for 2 hours before determining the optical density at 405 nm using a Biotek plate reader.

CHIKV-specific control human mAbs. In some assays, two previously described human CHIKV-specific mAbs, 5F10 and 8B10 (Wailer et al., 2011), were used as positive controls. These mAbs were expressed in 293F cells (Invitrogen) following transfection with an IgG1 expression plasmid (Lonza) containing a sequence-optimized cDNA of the 5F10 and 8B10 antibody variable gene regions based on sequences provided by Cheng-I Wang and Alessandra Nardin (Singapore Immunology Network, A*STAR, Singapore).

ELISA for mAb binding to E2 protein. Recombinant CHIKV E2 ectodomain protein (corresponding to the CHIKV-LR2006 strain) was generated in E. coli as described (Pal et al., 2013) and adsorbed to microtiter plates (100 μL of a 2 μg/mL E2 protein solution in 0.1 M $Na_2CO_3$, 0.1 M $NaHCO_3$, and 0.1% $NaN_3$ [pH 9.3]) at 4° C. overnight. Plates were rinsed three times with PBS containing 0.05% Tween-20, and incubated at 37° C. for 1 hour with blocking buffer (PBS, 0.05% Tween-20, and 2% [w/v] of BSA). Primary human mAb (diluted to 10 μg/mL in blocking buffer) was added to wells at room temperature for 1 hour. Plates were rinsed three times with PBS containing 0.05% Tween-20, and secondary antibody (biotin-conjugated goat anti-human IgG (H and L chains) with minimal cross-reactivity to mouse serum proteins (Jackson ImmunoResearch Laboratories) diluted 1/20,000 in blocking buffer) and streptavidin-conjugated horseradish peroxidase (diluted in PBS with 0.05% Tween-20; Vector Laboratories) were added sequentially, each at room temperature for 1 hour with plate rinsing in between steps. After four rinses with PBS, plates were incubated at room temperature with 100 μL of TMB (3,3',5,5'-tetramethylbenzidine) chromogenic substrate solution (Dako) for 5 min, and the reaction was stopped by addition of 2 N $H_2SO_4$. Product intensity was determined using an ELISA plate reader at an optical density of 450 nm.

Affinity measurements by surface plasmon resonance. Interactions of purified human mAbs and CHIKV proteins were analyzed kinetically using a Biacore T100 instrument as described (Austin et al., 2012). For the intact IgG with soluble CHIKV p62-E1, anti-human IgG antibodies (GE Life Sciences) were immobilized onto a Series S CMS chip and used to capture anti-CHIKV or control (hu-WNV E16) antibodies. The CHIKV p62-E1 was injected over the surface at 65 pt/min for 180 sec and allowed to dissociate for 1000 sec before regeneration with 3 M $MgCl_2$ between cycles. Some antibodies did not bind to the monomeric E1 protein, therefore the inventors tested them for binding to VLPs. For the kinetic measurements with the CHIKV VLP, anti-mouse IgG antibodies (GE Life Sciences) were immobilized to capture a set of mouse anti-CHIKV antibodies with sub-nanomolar affinities, which were in turn used to capture the CHIKV VLPs. Anti-CHIKV IgG or Fab was injected over the chip surface at 65 μL/min for 180 sec and allowed to dissociate for 1000 sec before regeneration with 10 mM glycine pH 1.7 between cycles. All data were processed using the Biacore Evaluation Software (Version 1.1.1) and a global 1:1 Langmuir fit of the curves. Results were obtained from at least three independent experiments.

Virus strains used in focus reduction neutralization tests. To determine mAb breadth and neutralization potency, the inventors used four representative strains with at least one representative from each CHIKV genotype, including one prototype virus from each of the three genotypes and also a strain from the current Caribbean outbreak. Strain LR2006_OPY1 (LR) (CHIKV East/Central/South African [ECSA] genotype) was provided by Stephen Higgs (Manhattan, Kans.). Strain NI 64 IbH 35 (West African genotype) and strains RSU1 and 99659 (Asian genotype; isolated in 2014 from a subject in the British Virgin Islands (Lanciotti & Valadere, 2014)) were provided by Robert Tesh (World Reference Center for Emerging Viruses and Arboviruses, Galveston, Tex.).

Focus reduction neutralization test (FRNT) with infectious CHIKV. Serial dilutions of purified human mAbs were incubated with 100 focus-forming units (FFU) of CHIKV at 37° C. for 1 hour. MAb-virus complexes were added to Vero cells in 96-well plates. After 90 min incubation, cells were overlaid with 1% (w/v) methylcellulose in Modified Eagle Media (MEM) supplemented to contain 2% FBS. Cells were incubated for 18 hours and fixed with 1% paraformaldehyde in PBS. Cells were incubated sequentially with 500 ng/mL of murine CHK-11 (Pal et al., 2013) and horseradish peroxidase (HRP)-conjugated goat anti-mouse IgG in PBS supplemented to contain 0.1% saponin and 0.1% bovine serum albumin (BSA). CHIKV-infected foci were visualized using TrueBlue peroxidase substrate (KPL) and quantified using an ImmunoSpot 5.0.37 macroanalyzer (Cellular Technologies Ltd). $EC_{50}$ values were calculated using nonlinear regression analysis after comparison to wells inoculated with CHIKV in the absence of antibody.

Biolayer interferometry competition binding assay. CHIKV-LR2006 E2 ectodomain protein containing a polyhistidine-tag (20 μg/mL) was immobilized onto Anti-Penta-His biosensor tips (ForteBio #18-5077) for 2 min. After determining the baseline signal in kinetics buffer (KB, 1×PBS, 0.01% BSA and 0.002% Tween 20) for 1 min, biosensor tips were immersed into wells containing primary antibody at a concentration of 100 μg/mL for 5 min and then immersed into wells containing competing mAbs at a concentration of 100 μg/mL for 5 min. The percent binding of the competing mAb in the presence of the first mAb was determined by comparing the maximal signal of the competing mAb applied after the initial mAb complex to the maximal signal of competing mAb alone. Antibodies were judged to compete for binding to the same site if maximum binding of the competing mAb was reduced to <30% binding affinity alone. Antibodies were considered non-competing if maximum binding of the competing mAb was >70% of non-competed binding. A level of 30-70% of non-competed binding was considered intermediate competition.

Mutagenesis epitope mapping. A CHIKV envelope protein expression construct (strain S27, Uniprot Reference #Q8JUX5) with a C-terminal V5 tag was subjected to alanine-scanning mutagenesis to generate a comprehensive mutation library. Primers were designed to mutate each residue within the E2, 6K, and E1 regions of the envelope proteins (residues Y326 to H1248 in the structural polyprotein) to alanine; alanine codons were mutated to serine (Fong et al., 2014). In total, 910 CHIKV envelope protein mutants were generated (98.5% coverage), sequence confirmed, and arrayed into 384-well plates. HEK-293T cells were transfected with the CHIKV mutation library in 384-well plates and incubated for 22 hours. Cells were fixed in 4% paraformaldehyde (Electron Microscopy Sciences) in PBS plus calcium and magnesium (PBS+/+) and stained with purified mAbs at 0.25 to 1.0 μg/mL or purified Fab fragments at 2.5 μg/mL diluted in 10% normal goat serum (NGS; Sigma). Primary antibody concentrations were determined using an independent immunofluorescence titration curve against wild-type CHIKV envelope proteins to ensure that signals were within the linear range of detection. Antibodies were detected using 3.75 μg/mL AlexaFluor488- conjugated secondary antibody (Jackson ImmunoResearch Laboratories) in 10% NGS. Cells were washed twice with PBS without magnesium and calcium (PBS −/−) and resuspended in Cellstripper (Cellgro) with 0.1% BSA (Sigma). Mean cellular fluorescence was detected using a high-throughput flow cytometer (HTFC, Intellicyt). Antibody reactivity against each mutant clone was calculated relative to wild-type protein reactivity by subtracting the signal from mock-transfected controls and normalizing to the signal from wild-type-transfected controls. Amino acids were identified as required for mAb binding if the corresponding alanine mutant did not react with the test mAb but did react with other CHIKV antibodies. This counter-screen strategy facilitates the exclusion of mutants that are misfolded or have an expression defect (Christian et al., 2013, Paes et al., 2009 and Selvarajah et al., 2013). Amino acids required for antibody binding were visualized on the CHIKV envelope protein crystal structure (monomer PDB ID #3N41 and trimer PDB ID #2XFB) using PyMol software.

Pre- and post-attachment neutralization assays. Vero 81 cells (ATCC CCL-81; ~7.5×10$^3$ cells/well) were seeded into wells of 96-well plates and incubated at 37° C. for ~24 hours. For pre-attachment assays, dilutions of mAb were prepared at 4° C. in virus dilution buffer (VDB) and pre-incubated with VRPs at 4° C. for 1 hour. Antibody-virus complexes were added to pre-chilled Vero 81 cells at 4° C. for 1 hour. Non-adsorbed virus was removed by three washes with VDB, and cells were incubated in complete medium at 37° C. for 18 hours. The post-attachment assay was performed similarly, except that an equivalent MOI of VRPs was first adsorbed to Vero 81 cells at 4° C. for 1 hour, unbound VRPs were removed by three washes with virus dilution buffer, and cells were incubated with pre-chilled VDB containing serial dilutions of mAb at 4° C. for 1 hour. Unbound mAbs were removed by three washes with VDB, and cells were incubated in complete medium at 37° C. for 18 hours. Cells were stained, imaged, and analyzed as described for VRP neutralization assays, with four fields of view per well, yielding a total of ~800 to 1,000 cells analyzed for GFP expression per sample.

Fusion inhibition assays. Virus fusion with the plasma membrane was assessed using an FFWO assay (Edwards & Brown, 1986). Vero 81 cells (~3.75×10$^3$ cells/well) were seeded into wells of 96-well plates and incubated at 37° C. for ~24 hours. Cells were washed once with binding medium (RPMI 1640 supplemented to contain 1% FBS, 25 mM HEPES [pH 7.4] and 20 mM NH$_4$Cl to prevent infection through endosomal fusion) and incubated in binding medium at 4° C. for 15 min. Inoculum containing VRPs was diluted in binding medium and incubated with cells at 4° C. for 1 hour. Unbound VRPs were removed by two washes with binding medium. Serial dilutions of mAbs in VDB were incubated with cells at 4° C. for 1 hour, and unbound mAb was removed by two washes with VDB. FFWO was induced by the addition of pre-warmed fusion medium (RPMI 1640, 1% FBS, 25 mM HEPES, and 30 mM succinic acid at pH 5.5) at 37° C. for 2 min. In parallel wells, control medium (RPMI 1640, 1% FBS, 25 mM HEPES at pH 7.4) was added at 37° C. for two min. The medium was removed and cells were incubated in DMEM supplemented to contain 5% FBS, 20 mM NH$_4$Cl (to ensure that infection occurred only through pH-dependent plasma membrane fusion), and 25 mM HEPES [pH 7.4]). At 18 hours post infection, cells were stained, imaged, and analyzed as described, with four fields of view per well, yielding a total of ~800-1,000 cells analyzed for GFP expression per sample.

In vivo protection studies in mice. This study was carried out in strict accordance with the recommendations in the Guide for the Care and Use of Laboratory Animals of the National Institutes of Health. The protocols were approved by the Institutional Animal Care and Use Committee at Washington University School of Medicine (Assurance Number: A3381-01). Ifnar$^{−/−}$ mice were bred in pathogen-free animal facilities at Washington University School of Medicine, and infection experiments were performed in A-BSL3 facilities with the approval of the Washington University Animal Studies Committee. Footpad injections were performed under anesthesia that was induced and maintained with ketamine hydrochloride and xylazine. For prophylaxis studies, human mAbs were administered by intraperitoneal injection to 6 week-old Ifnar$^{−/−}$ mice 1 day prior to subcutaneous inoculation in the footpad with 10 FFU of CHIKV-LR diluted in HBSS with 1% heat-inactivated FBS. For therapeutic studies, 10 FFU of CHIKV-LR was delivered 24, 48, or 60 hours prior to administration of a single dose of individual or combinations of human mAbs at specified doses.

Example 2—Results

Figure 4:
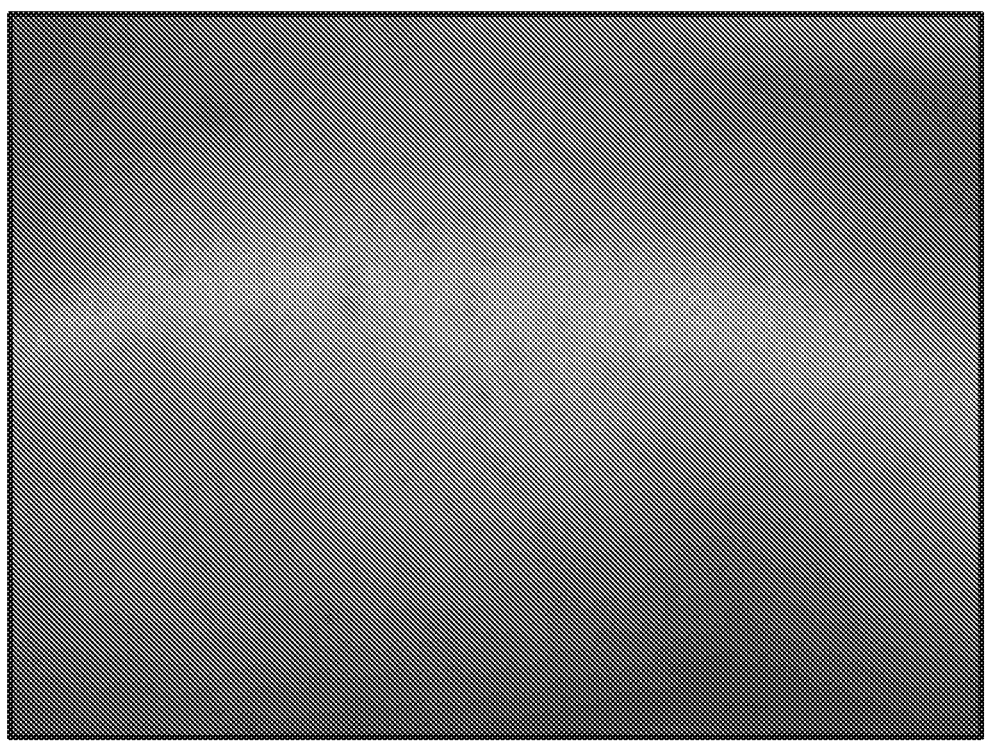
FIG. 4. Papular rash at time of acute presentation. The subject presented to the primary care physician with a fever (102° F.) of three days duration, with concurrent development of bilateral joint pain in elbows and fingers, and rash. Providers noted a raised, non-pruritic, blanching, papular rash (photograph shown in the figure) across the back, chest and abdomen.
Figure 6A:
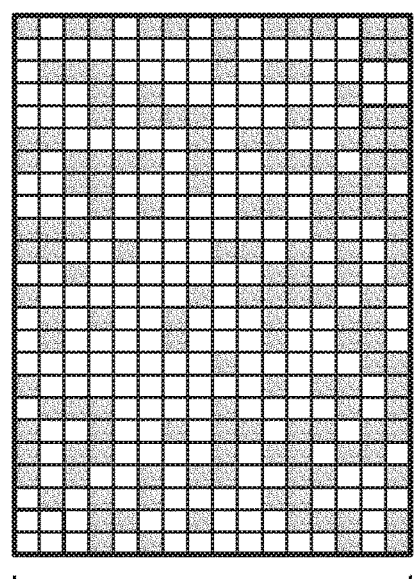
FIGS. 6A-E. High resolution epitope mapping of CHIKV MAbs. (A) An alanine scanning mutation library for CHIKV envelope protein encompassing 910 E2/E1 mutations was constructed where each amino acid was individually mutated to alanine. Each well of each mutation array plate contains one mutant with a defined substitution. A representative 384-well plate of reactivity results is shown. Eight positive (wild-type E2/E1) and eight negative (mock-transfected) control wells are included on each plate. (B) For epitope mapping, human HEK-293T cells expressing the CHIKV envelope mutation library were tested for immunoreactivity with a MAb of interest (MAb 4G20 shown here) and measured using an Intellicyt high-throughput flow cytometer. Clones with reactivity <30% relative to wild-type CHIKV E2/E1 yet >70% reactivity for a different CHIKV E2/E1 MAb were initially identified as critical for MAb binding. (C) Mutation of four individual residues reduced 4G20 binding (red bars) but did not greatly affect binding of other conformation-dependent MAbs (gray bars) or rabbit polyclonal antibody (rPAb, a gift from IBT Bioservices). Bars represent the mean and range of at least two replicate data points. (D-E) The epitopes of neutralizing MAbs with PRNT50<1,000 ng/ml are mapped onto the trimeric crystal structures of E2/E1 (PDB Entry 2XFC). All neutralizing epitopes map to well-exposed, membrane-distal domains of E2/E1. Each individual E2/E1 heterodimeric subunit is shown in a different color for clarity. Highly immunogenic regions in E2 domains A and B which contain critical epitope residues for multiple MAbs are outlined in red on a single subunit of E2.
Figure 6B:
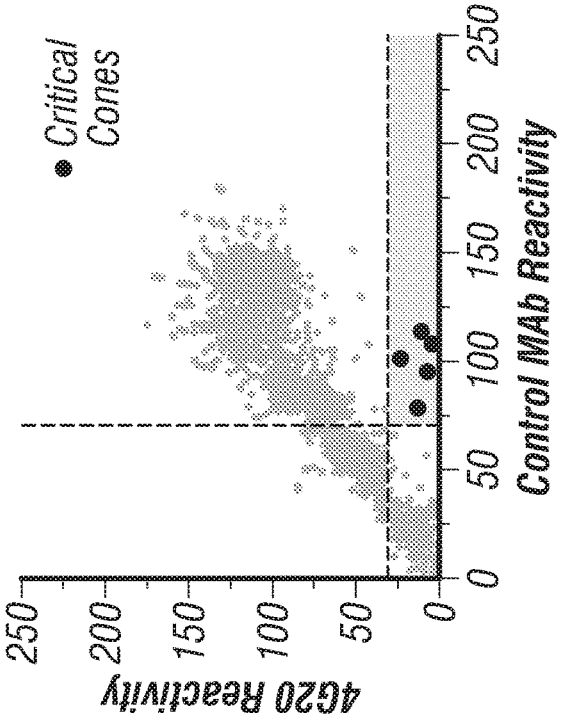
Figure 6C:
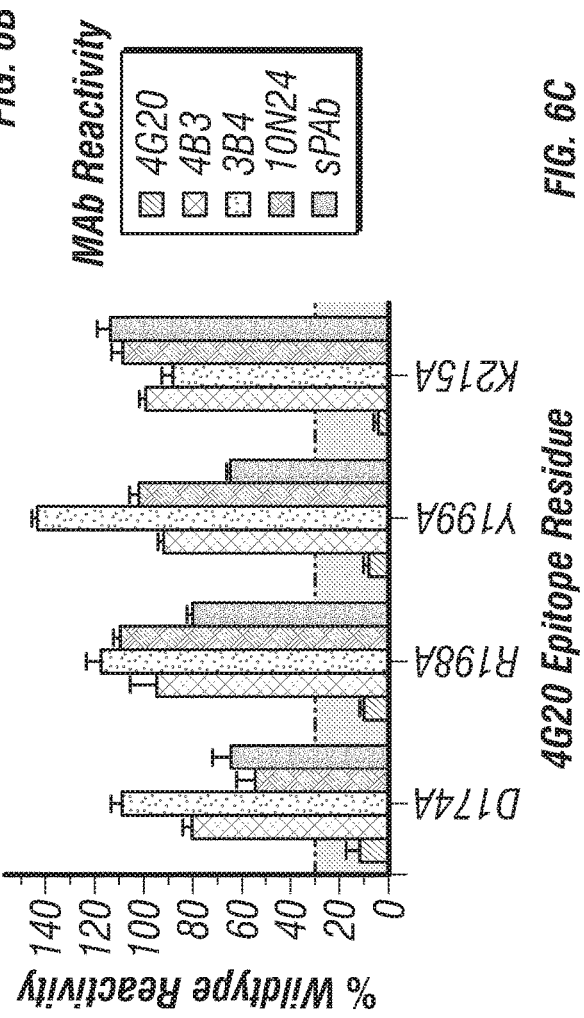
Figure 6D:
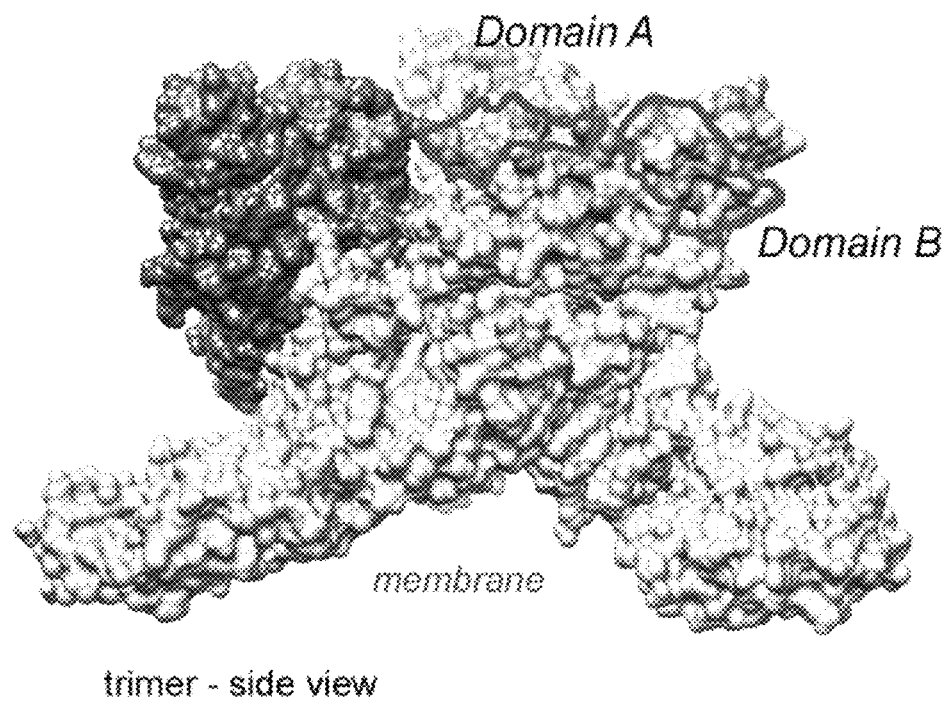
Figure 6E:
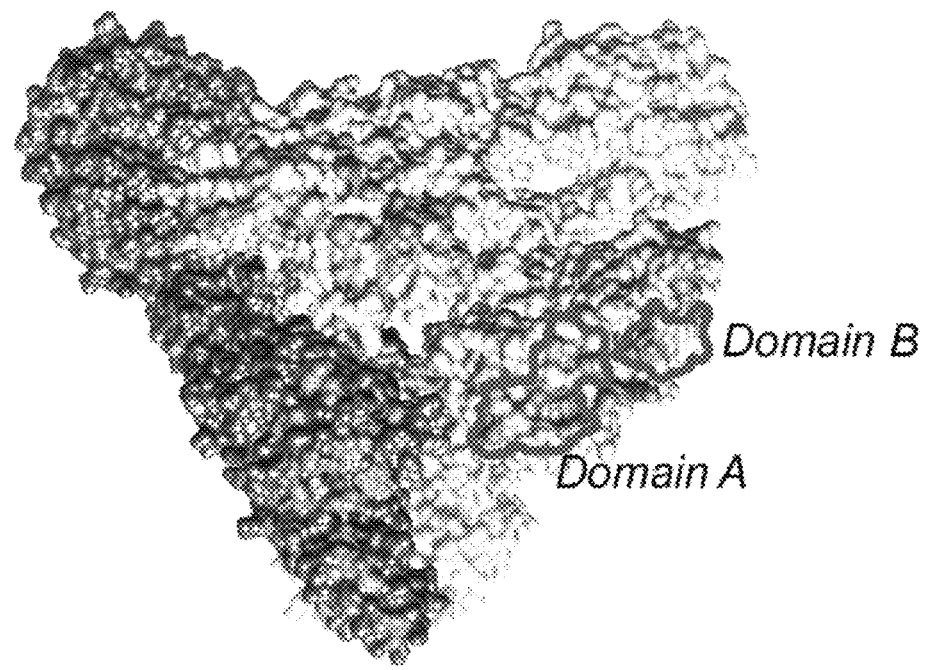
Figure 7:
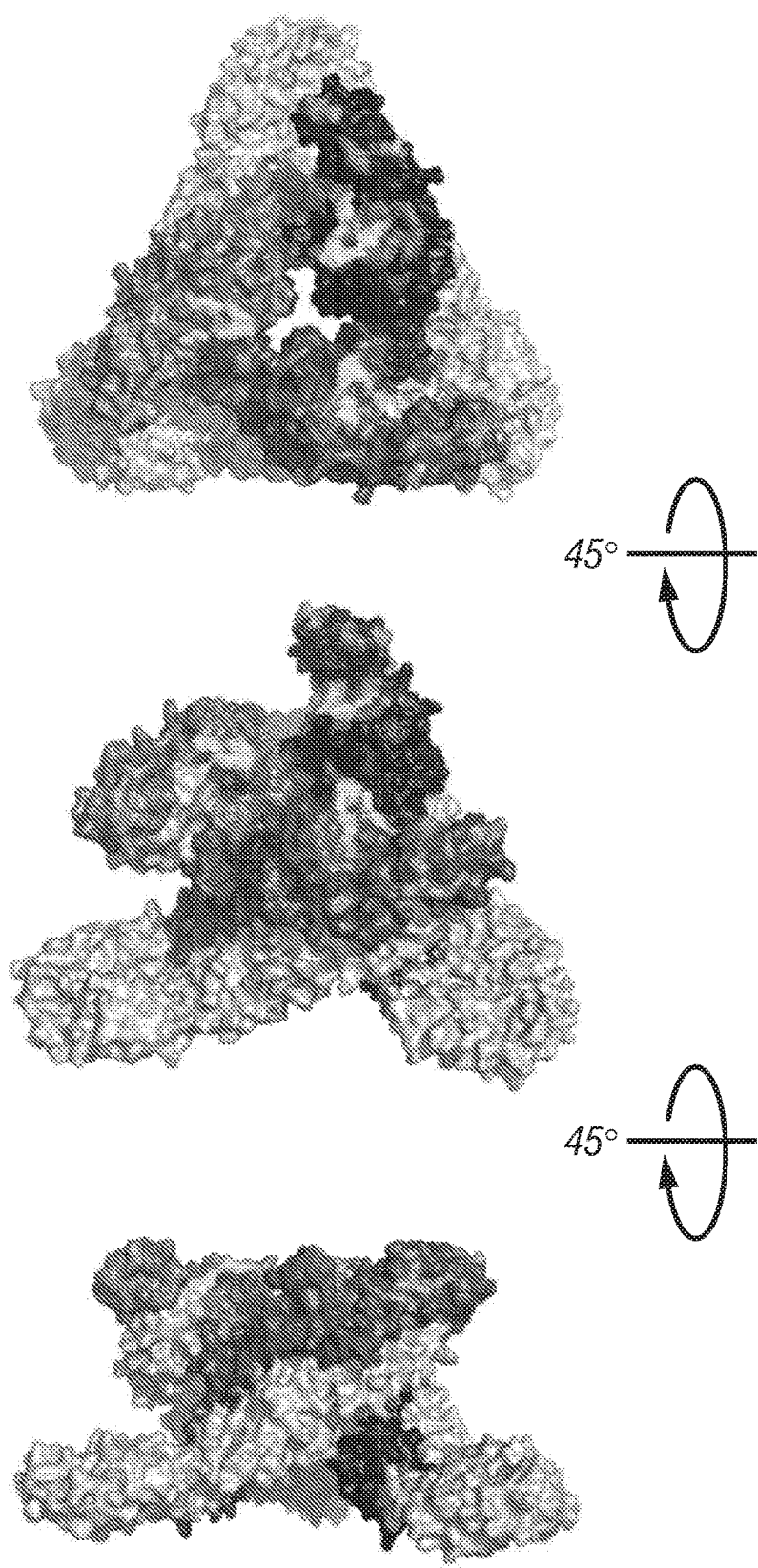
FIG. 7. Structural analysis of E2 residues important for mAb binding for antibodies mapped to competition groups. Location of residues required for binding of the human or mouse mAbs from different competition groups (FIGS. 1A-C) mapped onto the crystal structure of E1/E2 (PDB ID 2XFB). A space-filling model of the E1/E2 trimer with E1 colored in white and each E2 monomer colored with light grey, dark grey, or black. The residues required for antibody binding are color-coded according to the competition group (s) to which they belong. Red indicates residues D117 and I121, which are required for binding of 5N23, and belong to competition group 1. Blue indicates residues R80 and G253, which are required for binding by 106 or 5M16, belong to competition group 2. Green indicates residues Q184, S185, I190, V197, R198, Y199, G209, L210, T212, and 1217, which are required for binding by CHK-285, CHK-88, or 3A2, and belong to competition group 3. Orange indicates residues H18, which is required for binding of 5F19, and belongs to competition group 4. Purple indicates residues E24, A33, L34, R36, V50, D63, F100, T155, which are required for binding by 5N23, CHK-84, or CHK-141, and belong to competition groups 1 and 2. Teal indicates residues T58, D59, D60, R68, I74, D77, T191, N193, and K234, which are required for binding by 1H12, and belong to competition groups 2 and 3. Brown indicates residues D71, which is required for binding by CHK-84 and 1H12, and belongs to competition groups 1, 2, and 3. Yellow indicates residues (T58, D71, N72, I74, P75, A76, D77, 5118, and R119) that comprise the putative receptor-binding domain (RBD), with the exception of residue D71, which belongs to competition groups 1, 2, and 3. The upper panel shows a bird's eye view of the trimer, the middle panel shows an angled side view of the trimer rotated 45 in the x-axis from the structure in the upper panel, and the bottom panel shows a side view of the trimer rotated 45 in the x-axis from the structure in the middle panel.

Isolation of CHIKV-specific human mAbs. The inventors isolated a panel of mAbs from a single individual who acquired CHIKV infection in Sri Lanka in 2006 and presented with fever, arthralgias, and rash (FIG. 4). The clinical course and B cell transformation and screening procedures are provided in the Online Methods. They transformed B cells in two separate experiments from a single blood sample collected from the donor five and a half years following natural infection. They observed a virus-specific B cell frequency of approximately 1 in 1,000 total B cells and established 30 stable hybridomas from B cell lines secreting antibodies that bound to virus. The mAb panel contained IgGs of multiple subclasses, with 24 IgG1, three IgG2, and two IgG3; one was not determined due to poor hybridoma growth (Table 5).

Assessment of mAb neutralization. Eighteen of the mAbs exhibited neutralizing activity against Asian CHIKV strain SL15649-GFP virus reporter particles (VRPs) with EC$_{50}$ values <40 ng/mL, with eleven exhibiting ultrapotent inhibitory activity (defined as EC$_{50}$ values <10 ng/mL, Table 5). Four mAbs possessed weak inhibitory activity (EC$_{50}$ values in the 0.1 to 5 µg/mL range), and eight of the mAbs had no inhibitory activity at the highest concentration tested (EC$_{50}$ values >10 µg/mL).

Breadth of neutralizing activity. The inventors determined the EC$_{50}$ values for each antibody against representative infectious CHIKV strains of the East/Central/South African (ECSA) genotype (LR2006 OPY1 [LR] strain), the West African genotype (NI 64 IbH 35 strain), and the Asian genotype (RSU1 and 99659 [2014 Caribbean] strains) using a high-throughput focus reduction neutralization test (FRNT) (Pal et al., 2013). Twenty-five of the mAbs exhibited neutralizing activity against at least one CHIKV strain (EC$_{50}$ values <10 µg/mL), with eight mAbs exhibiting neutralization in a potent range (EC$_{50}$ values between 10-99 ng/mL), and thirteen mAbs exhibiting neutralization in an ultrapotent range (EC$_{50}$ values <10 ng/mL) (Table 5). For comparative purposes, the inventors also tested the previously reported human mAbs 5F10 and 8B10 against viruses of all three genotypes, and in every case the EC$_{50}$ values were >100 ng/mL (range 161-1337). In most cases, the mAbs the inventors isolated exhibited relatively similar neutralizing activity against virus from all three genotypes.

Six mAbs (2B4, 2H1, 4J21, 4N12, 5M16, and 9D14) inhibited viruses from all three genotypes with ultrapotent activity ($EC_{50}$ values <10 ng/mL). These data indicate that a single individual can develop multiple CHIKV-specific antibodies that are ultrapotent and broadly neutralizing.

Binding to E2 protein. The CHIKV E2 protein is a dominant target of murine (Goh et al., 2013; Lum et al., 2013), nonhuman primate (Kam et al., 2014), and human (Fong et al., 2014; Kam et al., 2012a; Kam et al., 2012b; Selvarajah et al., 2013) humoral responses. The inventors tested the human mAbs for binding to a monomeric form of the ectodomain of E2 protein expressed in *E. coli* (Pal et al., 2013). Nine mAbs bound strongly to the E2 ectodomain, six exhibited moderate binding, one bound weakly, and 14 failed to bind above background (Table 5). The capacity to bind purified E2 protein in vitro did not correlate directly with neutralizing potency (Table 5). A subset of 17 human mAbs was tested using a surface plasmon resonance assay for binding to the p62-E1 protein derived from mammalian cells (Voss et al., 2010). All mAbs bound in the nM range, with $K_D$ values from 0.5 to 20 nM. Differences in binding kinetics did not correlate with antigenic specificity or functional activity (Table S1).

Competition-binding studies. To identify non-overlapping antigenic regions in recombinant E2 protein recognized by different neutralizing mAbs, the inventors used a quantitative competition-binding assay. For comparison, they also evaluated four previously described murine mAbs (CHK-84, CHK-88, CHK-141, and CHK-265) (Pal et al., 2013) and the previously described human mAb 5F10 (Wailer et al., 2011) (FIG. 5). The pattern of competition was complex, but three major competition groups were evident, which the inventors designated group 1 (red box), group 2 (blue boxes) or group 3 (green box). The inventors also defined a fourth group containing the single human mAb, 5F19 (orange box). These competition studies suggest that there are three major antigenic regions recognized by CHIKV-specific antibodies.

Epitope mapping using alanine-scanning mutagenesis. The inventors used an alanine-scanning mutagenesis library coupled with cell-based expression and flow cytometry to identify amino acids in E2 and E1 proteins of CHIKV strain S27 (ECSA genotype) required for antibody binding (Fong et al., 2014) (FIGS. 6A-E). Residues required for antibody binding to CHIKV glycoproteins for a subset of 20 human mAbs are listed in Table 6. Mutations affecting binding of these 20 mAbs are indicated in an alignment of the full-length E2 sequences of strain S27 and strains representing all CHIKV genotypes that were used in this study (FIG. 1A). The amino acids in E2 that influence binding are located primarily in the solvent-exposed regions of domains A and B and arches 1 and 2 of the (β-ribbon connector, which links domains A and B (Voss et al., 2010) (FIG. 1A). Comparison of the antigenic sites identified by loss-of-binding experiments using alanine-scanning mutagenesis with the competition binding analysis (FIG. 5) demonstrated that competition groups 1 and 2 generally corresponded to sites within domain A and the arches, whereas group 3 corresponded to regions in domain B.

Figure 1C:
Figure 1B:
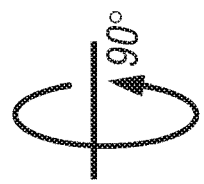
Figure 1B:

Structural analysis of antigenic regions. A large and diverse number of the surface residues in domains A and B and the arches are contacted by at least one of the mAbs (FIGS. 1B-C). Two principal antigenic regions in E2 accounted for the binding of multiple mAbs. The first region is located in domain A, between amino acids 58 and 80, and contains the putative receptor-binding domain (RBD) (Sun et al., 2014; Voss et al., 2010). The second region is located in domain B, between amino acids 190 and 215. Both sequence regions project away from the viral envelope and are located near the E2 trimer apex (FIGS. 6A-E and 7).

Figure 8:
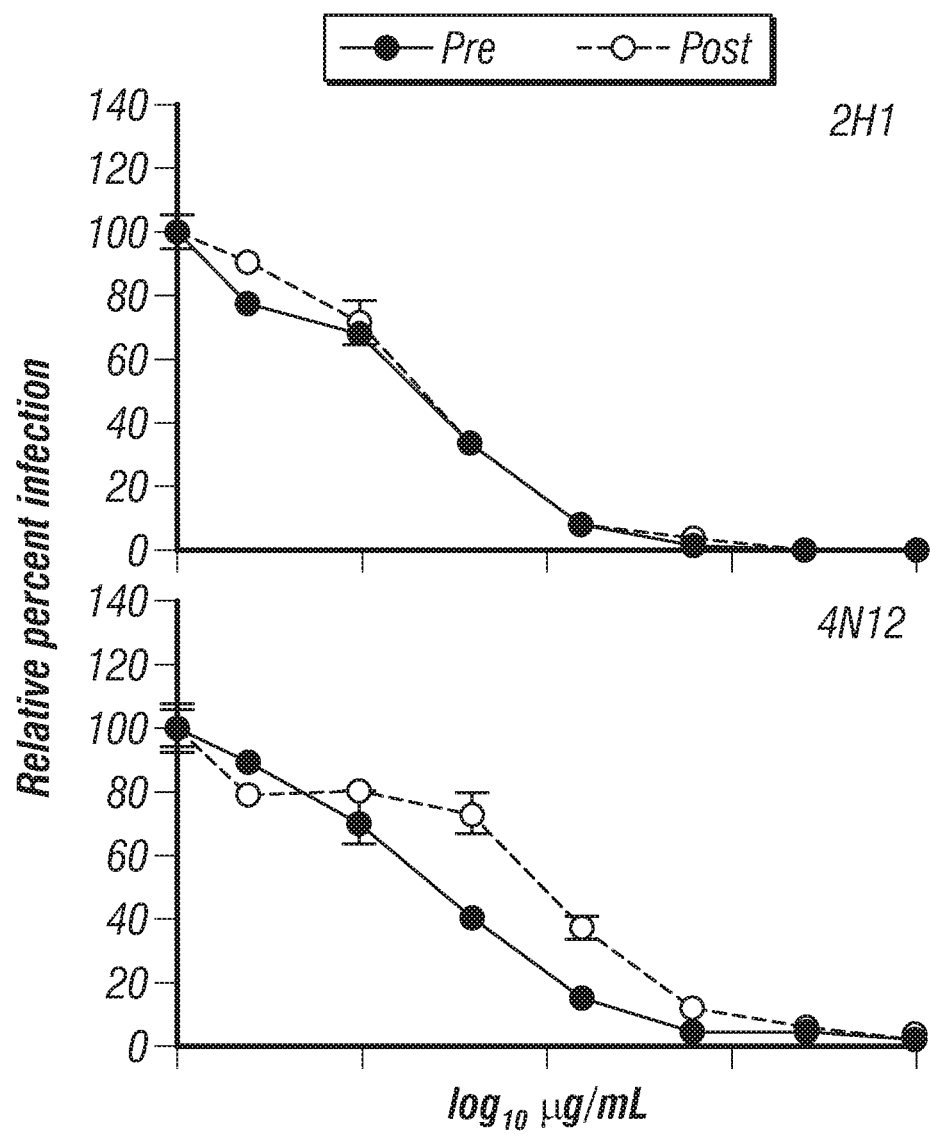
FIG. 8. Mechanism of Neutralization by Two Human Anti-CHIKV mAbs, 2H1 or 4N12. Pre- and post-attachment neutralization assays. CHIKV strain SL15649 virus replicon particles (VRPs) were (1) incubated with the mAbs shown (2H1 or 4N12) prior to addition to pre-chilled Vero cells, followed by removal of unbound virus by three washes (pre-attachment; filled circle) or (2) allowed to adsorb to pre-chilled Vero cells followed by addition of the indicated mAbs (post-attachment; open circles). These mAbs neutralized when added prior to or after attachment.
Figure 9:
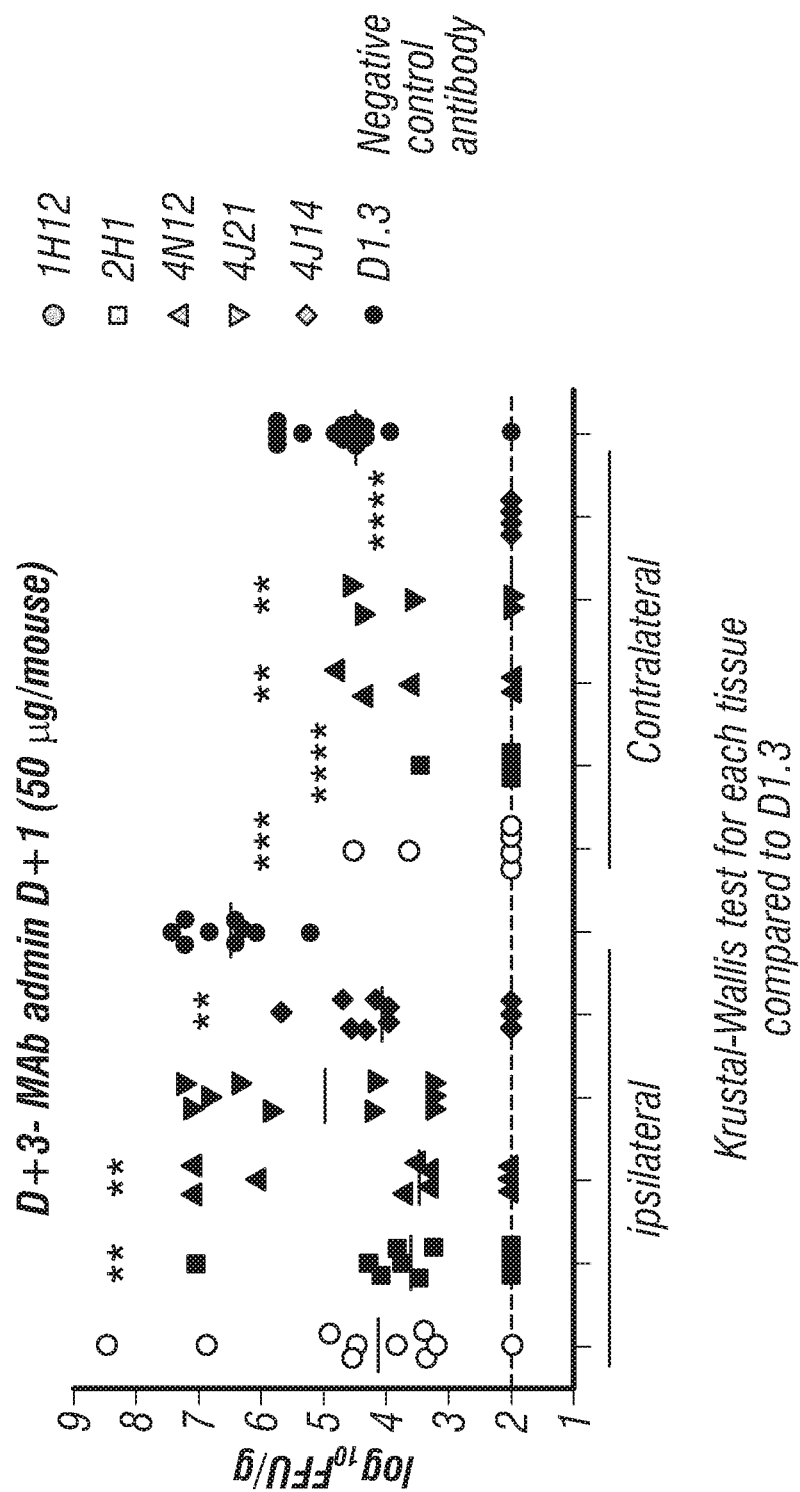
FIG. 9. B6 mouse acute disease model. CHO cell produced recombinant antibodies, given on day 1, reduce virus in ankles compared to control antibody treatment on D+3. Experiments were performed in 4 week-old WT mice after subcutaneous inoculation with $10^3$ FFU of CHIKV-LR. Antibodies were given on D+1 and tissues were harvested on D+3 for titration by focus-forming assay.
Figure 10:
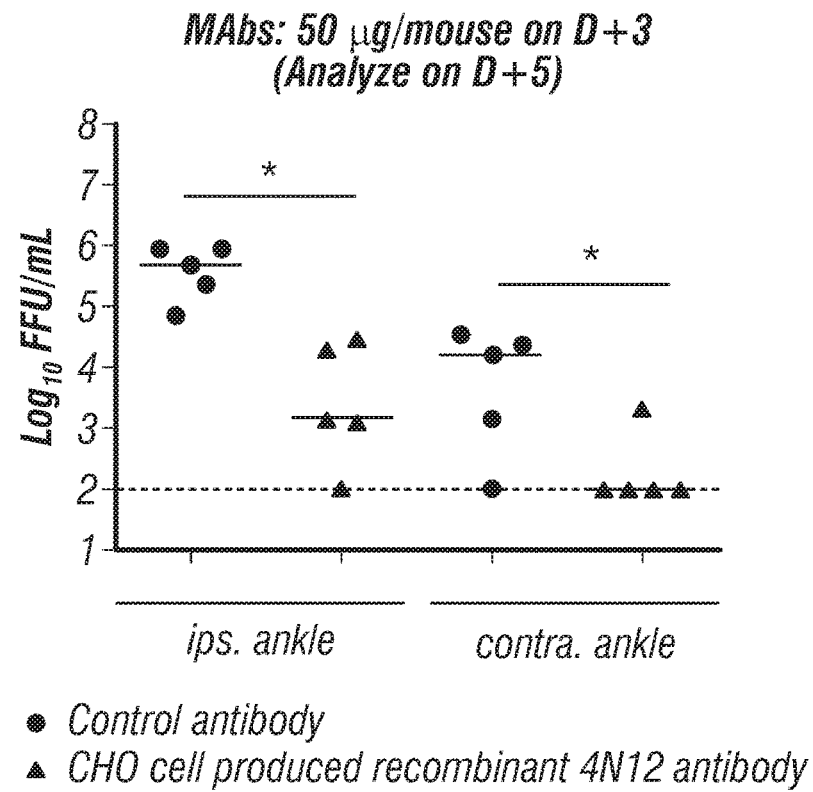
FIG. 10. B6 mouse acute disease model. CHKV mAb 4N12 produced in CHO cells, given systemically on day 3, reduces virus titer in ankles Experiments were performed in 4 week-old WT mice after subcutaneous inoculation with 10e3 FFU of CHIKV-LR. Antibodies were given on D+3 and tissues were harvested on D+5 for titration by focus-forming assay.
Figure 11:
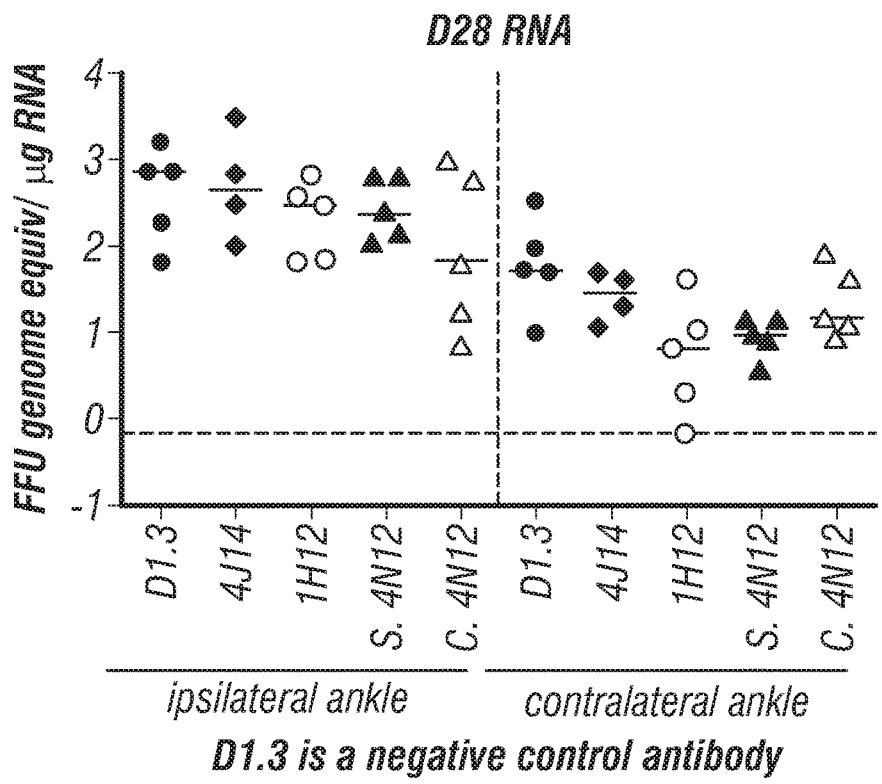
FIG. 11. B6 mouse chronic disease model. CHKV mAbs produced in CHO cells, given systemically on day 3, reduces virus genomic equivalents, on day 28, in ankles. Experiments were performed in 4 week-old WT mice after inoculation with 10e3 FFU of CHIKV-LR. Antibodies (300 μg) were given on D+3 and tissues were harvested on D+28 for analysis by qRT-PCR.
Figure 12:
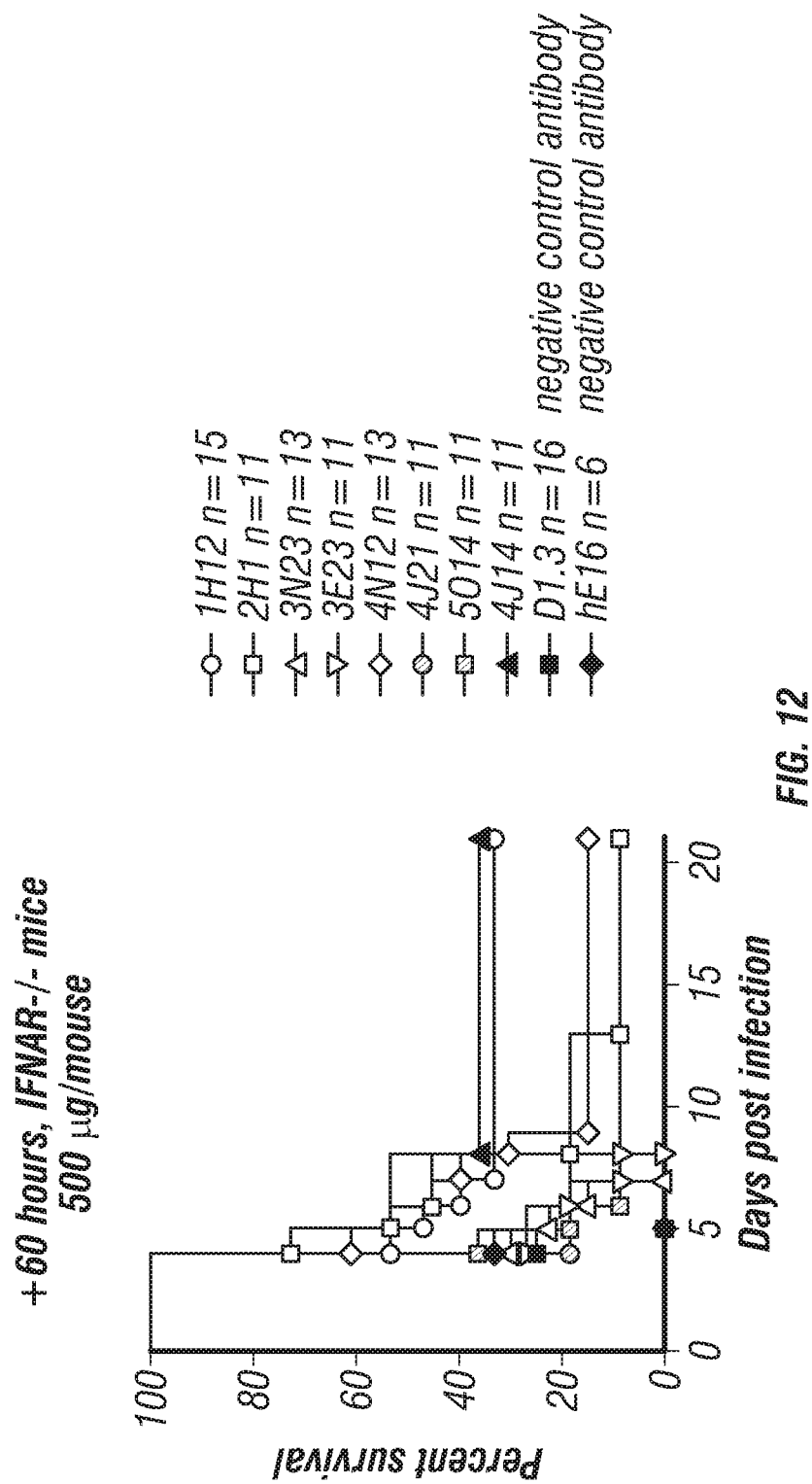
FIG. 12. INFNAR knockout lethal disease mouse model. CHKV mAbs produced in CHO cells, given systemically at 60 hours post-infection, enhance survival. Experiments were performed in 4-5 week-old IFNAR-/- mice after subcutaneous inoculation with 10e3 FFU of CHIKV-LR. Antibodies were given 60 hours after infection and mortality was followed for 21 days.
Figure 13:
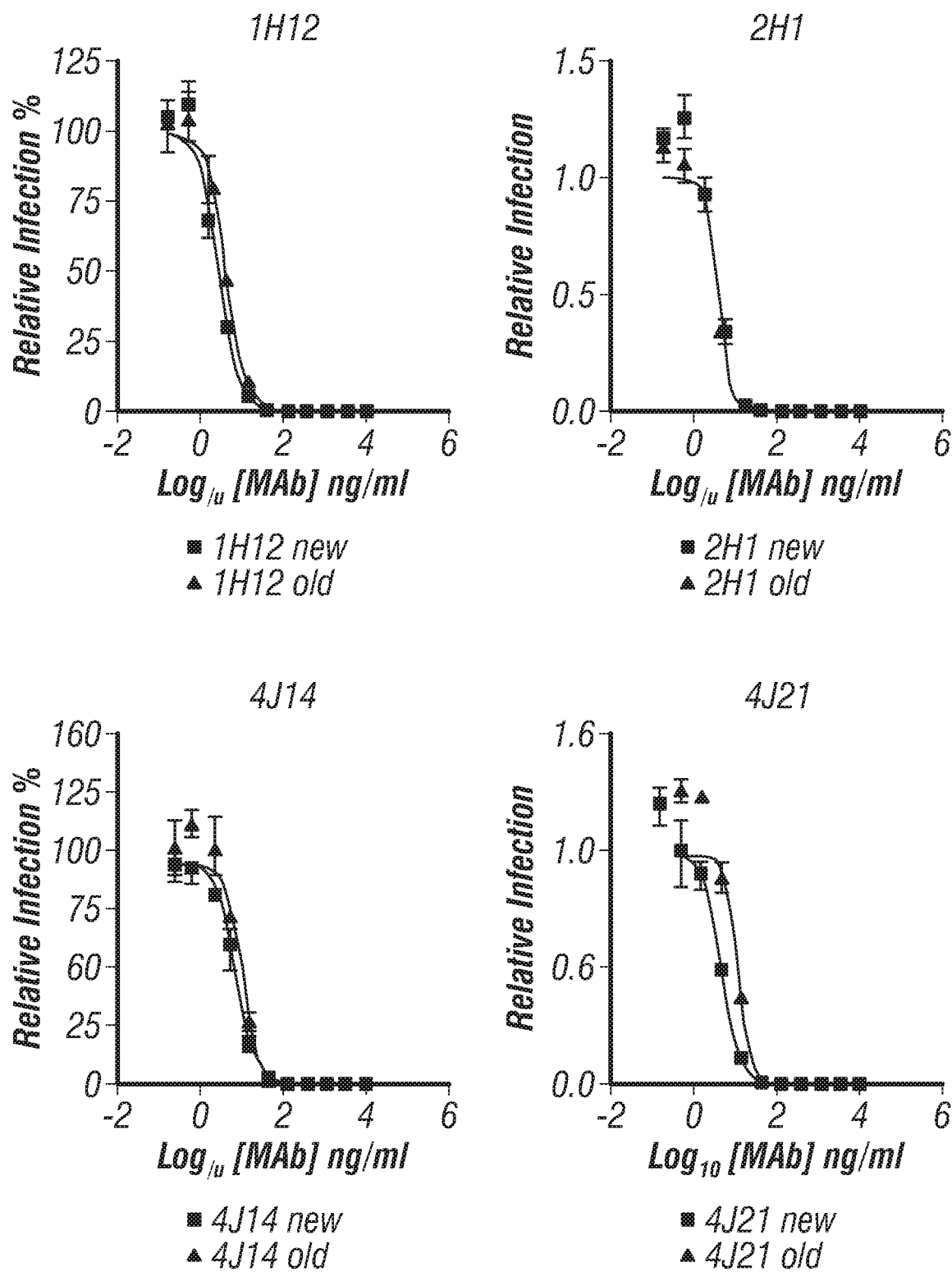
FIG. 13. Neutralization curves for hybridoma-produced ('old') or recombinant ('new') CHIKV-specific mAbs. Neutralization curves were performed in BHK21 cells. 100 FFU of CHIKV-LR was mixed with indicated mAbs for 1 h at 37° C. prior to addition to BHK21 cells. Infection was determined by a focus forming assay.
Figure 13:
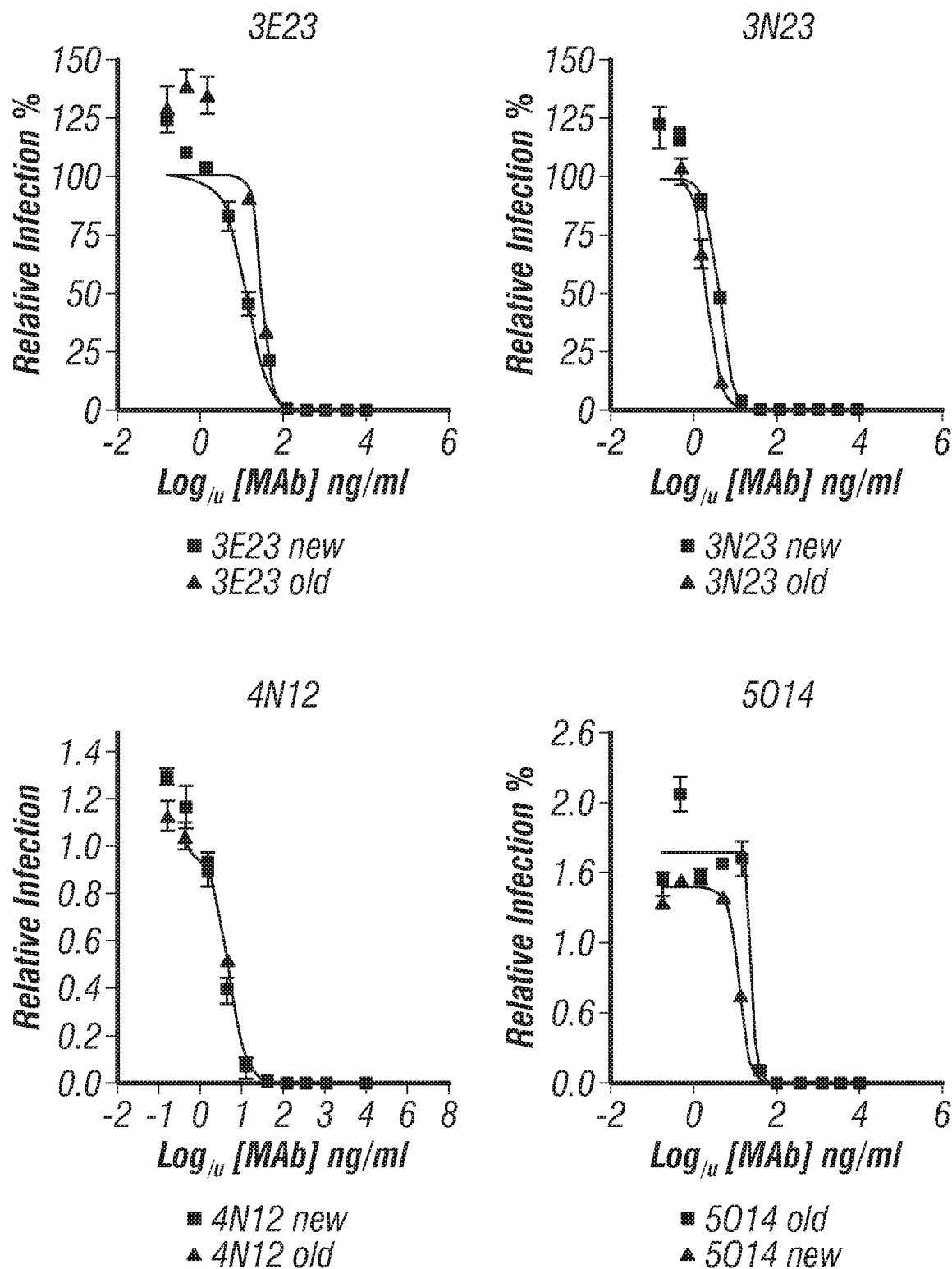

Mechanism of neutralization. The inventors conducted pre- and post-attachment neutralization assays using mAbs displaying a range of inhibitory activities. As expected, all five mAbs tested neutralized infection efficiently when pre-incubated with VRPs (FIG. 2A). However, mAb 4B8 did not neutralize VRPs completely even at high concentrations, suggesting the presence of a fraction of CHIKV virions resistant to this mAb; this pattern also was observed in assays using viable CHIKV strains corresponding to the three distinct CHIKV genotypes (data not shown). In contrast, mAbs 3E23, 4J21, 5M16, and 9D14 completely neutralized infection when administered before attachment. All five human mAbs also neutralized CHIKV infection when added following attachment, but the inventors observed three different patterns of activity (FIG. 2A). MAb 4B8 was incapable of complete neutralization when added post-attachment, and the fraction of resistant virions was larger compared with that observed following pre-attachment neutralization. MAb 9D14 neutralized VRPs with comparable efficiency whether added before or after attachment. MAbs 3E23, 4J21, and 5M16 displayed complete neutralization of VRPs, but the efficiency of neutralization post-attachment was lower than that following pre-attachment. The mAbs 2H1 and 4N12 also efficiently neutralized VRPs when added prior to or after attachment (FIG. 8).

Fusion-from-without (FFWO) assay testing of five of the ultrapotently neutralizing mAbs (3E23, 4B8, 4J21, 5M16, or 9D14) revealed that all inhibited fusion (Edwards and Brown, 1986). As expected, when virions pre-treated with mAbs were incubated continuously with medium buffered at neutral pH, little to no infection was observed (FIG. 2B). In the absence of antibody treatment, a short pulse of acidic pH-buffered medium resulted in infected cells, indicating fusion between the viral envelope and plasma membrane. Notably, all five human mAbs inhibited plasma membrane fusion and infection, with mAb 9D14 exhibiting the greatest potency in this assay. These studies suggest that ultrapotently neutralizing mAbs block CHIKV fusion.

Figures 3A, 3B, 3C, 3D:
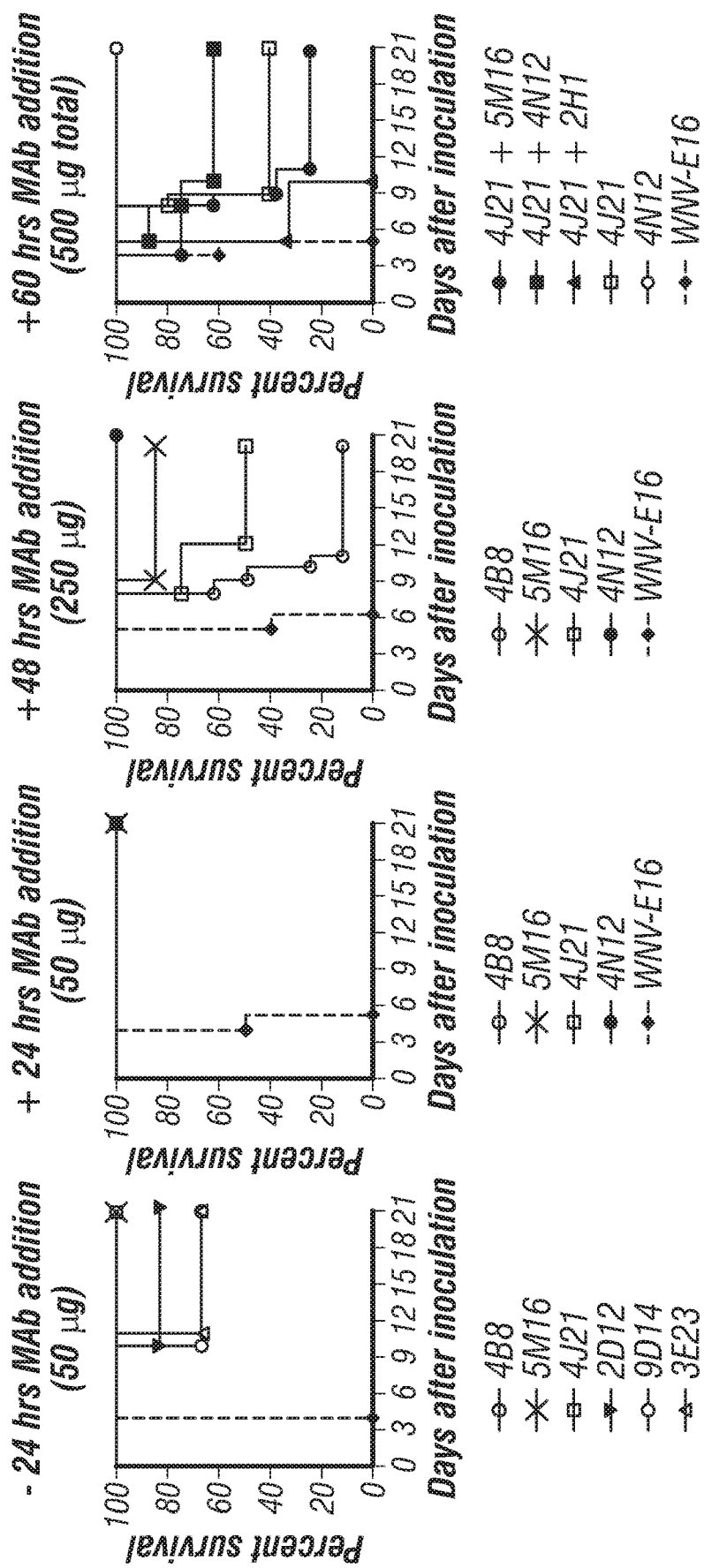
FIGS. 3A-D. Human mAb therapy against lethal CHIKV infection in Ifnar$^{-/-}$ mice.

MAb prophylaxis in vivo. The inventors tested a subset of mAbs exhibiting diverse levels of neutralizing activity (Table 7) in a lethal infection model with 6-week-old, highly immunodeficient $Ifnar^{-/-}$ mice. Mice were pre-treated with a single 50 µg dose (~3 mg/kg) of human anti-CHIKV mAbs or a West Nile virus-specific isotype control mAb (WNV hE16) 24 hours before subcutaneous injection with a lethal dose of CHIKV-LR2006. All mice treated with the isotype control mAb succumbed to infection by 4 days post-inoculation. Pretreatment with mAbs 4B8, 4J21, or 5M16 completely protected $Ifnar^{-/-}$ mice, whereas treatment with mAbs 3E23 or 9D14 partially protected the infected animals, with 67% survival rates (FIG. 3A). Surprisingly, mAb 2D12, which weakly neutralized in vitro, protected 83% of the animals.

MAb post-exposure therapy in vivo. $Ifnar^{-/-}$ mice were inoculated with a lethal dose of CHIKV-LR2006 and then administered a single 50 µg (~3 mg/kg) dose of representative mAbs 24 hours following virus inoculation. Therapeutic administration of these mAbs provided complete protection, whereas the isotype-control mAb provided no protection (FIG. 3B). To define further the therapeutic window of efficacy, $Ifnar^{-/-}$ mice were administered a single 250 µg (~14 mg/kg) dose of representative mAbs 48 hours after challenge with CHIKV-LR2006. Treatment with 5M16, 4J21, and 4B8 protected 85%, 50%, and 12.5% of the animals, respectively (FIG. 3C). Remarkably, monotherapy with 4N12 at the later time point of 60 hours protected 100% of animals when used at a dose of 500 µg, (~28 mg/kg) (FIG. 3D). These data establish that human mAbs can protect against CHIKV-induced death, even at intervals well after infection is established.

Analogously, studies were performed in WT mice to assess the effects of human mAbs on CHIKV acute and chronic arthritis. MAbs were administered on day 1 or 3 after infection and viral burden or RNA was analyzed at D3, 5 or 28 after infection. Depending on the tissue and time examined either 1H12 or 4J14 provide the most significant virological protection. 4N12 also provided significant protection in these assays.

Combination mAb therapy in vivo. Given the possibility of resistance selection in vivo in animals treated with a single anti-CHIKV mAb (Pal et al., 2013), the inventors tested whether a combination of two anti-CHIKV human mAbs could protect mice against lethal challenge. They chose pairs of neutralizing mAbs based on the potency of individual mAbs in vitro. Ifnar$^{-/-}$ mice were administered a single combination antibody treatment dose (250 µg of each, ~total of 28 mg/kg) of the most effective mAbs 60 hours after inoculation. Although some mAb combinations ([4J21+2H1] and [4J21+5M16]) provided little or no protection, others ([4J21+4N12]) resulted in a 63% survival rate at this very late time point (FIG. 3D). Thus, combination mAb therapy protected against lethal CHIKV infection in highly immunocompromised mice even when administered within 24 to 36 hours of when these animals succumb. In this setting, 4N12 worked less well in combination with 4J21 than it did as monotherapy, although the dosing of 4N12 in monotherapy experiments (500 µg) was twice that of the 4N12 component in combination therapy (250 µg).

display remarkable neutralizing activity in vitro and therapeutic efficacy in vivo. As a class, the most inhibitory antibodies also exhibited broad activity, neutralizing viruses from all three CHIKV genotypes, including a strain currently circulating in the Caribbean. The majority of human CHIKV-specific mAbs isolated in this study neutralized the virus at concentrations less than 100 ng/mL, and many exhibited inhibitory activity at less than 10 ng/mL. This activity is greater than the inventors have observed in previous studies of human mAbs against other pathogenic human viruses, including H1, H2, H3, or H5 influenza viruses (Hong et al., 2013; Krause et al., 2012; Krause et al., 2011a; Krause et al., 2011b; Krause et al., 2010; Thornburg et al., 2013; Yu et al., 2008), dengue viruses (Messer et al., 2014; Smith et al., 2013a; Smith et al., 2014; Smith et al., 2013b; Smith et al., 2012), and others. The potency of many human CHIKV mAbs is comparable to or exceeds that of best-in-class murine neutralizing CHIKV mAbs (Fong et al., 2014; Fric et al., 2013; Pal et al., 2013; Wailer et al., 2011), which were generated after iterative boosting and affinity maturation. Most other neutralizing human mAbs against CHIKV are substantially less potent (Fong et al., 2014; Selvarajah et al., 2013; Warter et al., 2011). A single previously reported human CHIKV-specific mAb (IM-CKV063) displays activity comparable to the ultrapotent neutralizing mAbs reported here (Fong et al., 2014).

The inventors observed a diversity of epitope recognition patterns in E2 by the different neutralizing CHIKV mAbs tested. Fine epitope mapping with alanine-substituted CHIKV glycoproteins showed that recognition of three structural regions in E2 is associated with mAb-mediated neutralization: domain A, which contains the putative RBD (Sun et al., 2013; Voss et al., 2010), domain B, which

TABLE S1

Kinetics of human CHIKV antibodies binding antigen measured by SPR

| CHKV MAb | Ligand | ka ($10^6$ M-1s-1) | kd ($10^{-4}$ s-1) | KD (nM) | $t_{1/2}$ (min) |
|---|---|---|---|---|---|
| 5M16 | p62-E1 | 1.09 ± 0.02 | 1.13 ± 0.02 | 1.03 ± 0.01 | 102 ± 2 |
| 5M16 Fab | VLP | 1.19 ± 0.01 | 0.84 ± 0.13 | 7.07 ± 1.05 | 137 ± 21 |
| 4J21 | p62-E1 | 1.19 ± 0.02 | 0.62 ± 0.05 | 0.54 ± 0.31 | 186 ± 11 |
| 4J21 Fab | VLP | 1.58 ± 0.03 | 14.2 ± 0.29 | 9.00 ± 0.03 | 8 ± 0.2 |
| 3E23 | p62-E1 | 3.18 ± 2.43 | 2.67 ± 0.87 | 6.11 ± 1.41 | 43 ± 19 |
| 3E23 Fab | VLP | 0.203 ± 0.03 | 3.93 ± 0.40 | 19.6 ± 3.16 | 29 ± 3 |
| 4B8 | p62-E1 | 2.98 ± 2.98 | 5.06 ± 1.10 | 5.57 ± 1.10 | 23 ± 5 |
| 4B8 Fab | VLP | 0.60 ± 0.04 | 3.33 ± 0.30 | 5.60 ± 0.46 | 35 ± 3 |
| 5N23 | p62-E1 | 2.98 ± 0.75 | 2.40 ± 0.66 | 0.87 ± 0.37 | 48 ± 17 |
| 1L1 | p62-E1 | 0.88 ± 0.44 | 2.73 ± 0.36 | 3.79 ± 2.10 | 42 ± 6 |
| 2C2 | p62-E1 | 1.54 ± 0.65 | 6.08 ± 1.45 | 4.59 ± 2.32 | 19 ± 6 |
| 2D12 | p62-E1 | 17.5 ± 1.64 | 5.41 ± 3.97 | 0.49 ± 0.08 | 13 ± 4 |
| 4N12 | p62-E1 | 1.24 ± 0.02 | 1.18 ± 0.01 | 0.95 ± 0.02 | 98 ± 1 |
| 5O14 | p62-E1 | 0.79 ± 0.02 | 9.11 ± 0.19 | 1.15 ± 0.01 | 13 ± 0.3 |
| 9D14 | p62-E1 | 2.70 ± 0.90 | 2.82 ± 0.14 | 1.13 ± 0.40 | 41 ± 2 |
| 8G18 | p62-E1 | 3.90 ± 0.21 | 1.88 ± 0.11 | 0.48 ± 0.02 | 62 ± 3 |
| 4J14 | p62-E1 | 1.61 ± 0.47 | 15.3 ± 2.52 | 9.94 ± 2.54 | 8 ± 1 |
| 5F | p62-E1 | 2.61 ± 0.04 | 50.9 ± 0.75 | 19.5 ± 0.2 | 2 ± 0.03 |
| 3A2 | p62-E1 | 2.12 ± 0.02 | 10.1 ± 0.12 | 4.78 ± 0.08 | 11 ± 0.1 |
| 1M9 | p62-E1 | 1.86 ± 0.99 | 3.98 ± 0.26 | 2.48 ± 0.99 | 29 ± 2 |
| 3B4 | p62-E1 | 2.91 ± 0.09 | 1.56 ± 0.11 | 0.54 ± 0.02 | 74 ± 5 |
| 6B | p62-E1 | 0.99 ± 0.03 | 2.74 ± 0.10 | 2.77 ± 0.18 | 42 ± 2 |
| 6E22 | p62-E1 | 0.48 ± 0.02 | 2.0 ± 0.13 | 4.22 ± 0.42 | 58 ± 4 |

Values for ka, kd, KD are means ± standard deviations.
KD = kd/ka; $t_{1/2}$ = (ln(2)/kd)/60.

Example 3—Discussion

The inventors report the isolation of a diverse panel of naturally-occurring human mAbs from a single individual, the majority of which recognize the CHIKV E2 protein and contacts and shields the fusion loop in E1 (Voss et al., 2010), and arches 1 and 2 of the β-ribbon connector, which contains an acid-sensitive region and links domains A and B (Voss et al., 2010). Of the antibodies mapped to epitopes in E2, the bulk (those in competition groups 1 and 2) preferentially recognized sites in domain A and arches 1 and 2, whereas a smaller group (in competition group 3) recognized sites in domain B. These data suggest that surface-exposed regions in domain A and the arches are dominant antigenic sites that elicit human neutralizing antibody responses. The inventors conclude that the highly conserved region in domain A and arch 2 might elicit a broadly protective immune response and serve as an attractive candidate for epitope-focused vaccine design.

Remarkably, almost a quarter of surface-exposed residues in the critical E2 domains appear to be engaged by one or more mAbs from a single individual. The existence of functionally diverse binding modes on the major antigenic sites is implied by two observations: (a) some mAbs bound to similar epitopes but exhibited inhibitory activity that varied by several orders of magnitude and (b) there was little correlation between neutralization capacity and affinity of binding to E2 protein. Seven of the most potently neutralizing human mAbs (2H1, 3E23, 4B8, 4J21, 4N12, 5M16, and 9D14) inhibited CHIKV infection at a step following attachment, likely via prevention of pH-dependent structural changes, which prevents nucleocapsid penetration into the cytoplasm (Kielian et al., 2010).

As therapeutic efficacy in mice appears to predict treatment outcomes in experimentally-induced infection and arthritis in nonhuman primates (Pal et al., 2013; Pal et al., 2014), the data here suggest that prophylaxis of humans with CHIKV-specific human mAbs would prevent infection. Given concerns about selection of resistant variants with monotherapy (Pal et al., 2013), combination therapy using ultrapotent neutralizing antibodies that target different regions of E2 may be desirable. Patient populations at markedly increased risk of severe disease could be targeted during outbreaks, including those with serious underlying medical conditions (e.g., late-term pregnant women, the immunocompromised, and the elderly). Further clinical testing is planned to determine whether neutralizing human mAbs can prevent or ameliorate established joint disease in humans.

TABLE 1

NUCLEOTIDE SEQUENCES FOR ANTIBODY VARIABLE REGIONS

| Clone | Variable Sequence Region | SEQ ID NO: |
|---|---|---|
| 1H12 heavy | CAGGTGCAGCTGGTGCAGTCTGGAGCTGAGGTGAAGAAGCCTGGGGCCTCAGTG AAGGTCTCCTGCAAGGCCTCTGGTTACAGCTTTACCAGCTACGGTATCAGCTGG GTGCGACAGGCCCCTGGACAAGGGCTTGAGTGGATGGGATGGATCAGCACTTAC AAAGGTTACACACAGTATGCACAGAACTTCCAGGGCAGAGTCACCATCACCACA GACACACCCGCGACTACAGTCTATATGGAGCTGAGGAGCCTGAGATCTGACGAC ACGGCCGTGTATTACTGCGCGAGAGTTCTTTCCGAGACTGGTTATTTCTACTAC TACTACTACGGTATGGACGTCTGGGGCCAAGGGACCCTGGTCACCGTCTCCTCA | 2 |
| 1H12 light | CAGGCTGTGGTGACTCAGCCGCCCTCAGTGTCTGGGGCCCCAGGGCAGAGGGTC ACCATCTCCTGTACTGGGAGCAGCTCCAACATCGGGGCAGATTATAATGTACAC TGGTACCAGCTGCTTCCAGGAACAGCCCCCAAACTCCTCATCTATGGTAACACC AATCGGCCCTCAGGGGTCCCTGACCGATTCTCTGGCTCCAAGTCTGGCACCTCA GCCTCCCTGGCCATCACTGGGCTCCAGGCTGAGGATGAGGCTGATTATTACTGC CAGTCCTATGACAGCAGCCTGAGTGCTTCGGTATTCGGCGGAGGGACCAAACTG ACCGTCCTAG | 3 |
| 2B4 heavy | caggtgcagctggtgcaatctgggtctgagttgaagaagcctgggGCCTCAGTG AAGGTCTCCTGCAAGGCTTCTGGATACAGTTTCACTAGCTATTCTATCAACTGG GTGCGACAGGCCCCTGGACAAGGGCCTGAGTGGATGGGATGGATCGACACCAAC ACTGGGAACCCAACCTATGCCCAGGACTTCGCAGGACGGTTTGTCTTCTCCTTG GACACCTCTGTCACCACGGCATATCTGCAGATCAGCAGCCTAAAGGCTGGGGAC ACTGCCGTTTATTACTGTGCAACATATTATGTTGACCTTTGGGGGAGTTATCGC CAAGACTACTACGGTATGGACGTCTGGGGCCAC | 4 |
| 2B4 light | cagtctgtgctgactcagccacccctcagcgtctgggaccccccgggcagagggtc accatCTCTTGTTCTGGAGGGAGCTCCAACATCGGGAGTAATCCTGTAAATTGG TACCAGATGGTCCCAGGAACGGCCCCCAAACTCCTCCTCTATACTAATAATCAG CGGCCCTCAGGGGTCCCTGACCGATTCTCTGGCTCCAAGTCTGGCACCTCAGCC TCCCTGGCCATCAATGGACTCCAGTCTGAGGATGAGGCTGATTATTACTGTGCA GTATGGGATGACAGCCTGAGTGGCCGTTGGGTGTTCGGCGGAGGGACCAAGGTG ACCGTCCTA | 5 |
| 2H1 heavy | CAGGTGCAGCTGGTGCAGTCTGGAGCTGAGGTGAAGAAGCCTGGGGCCTCAGTG AGGGTCTCCTGCAAGGCGTCTGGTTACACCTTTACCAGTTATGGTATCAGCTGG GTGCGACAGGCCCCTGGACAAGGGCTTGAGTGGATGGGATGGATCAGCACTTAC AATGGTGACACAAACTATGCACAGAAGTTCCAGGGCAGAGTCACCTTGACAACA GAGACATCCACGAGCACAGCCTACATGGAGCTGAGGCGCCTGAGATCTGACGAC ACGGCCGTTTACTACTGTGCGAGAGATTTTGAATTTCCCGGAGATTGTAGTGGT GGCAGCTGCTACTCCAGGTTCATCTACCAGCACAACGACATGGACGTCTGGGGC CACGGGACCCTGGTCACCGTCTCCTCAGCAAGC | 6 |
| 2H1 light | CAGGCTGTGGTGACTCAGCCGCCCTCAGTGTCTGCGGCCCAGGACAGAAGGTC ACCATCTCCTGCTCTGGAAGCAGCTCCAACATTGGGAATCATTATGTATCCTGG TACCAGCACCTCCCGGGAACAGCCCCCAAACTCCTCATTTATGACAATTATAAG CGACCCTCAGTGATTCCTGACCGATTCTCTGCCTCCAAGTCTGGCGCGTCAGCC ACCCTGGGCATCATCGGACTCCAGACTGGGGACGAGGCCGATTATTACTGCGGA ACATGGGATAGCAGCCTGAGTGCTGTGGTATTCGGCGGAGGGACCAAGCTGACC GTCCTA | 7 |

TABLE 1-continued

NUCLEOTIDE SEQUENCES FOR ANTIBODY VARIABLE REGIONS

| Clone | Variable Sequence Region | SEQ ID NO: |
|---|---|---|
| 3E23 heavy | CAGGTGCAGCTGGTGCAGTCGGGCCCAGGACTGGTGAAGCCTTCGGACACCCTG TCCCTCACCTGCAGTGTCTCAAGTGACGCCCTCCGCAGCAGGAGTTATTACTGG GGCTGGGTCCGCCAGCCCCCCGGGAAGGGATTGGAGTGGATTGGGACTGTCTCT TATAGTGGGGGCACCTACTACAACCCGTCCCTCCAGAGTCGAGTCACCGTGTCG GTGGACACGTCCAAGAACCACTTCTCCCTGAGGTTGAACTCTGTGACCGCCGCA GACGCGGCTGTTTATTACTGTGCGAGATCTTATTTCTATGATGGCAGTGGTTAC TACTACCTGAGCTACTTTGACTCCTGGGGCCAGGGAACCCTGGTCACCGTCTCC TCA | 8 |
| 3E23 light | CAGGCTGTGGTGACTCAGGAGCCCTCACTGACTGTGTCCCCAGGAGGGACAGTC ACTCTCACCTGTGCTTCCAGCACTGGAGCAGTCACCAGTGGTCACTATCCAAAC TGGTTCCAGCAGAAACCTGGACAACCACCCAGGGCCCTGATTTATAGCACAGAA AACAAGCACTCCTGGACCCCTGCCCGGTTCTCAGGCTCCCTCCTAGGGGTCAAG GCTGCCCTGACACTGTCAGATGTACAGCCTGAGGACGAGGCTGACTATTACTGC CTGCTCCATTTTGGTGGTGTCGTGGTCTTCGGCGGAGGGACCAAGCTGACCGTC CTA | 9 |
| 3N23 heavy | CAGGTGCAGCTGGTGCAGTCTGGGGGAGGCGTGGTCCAGCCTGGGAGGTCCCTG AGACTCTCCTGTGCAGTGTCTGGATTCACCTTCAGTAACTATGCCATGCACTGG GTCCGCCAGGCTCCAGGCAAGGGGCTGGACTGGGTGGCAGTTATATGGTATGAT GGAAGTAATAAATACTATGCAGACTCCGTGAAGGGCCGATTCACCATCTCCAGA GACAATTCCAAGAACACGCTGTATCTGCAAGTGAACAGCCTGAGAGCCGAGGAC ACGGCTGTGTATTACTGTGCGAGGGGTGACTACGTTCTTGACTACTGGGGCCAG GGAACCCTGGTCACCGTCTCCTCA | 10 |
| 3N23 light | GACATTGTGATGACCCAGTCTCCATCCTCCCTGTCTGCATCTGTAGGAGACAGA GTCACCATCAGTTGCCGGGCCAGTCAGAGCATTCCCAGCTATTTAAATTGGTAT CAACAGAAACCAGGGAAAGCCCCTAAGGTCCTGATCTATGCTACATCCACTTTG GAAGCTGGGGTCCCATCACGGTTCAGTGGCAGTGGATCTGGGACAGATTTCACT CTCACCATCACCAGTCTGCAACCTGAAGATTTTGCAACTTACTACTGTCAACAG AGTTACAATACGGGGATATTCACTTTCGGCCCTGGGACCAAAGTGGATATCAAA | 11 |
| 4J14 heavy | CAGGTGCAGCTGGTGCAGTCTGGGGCTGAGGTGAAGAAGCCTGGGTCCTCGGTG AAGGTCTCCTGCAAGGCTTCTGGAGGCACTTCCAGCACTTATGCTATCAGCTGG GTGCGACAGGCCCCTGGACAAGGGCTTGAGTGGATGGGAGGCAGCATCCCTGTC TTTGCTACAGTAAACTACGCACAGAAGTTCCAGGGCAGACTCACGATTACCGCG GACGAATCCACGAGCACAGTTTACATGGAACTGAGCAGCCTGAGATCTGAGGAC ACGGCCGTTTATTTCTGTGCGAGCCCCTATTGTAGTAGTATGAACTGCTATACG ACCTTTTACTACTTTGACTTCTGGGGCCAGGGAACCCTGGTCACCGTCTCCTCA | 12 |
| 4J14 light | CAGGCTGTGGTGACTCAGCCTGCCTCCGTGTTTGGGTTTCCTGGACAGTCGATC ACCATCTCCTGCACTGGAACCAGCAGTGACTTTGGTACTTATAACTATGTCTCT TGGTACCAGCAACACCCAGGCCAAGCCCCCAAACTCATGATTTTTGATGTCAGT AATCGGCCCTCAGGGGTTTCTAATCGCTTCTCTGGCTCCAAGTCTGGCAACACG GCCTCCCTGACCATCTCTGGGCTCCAGGCTGAGGACGAGGCTTCTTATTACTGC AGCTCCTATACAAGCGGCAGCACTCTCTACGGCGGAGGGACCAAGCTGACCGTC CTG | 13 |
| 4J21 heavy | CAGGTGCAGCTGGTGCAGTCTGGGTCTGAGTTGAAGAAGCCTGGGGCCTCAGTG AAGGTTTCCTGCAAGGCTTCTGGATACAGTTTCACTAGCTATTCTATCAACTGG GTGCGACAGGCCCCTGGACAAGGGCCTGAGTGGATGGGATGGATCGACACCAAC ACTGGGAACCCAACCTATGCCCAGGACTTCGCAGGACGGTTTGTCTTCTCCTTG GACACCTCTGTCACCACGGCATATCTGCAGATCAGCAGCCTAAAGGCTGGGGAC ACTGCCGTTATTACTGTGCAACATATTATGTTGACCTTTGGGGAGTTATCGC CAAGACTACTACGGTATGGACGTCTGGGGCCACGGGACCCTGGTCACCGTCTCC TCA | 14 |
| 4J21 light | CAGTCTGTGGTGACTCAGCCACCCTCAGTGTCTGGGACCCCCGGGCAGGGGGTC ACCATCTCTTGTTCTGGAGGGAGCTCCAACATCGGGAGTAATCCTGTAAATTGG TACCAGATGGTCCCAGGAACGGCCCCCAAACTCCTCCTCTATACTAATAATCAG CGGCCCTCAGGGGTCCCTGACCGATTCTCTGGCTCCAAGTCTGGCACCTCAGCC TCCCTGGCCATCAATGGACTCCAGTCTGAGGATGAGGCTGATTATTACTGTGCA GTATGGGATGACAGCCTGAGTGGCCGTTGGGTGTTCggcggagggaccaagctg accgtccta | 15 |
| 4N12 heavy | CAGGTGCAGCTGGTGCAGTCTGGGGCTGAGGTGAAGAAGCCTGGGGCCTCAGTG AAGGTCTCCTGCAAGGTTTCCGGATACATCCTCAGTAAATTATCCGTGCACTGG GTGCGACAGGCTCCTGGAAAAGGACTTGAATGGATGGGAGGTTCTGAACGTGAA GATGGCGAAACAGTCTACGCACAGAAGTTCCAGGGCAGAATCAGCTTGACCGAG GACACATCTATAGAGACAGCCTACATGGAGCTGAGCAGCCTGAGTTCTGAGGAC ACGGCCGTGTATTATTGTGCAACAGGAGGCTTCTGGAGTATGATTGGGGGAAAT GGAGTGGACTACTGGGGCCAGGGAACCCTGGTCACCGTCTCCTCA | 16 |

TABLE 1-continued

NUCLEOTIDE SEQUENCES FOR ANTIBODY VARIABLE REGIONS

| Clone | Variable Sequence Region | SEQ ID NO: |
|---|---|---|
| 4N12 light | CAGGCTGTGGTGACTCAGTCTCCATCGTCCCTGCCTGCATCTGTAGGAGACAGG GTCACCATCACTTGCCGGGCAAGTCAGGACATTAGAAATAATTTAGGCTGGTAT CAGCAGAAACCAGGGAAAGCCCCTGAGCGCCTGATCTATGGAACCTCCAATTTG CAGAGTGGGGTCCCGTCAAGGTTCAGCGGCAGTGGATCTGGGACAGAATTCACT CTCACAATCAGCAGCCTGCAGCCTGAAGATTTTGCAACTTATTACTGTCTACAG CATAATAGTTACCCTCCCACGTTCGGCCGCGGGACCAAGGTGGAAATCAAA | 17 |
| 5M16 heavy | CAGGTGCAGCTGGTGCAGTCTGGGGCTGAGGTGAAGAAGCCTGGGGCCTCAGTG AGAGTTTCCTGCAAGGCATCTGGGTACACCTTCACCAGTTACTTTATGCACTGG GTGCGACAGGCCCCTGGACAAGGACTTGAGTGGATGGCGATAACTTATCCTGGT GGTGGTAGCCCATCCTACGCACCGCAGTTCCAGGGCAGACTCACCATGACCGAC GACACGTCCGCGACCACAGTCTACATGGACCTGAGTGACCTGACTTCTAAAGAC ACGGCCGTGTATTACTGTGCGAGAGGTGCCCACCGTTCCATTGGGACGACCCCC CTTGACTCGTGGGGCCAGGGAACCCTGGTCACCGTCTCCTCAGCAAGCTTCAAG GG | 18 |
| 5O14 heavy | CAGGTGCAGCTGGTGCAGTCTGGGGGACGCGTGGTCCAGGCTGGGAGGTCCCTG AGACTCTCCTGTGCAGCGTCTGGATTCACCTTCAGTATGTATGGCGTCCACTGG GTCCGCCAGGCTCCAGGCAAGGGGCTGGAGTGGGTGGCAGTTATATGGAATGAT GGATCTAAAGAATACTATGGAGACTCCGTGAAGGGCCGATTCACCATCTCCAGA GACAATTCCAGGAACACGTTGTATCTGCAAATGAACAGCCTGAGAGTCGACGAC ACGGCAGTGTATTTTTGTGCGAGAGATGGAATTCCTGACCCTGAACGCGGTGAC TACGGGGGCTTGGACTACTGGGGCCAGGGAACCCTGGTCACCGTCTCCTCA | 19 |
| 5O14 light | CAGACTGTGGTGACTCAGTTTCCATCCTCCCCGTTTGCATCTGTAGGAGACGGA GTCACCATCACTTGCCGGGCAAGGCAGAGCATTAGCAGTTATGTTAATTGGTAT CAGCAGAAACCAGGGAAAGCCCCTAAGCTCCTGATTTACGCTACATCCAGTTTG CAAAGTGGGGTCCCATCAAGGTTCAGTGGCAGTGGATATGGGACAGATTTCACT CTCACCATCAGCGGTCTGCAACCTGAAGATTTTGCAACATATACTGTCAACAG AGTTACAGTTTTCCTCGAACGTTCGGCCAAGGGACCAAGGTGGAAATCAAAC | 20 |
| 8G18 heavy | CAGGTGCAGCTGGTGCAGTCTGGGGCTCAGGTGAAGAAGCCTGGGTCCTCGGTG AAGGTCTCCTGCAAGCCCTCTGGAGGCACCTTCAACAACAATGGGATCAGTTGG GTGCGACAGGCCCCTGGACAAGGGCTTGAGTGGATGGGAGGCATCGTCCCGAAC TTTGGAACCCCAACCTATGGACAAGACTTCCAGGGCAGAGTCACGATCACCGCG GACGAATCTACGAGCACAGTCTTCTTGGAGCTGACCAGACTGAGATCTGACGAC ACGGCCGTTTATTCTGTGCGCGAGGTCGCACGGCGGTGACTCCGATGCAATTG GGTTTACAGTTCTACTTTGACTTCTGGGGCCGGGGAACCCTGGTCACCGTCTCC TCA | 21 |
| 8G18 light | cagactgtggtgactCAGGAGCCCTCACTGACTGTGTCCCCAGGAGGGACAGTC ACTCTCACCTGTTCTGCCAACAGTGGAGCAGTCACCAGTGATTACTATCCAAAC TGGTTCCAGCAGAAACCTGGACAAGCACCCAGGGCACTGATTTATAGTGCAAGC AACAAATTCTCCTGGACGCCTGCCCGGTTCTCAGGCTCCCTCCTTGGGGGCAAA GCTGCCCTGACACTGTCAGGTGCGCAGCCTGAGGACGAGGCTGAGTATTACTGC CTGGTCTACTCTGGTGATGGTGTGGTTTTCGGCGGAGGGACCAAGCTGACCGTC C | 22 |
| 1I9 heavy | CAGGTGCAGCTGGTGCAGTCTGGGGCTGAGGTGAAGAAGCCCGGGGCCTCAGTG AAGGTCTCCTGCAAGACTTCTGGATATACGTTCACCGACACTCTGTACACTGG GTGCGACAGGCCCCTGGACAAGGGTTTGAGTGGATGGGACGGATCAACCCTAAC ACTGGTGTCTCAACTTCTGCCCAGAAGTTTCAGGGCAGGGTCACCATGACCAGG GACACGTCCATCAGCACAACCTACATGGAGCTGAGCAGTTTGAGATCTGACGAC ACGGCCGTCTATTACTGTGCGAGAGAGGAGAACGATAGTAGTGGGTATTACCTT TGGGGTCAGGGAACCCTGGTCACCGTCTCCTCA | 23 |
| 1I9 light | CAGATTGTGGTGACTCAGTCTCCATCCTCCCTGTTTGCATCTGTAGGAGACAGA GTCACCATCACTTGCCGGGCAAGTCAGAGCATTAGCACCTATTTAAATTGGTAT CAGCAAAAACCAGGGAAAGCCCCTAAGCTCCTGATCTATGCTGCATCCAGTTTG GAGAGTGGGGTCCCATCAAGGTTCGGTGGCAGTAGATCTGGGACAGATTTCACT CTCACCATCAGCAGTCTGCAACCTGAAGATTTTGCAACTTACTACTGTCAACAG AGTTACAGGACCCCGTGGACGTTCGGCCAAGGGACCAAGGTGGACATCAAA | 24 |
| 1L1 heavy | CAGGTGCAGCTGGTGCAGTCTGGTCCTACGCTGGTGAAACCCACACAGACCCTC ACGCTGACCTGCACCTTCTCTGGGTTCTCACTCAGTATTAGTGGAGTGGGTGTG GGCTGGATCCGTCAGCCCCCAGGAAAGGCCCTGGAGTGGCTTGCACTCATTTAT TGGGATGATGATAAGCGCTACAGCCCATCTCTGAAGAGCAGGCTCACCATCACC AAGGACACCTCCGAAAACCAGGTGGTCCTTACAATGACCAACATGGACCCTGTG GACACAGCCACATATTACTGTGCACACAGTATGACTAAAGGCGGGGCTATCTAT GGTCAGGCCTACTTTGAATACTGGGGCCAGGGAACCCTGGTC | 25 |

TABLE 1-continued

NUCLEOTIDE SEQUENCES FOR ANTIBODY VARIABLE REGIONS

| Clone | Variable Sequence Region | SEQ ID NO: |
|---|---|---|
| 1L1 light | CCATCTCCTGCACTGGAACCAGACAGTGACGTTGGTGGTTATAACTATGTCTCC TGGTACCAACAACACCCAGGCAAAGCCCCCAAACTCATCATTTATGATGTCACT GATCGGCCCTCAGGGGTTTCTAATCGCTTCTCTGCCTCCAAGTCTGCCAACACG GCCTCCCTGACCATCTCTGGGCTCCAGGCTGAGGACGAGGCTGATTATTACTGC AGCTCATATACAAGCAGCAGCACTCTGGTTTTCGGCGGAGGGACCAAGCTGACC GTCCTA | 26 |
| 1M9 heavy | caggtccagctggtacagtctggggctgaggtgaagaagcctggGGCCTCAGTG AAGGTCTCCTGCAAGGTTTCCGGATACACCCTCACTGAATTATCCATGCACTGG GTGCGACAGGCTCCTGGAAAAGGCCTAGAGTGGATGGGAGGTTTTGAGCCTGAA GATGGTGAAACAATCTACGCACAGAAGTTCCAGGGCAGAGTCACCATGACCGAG GACACATCTAGAGACACAGCCTACATGGAGCTGAGTAGCCTGAGATCTGAGGAC ACGGCCGTCTATTACTGTACAACAGATCAGGTCTACTATCGTTCGGGGAGTTAT TCTGGATATGTTGACTACTGGGGCCAGGGAACCCTGGTC | 27 |
| 1O5 heavy | caggtccagctggtgcagtctggggctgaggtgaagaagcctgggtCCTCAGTG AAGGTCTCCTGCAAGGCTTCTGGACGCACCTTCAGCAGCTATGTTATCAGCTGG GTGCGACAGGCCCCTGGACAAGGGCTTGAGTGGATGGGAGGGATCATCCCTCTG TTTGGTACAGCAAACTACGCACAGAAATTCCAGGGCAGAGTCACGATTACCGCG GACGAATCCACGAGCACAGCCTACATGGAGCTGAGCAGCCTGAGATCTGACGAC ACGGCCGTCTATTACTGTGCGAGGGGCGCCCAGCTATATTACAATGATGGTAGT GGTTACATTTTTGACTACTGGGGCCAGGGAGCCCTGGTC | 28 |
| 1O6 heavy | CAGGTGCAGCTGGTGCAGTCTGGGCCTGAGGTGAAGAAGCCTGGGACCTCAGTG AAGGTCTCCTGCAAGGCTTCTGGATTCAGCTTTATTAGCTCTGCTGTGCAGTGG GTGCGACAGGCTCGTGGACAACGCCTTGAGTGGATAGGATGGATCGTCGTTGCC AGTGCTAACACAAACTACGCACAGAAGTTCCGGGAAAGAGTCACCATTACTAGG GACATGTCCACAAACACAGCCTATATGGAACTGACCAGCCTGAGATCCGAGGAC ACGGCCGTTTATTACTGTGCGGCAGAGCACCGGTCCCCTTGTAGTGGTGGTGAT AGCTGCTACAGTCTCTACTACGGTATGGACGTCTGGGGCCAAGGGACCCTGGTC ACCGTCTCCTCA | 29 |
| 2A2 heavy | CAGGTGCAGCTGGTGCAGTCTGGGGGAGGCTTGGTTCCGCCTGGGGGGTCCCTG AGACTGTCCTGTACAGCCTCTGGATTCACCGTTAGTAACTATGGCATGAGCTGG GTCCGCCAGACTCCAGGGAAGGGGCTGGAGTGGGTCTCAACTATTAGTACTAGT AGTGGTAGAACATTCTACGCAGACTCCGTGGAGGGCCGGTTCACCATCTCCGGA GACAATTCCAAGAACACGCTGTATCTGCAAATGAACAGCCTGAGAGTCGAAGAC ACGGCCGTATATTACTGTGCGAAAGGCCCGTTCGGGGGCGACTTTGACTACTGG GGCCAGGGAACCCTGGTCACCGTCTCCTCA | 30 |
| 2A2 light | CAGGCTGTGGTGACTCAGTCTCCAGCCACCCTGTCTTTGTCTCCAGGGGAAAGA GCCACCCTCTCCTGCAGGGCCAGTCAGAGTGTTGCCATCTACTTAGCCTGGTAT CAACAGAAACCTGGCCAGGCTCCCAGGCTCCTCATCTATGATGCATCCAACAGG GCCACTGGCATCCCAGCCAGGTTCAGTGGCAGTGGGTCTGGGACAGACTTCACT CTCACCATCAGCAGCCTAGAGCCTGAAGATTTTGCAGTTTATTACTGTCAGCAG CGTGGCAACTGGCAGTACACTTTTGGCCAGGGGACCAAACTGGAGATCAAA | 31 |
| 2C2 heavy | CAGGTGCAGCTGGTGCAGTCTGGGGGAGGCCTGGTACAGCCTGGCAGGTCCCTG ACACTCTCCTGTGCAGCCTCTGGATTCACCTTTGATGTTTATGCCATGCACTGG GTCCGCCAAGCTCCAGGGAAGGGCTTGAGTGGGTCGCAGGTATTAGTTGGAAT AGTGGTAGCGTAGGCTATGCGGACTCTATGAAGGGCCGATTCACCATCTCCAGA GACAACGCCAAGAACTCCCTGTATCTGCAAATTAACAGTCTGAGAGCTGAGGAC ACGGCCTTATATTACTGTGCAAAAGCATTCTGGTTCGGGGAGTTATCGGGTTAC GGTATGGACGTCTGGGGCCAAGGGACCCTGGTCACCGTCTCCTCA | 32 |
| 2C2 light | CAGGCTGTGGTGACTCAGCCTCCCTCCGCGTCCGGGTTTCCTGGACAGTCAGTC ACCATCTCCTGCACTGGAACCAGCAGTGACGTTGGTAGTTATAACTATGTCTCC TGGTACCAACAGCACCCAGGCAAAGCCCCCAAACTCATAATTTATGCGGTCACT AGGCGGCCCTCAGGGGTCCCTGAGCGCTTCTCTGGCTCCAAGTCTGGCAACACG GCCTCCCTGACCGTCTCTGGGCTCCAGGCTGAGGATGAGGCTGATTATTACTGC ACCTCATATGCAGGCAACAACAAGGATGTCTTCGGAACTGGGACCAAGGTCACC GTCCTA | 33 |
| 2D12 heavy | CAGGTGCAGCTGGTGCAGTCTGGAGCTGAGGTGAAGAAGCCTGGGGCCTCAGTG AAGGTCTCCTGCAAGGCTTCTGGTTACAGCTTTAACATCTATGGTATCAGCTGG GTGCGACAGGCCCCTGGACAAGGGCTTGAGTGGATGGGATGGATCAGCGCTTAC AATGGTAACACAAACTATGCACAGAAACTCCAGGGCAGAGTCACCATGACCACA GACACATCCACGAGCACAGCCTACATGGAACTGAGGAGCCTGAGATCTGACGAC ACGGCCGTGTATTACTGTGCGAGACCACTTTGGGGGGAATTTTACTATGATATC TGGGGCCAAGGGACCCTGGTCACCGTCTCCTCA | 34 |

TABLE 1-continued

NUCLEOTIDE SEQUENCES FOR ANTIBODY VARIABLE REGIONS

| Clone | Variable Sequence Region | SEQ ID NO: |
|---|---|---|
| 2D12 light | CAGGCTGTGGTGACTCAGTCTCCAGGCACCCTGTCCTTGTCTCCAGGGGAAAGA GCCACCCTCTCTTGCAGGGCCAGTCAGAGTGTTAGCAGCGGGTACTCAGCCTGG TACCAGCAGAAACCTGGCCAGGCTCCCAGGCTCCTCATCTATGGTGCATCCAAA AGGGCCGCTGGCATCCCAGACAGGTTCAGTGGCAGTGGGTCTGGGACAGACTTC ACTCTCACCATCAGCAGACTGGAGCCTGAAGATTTTGCAGTGTATTACTGTCAG CTGTTTGCTACCTCACCTCCGCCCTTCGGCCAAGGGACACGACTGGAGATTAAA | 35 |
| 3A2 heavy | CAGGTGCAGCTGGTGCAGTCTGGGGAGGCGTGGTCCAGCCTGGGAGGTCCCTG AGACTCTCCTGTGCAGCCTCTGGATTCACCTTCAGTAATTATGTTATGGAGTGG GTCCGCCAGGCTCCAGGCAAGGGGCTGGAGTGGGTGGCAGTTATATCATATGAT GGAAGCAATAAATACTATGCAGACTCCGTGAAGGGCCGATTCACCATCTCCAGA GACAATTCCAAGAACACGTTGTATCTGCAAATGAACAGCCTGAGAGCTGAGGAC ACGGCTGTGTATTACTGTGCGAGATCAGAGTGGGAGTCTTCCTATGGTTCGGGG AATTATTATACAGATTACTTCTACTACTACGCTATGGACGTCTGGGGCCCAGGG ACCCTGGTCACCGTCTCCTCA | 36 |
| 3A2 light | CAGGCTGTGGTGACTCAGTCTCCACTCTCCCTGCCCGTCACCCCTGGAGAGCCG GCCTCCATCTCCTGCAGGTCTAATCAGAGCCTCCTGCGTGGTATTAGATACAAC TATTTGGATTGGTACCTGCAGAAACCAGGGCAGTCTCCACAGCTCCTGATCTAT TTGGGTTCTAATCGGGCCTCCGGGGTCCCTGACAGGTTCAGTGGCAGTGGATCA GCCACAGATTTTACACTGAAAATCAGCAGAGTGGAGGCTGAGGATGTTGGGGTT TATTACTGCATGCAAGCTCTACAAACTCCTACCACCTTCGGCCAAGGGACACGA CTGGAGATTAAA | 37 |
| 3B4 heavy | CAGGTGCAGCTGGAGGAGTCTGGTCCTACGCTGGTGAAACCCACACAGACCCTC ACGCTGACCTGTTCCTTCTCTGGGTTCTCACTCACCACTACTGGAGTGACTGTG GGCTGGATCCGTCAGCCCCCAGGAAAGGCCTTGGAGTGGCTTGCACTCATTTAT TGGGATGATGATAAGCGCTACAGCCCATCTCTGAAGAGCAGGCTCACCATCACC AAGGACACCTCCAAAAACCAGGTGGTCCTTACCATGACCAACATGGACCCTGTG GACACTGCCACATATTACTGTGCGCACTCCACCGGCTACTATGATAGTAGTGGC TATCGAGGGGCCCTTGATGCTTTTGCTGTCTGGGGCCAAGGGACCCTGGTCACC GTCTCCTCA | 38 |
| 3B4 light | CAGATTGTGGTGACTCAGTTTCCAGACTCCCCGGCTGTGTCTTTGGGCGAGAGG GCCACCATCAACTGCAAGTCCAGCCAGAGTGTTTTATACCACTCCAACAATAAA AACTACTTAGCTTGGTACCAGCAGAAACCAGGACAGCCTCCTAAACCTGCTCATT TACTGGGCATCTGCCCGACAATCGGGGTCCCTGACCGATTCAGTGGCAGCGGG TCTGGGACAGATTTCACTCTCACCATCAGCAGCCTGCAGGCTGAAGATGTGGCA GTTTATTACTGTCAGCAATATTATAGTACTCCGTACACTTTTGGCCAGGGGACC AAGCTGGAGATCAAA | 39 |
| 3E23 heavy | CAGGTGCAGCTGGTGCAGTCGGGCCCAGGACTGGTGAAGCCTTCGGACACCCTG TCCCTCACCTGCAGTGTCTCAAGTGACGCCCTCCGCAGCAGGAGTTATTACTGG GGCTGGGTCCGCCAGCCCCCCGGGAAGGGATTGGAGTGGATTGGGACTGTCTCT TATAGTGGGGGCACCTACTACAACCCGTCCCTCCAGAGTCGAGTCACCGTGTCG GTGGACACGTCCAAGAACCACTTCTCCCTGAGGTTGAACTCTGTGACCGCCGCA GACGCGGCTGTTTATTACTGTGCGAGATCTTATTTCTATGATGGCAGTGGTTAC TACTACTGAGCTACTTTGACTCCTGGGGCCAGGGAACCCTGGTCACCGTCTCC TCA | 40 |
| 3E23 light | CAGGCTGTGGTGACTCAGGAGCCCTCACTGACTGTGTCCCCAGGAGGGACAGTC ACTCTCACCTGTGCTTCCAGCACTGGAGCAGTCACCAGTGGTCACTATCCAAAC TGGTTCCAGCAGAAACCTGGACAACACCCAGGGCCCTGATTTATAGCACAGAC AACAAGCACTCCTGGACCCCTGCCCGGTTCTCAGGCTCCCTCCTAGGGGTCAAG GCTGCCCTGACACTGTCAGATGTACAGCCTGAGGACGAGGCTGACTATTACTGC CTGCTCCATTTTGGTGGTGTCGTGGTCTTCGGCGGAGGGACCAAGCTGACCGTC CTA | 41 |
| 3H5 heavy | CAGGTGCAGCTGGTGCAGTCTGGGGAGGCGTGGTCCAGCCTGGGAGGTCCCTG AGACTCTCCTGTTCAACGTCTGGATTCACCTTCAGGATGTATGGCATGCACTGG GTCCGCCAGGCTCCAGGCAAGGGGCTGGAGTGGGTGGCCGTTATTTTTAACGAT GGAGTTAAGAAATATTATGGAGACGCCGTGAAGGGCCGATTCACCGTCTCCAGA GACAATTCCAGGAACACCCTGTATCTGGAAATGAAAAGCCTGAGAGTCGACGAC ACGGCTGCCTACTACTGTGCGAGAGACGGGATTCCTGACCCCGAACGCGGTGAC TACGGGGGCTTGGACTACTGGGGCCAGGGAACCCTGGTCACCGTCTCCTCA | 42 |
| 3H5 light | CAGACTGTGGTGACTCAGTCTCCATCCTCCCTGTCTGCATCTGTAGGAGACACA GTCACCATCACTTGCCGGGCAAGTCAGAGCATTACCAGTTATTTAAACTGGTAT CAGCAGAAACCAGGAAAAGCCCCAAAGCTCCTCATCTATGCTACATCCAGTTTG CAAAGTGGGCTCCCCTCAAGGTTCAGTGGCAGTGGCTATGGGACAGAATTCACT CTCACCATCAGTGGTCTGCAACCTGAAGATTTTGCAACATACTACTGTCAACAG AGTTACAGTTTTCCTCGAACGTTCGGCCAAGGGACCAAGGTGGAAATGGATA | 43 |

TABLE 1-continued

NUCLEOTIDE SEQUENCES FOR ANTIBODY VARIABLE REGIONS

| Clone | Variable Sequence Region | SEQ ID NO: |
|---|---|---|
| 3I21 heavy | CAGGTGCAGCTGGTGCAGTCTGGGGGAGGCTTGGTACAGCCTGGCAGGTCCCTG AGACTCTCCTGTGCAACCTCTGGATTCATCTTTGATGATTATGCCATGTACTGG GTCCGGCAAGCTCCAGGGAAGGGCCTGGAGTGGGTCTCAGGTATTAGTTGGAAT AGTGGAAACATAGCCTATGCGGACTCTGTGAAGGGCCGATTCACCATCTCCAGA GACAACGCCAAGAACTCCCTGTATTTGGAAATGAACAGTCTGAGAGCTGAGGAC ACGGCCTTGTATTACTGTGTAAAAGATCTTTACGGGTACGATATTTTGACTGGT AATGGATATGATTACTGGGGCCAGGGAACCCTGGTCACCGTCTCCTCA | 44 |
| 3I21 light | CAGGCTGTGGTGACTCAGTCTTCACTCTCCCTGCCCGTCACCCCTGGAGAGCCG GCCTCCATCTCCTGCAGGTCTAGTCAGAGCCTCCTGCAAAGTAATGGATACAAC TATTTGGATTGGTACCTGCAGAAGCCAGGGCAGTCTCCACAGCTCCTGATCTAT TTGGGTTCTAATCGGGCCTCCGGGGTCCCTGACAGGTTCAGTGGCAGTGGATCA GGCACAGATTTTACACTGAAAATCAGCAGAGTGGAGGCTGAGGATGTTGGGGTT TATTACTGCATGCAAGCTCTACAAACTCCTCCGACGTTCGGCCAAGGGACCAAG GTGGAAATCAA | 45 |
| 3K11 heavy | CAGGTGCAGCTGGTGCAGTCTGGGGCTGAGGTGAAGAAGCCTGGGTCCTCGGTG AAGGTCCCTGCAAGGCTTCTGGAGACACCCTCAGTTACTACGGAATCACTTGG GTGCGACGGGCCCCTGGACAAGGGCTTGAGTGGATGGGACAGATCATCCCTTTC TTTGCTACAACAATCTCCGCACAGAAGTTCCAGGGCAGACTCACCATGACCGCG GAAGAATCCACGAGCACTGGCTACATGGAGCGCACATTTTACATGGACTTGAGT AGCCTTAGACCTGAGGACACGGCCGTATACTACTGTGCGGGGGGCTACTATGGT TCGGGGAGTTCGGGCGACTACGGTTTGGACGTCTGGGGCCAAGGGACCCTGGTC ACCGTCTCCTCA | 46 |
| 3K11 light | CAGGCTGTGGTGACTCAGCCGCCCTCAGTGTCTGGGGCCCCAGGGCAGAGGGTC ACCATCTCCTGCACTGGGAGCAGCTCCAACATCGGGGCAGGTTATGATGTAAAC TGGTACCAGCAGCTTCCAGGAACAGCCCCCAAACTCCTCATCTATGGTAACAAC AATCGGCCCTCAGGGGTCCCTGACCGATTCTCTGGCTCCAAGTCTGGCACCTCA GCCTCCCTGGCCATCACTGGGCTCCAGGCTGAGGATGAGGCTGATTATTACTGC CAGTCCTATGACAGCAGCCTGAGTGGTTCGGGAGTCTTCGGAACTGGGACCGAG GTCACCGTCCTA | 47 |
| 4B8 heavy | CAGGTGCAGCTGGTGCAGTCGGGCCCAGGACTGGTGAAGCCTTCGGAGACCCTG TCCCTGACGTGCGCTGTTTCTGGTGACTCCATCGGCAGTAGAAGTTTCTACTGG GGCTGGATCCGCCAGCCCCCAGGGAAGGGGCTGGAGTGGATTGGAAGTATCTAT TATAATGGACACCTACTACAAGCCGTCCCTCAAGAGTCGAGTCACCATATCC CTAGACACGTCCAAGAACCAGTTCTCCCTGAGGCTGAGCTCTCTGACCGCCACA GACACGGGTGTCTATTACTGTGCGCGGGCGCCAACCTACTGTAGTCCTTCCAGC TGCGCAGTTCACTGGTACTTCAATCTCTGGGGCCGTGGCACCCTGGTCACCGTC TCCTCA | 48 |
| 4B10 heavy | CAGGTGCAGCTGGTGCAGTCTGGAGCTGAGCTGAAGAAGCCTGGGGCCTCAGTG AAGGTCTCCTGCAAGGCTTCTGGTTACATATTTACCAAATATGGTATCAGTTGG CTGCGACAGGCCCCTGGACAAGGGCTTGAGTGGGTGGGATGGATCAGCGCTTAC AATGAAAACACAAACTATGCAGAGAAGTTCCAGGGCAGAGTCACCTTGACCACA GATGCATCCACGAGCACGGCCTACATGGAGCTGAGGAACCTGAGATCTGACGAC ACGGCCGTATACTTCTGTGCGAGAGAAGTCTGGTTCGCGGAGTATATTTACTGG GGCCAGGGAACCCTGGTCACCGTCTCCTCA | 49 |
| 8E22 light | CAGGCTGTGGTGACTCAGGAGCCCTCACTGACTGTGTCCCAGGAGGGACAGTC ACTCTCACCTGTTCTGCCAACAGTGGAGCAGTCACCAGTGATTACTATCCAAAC TGGTTCCAGCAGAAACCTGGACAAGCACCCAGGGCACTGATTTATAGTGCAAGC AACAAATTCTCCTGGACGCCTGCCCGGTTCTCAGGCTCCCTCCTTGGGGCAAA GCTGCCCTGACACTGTCAGGTGCGCAGCCTGAGGACGAGGCTGAGTATTACTGC CTGGTCTACTCTGGTGATGGTGTGGTTTTCGGCGGAGGGACCAAGCTGACCGTC CTAA | 50 |
| 9A11 light | CAGTCTGTGGTGACTCAGCCTGCCTCCGTGTCTGGGTCTCCTGGACAGTCGATC ACCATCTCCTGCACTGGAACCAGCAGTGACGTTGGTGCTTATAACTATGTCTCC TGGTACCAACAACACCCAGGCAAAGCCCCCAAACTCGTGATTTATGATGTCGCT AATCGGCCCTCAGGGATTTCTGACCGCTTCTCTGGCTCCAAGTCTGGCAACACG GCCTCCCTGACCATCTCTGGGCTCCAGGCTGAGGACGAGGCTGATTATTACTGC GGCTCATATACCAGCGACGTCTCGCCGGTTTTCAGCGGGGGACCAAGCTGACC GTCCTCA | 51 |
| 9D14 heavy | CAGGTGCAGCTGGTGCAGTCTGGGTCTGAGTTGAAGAAGCCTGGGGCCTCAGTG AAGTTTCCTGCAAGGCTTCTGGATACACCTTCACAAGTCATCCTATGAATTGG GTGCGACAGGCCCCTGGACAAGGGCTTGAGTGGATGGGATGGATCAACACCAAG ACTGGGAACCTAACTTATGCCCAGGGCTTCACAGGACGGTTTGTCTTCTCCTTG GACACCTCTGTCAGGACGGCGTATCTGCAGATCAGCGGCCTAAAGGCTGAGGAC ACTGCCATTATTACTGTGCGAGAGATGAGTATAGTGGCTACGATTCGGTAGGG GTGTTCCGTGGTTCTTTTGACGCTTCTACGGTATGGACGTCTGGGGCCAAGGG ACCCTGGTCACCGTCTCCTCA | 52 |

TABLE 2

| | PROTEIN SEQUENCES FOR ANTIBODY VARIABLE REGIONS | |
|---|---|---|
| Clone | Variable Sequence | SEQ ID NO: |
| 1H12 heavy | QVQLVQSGAEVKKPGASVKVSCKASGYSFTSYGISWVRQAPGQGLEWMG WISTYKGYTQYAQNFQGRVTITTDTPATTVYMELRSLRSDDTAVYYCAR VLSETGYFYYYYGMDVWGQGTLVTVSS | 53 |
| 1H12 light | QAVVTQPPSVSGAPGQRVTISCIGSSSNIGADYNVHWYQLLPGTAPKLL IYGNINRPSGVPDRFSGSKSGTSASLAITGLQAEDEADYYCQSYDSSLS ASVFGGGTKLTVL | 54 |
| 2B4 heavy | QVQLVQSGSELKKPGASVKVSCKASGYSFTSYSINWVRQAPGQGPEWMG WIDTNIGNPTYAQDFAGRFVFSLDTSVITAYLQISSLKAGDTAVYYCAT YYVDLWGSYRQDYYGMDVWGH | 55 |
| 2B4 light | QSVLIQPPSASGTPGQRVTISCSGGSSNIGSNPVNWYQMVPGTAPKLLL YTNNQRPSGVPDRFSGSKSGTSASLAINGLQSEDEADYYCAVWDDSLSG RWVFGGGTKVTVL | 56 |
| 2H1 heavy | QVQLVQSGAEVKKPGASVRVSCKASGYTFTSYGISWVRQAPGQGLEWMG WISTYNGDTNYAQKFQGRVILTTETSTSTAYMELRRLRSDDTAVYYCAR DFEFPGDCSGGSCYSRFIYQHNDMDVWGHGTLVTVSSAS | 57 |
| 2H1 light | QAVVTQPPSVSAAPGQKVTISCSGSSSNIGNHYVSWYQHLPGTAPKLLI YDNYKRPSVIPDRFSASKSGASATLGIIGLQTGDEADYYCGTWDSSLSA VVFGGGTKLTVL | 58 |
| 3E23 heavy | QVQLVQSGPGLVKPSDILSLICSVSSDALRSRSYYWGWVRQPPGKGLEW IGTVSYSGGTYYNPSLQSRVTVSVDTSKNHFSLRLNSVTAADAAVYYCA RSYFYDGSGYYYLSYFDSWGQGTLVTVSS | 59 |
| 3E23 light | QAVVTQEPSLTVSPGGIVTLICASSTGAVISGHYPNWFQQKPGQPPRAL IYSTDNKHSWTPARFSGSLLGVKAALTLSDVQPEDEADYYCLLHFGGVV VFGGGTKLTVL | 60 |
| 3N23 heavy | QVQLVQSGGGVVQPGRSLRLSCAVSGFTFSNYAMHWVRQAPGKGLDWVA VIWYDGSNKYYADSVKGRFTISRDNSKNTLYLQVNSLRAEDTAVYYCAR GDYVLDYWGQGTLVTVSS | 61 |
| 3N23 light | DIVMTQSPSSLSASVGDRVTISCRASQSIPSYLNWYQQKPGKAPKVLIY ATSTLEAGVPSRFSGSGSGTDFTLTITSLQPEDFATYYCQQSYNTGIFT FGPGTKVDIK | 62 |
| 4J14 heavy | QVQLVQSGAEVKKPGSSVKVSCKASGGTSSTYAISWVRQAPGQGLEWMG GSIPVFATVNYAQKFQGRLTITADESTSTVYMELSSLRSEDTAVYFCAS PYCSSMNCYTTFYYFDFWGQGTLVTVSS | 63 |
| 4J14 light | QAVVTQPASVFGFPGQSITISCTGTSSDFGTYNYVSWYQQHPGQAPKLM IFDVSNRPSGVSNRFSGSKSGNTASLTISGLQAEDEASYYCSSYTSGST LYGGGTKLTVL | 64 |
| 4J21 heavy | QVQLVQSGSELKKPGASVKVSCKASGYSFTSYSINWVRQAPGQGPEWMG WIDINTGNPTYAQDFAGRFVFSLDTSVTTAYLQISSLKAGDTAVYYCAT YYVDLWGSYRQDYYGMDVWGHGTLVTVSS | 65 |
| 4J21 light | QSVVTQPPSVSGTPGQGVTISCSGGSSNIGSNPVNWYQMVPGTAPKLLL YTNNQRPSGVPDRFSGSKSGTSASLAINGLQSEDEADYYCAVWDDSLSG RWVFGGGTKLTVL | 66 |
| 4N12 heavy | QVQLVQSGAEVKKPGASVKVSCKVSGYILSKLSVHWVRQAPGKGLEWMG GSEREDGETVYAQKFQGRISLTEDTSIETAYMELSSLSSEDTAVYYCAT GGFWSMIGGNGVDYWGQGTLVTVSS | 67 |
| 4N12 light | QAVVTQSPSSLPASVGDRVTITCRASQDIRNNLGWYQQKPGKAPERLIY GTSNLQSGVPSRFSGSGSGTEFTLTISSLQPEDFATYYCLQHNSYPPTF GRGTKVEIK | 68 |
| 5M16 heavy | QVQLVQSGAEVKKPGASVRVSCKASGYTFTSYFMHWVRQAPGQGLEWMA ITYPGGGSPSYAPQFQGRLTMTDDTSATTVYMDLSDLTSKDTAVYYCAR GAHRSIGTTPLDSWGQGTLVTVSSASFK | 69 |
| 5O14 heavy | QVQLVQSGGRVVQAGRSLRLSCAASGFTFSMYGVHWVRQAPGKGLEWVA VIWNDGSKEYYGDSVKGRFTISRDNSRNTLYLQMNSLRVDDTAVYFCAR DGIPDPERGDYGGLDYWGQGTLVTVSS | 70 |
| 5O14 light | QTVVTQFPSSPFASVGDGVTITCRARQSISSYVNWYQQKPGKAPKLLIY ATSSLQSGVPSRFSGSGYGTDFILTISGLQPEDFATYYCQQSYSFPRIF GQGTKVE1K | 71 |

TABLE 2-continued

PROTEIN SEQUENCES FOR ANTIBODY VARIABLE REGIONS

| Clone | Variable Sequence | SEQ ID NO: |
|---|---|---|
| 8G18 heavy | QVQLVQSGAQVKKPGSSVKVSCKPSGGTFNNNGISWVRQAPGQGLEWMG GIVPNFGTPTYGQDFQGRVTITADESTSTVFLELTRLRSDDTAVYFCAR GRTAVTPMQLGLQFYFDFWGRGTLVTVSS | 72 |
| 8G18 light | QTVVTQEPSLTVSPGGIVTLICSANSGAVISDYYPNWFQQKPGQAPRAL IYSASNKFSWTPARFSGSLLGGKAALTLSGAQPEDEAEYYCLVYSGDGV VFGGGTKLTV | 73 |
| 1I9 heavy | QVQLVQSGAEVKKPGASVKVSCKTSGYTFTDNSVHWVRQAPGQGFEWMG RINPNTGVSTSAQKFQGRVTMTRDTSISTTYMELSSLRSDDTAVYYCAR EENDSSGYYLWGQGTLVTVSS | 74 |
| 1I9 light | QIVVTQSPSSLFASVGDRVTITCRASQSISTYLNWYQQKPGKAPKLLIY AASSLESGVPSRFGGSRSGTDFTLTISSLQPEDFATYYCQQSYRTPWTF GQGTKVDIK | 75 |
| 1L1 heavy | QVQLVQSGP.TLVKPTQTLTLTCTFSGFSLSISGVGVGWIRQPPGKALE WLALIYWDDDKRYSPSLKSRLTITKDTSENQVVLTMTNMDPVDTATYYC AHSMTKGGAIYGQAYFEYWGQGTLV | 76 |
| 1L1 light | PSPALEPDSDVGGYNYVSWYQQHPGKAPKLIIYDVTDRPSGVSNRFSAS KSANTASLTISGLQAEDEADYYCSSYTSSST | 77 |
| 1M9 heavy | QVQLVQSGAEVKKPGASVKVSCKVSGYTLTELSMHWVRQAPGKGLEWMG GFEPEDGETIYAQKFQGRVIMTEDTSRDTAYMELSSLRSEDTAVYYCIT DQVYYRSGSYSGYVDYWGQGTLV | 78 |
| 1O5 heavy | QVQLVQSGAEVKKPGSSVKVSCKASGRTFSSYVISWVRQAPGQGLEWMG GIIPLFGTANYAQKFQGRVTITADESTSTAYMELSSLRSDDTAVYYCAR GAQLYYNDGSGYIFDYWGQGALV | 79 |
| 1O6 heavy | QVQLVQSGPEVKKPGTSVKVSCKASGFSFISSAVQWVRQARGQRLEWIG WIVVASANTNYAQKFRERVTITRDMSTNTAYMELTSLRSEDTAVYYCAA EHRSPCSGGDSCYSLYYGMDVWGQGTLVTVSS | 80 |
| 2A2 heavy | QVQLVQSGGGLVPPGGSLRLSCTASGFTVSNYGMSWVRQTPGKGLEWVS TISTSSGRTFYADSVEGRFTISGDNSKNTLYLQMNSLRVEDTAVYYCAK GPFGGDFDYWGQGTLVTVSS | 81 |
| 2A2 light | QAVVTQSPATLSLSPGERATLSCRASQSVAIYLAWYQQKPGQAPRLLIY DASNRATGIPARFSGSGSGTDFTLTISSLEPEDFAVYYCQQRGNWQYTF GQGTKLEIK | 82 |
| 2C2 heavy | QVQLVQSGGGLVQPGRSLTLSCAASGFTFDVYAMHWVRQAPGKGLEWVA GISWNSGSVGYADSMKGRFTISRDNAKNSLYLQINSLRAEDTALYYCAK AFWFGELSGYGMDVWGQGTLVTVSS | 83 |
| 2C2 light | QAVVTQPPS.ASGFPGQSVTISCTGTSSDVGSYNYVSWYQQHPGKAPKL IIYAVTRRPSGVPERFSGSKSGNTASLTVSGLQAEDEADYYCTSYAGNN KDVFGTGTKVTVL | 84 |
| 2D12 heavy | QVQLVQSGAEVKKPGASVKVSCKASGYSFNIYGISWVRQAPGQGLEWMG WISAYNGNTNYAQKLQGRVIMITDTSTSTAYMELRSLRSDDTAVYYCAR PLWGEFYYDIWGQGTLVTVSS | 85 |
| 2D12 light | QAVVTQSPGTLSLSPGERATLSCRASQSVSSGYSAWYQQKPGQAPRLLI YGASKRAAGIPDRFSGSGSGTDFTLTISRLEPEDFAVYYCQLFATSPPP FGQGTRLEIK | 86 |
| 3A2 heavy | QVQLVQSGGGVVQPGRSLRLSCAASGFTFSNYVMEWVRQAPGKGLEWVA VISYDGSNKYYADSVK.GRFTISRDNSKNTLYLQMNSLRAEDTAVYYCA RSEWESSYGSGNYYTDYFYYYAMDVWGPGTLVTVSS | 87 |
| 3A2 light | QAVVTQSPLSLPVTPGEPASISCRSNQSLLRGIRYNYLDWYLQKPGQSP QLLIYLGSNRASGVPDRFSGSGSATDFTLKISRVEAEDVGVYYCMQALQ TPTTFGQGTRLEIK | 88 |
| 3B4 heavy | QVQLEESGPTLVKPTQTLTLICSFSGFSLITTGVTVGWIRQPPGKALEW LALIYWDDDKRYSPSLKSRLTITKDTSKNQVVLTMTNMDPVDTATYYCA HSTGYYDSSGYRGALDAFAVWGQGTLVTVSS | 89 |
| 3B4 light | QIVVTQFPDSPAVSLGERATINCKSSQSVLYHSNNKNYLAWYQQKPGQP PNLLIYWASARQSGVPDRFSGSGSGTDFTLTISSLQAEDVAVYYCQQYY STPYTFGQGTKLEIK | 90 |

TABLE 2-continued

PROTEIN SEQUENCES FOR ANTIBODY VARIABLE REGIONS

| Clone | Variable Sequence | SEQ ID NO: |
|---|---|---|
| 3E23 heavy | QVQLVQSGPGLVKPSDILSLICSVSSDALRSRSYYWGWVRQPPGKGLEW IGTVSYSGGTYYNPSLQSRVTVSVDTSKNHFSLRLNSVTAADAAVYYCA RSYFYDGSGYYYLSYFDSWGQGTLVTVSS | 91 |
| 3E23 light | QAVVTQEPS.LTVSPGGTVTLICASSTGAVTSGHYPNWFQQKPGQPPRA LIYSTDNKHSWTPARFSGSLLGVKAALTLSDVQPEDEADYYCLLHFGGV VVFGGGTKLTVL | 92 |
| 3H5 heavy | QVQLVQSGGGVVQPGRSLRLSCSTSGFTFRMYGMHWVRQAPGKGLEWVA VIFNDGVKKYYGDAVKGRFTVSRDNSRNTLYLEMKSLRVDDTAAYYCAR DGIPDPERGDYGGLDYWGQGTLVTVSS | 93 |
| 3H5 light | QTVVTQSPSSLSASVGDTVTITCRASQSITSYLNWYQQKPGKAPKLLIY ATSSLQSGLPSRFSGSGYGTEFTLTISGLQPEDFATYYCQQSYSFPRTF GQGTKVEMD | 94 |
| 3I21 heavy | QVQLVQSGGGLVQPGRSLRLSCATSGFIFDDYAMYWVRQAPGKGLEWVS GISWNSGNIAYADSVKGRFTISRDNAKNSLYLEMNSLRAEDTALYYCVK DLYGYDILTGNGYDYWGQGTLVTVSS | 95 |
| 3I21 light | QAVVTQSSLSLPVTPGEPASISCRSSQSLLQSNGYNYLDWYLQKPGQSP QLLIYLGSNRASGVPDRFSGSGSGTDFTLKISRVEAEDVGVYYCMQALQ TPPTFGQGTKVEIK | 96 |
| 3K11 heavy | QVQLVQSGAEVKKPGSSVKVPCKASGDTLSYYGITWVRRAPGQGLEWMG QIIPFFATTISAQKFQGRLTMTAEESTSTGYMERTFYMDLSSLRPEDTA VYYCAGGYYGSGSSGDYGLDVWGQGTLVTVSS | 97 |
| 3K11 light | QAVVTQPPS.VSGAPGQRVTISCIGSSSNIGAGYDVNWYQQLPGTAPKL LIYGNNNRPSGVPDRFSGSKSGTSASLAITGLQAEDEADYYCQSYDSSL SGSGVFGTGTEVTVL | 98 |
| 4B8 heavy | QVQLVQSGPGLVKPSETLSLTCAVSGDSIGSRSFYWGWIRQPPGKGLEW IGSIYYNGTTYYKPSLKSRVTISLDTSKNQFSLRLSSLTATDTGVYYCA RAPTYCSPSSCAVHWYFNLWGRGTLVTVSS | 99 |
| 4B10 heavy | QVQLVQSGAELKKPGASVKVSCKASGYIFTKYGISWLRQAPGQGLEWVG WISAYNENTNYAEKFQGRVILTTDASTSTAYMELRNLRSDDTAVYFCAR EVWFAEYIYWGQGTLVTVSS | 100 |
| 9A11 light | QSVVTQPASVSGSPGQSITISCTGTSSDVGAYNYVSWYQQHPGKAPKLV IYDVANRPSGISDRFSGSKSGNTASLTISGLQAEDEADYYCGSYTSDVS PVFSGGTKLTVL | 101 |
| 9D14 heavy | QVQLVQSGSELKKPGASVKLSCKASGYTFTSHPMNWVRQAPGQGLEWMG WINTKIGNLTYAQGFTGRFVFSLDTSVRTAYLQISGLKAEDTAIYYCAR DEYSGYDSVGVFRGSFDDFYGMDVWGQGTLVTVSS | 102 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 1H12 | GYSFTSYG (103) | ISTYKGYT (104) | ARVLSETGYFYY YYYGMDV (105) |
| 2B4 | GYSFTSYS (106) | IDTNTGNP (107) | ATYYVDLWGSYR QDYYGMDV (108) |
| 2H1 | GYTFTSYG (109) | ISTYNGDT (110) | ARDFEFPGDCSG GSCYSRFIYQHN DMDV (111) |
| 3E23 | SDALRSRSYY (112) | VSYSGGT (113) | ARSYFYDGSGYY YLSYFDS (114) |
| 3N23 | GFTFSNYA (115) | IWYDGSNK (116) | ARGDYVLDY (117) |
| 4J14 | GGTSSTYA (118) | SIPVFATV (119) | ASPYCSSMNCYT TFYYFDF (120) |
| 4J21 | GYSFTSYS (121) | IDTNTGNP (122) | ATYYVDLWGSYR QDYYGMDV (123) |
| 4N12 | GYILSKLS (124) | SEREDGET (125) | ATGGFWSMIGGN GVDY (126) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 5M16 | GYTFTSYF (127) | TYPGGGSP (128) | ARGAHRSIGTTPLDS (129) |
| 5O14 | GFTFSMYG (130) | IWNDGSKE (131) | ARDGIPDPERGDYGGLDY (132) |
| 8G18 | GGTFNNNG (133) | IVPNFGTP (134) | ARGRTAVTPMQLGLQFYFDF (135) |
| 1I9 | GYTFTDNS (136) | INPNTGVS (137) | AREENDSSGYYL (138) |
| 1L1 | GFSLSISGVG (139) | IYWDDDK (140) | AHSMTKGGAIYGQAYFEY (141) |
| 1M9 | GYTLTELS (142) | FEPEDGET (143) | TTDQVYYRSGSYSGYVDY (144) |
| 1O5 | GRTFSSYV (145) | IIPLFGTA (146) | ARGAQLYYNDGSGYIFDY (147) |
| 1O6 | GFSFISSA (148) | IVVASANT (149) | AAEHRSPCSGGDSCYSLYYGMDV (150) |
| 2A2 | GFTVSNYG (151) | ISTSSGRT (152) | AKGPFGGDFDY (153) |
| 2C2 | GFTFDVYA (154) | ISWNSGSV (155) | AKAFWFGELSGYGMDV (156) |
| 2D12 | GYSFNIYG (157) | ISAYNGNT (158) | ARPLWGEFYYDI (159) |
| 3A2 | GFTFSNYV (160) | ISYDGSNK (161) | ARSEWESSYGSGNYYTDYFYYYAMDV (162) |
| 3B4 | GFSLTTTGVT (163) | IYWDDDK (164) | AHSTGYYDSSGYRGALDAFAV (165) |
| 3E23 | SDALRSRSYY (166) | VSYSGGT (167) | ARSYFYDGSGYYYLSYFDS (168) |
| 3H5 | GFTFRMYG (169) | IFNDGVKK (170) | ARDGIPDPERGDYGGLDY (171) |
| 3I21 | GFIFDDYA (172) | ISWNSGNI (173) | VKDLYGYDILTGNGYDY (174) |
| 3K11 | GDTLSYYG (175) | IIPFFATT (176) | TAVYYCAGGYYGSGSSGDYGLDV (177) |
| 4B8 | GDSIGSRSFY (178) | IYYNGTT (179) | ARAPTYCSPSSCAVHWYFNL (180) |
| 4B10 | GYIFTKYG (181) | ISAYNENT (182) | AREVWFAEYIY (183) |
| 9D14 | GYTFTSHP (184) | INTKTGNL (185) | ARDEYSGYDSVGVFRGSFDDFYGMDV (186) |

TABLE 4

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 1H12 | SSNIGADYN (187) | GNT (188) | QSYDSSLSASV (189) |
| 2B4 | SSNIGSNP (190) | TNN (191) | AVWDDSLSGRWV (192) |
| 2H1 | SSNIGNHY (193) | DNY (194) | GTWDSSLSAVV (195) |
| 3E23 | TGAVTSGHY (196) | STD (197) | LLHFGGVVV (198) |
| 3N23 | QSIPSY (199) | ATS (200) | QQSYNTGIFT (201) |
| 4J14 | SSDFGTYNY (202) | DVS (203) | SSYTSGSTLYGGG (204) |
| 4J21 | SSNIGSNP (205) | TNN (206) | AVWDDSLSGRWV (207) |
| 4N12 | QDIRNN (208) | GTS (209) | LQHNSYPPT (210) |
| 5O14 | QSISSY (211) | ATS (212) | QQSYSFPRT (213) |
| 8G18 | SGAVTSDYY (214) | SAS (215) | LVYSGDGVV (216) |
| 1I9 | QSISTY (217) | AAS (218) | QQSYRTPWT (219) |
| 1L1 | DSDVGGYNY (220) | DVT (221) | SSYTSSSTLV (222) |
| 2A2 | QSVAIY (223) | DAS (224) | QQRGNWQYT (225) |
| 2C2 | SSDVGSYNY (226) | AVT (227) | TSYAGNNKDV (228) |
| 2D12 | QSVSSGY (229) | GAS (230) | QLFATSPPP (231) |
| 3A2 | QSLLRGIRYNY (232) | LGS (233) | MQALQTPTT (234) |
| 3B4 | QSVLYHSNNKNY (235) | WAS (236) | QQYYSTPYT (237) |
| 3E23 | TGAVTSGHY (238) | STD (239) | LLHFGGVVV (240) |
| 3H5 | QSITSY (241) | ATS (242) | QQSYSFPRT (243) |
| 3I21 | QSLLQSNGYNY (244) | LGS (245) | MQALQTPPT (246) |

TABLE 4-continued

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 3K11 | SSNIGAGYD (247) | GNN (248) | QSYDSSLSGSGV (249) |
| 9A11 | SSDVGAYNY (250) | DVA (251) | GSYTSDVSPV (252) |

TABLE 5

CHARACTERISTICS OF CHIKUNGUNYA VIRUS-SPECIFIC HUMAN MONOCLONAL ANTIBODIES

| mAb[1] | IgG subclass[2] | λ/κ light chain[2] | ELISA binding to E2 ectodomain (10 μg/mL)[3] | Neutralization against CHIKV VRP (strain SL15649)[4] EC$_{50}$ in ng/mL[5] [95% confidence interval] |
|---|---|---|---|---|
| 2H1 | IgG2 | λ | ++ | 8 [6-10] |
| 4N12 | IgG2 | κ | − | 8 [7-10] |
| 2B4 | IgG1 | λ | ++ | 14 [11-17] |
| 4J21 | IgG1 | λ | ++ | 5 [4-6] |
| 5M16 | IgG1 | κ | +++ | 5 [4-6] |
| 9D14 | IgG1 | λ | +++ | 6 [5-7] |
| 1H12 | IgG1 | λ | +++ | 17 [14-20] |
| 8E22 | IgG1 | λ | ++ | 17 [14-19] |
| 8G18 | IgG1 | λ | ++ | 17 [14-19] |
| 10N24 | IgG1 | κ | − | 21 [17-26] |
| 8I4 | IgG1 | κ | +++ | 8 [5-14] |
| 3N23 | IgG1 | κ | − | 25 [21-30] |
| 5O14 | IgG1 | κ | +++ | 38 [30-47] |
| 4J14 | IgG1 | λ | ++ | 23 [20-26] |
| 3E23 | IgG2 | λ | − | 11 [9-13] |
| 1L1 | IgG1 | λ | +/− | 18 [15-22] |
| 3B4 | IgG3 | κ | − | > |
| 4B8 | IgG1 | λ | +++ | 0.6 [0.4-0.8] |
| 4G20 | IgG1 | λ | − | 95 [60-160] |
| 1O5 | IgG1 | λ | − | 138 [110-170] |
| 1O6 | IgG3 | λ | − | 5,200 [4,100-6,600] |
| 2L5 | NT | NT | − | 4,600 [2,400-9,500] |
| 3A2 | IgG1 | κ | +++ | 1,300 [830-1,900] |
| 5F19 | IgG1 | λ | +++ | > |
| 1M9 | IgG1 | κ | − | > |
| 1I9 | IgG1 | κ | − | > |
| 4B10 | IgG1 | κ | − | > |
| 2C2 | IgG1 | λ | − | > |
| 2D12 | IgG1 | κ | − | > |
| 5N23 | IgG1 | λ | +++ | > |
| murine CHK-152 | IgG2c | κ | − | 3 [2-4] |

[1]Order of antibodies reflects the level of potency degree and breadth of the antibodies in neutralization assays against clinical CHIKV isolates of diverse genotypes.
[2]Immunoglobulin isotype, subtype, and light chain use were determined by ELISA. NT indicates not tested due to poor growth of B cell line.
[3](−) denotes no detectable binding [OD < 0.1]; (+/−) denotes weak binding [OD 0.31-0.499]; (++) denotes moderate binding [OD 0.5-0.99]; (+++) denotes strong binding [OD > 1.0].
[4]Values shown represent combined data from two or more independent experiments.
[5]Concentration (ng/mL) at which 50% of virus was neutralized (EC$_{50}$). (>) indicates EC$_{50}$ value is greater than the highest mAb concentration tested (10 μg/ml). N.D. = Not Done.

TABLE 6

MAJOR ANTIGENIC SITES OF CHIKUNGUNYA VIRUS-SPECIFIC HUMAN MONOCLONAL ANTIBODIES

| mAb[1] | Competition binding group for purified E2 protein[2] | Mutagenesis mapping E2 Domain[3] | E2 residues for which reduced binding was noted when altered to alanine |
|---|---|---|---|
| 2H1 | Low binding | E2-DA | R80, T116 |
| 4N12 | NT | Arch | D250 |
| 2B4 | Low binding | NoReduct ## | — |
| 4J21 | Low binding | NoReduct | — |
| 5M16 | 2 | Arch | G253 |
| 9D14 | 2 | NoReduct | — |
| 1H12 | 1/2 | DA/B, Arch | T58, D59, D60, R68, D71, I74, D77, T191, N193, K234 |
| 8E22 | Low binding | DA, Arch | H62, W64, R68, H99, D117, I255 |
| 8G18 | Low binding | DA | H62, W64, D117 |
| 10N24 | NT | DA, B | W64, D71, R80, T116, D117, I121, N187, I190 |
| 8I4 | NSF Ab | DB, Arch | M171, Q184, I190, N193, V197, R198, Y199, G209, L210, K215, K234, V242, I255 |
| 3N23 | NT | DA, Arch | D60, R68, G98, H170, M171, K233, K234 |
| 5O14 | 2 | NoReduct | — |
| 4J14 | Low binding | DA/B | D63, W64, T65, R80, I121, A162, N193 |
| 3E23 | NT | DA | W64 |
| 1L1 | Low binding | Arch | G253 |
| 3B4 | NT | DB | V192, Q195 |
| 4B8 | 2 | NoReduct | — |
| 4G20 | NT | DB | D174, R198, Y199, K215 |
| 1O5 | NT | DA | W64, T65 |
| 1O6 | 2 | DA | R80 |
| 2L5 | NT | NoReduct | — |
| 3A2 | 3 | DB | I190, R198, Y199, G209, L210, T212 |
| 5F19 | 4 | DA | H18 |
| 1M9 | NT | DA, Arch | R36, H62, R80, Q146, E165, E166, N231, D250, H256 |
| 1I9 | NT | E2 | Inconclusive |
| 4B10 | NT | NoReduct | — |
| 2C2 | NT | NoReduct | Inconclusive |
| 2D12 | NT | E2 | Inconclusive |
| 5N23 | 1 | DA, Arch | E24, D117, I121 |
| murine CHK-152 | NT | E2-DA, E2-DB | D59, W235, A11, M74, G194, N193, T212, H232[4] |

[1]Order of antibodies reflects the level of potency degree and breadth of the antibodies in neutralization assays against clinical CHIKV isolates of diverse genotypes.
[2]Values shown represent combined data from two independent experiments. Low binding indicates incomplete mAb binding to E2 on biosensor for assessing competition. NT indicates not tested since Ab did not bind E2 ectodomain in ELISA; NSF Ab indicates insufficient supply of mAb.
[3]NotReact indicates that the mAb did not react against the wild-type envelope proteins and could not be tested in this system. NoReduct indicates the mAb did bind to the wild-type E proteins, but no reduction was noted reproducibly for any mutant. DA indicates domain A; DB indicates domain B; Arch indicates either arch 1, arch 2, or both.
[4]Residues identified by contacts with mAb in a previous cryo-EM reconstruction.

TABLE 7

IN VITRO NEUTRALIZING POTENCY AND BREADTH OF CHIKUNGUNYA
VIRUS-SPECIFIC HUMAN MONOCLONAL ANTIBODIES

| | Neutralization against CHKV against indicated genotype and strain* $EC_{50}$, $ng/mL^2$ (95% confidence interval) | | | |
|---|---|---|---|---|
| | West African genotype | ECSA genotype | Asian genotype | |
| $mAb^1$ | NI 64 IbH 35 strain | LR2006 OPY1 (LR) strain | RSU1 strain | 2014 Caribbean 99659 strain |
| 2H1 | 3.7 (3.3-4.3) | 5.6 (4.9-6.3) | 5.9 (5.3-6.7) | 5.5 (4.7-6.5) |
| 4N12 | 2.5 (2.0-3.1) | 4.0 (3.3-5.0) | 6.5 (5.7-7.3) | 7.3 (5.9-9.2) |
| 2B4 | 3.2 (2.8-3.7) | 5.6 (4.6-6.7) | 6.5 (5.6-7.7) | 7.0 (6.0-8.2) |
| 4J21 | 5.2 (4.3-6.4) | 7.4 (6.6-8.3) | 7.7 (7.0-8.6) | 7.2 (5.3-9.8) |
| 5M16 | 6.0 (5.5-6.6) | 5.9 (5.0-6.8) | 8.4 (6.7-10.4) | 11.7 (9.7-14.1) |
| 9D14 | 2.1 (1.6-2.7) | 2.9 (2.3-3.7) | 6.3 (4.7-8.4) | 86.0 (31.5-235) |
| 1H12 | 3.0 (2.5-3.5) | 7.5 (6.7-8.4) | 11.7 (9.3-14.8) | 11.6 (8.2-16.2) |
| 8E22 | 8.2 (7.0-9.7) | 7.2 (6.4-8.3) | 42.5 (30.8-58.5) | 138.9 (64.7-298) |
| 8G18 | 4.7 (4.1-5.3) | 7.3 (6.3-8.4) | 34.9 (24.9-48.9) | 52.4 (24.1-114) |
| 10N24 | 7.9 (6.9-9.0) | 9.5 (8.2-11.0) | 15.9 (13.2-19.2) | 23.6 (18.3-30.5) |
| 8I4 | 6.9 (3.8-12.3) | 6.2 (4.5-8.4) | 153 (78-299) | > |
| 3N23 | 6.0 (5.0-7.2) | 10.1 (8.9-11.5) | 14.1 (11.6-17.1) | 8.7 (7.0-10.9) |
| 5O14 | 6.7 (5.5-8.3) | 12.1 (10.9-13.5) | 17.3 (14.2-21.1) | 6.2 (5.3-7.2) |
| 4J14 | 12.9 (11.2-15.0) | 17.7 (16.1-19.4) | 23.1 (20-27) | 23.0 (18.5-28.4) |
| 3E23 | 19.4 (15.2-25.0) | 18.7 (16.3-21.5) | 36.0 (30.3-42.9) | 38.0 (30.3-47.5) |
| 1L1 | 18.6 (15.5-22.4) | 24.2 (21.3-27.5) | 34.3 (29-40.7) | N.D. |
| 3B4 | 18.7 (10.7-32.8) | 29.6 (18.7-46.8) | 271 (144-511) | N.D. |
| 4B8 | 22.8 (12.4-41.8) | 28.1 (19.8-39.9) | 234 (142-386) | N.D. |
| 4G20 | 22.3 (17.3-29.0) | 34.9 (28.2-43.8) | 131.4 (88.5-195) | N.D. |
| 1O5 | 30.1 (22.6-35.3) | 37.6 (32.6-43.4) | 48.9 (37.8-63.2) | N.D. |
| 1O6 | 61.7 (50.8-74.8) | 57.5 (48.8-68.1) | N.D. | N.D. |
| 2L5 | 1,076 (748-1,548) | 2,361 (1,460-3,819) | 5,632 (3,904-8,128) | N.D. |
| 3A2 | 1,566 (1,111-2,207) | 1,396 (952-2,046) | > | N.D. |
| 5F19 | > | 9,064 (2,911-28,249) | > | N.D. |
| 1M9 | > | > | 6,187 (2,795-13,709) | N.D. |
| 1I9 | > | > | > | N.D. |
| 4B10 | > | > | > | N.D. |
| 2C2 | > | > | > | N.D. |
| 2D12 | > | > | > | N.D. |
| 5N23 | > | > | > | N.D. |
| murine CHK-152 | | | | |

[1] Order of antibodies reflects the level of potency degree and breadth of the antibodies in neutralization assays against clinical CHIKV isolates of diverse genotypes.
[2] Concentration (ng/mL) at which 50% of virus was neutralized ($EC_{50}$). (>) indicates $EC_{50}$ value is greater than the highest mAb concentration tested (10 μg/ml). N.D. = Not Done.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, N.Y., 1988.

Abbondanzo et al., Am. J. Pediatr. Hematol. Oncol., 12(4), 480-489, 1990.

Allred et al., Arch. Surg., 125(1), 107-113, 1990.

Atherton et al., Biol. of Reproduction, 32, 155-171, 1985.

Austin et al., PLoS Pathog 8, e1002930, 2012.

Brehin, et al., Virology 371:185-195, 2008.

Brown et al., J. Immunol. Meth., 12; 130(1):111-121, 1990.

Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.

Capaldi et al., Biochem. Biophys. Res. Comm., 74(2):425-433, 1977.

CDC, Chikungunya in the Americas. (Atlanta, Ga.: US Department of Health and Human Services). world-wide-web at cdc.gov/chikungunya/geo/americas.html, 2014.

CDC, Chikungunya virus (Atlanta, Ga.: US Department of Health and Human Services). world-wide-web at cdc.gov/media/releases/2013/p1218-chikungunyas.html, 2013.

Christian et al., Proc Natl Acad Sci USA, 110:18662-18667, 2013.

Chu et al., Deciphering the protective role of adaptive immunity to CHIKV/IRES a novel candidate vaccine against Chikungunya in the A129 mouse model. Vaccine 31:3353-3360, 2013.

Couderc et al., J. Infect. Dis. 200, 516-523, 2009.
De Jager et al., Semin. Nucl. Med. 23(2), 165-179, 1993.
Dholakia et al., J. Biol. Chem., 264, 20638-20642, 1989.
Doolittle and Ben-Zeev, Methods Mol. Biol., 109:215-237, 1999.
Edwards & Brown, J. Gen. Virol. 67 (Pt 2), 377-380, 1986.
Edwards et al., J. Gen. Virol. 67 (Pt 2), 377-380, 1986.
Fong et al., J. Virol. 88:14364-14379, 2014.
Fric et al., J. Infect. Dis. 207:319-322, 2013.
Gefter et al., Somatic Cell Genet., 3:231-236, 1977.
Goh et al., Clin. Immunol. 149:487-497, 2013.
Gulbis and Galand, Hum. Pathol. 24(12), 1271-1285, 1993.
Guo et al., Sci. Transl. Med. 3:99 ra85, 2001.
Hallengard, et al., J. Virol. 88:13333-13343, 2014.
Hawman et al., J. Virol. 87, 13878-13888, 2013.
Hong et al., J. Virol. 87:12471-12480, 2013.
Kam et al., EMBO Mol. Med. 4, 330-343, 2012b.
Kam et al., J. Virol. 86, 13005-13015, 2012a.
Kam et al., PLoS One 9, e95647, 2014.
Khatoon et al., Ann. of Neurology, 26, 210-219, 1989.
Kielian et al., Viruses 2:796-825, 2010.
King et al., J. Biol. Chem., 269, 10210-10218, 1989.
Kohler and Milstein, Eur. J. Immunol., 6, 511-519, 1976.
Kohler and Milstein, Nature, 256, 495-497, 1975.
Krause et al., J. Immunol. 187:3704-3711, 2011b.
Krause et al., J. Virol. 84:3127-3130, 2010.
Krause et al., J. Virol. 85:10905-10908, 2011a.
Krause et al., J. Virol. 86:6334-6340, 2012.
Kyte and Doolittle, J. Mol. Biol., 157(1):105-132, 1982.
Lanciotti & Valadere, Emerg Infect Dis 20, 2014.
Lee et al., PLoS Pathog. 7:e1002390, 2011.
Levitt et al., Vaccine 4, 157-162, 1986.
Lum et al., J. Immunol. 190:6295-6302, 2013.
Mainou et al., MBio 4, 2013.
Masrinoul et al., Virology 464-465, 111-117, 2014.
Messer et al., Proc. Natl. Acad. Sci. U.S.A 111:1939-1944, 2014.
Morrison et al., Am J Pathol, 178:32-40, 2011.
Nakamura et al., In: *Enzyme Immunoassays: Heterogeneous and Homogeneous Systems,*
Chapter 27, 1987.
O'Shannessy et al., J. Immun. Meth., 99, 153-161, 1987.
Paes et al., J. Am. Chem. Soc., 131:6952-6954, 2009.
Pal et al., J. Virol. 88:8213-8226, 2014.
Pal et al., PLoS Pathog 9, e1003312, 2013.
Persic et al., Gene 187:1, 1997
Potter and Haley, Meth. Enzymol., 91, 613-633, 1983.
Remington's Pharmaceutical Sciences, 15th Ed., 3:624-652, 1990.
R.C. Team, R Foundation for Statistical Computing, Vienna, Austria, 2014.
Schilte et al., PLoS Negl. Trop. Dis. 7:e2137, 2013.
Selvarajah et al., PLoS Negl. Trop. Dis. 7:e2423, 2013.
Sissoko et al., PLoS Negl. Trop. Dis. 3:e389, 2009.
Smith et al., J. Virol. 86, 2665-2675, 2012.
Smith et al., J. Virol. 88, 12233-12241, 2014.
Smith et al., J. Virol., 86:2665-2675, 2012.
Smith et al., MBio 4, e00873-00813, 2013a.
Smith et al., J. Infect. Dis. 207, 1898-1908, 2013b.
Staples et al., Clin. Infect. Dis., 49, 942-948, 2009.
Sun et al., Elife, 2:e00435, 2013.
Sun et al., J. Steroid Biochem., 26(1):83-92, 1987.
Sun et al., J. Virol., 88:2035-2046, 2014.
Tang et al., J. Biol. Chem., 271:28324-28330, 1996.
Thornburg et al., J. Clin. Invest., 123:4405-4409, 2013.
U.S. Pat. Nos. 3,817,837
3,850,752
3,939,350
3,996,345
4,196,265
4,275,149
4,277,437
4,366,241
4,472,509
4,554,101
4,680,338
4,816,567
4,867,973
4,938,948
5,021,236
5,141,648
5,196,066
5,563,250
5,565,332
5,856,456
5,880,270
Vander Veen et al., Anim Health Res Rev, 13:1-9, 2012.
Voss et al., Nature, 468:709-712, 2010.
Voss et al., Nature, 468:709-712, 2010.
Wailer et al., J. Immunol., 186:3258-3264, 2011.
Wailer et al., J. Immunol., 186:3258-3264, 2011.
Wawrzynczak & Thorpe, In: *Immunoconjugates, Antibody Conjugates In Radioimaging And Therapy Of Cancer,* Vogel (Ed.), NY, Oxford University Press, 28, 1987.
Yu et al., Nature 455:532-536, 2008.

What is claimed is:

1. A method of detecting a Chikungunya virus infection in a subject comprising:
   (a) contacting a sample from said subject with an antibody or antibody fragment comprising clone-paired heavy and light chain CDR sequences as set out below:
   Clone 1H12 ($V_H$ CDRs 1-3 consisting of SEQ ID NOS: 103-105, respectively; and $V_L$ CDRs 1-3 consisting of SEQ ID NOS: 187-189, respectively);
   Clone 4N12 ($V_H$ CDRs 1-3 consisting of SEQ ID NOS: 124-126, respectively; and $V_L$ CDRs 1-3 consisting of SEQ ID NOS: 208-210);
   Clone 2H1 ($V_H$ CDRs 1-3 consisting of SEQ ID NOS: 109-111, respectively; and $V_L$ CDRs 1-3 consisting of SEQ ID NOS: 193-195, respectively);
   Clone 4J14 ($V_H$ CDRs 1-3 consisting of SEQ ID NOS: 118-120, respectively; and $V_L$ CDRs 1-3 consisting of SEQ ID NOS: 202-204, respectively);
   Clone 3N23 ($V_H$ CDRs 1-3 consisting of SEQ ID NOS: 115-117, respectively; and $V_L$ CDRs 1-3 consisting of SEQ ID NOS: 199-201, respectively);
   Clone 5O14 ($V_H$ CDRs 1-3 consisting of SEQ ID NOS: 130-132, respectively; and $V_L$ CDRs 1-3 consisting of SEQ ID NOS: 211-213, respectively); or
   Clone 3E23 ($V_H$ CDRs 1-3 consisting of SEQ ID NOS: 112-114, respectively; and $V_L$ CDRs 1-3 consisting of SEQ ID NOS: 196-198, respectively); and
   (b) detecting Chikungunya virus glycoprotein E2 in said sample by binding of said antibody or antibody fragment to E2 in said sample.

2. The method of claim 1, wherein said sample is a body fluid.

3. The method of claim 1, further comprising performing steps (a) and (b) a second time and determining a change in the E2 levels as compared to the first assay.

4. A method of treating a subject infected with Chikungunya Virus, or reducing the likelihood of infection of a subject at risk of contracting Chikungunya virus, comprising delivering to said subject an antibody or antibody fragment comprising clone-paired heavy and light chain CDR sequences as set out below:
   Clone 1H12 ($V_H$ CDRs 1-3 consisting of SEQ ID NOS: 103-105, respectively; and $V_L$ CDRs 1-3 consisting of SEQ ID NOS: 187-189, respectively);
   Clone 4N12 ($V_H$ CDRs 1-3 consisting of SEQ ID NOS: 124-126, respectively; and $V_L$ CDRs 1-3 consisting of SEQ ID NOS: 208-210);
   Clone 2H1 ($V_H$ CDRs 1-3 consisting of SEQ ID NOS: 109-111, respectively; and $V_L$ CDRs 1-3 consisting of SEQ ID NOS: 193-195, respectively);
   Clone 4J14 ($V_H$ CDRs 1-3 consisting of SEQ ID NOS: 118-120, respectively; and $V_L$ CDRs 1-3 consisting of SEQ ID NOS: 202-204, respectively);
   Clone 3N23 ($V_H$ CDRs 1-3 consisting of SEQ ID NOS: 115-117, respectively; and $V_L$ CDRs 1-3 consisting of SEQ ID NOS: 199-201, respectively);
   Clone 5O14 ($V_H$ CDRs 1-3 consisting of SEQ ID NOS: 130-132, respectively; and $V_L$ CDRs 1-3 consisting of SEQ ID NOS: 211-213, respectively); or
   Clone 3E23 ($V_H$ CDRs 1-3 consisting of SEQ ID NOS: 112-114, respectively; and $V_L$ CDRs 1-3 consisting of SEQ ID NOS: 196-198, respectively).

5. The method of claim 4, wherein said antibody or antibody fragment is administered prior to infection.

6. The method of claim 4, wherein said antibody or antibody fragment is administered after infection.

7. The method of claim 4, wherein delivering comprises antibody or antibody fragment administration, or genetic delivery with an RNA or DNA sequence or vector encoding the antibody or antibody fragment.

8. A recombinant monoclonal antibody or antibody fragment binding immunologically to Chikungunya virus, wherein the antibody or antibody fragment comprises clone-paired heavy and light chain CDR sequences as set out below:
   Clone 1H12 ($V_H$ CDRs 1-3 consisting of SEQ ID NOS: 103-105, respectively; and $V_L$ CDRs 1-3 consisting of SEQ ID NOS: 187-189, respectively);
   Clone 4N12 ($V_H$ CDRs 1-3 consisting of SEQ ID NOS: 124-126, respectively; and $V_L$ CDRs 1-3 consisting of SEQ ID NOS: 208-210);
   Clone 2H1 ($V_H$ CDRs 1-3 consisting of SEQ ID NOS: 109-111, respectively; and $V_L$ CDRs 1-3 consisting of SEQ ID NOS: 193-195, respectively);
   Clone 4J14 ($V_H$ CDRs 1-3 consisting of SEQ ID NOS: 118-120, respectively; and $V_L$ CDRs 1-3 consisting of SEQ ID NOS: 202-204, respectively);
   Clone 3N23 ($V_H$ CDRs 1-3 consisting of SEQ ID NOS: 115-117, respectively; and $V_L$ CDRs 1-3 consisting of SEQ ID NOS: 199-201, respectively);
   Clone 5O14 ($V_H$ CDRs 1-3 consisting of SEQ ID NOS: 130-132, respectively; and $V_L$ CDRs 1-3 consisting of SEQ ID NOS: 211-213, respectively); or
   Clone 3E23 ($V_H$ CDRs 1-3 consisting of SEQ ID NOS: 112-114, respectively; and $V_L$ CDRs 1-3 consisting of SEQ ID NOS: 196-198, respectively).

9. The recombinant monoclonal antibody or antibody fragment of claim 8, wherein said antibody or antibody fragment is encoded by light and heavy chain variable sequences according to clone-paired sequences from Table 1.

10. The recombinant monoclonal antibody or antibody fragment of claim 8, wherein said antibody or antibody fragment is encoded by light and heavy chain variable sequences having at least 70%, 80%, or 90% identity to clone-paired sequences from Table 1 and comprises clone-paired heavy and light chain CDR sequences as set out below:
   Clone 1H12 ($V_H$ CDRs 1-3 consisting of SEQ ID NOS: 103-105, respectively; and $V_L$ CDRs 1-3 consisting of SEQ ID NOS: 187-189, respectively);
   Clone 4N12 ($V_H$ CDRs 1-3 consisting of SEQ ID NOS: 124-126, respectively; and $V_L$ CDRs 1-3 consisting of SEQ ID NOS: 208-210);
   Clone 2H1 ($V_H$ CDRs 1-3 consisting of SEQ ID NOS: 109-111, respectively; and $V_L$ CDRs 1-3 consisting of SEQ ID NOS: 193-195, respectively);
   Clone 4J14 ($V_H$ CDRs 1-3 consisting of SEQ ID NOS: 118-120, respectively; and $V_L$ CDRs 1-3 consisting of SEQ ID NOS: 202-204, respectively);
   Clone 3N23 ($V_H$ CDRs 1-3 consisting of SEQ ID NOS: 115-117, respectively; and $V_L$ CDRs 1-3 consisting of SEQ ID NOS: 199-201, respectively);
   Clone 5O14 ($V_H$ CDRs 1-3 consisting of SEQ ID NOS: 130-132, respectively; and $V_L$ CDRs 1-3 consisting of SEQ ID NOS: 211-213, respectively); or
   Clone 3E23 ($V_H$ CDRs 1-3 consisting of SEQ ID NOS: 112-114, respectively; and $V_L$ CDRs 1-3 consisting of SEQ ID NOS: 196-198, respectively).

11. The recombinant monoclonal antibody or antibody fragment of claim 8, wherein said antibody or antibody fragment is encoded by light and heavy chain variable sequences having at least 95% identity to clone-paired sequences from Table 1 and comprises clone-paired heavy and light chain CDR sequences as set out below:
   Clone 1H12 ($V_H$ CDRs 1-3 consisting of SEQ ID NOS: 103-105, respectively; and $V_L$ CDRs 1-3 consisting of SEQ ID NOS: 187-189, respectively);
   Clone 4N12 ($V_H$ CDRs 1-3 consisting of SEQ ID NOS: 124-126, respectively; and $V_L$ CDRs 1-3 consisting of SEQ ID NOS: 208-210);
   Clone 2H1 ($V_H$ CDRs 1-3 consisting of SEQ ID NOS: 109-111, respectively; and $V_L$ CDRs 1-3 consisting of SEQ ID NOS: 193-195, respectively);
   Clone 4J14 ($V_H$ CDRs 1-3 consisting of SEQ ID NOS: 118-120, respectively; and $V_L$ CDRs 1-3 consisting of SEQ ID NOS: 202-204, respectively);
   Clone 3N23 ($V_H$ CDRs 1-3 consisting of SEQ ID NOS: 115-117, respectively; and $V_L$ CDRs 1-3 consisting of SEQ ID NOS: 199-201, respectively);
   Clone 5O14 ($V_H$ CDRs 1-3 consisting of SEQ ID NOS: 130-132, respectively; and $V_L$ CDRs 1-3 consisting of SEQ ID NOS: 211-213, respectively); or
   Clone 3E23 ($V_H$ CDRs 1-3 consisting of SEQ ID NOS: 112-114, respectively; and $V_L$ CDRs 1-3 consisting of SEQ ID NOS: 196-198, respectively).

12. The recombinant monoclonal antibody or antibody fragment of claim 8, wherein said antibody or antibody fragment comprises light and heavy chain variable sequences according to clone-paired sequences from Table 2.

13. The recombinant monoclonal antibody or antibody fragment of claim 8, wherein said antibody or antibody fragment comprises light and heavy chain variable sequences having 95% identity to clone-paired sequences from Table 2 and comprises clone-paired heavy and light chain CDR sequences as set out below:
   Clone 1H12 ($V_H$ CDRs 1-3 consisting of SEQ ID NOS: 103-105, respectively; and $V_L$ CDRs 1-3 consisting of SEQ ID NOS: 187-189, respectively);
   Clone 4N12 ($V_H$ CDRs 1-3 consisting of SEQ ID NOS: 124-126, respectively; and $V_L$ CDRs 1-3 consisting of SEQ ID NOS: 208-210);
   Clone 2H1 ($V_H$ CDRs 1-3 consisting of SEQ ID NOS: 109-111, respectively; and $V_L$ CDRs 1-3 consisting of SEQ ID NOS: 193-195, respectively);
   Clone 4J14 ($V_H$ CDRs 1-3 consisting of SEQ ID NOS: 118-120, respectively; and $V_L$ CDRs 1-3 consisting of SEQ ID NOS: 202-204, respectively);
   Clone 3N23 ($V_H$ CDRs 1-3 consisting of SEQ ID NOS: 115-117, respectively; and $V_L$ CDRs 1-3 consisting of SEQ ID NOS: 199-201, respectively);
   Clone 5O14 ($V_H$ CDRs 1-3 consisting of SEQ ID NOS: 130-132, respectively; and $V_L$ CDRs 1-3 consisting of SEQ ID NOS: 211-213, respectively); or
   Clone 3E23 ($V_H$ CDRs 1-3 consisting of SEQ ID NOS: 112-114, respectively; and $V_L$ CDRs 1-3 consisting of SEQ ID NOS: 196-198, respectively).

14. The recombinant monoclonal antibody or antibody fragment of claim 8, wherein the antibody fragment is a recombinant ScFv (single chain fragment variable) antibody, Fab fragment, F(ab')$_2$ fragment, or Fv fragment.

15. The recombinant monoclonal antibody or antibody fragment of claim 8, wherein said antibody is a chimeric antibody, or is bispecific antibody that targets a Chikungunya virus antigen other than glycoprotein.

16. The recombinant monoclonal antibody or antibody fragment of claim 8, wherein said antibody is an IgG.

17. The recombinant monoclonal antibody or antibody fragment of claim 8, wherein said antibody or antibody fragment further comprises a cell penetrating peptide and/or is an intrabody.

18. A hybridoma or engineered cell comprising a nucleic acid encoding an antibody or antibody fragment, wherein the antibody or antibody fragment comprises clone-paired heavy and light chain CDR sequences as set out below:
Clone 1H12 ($V_H$ CDRs 1-3 consisting of SEQ ID NOS: 103-105, respectively; and $V_L$ CDRs 1-3 consisting of SEQ ID NOS: 187-189, respectively);
Clone 4N12 ($V_H$ CDRs 1-3 consisting of SEQ ID NOS: 124-126, respectively; and $V_L$ CDRs 1-3 consisting of SEQ ID NOS: 208-210);
Clone 2H1 ($V_H$ CDRs 1-3 consisting of SEQ ID NOS: 109-111, respectively; and $V_L$ CDRs 1-3 consisting of SEQ ID NOS: 193-195, respectively);
Clone 4J14 ($V_H$ CDRs 1-3 consisting of SEQ ID NOS: 118-120, respectively; and $V_L$ CDRs 1-3 consisting of SEQ ID NOS: 202-204, respectively);
Clone 3N23 ($V_H$ CDRs 1-3 consisting of SEQ ID NOS: 115-117, respectively; and $V_L$ CDRs 1-3 consisting of SEQ ID NOS: 199-201, respectively);
Clone 5O14 ($V_H$ CDRs 1-3 consisting of SEQ ID NOS: 130-132, respectively; and $V_L$ CDRs 1-3 consisting of SEQ ID NOS: 211-213, respectively); or
Clone 3E23 ($V_H$ CDRs 1-3 consisting of SEQ ID NOS: 112-114, respectively; and $V_L$ CDRs 1-3 consisting of SEQ ID NOS: 196-198, respectively).

19. The recombinant monoclonal antibody or antibody fragment of claim 8, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

20. The recombinant monoclonal antibody or antibody fragment of claim 8, wherein the variable region of its heavy chain comprises or consists of SEQ ID NO: 53 and the variable region of its light chain comprises or consists of SEQ ID NO: 54.

21. A pharmaceutical composition comprising the recombinant monoclonal antibody or antibody fragment according to claim 8.

22. A cell line producing a monoclonal antibody or antibody fragment comprising clone-paired heavy and light chain CDR sequences as set out below:
Clone 1H12 ($V_H$ CDRs 1-3 consisting of SEQ ID NOS: 103-105, respectively; and $V_L$ CDRs 1-3 consisting of SEQ ID NOS: 187-189, respectively);
Clone 4N12 ($V_H$ CDRs 1-3 consisting of SEQ ID NOS: 124-126, respectively; and $V_L$ CDRs 1-3 consisting of SEQ ID NOS: 208-210);
Clone 2H1 ($V_H$ CDRs 1-3 consisting of SEQ ID NOS: 109-111, respectively; and $V_L$ CDRs 1-3 consisting of SEQ ID NOS: 193-195, respectively);
Clone 4J14 ($V_H$ CDRs 1-3 consisting of SEQ ID NOS: 118-120, respectively; and $V_L$ CDRs 1-3 consisting of SEQ ID NOS: 202-204, respectively);
Clone 3N23 ($V_H$ CDRs 1-3 consisting of SEQ ID NOS: 115-117, respectively; and $V_L$ CDRs 1-3 consisting of SEQ ID NOS: 199-201, respectively);
Clone 5O14 ($V_H$ CDRs 1-3 consisting of SEQ ID NOS: 130-132, respectively; and $V_L$ CDRs 1-3 consisting of SEQ ID NOS: 211-213, respectively); or
Clone 3E23 ($V_H$ CDRs 1-3 consisting of SEQ ID NOS: 112-114, respectively; and $V_L$ CDRs 1-3 consisting of SEQ ID NOS: 196-198, respectively.

23. A method of producing a monoclonal antibody or antibody fragment, said method comprising the steps of:
(a) culturing a cell line producing monoclonal antibody or antibody fragment;
(b) purifying the produced monoclonal antibody or antibody fragment; and optionally
(c) formulating said monoclonal antibody or antibody fragment into a pharmaceutical composition,
wherein the antibody or antibody fragment is characterized by clone-paired heavy and light chain CDR sequences as set out below:
Clone 1H12 ($V_H$ CDRs 1-3 consisting of SEQ ID NOS: 103-105, respectively; and $V_L$ CDRs 1-3 consisting of SEQ ID NOS: 187-189, respectively);
Clone 4N12 ($V_H$ CDRs 1-3 consisting of SEQ ID NOS: 124-126, respectively; and $V_L$ CDRs 1-3 consisting of SEQ ID NOS: 208-210);
Clone 2H1 ($V_H$ CDRs 1-3 consisting of SEQ ID NOS: 109-111, respectively; and $V_L$ CDRs 1-3 consisting of SEQ ID NOS: 193-195, respectively);
Clone 4J14 ($V_H$ CDRs 1-3 consisting of SEQ ID NOS: 118-120, respectively; and $V_L$ CDRs 1-3 consisting of SEQ ID NOS: 202-204, respectively);
Clone 3N23 ($V_H$ CDRs 1-3 consisting of SEQ ID NOS: 115-117, respectively; and $V_L$ CDRs 1-3 consisting of SEQ ID NOS: 199-201, respectively);
Clone 5O14 ($V_H$ CDRs 1-3 consisting of SEQ ID NOS: 130-132, respectively; and $V_L$ CDRs 1-3 consisting of SEQ ID NOS: 211-213, respectively); or
Clone 3E23 ($V_H$ CDRs 1-3 consisting of SEQ ID NOS: 112-114, respectively; and $V_L$ CDRs 1-3 consisting of SEQ ID NOS: 196-198, respectively).

24. A kit comprising a recombinant monoclonal antibody or antibody fragment according to claim 8 and optionally packaging material.

25. The pharmaceutical composition of claim 21, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

26. The pharmaceutical composition of claim 21, wherein the variable region of the heavy chain comprises or consists of SEQ ID NO: 53 and the variable region of the light chain comprises or consists of SEQ ID NO: 54.

27. The hybridoma or engineered cell of claim 18, wherein said antibody or antibody fragment is encoded by light and heavy chain variable sequences according to clone-paired sequences from Table 1.

28. The hybridoma or engineered cell of claim 18, wherein said antibody or antibody fragment is encoded by light and heavy chain variable sequences having at least 70%, 80%, or 90% identity to clone-paired sequences from Table 1 and comprises heavy and light chain CDR sequences as set out below:
Clone 1H12 ($V_H$ CDRs 1-3 consisting of SEQ ID NOS: 103-105, respectively; and $V_L$ CDRs 1-3 consisting of SEQ ID NOS: 187-189, respectively);
Clone 4N12 ($V_H$ CDRs 1-3 consisting of SEQ ID NOS: 124-126, respectively; and $V_L$ CDRs 1-3 consisting of SEQ ID NOS: 208-210);
Clone 2H1 ($V_H$ CDRs 1-3 consisting of SEQ ID NOS: 109-111, respectively; and $V_L$ CDRs 1-3 consisting of SEQ ID NOS: 193-195, respectively);

Clone 4J14 (V_H CDRs 1-3 consisting of SEQ ID NOS: 118-120, respectively; and V_L CDRs 1-3 consisting of SEQ ID NOS: 202-204, respectively);

Clone 3N23 (V_H CDRs 1-3 consisting of SEQ ID NOS: 115-117, respectively; and V_L CDRs 1-3 consisting of SEQ ID NOS: 199-201, respectively);

Clone 5O14 (V_H CDRs 1-3 consisting of SEQ ID NOS: 130-132, respectively; and V_L CDRs 1-3 consisting of SEQ ID NOS: 211-213, respectively); or Clone 3E23 (V_H CDRs 1-3 consisting of SEQ ID NOS: 112-114, respectively; and V_L CDRs 1-3 consisting of SEQ ID NOS: 196-198, respectively).

29. The hybridoma or engineered cell of claim 18, wherein said antibody or antibody fragment is encoded by light and heavy chain variable sequences having at least 95% identity to clone-paired sequences from Table 1 and comprises heavy and light chain CDR sequences as set out below:

Clone 1H12 (V_H CDRs 1-3 consisting of SEQ ID NOS: 103-105, respectively; and V_L CDRs 1-3 consisting of SEQ ID NOS: 187-189, respectively);

Clone 4N12 (V_H CDRs 1-3 consisting of SEQ ID NOS: 124-126, respectively; and V_L CDRs 1-3 consisting of SEQ ID NOS: 208-210);

Clone 2H1 (V_H CDRs 1-3 consisting of SEQ ID NOS: 109-111, respectively; and V_L CDRs 1-3 consisting of SEQ ID NOS: 193-195, respectively);

Clone 4J14 (V_H CDRs 1-3 consisting of SEQ ID NOS: 118-120, respectively; and V_L CDRs 1-3 consisting of SEQ ID NOS: 202-204, respectively);

Clone 3N23 (V_H CDRs 1-3 consisting of SEQ ID NOS: 115-117, respectively; and V_L CDRs 1-3 consisting of SEQ ID NOS: 199-201, respectively);

Clone 5O14 (V_H CDRs 1-3 consisting of SEQ ID NOS: 130-132, respectively; and V_L CDRs 1-3 consisting of SEQ ID NOS: 211-213, respectively); or Clone 3E23 (V_H CDRs 1-3 consisting of SEQ ID NOS: 112-114, respectively; and V_L CDRs 1-3 consisting of SEQ ID NOS: 196-198, respectively).

30. The hybridoma or engineered cell of claim 18, wherein said antibody or antibody fragment comprises light and heavy chain variable sequences according to clone-paired sequences from Table 2.

31. The hybridoma or engineered cell of claim 18, wherein said antibody or antibody fragment comprises light and heavy chain variable sequences having 95% identity to clone-paired sequences from Table 2 and comprises heavy and light chain CDR sequences as set out below:

Clone 1H12 (V_H CDRs 1-3 consisting of SEQ ID NOS: 103-105, respectively; and V_L CDRs 1-3 consisting of SEQ ID NOS: 187-189, respectively);

Clone 4N12 (V_H CDRs 1-3 consisting of SEQ ID NOS: 124-126, respectively; and V_L CDRs 1-3 consisting of SEQ ID NOS: 208-210);

Clone 2H1 (V_H CDRs 1-3 consisting of SEQ ID NOS: 109-111, respectively; and V_L CDRs 1-3 consisting of SEQ ID NOS: 193-195, respectively);

Clone 4J14 (V_H CDRs 1-3 consisting of SEQ ID NOS: 118-120, respectively; and V_L CDRs 1-3 consisting of SEQ ID NOS: 202-204, respectively);

Clone 3N23 (V_H CDRs 1-3 consisting of SEQ ID NOS: 115-117, respectively; and V_L CDRs 1-3 consisting of SEQ ID NOS: 199-201, respectively);

Clone 5O14 (V_H CDRs 1-3 consisting of SEQ ID NOS: 130-132, respectively; and V_L CDRs 1-3 consisting of SEQ ID NOS: 211-213, respectively); or Clone 3E23 (V_H CDRs 1-3 consisting of SEQ ID NOS: 112-114, respectively; and V_L CDRs 1-3 consisting of SEQ ID NOS: 196-198, respectively).

32. The hybridoma or engineered cell of claim 18, wherein the antibody fragment is a recombinant ScFv (single chain fragment variable) antibody, Fab fragment, F(ab')_2 fragment, or Fv fragment.

33. The hybridoma or engineered cell of claim 18, wherein said antibody is a chimeric antibody, or is bispecific antibody that targets a Chikungunya virus antigen other than glycoprotein.

34. The hybridoma or engineered cell of claim 18, wherein said antibody is an IgG.

35. The hybridoma or engineered cell of claim 18, wherein said antibody or antibody fragment further comprises a cell penetrating peptide and/or is an intrabody.

36. The hybridoma or engineered cell of claim 18, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

37. The hybridoma or engineered cell of claim 18, wherein the variable region of the heavy chain comprises or consists of SEQ ID NO: 53 and the variable region of the light chain comprises or consists of SEQ ID NO: 54.

38. The method of claim 1, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

39. The method of claim 1, wherein the variable region of the heavy chain comprises or consists of SEQ ID NO: 53 and the variable region of the light chain comprises or consists of SEQ ID NO: 54.

40. The method of claim 4, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

41. The cell line producing a monoclonal antibody or antibody fragment of claim 22, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

42. The method of claim 23, wherein said antibody or antibody fragment comprises:
a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

43. The kit of claim 24, wherein said antibody or antibody fragment comprises:

a CDRH1 consisting of SEQ ID NO: 103;
a CDRH2 consisting of SEQ ID NO: 104;
a CDRH3 consisting of SEQ ID NO: 105;
a CDRL1 consisting of SEQ ID NO: 187;
a CDRL2 consisting of SEQ ID NO: 188;
a CDRL3 consisting of SEQ ID NO: 189.

* * * * *